US010787494B2

(12) United States Patent
Struthers et al.

(10) Patent No.: US 10,787,494 B2
(45) Date of Patent: *Sep. 29, 2020

(54) INTERLEUKIN-2/INTERLEUKIN-2 RECEPTOR ALPHA FUSION PROTEINS AND METHODS OF USE

(71) Applicant: Bristol-Myers Squibb Company, Princeton, NJ (US)

(72) Inventors: Mary Struthers, Edison, NJ (US); Jonathan Harry Davis, Madison, WI (US); Michael Louis Doyle, Yardley, PA (US); Priyanka Apurva Madia, Franklin Park, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/435,420

(22) Filed: Jun. 7, 2019

(65) Prior Publication Data

US 2019/0359672 A1 Nov. 28, 2019

Related U.S. Application Data

(63) Continuation of application No. 16/366,838, filed on Mar. 27, 2019.

(60) Provisional application No. 62/649,379, filed on Mar. 28, 2018.

(51) Int. Cl.
| | | |
|---|---|---|
| *A61K 38/20* | (2006.01) | |
| *A61K 38/17* | (2006.01) | |
| *C07K 14/55* | (2006.01) | |
| *C07K 14/715* | (2006.01) | |
| *C12N 15/62* | (2006.01) | |
| *A61K 47/65* | (2017.01) | |
| *A61P 37/04* | (2006.01) | |
| *C07K 16/28* | (2006.01) | |
| *A61K 38/00* | (2006.01) | |

(52) U.S. Cl.
CPC .......... *C07K 14/55* (2013.01); *A61K 38/1793* (2013.01); *A61K 38/2013* (2013.01); *A61K 47/65* (2017.08); *A61P 37/04* (2018.01); *C07K 14/7155* (2013.01); *C07K 16/2818* (2013.01); *C07K 16/2827* (2013.01); *C12N 15/62* (2013.01); *A61K 38/00* (2013.01); *C07K 2317/30* (2013.01); *C07K 2319/00* (2013.01); *C07K 2319/30* (2013.01); *C07K 2319/31* (2013.01); *C07K 2319/32* (2013.01); *C07K 2319/75* (2013.01); *C07K 2319/91* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 4,873,192 | A | 10/1989 | Kunkel |
| 5,250,296 | A | 10/1993 | Ootsu |
| 5,605,793 | A | 2/1997 | Stemmer |
| 5,837,458 | A | 11/1998 | Minshull et al. |
| 6,967,092 | B1 | 11/2005 | McKearn et al. |
| 9,359,415 | B2 | 6/2016 | Alvarez |
| 2004/0265272 | A1 | 12/2004 | Iwamoto |
| 2006/0160187 | A1 | 7/2006 | Denis-Mize et al. |
| 2006/0263857 | A1 | 11/2006 | Lefrancois et al. |
| 2006/0269515 | A1 | 11/2006 | Denis-Mize et al. |
| 2013/0336924 | A1 | 12/2013 | Alvarez |
| 2017/0233448 | A1 | 8/2017 | Malek |
| 2019/0300592 | A1 | 10/2019 | Struthers |

FOREIGN PATENT DOCUMENTS

| | | | |
|---|---|---|---|
| EP | 0075444 A2 | 3/1983 | |
| JP | H10-511846 A | 11/1998 | |
| JP | 2008-545397 A | 12/2008 | |
| WO | WO-199620277 A | 7/1996 | |
| WO | WO-9960128 A1 | 11/1999 | |
| WO | WO-2003029475 A | 4/2003 | |
| WO | WO-2007001677 A | 1/2007 | |
| WO | WO-2010020766 A2 | 2/2010 | |
| WO | WO-2011123683 A2 | 10/2011 | |
| WO | WO-2013184942 A1 | 12/2013 | |
| WO | WO-2014023752 A1 | 2/2014 | |
| WO | WO-2016022671 A1 * | 2/2016 | ......... C07K 14/7155 |
| WO | WO-2016100788 A1 | 6/2016 | |
| WO | WO-2017201432 A2 | 11/2017 | |

OTHER PUBLICATIONS

Office action dated Mar. 8, 2019 in U.S. Appl. No. 15/501,392, inventor Malek, T., int'l filed Aug. 6, 2015, 10 pages.
Office action dated Aug. 27, 2018 in U.S. Appl. No. 15/501,392, inventor Malek, T., int'l filed Aug. 6, 2015, 13 pages.
Rao, B., et al., High-Affinity CD25-Binding IL-2 Mutants Potently Stimulate Persistent T Cell Growth, Biochemistry 44:10696-10701, American Chemical Society, United States (2007).
Office action dated Mar. 5, 2020, in U.S. Appl. No. 15/501,392, inventor Malek, T., int'l filed Aug. 6, 2015, 13 pages.
Buchwald, H., et al., "Long-term, Continuous Intravenous Heparin Administration by an Implantable Infusion Pump in Ambulatory Patients with Recurrent Venous Thrombosis," Surgery 88(4):507-516, Mosby, United States (1980).

(Continued)

*Primary Examiner* — Xiaozhen Xie
(74) *Attorney, Agent, or Firm* — Sterne, Kessler, Goldstein & Fox, P.L.L.C.

(57) ABSTRACT

Disclosed herein are fusion proteins comprising: (a) a first polypeptide comprising Interleukin-2 (IL2); and (b) a second polypeptide, fused in frame to the first polypeptide, wherein the second polypeptide comprises an extracellular domain of Interleukin-2 Receptor alpha (IL2Rα), wherein IL2 or IL2Rα comprises at least one fewer glycosylation site compared to native IL2 or native IL2Rα. Methods of production and methods of therapeutic use of the fusion proteins are also disclosed.

8 Claims, 11 Drawing Sheets

Specification includes a Sequence Listing.

(56) References Cited

OTHER PUBLICATIONS

Centers for Disease Control and Prevention (CDC)., "FDA Approval for Infants of a Haemophilus Influenzae Type B Conjugate and Hepatitis B (Recombinant) Combined Vaccine," MMWR. Morbidity and Mortality Weekly Report 46(5):107-109, Centers for Disease Control, United States (1997).
Crameri, A., "DNA Shuffling of a Family of Genes from Diverse Species Accelerates Directed Evolution," Nature 391(6664):288-291, Nature America Publishing, United States (1998).
Crameri, A., "Molecular Evolution of an Arsenate Detoxification Pathway by DNA Shuffling," Nature Biotechnology 15(5):436-438, Nature America Publishing, United States (1997).
During, M.J., et al., "Controlled Release of Dopamine From a Polymeric Brain Implant: in Vivo Characterization," Annals of Neurology 25(4):351-356, Wiley-Liss, United States (1989).
Gait., et al., Oligonucleotide Synthesis: A Practical Approach, IRL Press, MRC Laboratory of Molecular Biology(1984).
Genbank, "Canis lupus familiaris interleukin 2 receptor, alpha (IL2RA), mRNA," accession No. NM_001003211.1, accessed at https://www.ncbi.nlm.nih.gov/nuccore/NM_001003211.1, Feb. 2014.
Genbank, "interleukin-2 receptor subunit alpha precursor [Bos taurus]," accession No. NP_776783.1, accessed at https://www.ncbi.nlm.nih.gov/protein/NP_776783.1, Jun. 2018.
Genbank, "interleukin-2 receptor subunit alpha precursor [Macaca mulatta]," accession No. NP_001028089.1, accessed at https://www.ncbi.nlm.nih.gov/protein/NP_001028089.1, Nov. 2017.
Genbank, "interleukin-2 receptor subunit alpha precursor [Mus musculus]," accession No. NP_032393.3, accessed at https://www.ncbi.nlm.nih.gov/protein/NP_032393.3, Jun. 2018.
Genbank, "interleukin-2 receptor subunit alpha precursor [Pan troglodytes]," accession No. NP_001030597.1, accessed at https://www.ncbi.nlm.nih.gov/protein/78486568/, Nov. 2017.
Genbank, "interleukin-2 receptor subunit alpha precursor [Rattus norvegicus]," accession No. NP_037295.1, accessed at https://www.ncbi.nlm.nih.gov/protein/NP_037295.1, Aug. 2018.
Howard, M.A. 3rd., "Intracerebral Drug Delivery in Rats With Lesion-induced Memory Deficits," Journal of Neurosurgery 71(1):105-112, American Association of Neurological Surgeons, United States (1989).
International Preliminary Report on Patentability, European Patent Office, PCT/US2015/043792, dated Feb. 7, 2017.
International Search Report and Written Opinion of the International Search Authority, European Patent Office, PCT/US2015/043792, dated Nov. 20, 2015.
Kunkel, T.A., et al., "Rapid and Efficient Site-specific Mutagenesis Without Phenotypic Selection," Methods in Enzymology 154:367-382, Academic Press, United States (1987).
Kunkel, T.A., "Rapid and Efficient Site-Specific Mutagenesis Without Phenotypic Selection," Proceedings of the National Academy of Sciences USA 82(2):488-492, National Academy of Sciences, United States (1985).
Langer, R., "New Methods of Drug Delivery," Science 249(4976):1527-1533, American Association for the Advancement of Science, United States (1990).
Levy, R.J., et al., "Inhibition of Calcification of Bioprosthetic Heart Valves by Local Controlled-release Diphosphonate," Science 228(4696):190-192, American Association for the Advancement of Science, United States (1985).
Lowenthal, J.W., et al., "Contrasting Interleukin 2 Binding Properties of the Alpha (P55) and Beta (P70) Protein Subunits of the Human High-Affinity Interleukin 2 Receptor," Journal of Experimental Medicine, 166(4):1156-1161, Rockefeller University Press, United States (1987).
Malek, T.R and Castro, I., "Interleukin-2 Receptor Signaling: at the Interface Between Tolerance and Immunity," Immunity 33(2):153-165, Cell Press, United States (2010).

Malek, T.R and Korty, P.E., "The Murine Interleukin 2 Receptor. IV. Biochemical Characterization," Journal of Immunology 136(11):4092-4098, American Association of Immunologists, United States (1986).
Melder, R.J., et al. "Pharmacokinetics and in Vitro and in Vivo Anti-tumor Response of an Interleukin-2-Human Serum Albumin Fusion Protein in Mice," Cancer Immunology, Immunotherapy, 54(6):535-547, Springer Verlag, Germany (2005).
Millington, T., et al. "Effects of an Agonist Interleukin-2/FC Fusion Protein, a Mutant Antagonist Interleukin-15/FC Fusion Protein, and Sirolimus on Cardiac Allograft Survival in Non-Human Primates," The Journal of Heart and Lung Transplantation, 31(4):427-435, Elsevier, United States (2012).
Nikaido, T., et al., "Molecular Cloning of cDNA Encoding Human Interleukin-2 Receptor," Nature, 311(5987):631-635, Nature Publishing Group, England (1984).
Wang, H.M and Smith, K.A., "The Interleukin 2 Receptor. Functional Consequences of its Bimolecular Structure," Journal of Experimental Medicine, 166(4):1055-1069, Rockefeller University Press, United States (1987).
Puskas, J., et al. "Development of an Attenuated Interleukin-2 Fusion Protein That Can Be Activated by Tumour-expressed Proteases," Immunology, 133(2):206-220, Blackwell Scientific Publications, England (2011).
Robb, R.J., et al., "Structure-function Relationships for the Interleukin 2 Receptor: Location of Ligand and Antibody Binding Sites on the Tac Receptor Chain by Mutational Analysis," Proceedings of the National Academy of Sciences of the United States of America 85(15):5654-5658, National Academy of Sciences, United States (1988).
Zhang, J.H., "Directed Evolution of a Fucosidase From a Galactosidase by DNA Shuffling and Screening," Proceedings of the National Academy of Sciences of the United States of America 94(9):4504-4509, National Academy of Sciences, United States (1997).
Saudek, C.D., et al., "A Preliminary Trial of the Programmable Implantable Medication System for Insulin Delivery," The New England Journal of Medicine 321(9):574-579, Massachusetts Medical Society, United States (1989).
Sefton, M.V., "Implantable Pumps," Critical Reviews in Biomedical Engineering 14(3):201-240, Begell House, United States (1987).
Speck, L.M and Tyring, S.K., "Vaccines for the Prevention of Human Papillomavirus Infections," Skin Therapy Letter 11(6):1-3, International Skin Therapy Newsletter, Canada (2006).
Stemmer, W.P., "DNA Shuffling by Random Fragmentation and Reassembly: in Vitro Recombination for Molecular Evolution," Proceedings of the National Academy of Sciences of the United States of America 91(22):10747-10751, National Academy of Sciences, United States (1994).
Stoklasek, T.A., et al. "Combined IL-15/IL-15 Ralpha Immunotherapy Maximizes IL-15 Activity in Vivo," Journal of Immunology, 177(9):6072-6080, American Association of Immunologists, United States (2006).
UniProtKB, "RecName: Full=Interleukin-2; Short=IL-2; AltName: Full=T-cell growth factor; Short=TCGF; Flags: Precursor," accession No. P05016.1, accessed at https://www.ncbi.nlm.nih.gov/protein/P05016, Nov. 2017.
UniProtKB, "RecName: Full=Interleukin-2; Short=IL-2; AltName: Full=T-cell growth factor; Short=TCGF; Flags: Precursor," accession No. P36835.1, accessed at https://www.ncbi.nlm.nih.gov/protein/P36835, Nov. 2017.
UniProtKB, "RecName: Full=Interleukin-2; Short=IL-2; AltName: Full=T-cell growth factor; Short=TCGF; Flags: Precursor," accession No. p37997.2, accessed at https://www.ncbi.nlm.nih.gov/protein/P37997, May 2018.
UniProtKB, "RecName: Full=Interleukin-2; Short=IL-2; AltName: Full=T-cell growth factor; Short=TCGF; Flags: Precursor," accession No. Q29416.1, accessed at https://www.ncbi.nlm.nih.gov/protein/Q29416, May 2018.
UniProtKB, "RecName: Full=Interleukin-2; Short=IL-2; AltName: Full=T-cell growth factor; Short=TCGF; Flags: Precursor," accession No. Q7JFM2.1, accessed at https://www.ncbi.nlm.nih.gov/protein/61213128/, Nov. 2017.

(56) References Cited

OTHER PUBLICATIONS

UniProtKB, "RecName: Full=Interleukin-2; Short=IL-2; AltName: Full=T-cell growth factor; Short=TCGF; Flags: Precursor," accession No. Q7JFM5.1, accessed at https://www.ncbi.nlm.nih.gov/protein/Q7JFM5, May 2018.
Wilkinson, I.R., et al. "A Ligand-receptor Fusion of Growth Hormone Forms a Dimer and is a Potent Long-acting Agonist," Nature Medicine, 13(9):1108-1113, Nature Publishing Company, United States (2007).
Rickert, M., et al., "The structure of interleukin-2 complexed with its alpha receptor," Science; 308(5727):1477-80, United States (2005).
Fehniger, T.A., et al., "Interleukin 15: biology and relevance to human disease," Blood;97(1):14-32 United States (2001).
Girt, J.G., et al., "IL-15, a novel T cell growth factor that shares activities and receptor components with IL-2," J Leukoc Biol.;57(5):763-6, United States (1995).
Rubinstein, M.P., et al. "Converting IL-15 to a superagonist by binding to soluble IL-15R{alpha}," Proc Natl Acad Sci U S A.;103(24):9166-71, United States (2006).
Co-Pending U.S. Appl. No. 16/366,838, inventor Struthers, M., et al., filed Mar. 27, 2019 (Unpublished).
International Search Report and Written Opinion of the International Search Authority, European Patent Office, PCT/US2019/024376, dated Jun. 13, 2019.

\* cited by examiner

INTERLEUKIN-2/INTERLEUKIN-2 RECEPTOR ALPHA FUSION PROTEINS AND METHODS OF USE

1. CROSS-REFERENCE TO RELATED APPLICATIONS

This application is a continuation application of U.S. application Ser. No. 16/366,838, filed Mar. 27, 2019, which claims the benefit of U.S. Provisional Application No. 62/649,379, filed Mar. 28, 2018, which is incorporated by reference herein in its entirety.

2. REFERENCE TO SEQUENCE LISTING SUBMITTED ELECTRONICALLY VIA EFS-WEB

The content of the electronically submitted sequence listing in ASCII text file (Name: 3338_1000002_Seqlisting_ST25.txt; Size: 354,585 bytes; and Date of Creation: Jun. 7, 2019) filed with the application is herein incorporated by reference in its entirety.

3. FIELD

The presently disclosed subject matter generally relates to methods and compositions for modulating the immune response employing an Interleukin-2/Interleukin-2 Receptor-alpha fusion protein.

4. BACKGROUND OF THE DISCLOSURE

Interleukin-2 (IL2 or IL-2) is a biologic cytokine that regulates key aspects of the immune system. IL2 has been used in attempts to boost immune responses in patients with cancer, inflammatory disease, or an autoimmune disease. IL2 is a potent T cells growth factor that promotes immune responses, including clonal expansion of antigen-activated T cells, drives development of CD4+ T-helper (Th)1 and Th2 cells, terminally differentiates CD8+ cytotoxic T lymphocytes (CTLs), and opposes development of CD4+ Th17 and T-follicular helper (Tfh) cells. IL2 also shapes T cell memory recall responses.

Clinical trials have harnessed the T cell activating properties of IL2 in patients with cancer and HIV/AIDS by infusion of high doses of IL2 (typically >500,000 units/kg, repeatedly) to boost T and NK cells. Indeed, IL2 was approved by the FDA for use in patients with melanoma and renal cell carcinoma as some (approximately 5%) exhibited complete remissions. Nevertheless, response rates were low in these and other cancers while this therapy was accompanied by severe toxicity. Just the same, IL2 was deemed to be not effective in promoting immunity in HIV/AIDS patients. The poor efficacy of high dose IL2 in these settings is due in part to the accompanying expansion of Tregs.

More recently, lower doses of IL2 have been used to selectively boost tolerance to suppress unwanted immune responses associated with autoimmune-like attack of self tissues. These low doses of IL2 have not shown any signs of enhancing or re-activation of autoreactive T cells. Preclinical studies showed that low IL2R signaling selectively promoted key activities of Tregs but not T effector (Teff) cells and that treatment of mice with low levels of IL2 prevented autoimmunity. Currently, a number of patients with hyperactive immune responses have been treated with low-dose IL2 (0.5-2 million units, periodically). The experience thus far has been that this therapy is safe, with no indication of reactivation of auto-aggressive T cells, while Tregs increase in nearly all patients, which is often accompanied by clinical improvement. Nevertheless, IL2 has important drawbacks as a therapeutic, including a very short-half life in vivo, which limits its efficacy, and toxicity at high doses. For these reasons new IL2 biologics are needed having improved pharmacokinetics and durability of responses for use.

5. SUMMARY OF THE DISCLOSURE

The present disclosure includes a fusion protein comprising (a) a first polypeptide comprising an Interleukin-2 (IL2) polypeptide; and (b) a second polypeptide comprising an extracellular domain of an Interleukin-2 Receptor alpha (IL2Rα) polypeptide; wherein (i) the extracellular domain of the IL2Rα polypeptide has at least one fewer glycosylation compared to the extracellular domain of native IL2Rα (SEQ ID NO:7); and/or (ii) the IL2 polypeptide has at least one fewer glycosylation compared to native IL2 (SEQ ID NO:2); and wherein the fusion protein has IL2 activity. In some embodiments, the extracellular domain of the IL2Rα polypeptide has at least one fewer glycosylation, at least two fewer glycosylations, at least three fewer glycosylations, at least four fewer glycosylations, at least five fewer glycosylations, at least six fewer glycosylations, at least seven fewer glycosylations, at least eight fewer glycosylations, or at least nine fewer glycosylations compared to the extracellular domain of native IL2Rα (SEQ ID NO:7). In some embodiments, the IL2 polypeptide has at least one fewer glycosylation compared to native IL2 (SEQ ID NO:2).

In some embodiments, the fusion protein comprises a first polypeptide, wherein the first polypeptide comprises an amino acid sequence at least about 60%, at least about 70%, at least about 80%, at least about 85%, at least about 90%, at least about 95%, at least about 96%, at least about 97%, at least about 98%, at least about 99% or about 100% identical to SEQ ID NO:2. In some embodiments, the fusion protein comprises a second polypeptide, wherein the second polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO:12.

In some embodiments, the extracellular domain of the IL2Rα polypeptide having at least one fewer glycosylation comprises a mutation that removes a glycosylation. In some embodiments, the mutation removes an O-glycosylation and/or an N-glycosylation. In some embodiments, the mutation removes an O-glycosylation. In some embodiments, the mutation removes an N-glycosylation.

In some embodiments, the mutation in the extracellular domain of the IL2Rα polypeptide is a deletion of amino acids 167 to 219, amino acids 168 to 219, amino acids 169 to 219, amino acids 170 to 219, amino acids 171 to 219, amino acids 172 to 219, amino acids 173 to 219, amino acids 174 to 219, amino acids 175 to 219, amino acids 176 to 219, amino acids 177 to 219, amino acids 178 to 219, amino acids 179 to 219, amino acids 180 to 219, amino acids 181 to 219, amino acids 182 to 219, amino acids 183 to 219, amino acids 184 to 219, amino acids 185 to 219, amino acids 186 to 219, amino acids 187 to 219, amino acids 188 to 219, amino acids 189 to 219, amino acids 190 to 219, amino acids 191 to 219, or amino acids 192 to 219, corresponding to SEQ ID NO:7. In some embodiments, the mutation is a deletion of amino acids from 167, 169, 171 through 192 to 219, corresponding to SEQ ID NO:7. In some embodiments, the mutation does not include a deletion of 170 to 219, corresponding to SEQ ID NO:7. In some embodiments, the second polypeptide is SEQ ID NO:11. In some embodiments, the second polypeptide is SEQ ID NO:12.

In some embodiments, the mutation is one or more substitutions of an amino acid that is glycosylated with an amino acid that is not glycosylated. In some embodiments, the mutation is one or more substitutions of an amino acid that allows glycosylation at a nearby amino acid with an amino acid that does not allow glycosylation at the nearby amino acid. In some embodiments, the one or more substitutions are at amino acid N49, amino acid N68, amino acid T74, amino acid T85, amino acid T197, amino acid T203, amino acid T208, and amino acid T216, or any combination thereof, wherein the amino acid locations correspond to SEQ ID NO:7. In some embodiments, the one or more substitutions are from asparagine to an amino acid selected from the group consisting of alanine, threonine, serine, arginine, aspartic acid, glutamine, glutamic acid, glycine, histidine, isoleucine, leucine, lysine, methionine, phenylalanine, proline, tryptophan, tyrosine, and valine. In some embodiments, the one or more substitutions are from threonine to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the one of the substitutions is amino acid N49. In some embodiments, N49 is mutated to an amino acid selected from the group consisting of alanine, threonine, serine, arginine, aspartic acid, glutamine, glutamic acid, glycine, histidine, isoleucine, leucine, lysine, methionine, phenylalanine, proline, tryptophan, tyrosine, and valine.

In some embodiments, the one the substitutions is amino acid N68. In some embodiments, N68 is mutated to an amino acid selected from the group consisting of alanine, threonine, serine, arginine, aspartic acid, glutamine, glutamic acid, glycine, histidine, isoleucine, leucine, lysine, methionine, phenylalanine, proline, tryptophan, tyrosine, and valine.

In some embodiments, the one of the substitutions is amino acid T74. In some embodiments, T74 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the one of the substitutions is amino acid T85. In some embodiments, T85 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the one of the substitutions is amino acid T197. In some embodiments, T197 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the one of the substitutions is amino acid T203. In some embodiments, T203 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the one of the substitutions is amino acid T208. In some embodiments, T208 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the one of the substitutions is amino acid T216. In some embodiments, T216 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the one or more substitutions are at amino acid S50, amino acid S51, amino acid T69, amino acid T70, amino acid C192, or any combination thereof, wherein the amino acid locations correspond to SEQ ID NO:7.

In some embodiments, the one of the substitutions is at amino acid S50. In some embodiments, S50 is mutated to proline.

In some embodiments, the one of the substitutions is amino acid S51. In some embodiments, S51 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the one of the substitution is amino acid T69. In some embodiments, T69 is mutated to proline.

In some embodiments, the one of the substitutions is amino acid T70. In some embodiments, T70 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, threonine, tryptophan, tyrosine, and valine.

In some embodiments, the one of the substitutions is amino acid C192. In some embodiments, C192 is mutated to an amino acid selected from the group consisting of alanine, arginine, asparagine, aspartic acid, glutamine, glutamic acid, glycine, histidine, isoleucine, leucine, lysine, methionine, phenylalanine, proline, serine, threonine, tryptophan, tyrosine, and valine.

In some embodiments, the IL2 polypeptide having at least one fewer glycosylation comprises a mutation that removes a glycosylation. In some embodiments, the mutation is one or more substitutions of an amino acid that is glycosylated with an amino acid that is not glycosylated. In some embodiments, the mutation is one or more substitutions of an amino acid that allows glycosylation at a nearby amino acid with an amino acid that does not allow glycosylation at the nearby amino acid. In some embodiments, the one or more substitutions are from an alanine to an amino acid selected from the group consisting of arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some embodiments, the one or more substitutions are from a threonine to an amino acid selected from the group consisting of alanine, arginine, asparagine, aspartic acid, cysteine, glutamine, glutamic acid, glycine, histidine, isoleucine, leucine, lysine, methionine, phenylalanine, proline, tryptophan, tyrosine, and valine. In some embodiments, the one or more substitutions are from a cysteine to an amino acid selected from the group consisting of alanine, arginine, asparagine, aspartic acid, glutamine, glutamic acid, glycine, histidine, isoleucine, leucine, lysine, methionine, phenylalanine, proline, serine, threonine, tryptophan, tyrosine, and valine. In some embodiments, the one or more substitutions are from a cysteine to a serine. In some embodiments, the one or more substitutions are from a cysteine to an alanine. In some embodiments, the one or more substitutions are from a cysteine to a valine.

In some embodiments, the one or more substitutions are at amino acid T3 compared to corresponding to SEQ ID NO:2. In some embodiments, one of the substitutions is at amino acid C125. In some embodiments, the substitution at amino acid C125 is selected from the group consisting of C125S, C125A, and C125V.

In some embodiments, the mutation is a deletion. In some embodiments, the deletion is at amino acid A1.

In some embodiments, the fusion protein is deglycosylated enzymatically or chemically. In some embodiments, the fusion protein is deglycosylated by alkali, hydrazinolysis, PNGase F, Endo H, O-glycosidase, or any combination thereof.

In some embodiments, the fusion protein further comprises a linker fused in frame between the first polypeptide and the second polypeptide. In some embodiments, the linker is a glycine/serine linker. In some embodiments, the glycine/serine linker comprises an amino acid sequence of $(GS)_n$, $(GGS)_n$, $(GGGS)_n$, $(GGGGS)_n$, or $(GGGGS)_n$, wherein n is an integer of 1, 2, 3, 4, 5, 6, 7, 8, 9, or 10. In some embodiments, the glycine/serine linker comprises the amino acid sequence of $(GGGS)_3$.

In some embodiments, the fusion protein further comprises a heterologous moiety fused to the first polypeptide and/or the second polypeptide. In some embodiments, the heterologous moiety is a half-life extending moiety. In some embodiments, the heterologous moiety comprises a non-polypeptide moiety. In some embodiments, the heterologous moiety comprises a polypeptide. In some embodiments, the heterologous moiety comprises albumin, an immunoglobulin constant region or a portion thereof, an immunoglobulin-binding polypeptide, an immunoglobulin G (IgG), albumin-binding polypeptide (ABP), a PASylation moiety, a HESylation moiety, XTEN, a PEGylation moiety, an Fc region, and any combination thereof.

In some embodiments, the fusion protein is more stable than the polypeptide consisting of SEQ ID NO:2 or SEQ ID NO:13. In some embodiments, the fusion protein has one or more properties selected from the group consisting of (i) increased thermodynamic stability compared to a reference protein; (ii) increased TM compared to a reference protein; (iii) increased resistant to degradation compared to a reference protein; (iv) increased resistance to modifications compared to a reference protein; (v) increased stability in vivo compared to a reference protein; and (vi) any combination thereof, wherein the reference protein comprises (i) a first polypeptide comprising an Interleukin-2 (IL2) polypeptide; and (b) a second polypeptide comprising an extracellular domain of an Interleukin-2 Receptor alpha (IL2Rα) polypeptide; and has at least one fewer glycosylation compared to the fusion protein.

In some embodiments, the fusion protein is a monomer. In some embodiments, the fusion protein is a dimer. In some embodiments, the dimer comprises two monomers, and the monomers are associated with each other via covalent bonds. In some embodiments, the dimer comprises two monomers, and the monomers are associated via non-covalent bonds.

In some embodiments, the fusion protein has one or more pharmacokinetic properties selected from the group consisting of an increased half-life, increased $C_{max}$, increased AUC, increased $C_{min}$, decreased clearance, improved bioavailability, and any combination thereof, compared to the pharmacokinetic property of the polypeptide consisting of SEQ ID NO:2 or SEQ ID NO:13. In some embodiments, the fusion protein has an extended half-life. In some embodiments, the extended half-life is at least about 1.5 fold, at least about 2 fold, at least about 3 fold, at least about 4 fold, at least about 5 fold, at least about 6 fold, at least about 7 fold, at least about 8 fold, at least about 9 fold, at least about 10 fold, at least about 11 fold, at least about 12 fold, at least about 13 fold, at least about 14 fold, at least about 15 fold, at least about 16 fold, at least about 17 fold, at least about 18 fold, at least about 19 fold, at least about 20 fold, at least about 21 fold, or at least about 22 fold compared to the half-life of a polypeptide consisting of SEQ ID NO:2 or SEQ ID NO:13.

In some embodiments, disclosed herein is one or more fusion proteins. In some embodiments, provided herein is a composition comprising one or more fusion proteins disclosed herein.

In some embodiments, disclosed herein is a nucleic acid that encodes any one of the fusion proteins disclosed herein. In some embodiments, disclosed herein is a vector comprising a nucleic acid that encodes any one of the fusion proteins disclosed herein. In some embodiments, disclosed herein is a host cell comprising the nucleic acid that encodes any one of the fusion proteins disclosed herein. In some embodiments, the host cell is a eukaryotic cell. In some embodiments, the host cell is selected from the group consisting of a mammalian cell, an insect cell, a yeast cell, a transgenic mammalian cell, and a plant cell. In some embodiments, the host cell is a mammalian cell. In some embodiments, the host cell is a prokaryotic cell. In some embodiments, the prokaryotic cell is a bacterial cell.

In some embodiments, provided herein is a pharmaceutical composition comprising (a) a fusion protein disclosed herein, a composition disclosed herein, a nucleic acid disclosed herein, a vector disclosed herein, or a host cell disclosed herein; and (b) a pharmaceutically acceptable excipient.

In some embodiments, provided herein is a kit comprising the fusion protein disclosed herein, the composition disclosed herein, the nucleic acid disclosed herein, the vector disclosed herein, or the host cell disclosed herein and instructions for administering the fusion protein to a subject in need thereof.

In some embodiments, provided herein is a method of producing the fusion protein disclosed herein, comprising: culturing the host cell disclosed herein under suitable conditions and recovering the fusion protein. In some embodiments, the host cell is a eukaryotic cell or a prokaryotic cell. In some embodiments, the host cell is a mammalian cell, an insect cell, a fungal cell, a plant cell, a transgenic mammalian cell, or a bacterial cell. In some embodiments, the host cell is selected from the group consisting of a CHO cell, a HEK 293 cell, a NS0 cell, a Per C6 cell, a BHK cell, and a COS cell. In some embodiments, the bacterial cell is *Escherichia coli*.

In some embodiments, provided herein is a method of treating a disease or disorder a subject in need thereof, comprising administering to the subject an effective amount of a fusion protein disclosed herein, a composition disclosed herein, a nucleic acid disclosed herein, a vector disclosed herein, a host cell disclosed herein, or a pharmaceutical composition disclosed herein. In some embodiments, the disease or disorder is cancer. In some embodiments, the cancer is a bladder cancer, breast cancer, uterine cancer, endometrial carcinoma, ovarian cancer, colorectal cancer, colon cancer, head and neck cancer, lung cancer, stomach cancer, germ cell cancer, bone cancer, squamous cell cancer, skin cancer, neoplasm of the central nervous system, lymphoma, leukemia, sarcoma, virus-related cancer, small-cell lung cancer, non-small cell lung cancer, gastrointestinal cancer, Hodgkin's or non-Hodgkin's lymphoma, pancreatic cancer, glioblastoma, glioma, cervical cancer, ovarian cancer, liver cancer, myeloma, salivary gland carcinoma, kidney cancer, basal cell carcinoma, melanoma, prostate cancer, vulval cancer, thyroid cancer, testicular cancer, esophageal cancer, or head or neck cancer, and any combinations thereof.

In some embodiments, the disease or disorder is an inflammatory disease or an autoimmune disease. In some embodiments, the inflammatory disease or an autoimmune disease is selected from the group consisting of type 1 diabetes, multiple sclerosis, rheumatoid arthritis, celiac disease, systemic lupus erythematous, lupus nephritis, cutaneous lupus, juvenile idiopathic arthritis, Crohn's disease, ulcerative colitis or systemic sclerosis, graft versus host disease, psoriasis, alopecia areata, HCV-induced vasculitis, Sjogren's syndrome, Pemphigus, Ankylosing Spondylitis, Behcet's Disease, Wegener's Granulomatosis, Takayasu's Disease, Autoimmune Hepatitis, Sclerosing Cholangitis, Gougerot-sjögren, and Macrophage Activation Syndrome.

In some embodiments, the disease or disorder is an infectious disease. In some embodiments, the infectious disease is caused by a pathogenic virus. In some embodiments, the pathogenic virus is selected from the group consisting of human immunodeficiency virus (HIV), hepatitis A, hepatitis B, hepatitis C, herpes virus, adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, human T-lymphotropic (HTL) virus, dengue virus, papillomavirus, molluscum virus, poliovirus, rabies virus, John Cunningham (JC) virus and arboviral encephalitis virus. In some embodiments, the infectious disease is caused by pathogenic bacteria. In some embodiments, the pathogenic bacteria is selected from the group consisting of *Chlamydia*, rickettsial bacteria, mycobacteria, staphylococci, streptococci, pneumonococci, meningococci and gonococci, *Klebsiella, Proteus, Serratia, Pseudomonas, Legionella, Diphtheria, Salmonella*, bacilli, cholera, tetanus, botulism, anthrax, plague, leptospirosis, and Lymes disease bacteria. In some embodiments, the infectious disease is caused by pathogenic fungi. In some embodiments, the pathogenic bacteria is selected from the group consisting of *Candida (albicans, krusei, glabrata, tropicalis*, etc.), *Cryptococcus neoformans, Aspergillus (fumigatus, niger,* etc.), Genus *Mucorales (mucor, absidia, rhizopus), Sporothrix schenkii, Blastomyces dermatitidis, Paracoccidioides brasiliensis, Coccidioides immitis* and *Histoplasma capsulatum*. In some embodiments, the infectious disease is caused by pathogenic parasite. In some embodiments, the pathogenic parasite is selected from the group consisting of *Entamoeba histolytica, Balantidium coli*, Naegleriafowleri, *Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii,* and *Nippostrongylus brasiliensis*.

In some embodiments, the methods disclosed herein further comprise administering to the subject a second agent. In some embodiments, the second agent is a PD-1 antagonist, a CTLA-4 antagonist, a TIM3 antagonist, a GITR antagonist, a KIR antagonist, a LAG3 antagonist, or any combination thereof. In some embodiments, the second agent is an anti-PD-1 antibody, an anti-PD-L1 antibody, an anti-CTLA-4 antibody, an anti-TIM3 antibody, an anti-KIR antibody, an anti-GITR antibody, an anti-LAG3 antibody, or any combination thereof. In some embodiments, the second agent is a cytokine inhibitor. In some embodiments, the cytokine inhibitor targets one or more of IL-6, IL-10, TGF-β, VEGF, IFN-γ, or any combination thereof.

In some embodiments, the fusion protein is administered via a topical, epidermal mucosal, intranasal, oral, vaginal, rectal, sublingual, topical, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural or intrasternal route.

6. BRIEF DESCRIPTION OF THE DRAWINGS

FIG. 1 shows that molecular mass of SEQ ID NO:16 is 93 kDa as measured by SEC/MALS static light scattering. Theoretical mass of the polypeptide chain alone is 37,812 Da reduced. The observed solution mass demonstrates it exists as a homogeneous homo-dimer with about 19% of the mass due to glycosylation.

FIG. 2 shows prototypical binding of the IL2-CD25 fusion protein (SEQ ID NO: 16) to human sCD25 using surface plasmon resonance measurements.

FIG. 3 shows serum concentration-time profiles of indicated fusion proteins in Balb/C mice following a 0.5 mg/kg single intravenous (IV) or subcutaneous (SC) dose. Each time-point represents a mean of samples from 3 mice. Error bars represent standard deviation.

FIG. 4 shows serum concentration-time profiles of indicated fusion proteins in Balb/C mice following a 0.5 mg/kg single intravenous (IV) or subcutaneous (SC) dose. Each time-point represents a mean of samples from 3 mice. Error bars represent standard deviation.

FIG. 5 shows serum concentration-time profiles of hIL2-CD25 (22-212) in cynomolgus monkey following a 0.075 mg/kg single subcutaneous (SC) dose. Each time-point represents a mean of samples from 3 monkeys. Error bars represent standard deviation.

FIG. 6 shows the activity of IL2-CD25 fusion proteins to induce STAT5 phosphorylation in human PBMCs from a representative donor. Cells were gated on Treg (CD4$^+$, foxp3$^+$, CD25$^+$) or Tconv (CD4$^+$, foxp3$^-$), CD8$^+$, and NK cells (CD3$^-$, CD56$^+$) and the percent of cells which stained positive for pSTAT5 after incubation was quantitated. The EC$_{50}$ for pSTAT5 induction in Treg determined from these experiments was 10 ng/ml, 4.4 ng/ml, and 4.6 ng/ml for hIL2-CD25(22-240), hIL2-CD25(22-212), and hIL2-CD25 (22-187) respectively.

FIG. 7 shows the ability of truncated fusions proteins to stimulate IL2R in whole blood resulting in induction of phosphorylated STAT5 in various cell types. IL2R signaling was detected by measuring by flow cytometry after intracellular staining for pSTAT5 and determining the percent of cells staining positive for pSTAT5 in the whole blood mixture. The potency of hIL2-CD25(22-240) was compared to hIL2-CD25(22-212) in a representative donor. Protein was titrated in human whole blood and the intensity of intracellular pSTAT5 staining measured by flow cytometry. EC50 for pSTAT5 induction in Treg was 22 ng/ml for hIL2-CD25(22-240) and 36 ng/ml for hIL2-CD25(22-212).

FIG. 8A-FIG. 8C show the similar ability of hIL2-CD25 (22-240), hIL2-CD25(22-212) and hIL2-CD25(22-184) to increase T cells in mice with a humanized immune system. Administration (s.c.) of fusion protein to NSG-huCD34 engrafted mice was performed every third day for three doses. Analysis of the Treg (FIG. 8A), CD8 (FIG. 8B), and NK cells (FIG. 8C) from the spleen of dosed mice was determined by flow cytometry.

7. DETAILED DESCRIPTION OF THE DISCLOSURE

Figure 1:
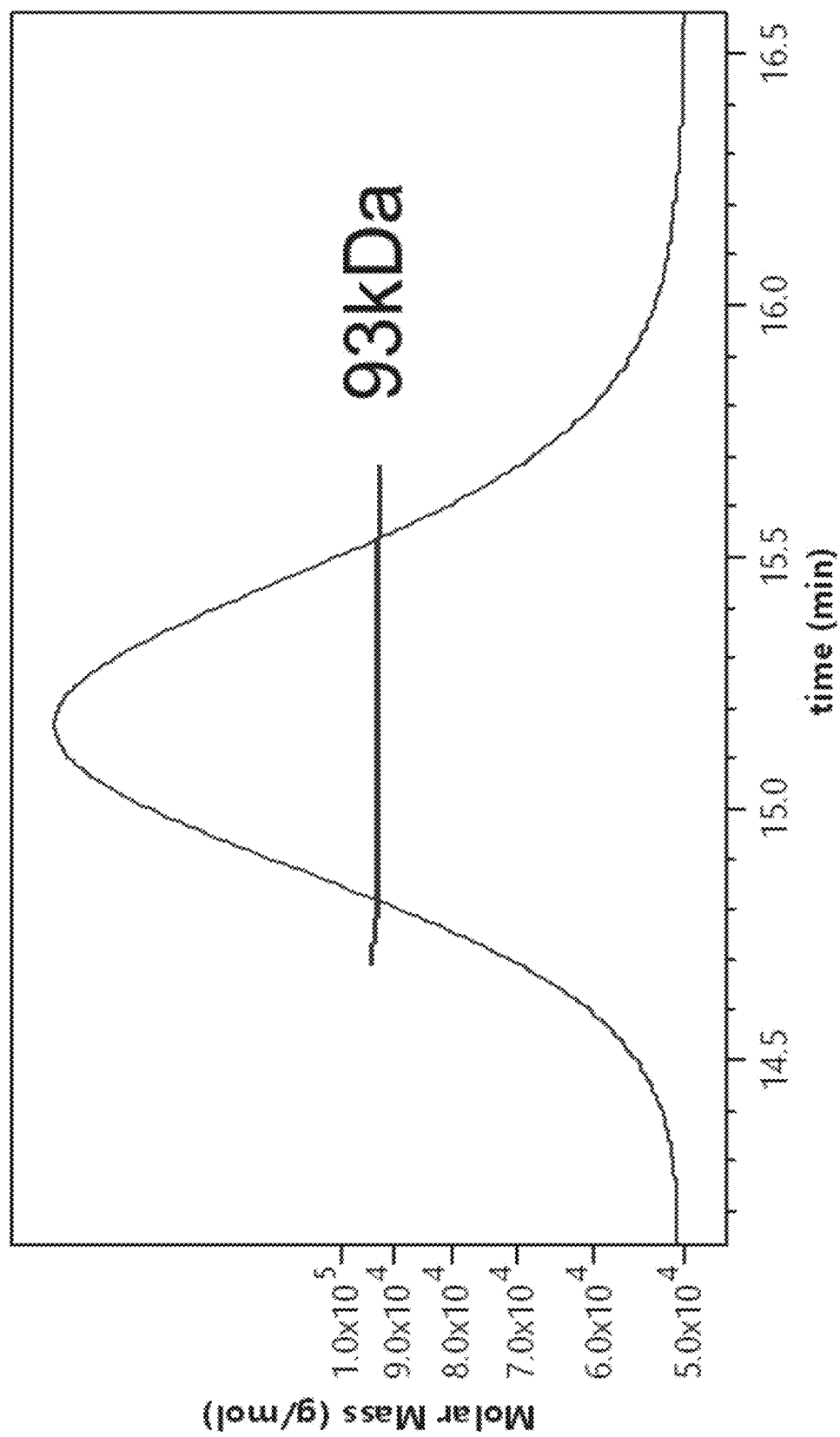

The present disclosure is described more fully hereinafter with reference to the accompanying drawings, in which some, but not all embodiments of the disclosure are shown. Indeed, these disclosures can be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

7.1 Overview

Various methods and compositions are provided which can be employed to modulate the immune system. Compositions include a fusion protein comprising: (a) a first polypeptide comprising Interleukin-2 (IL2) polypeptide; and (b) a second polypeptide comprising an extracellular domain of Interleukin-2 Receptor alpha (IL2Rα) polypeptide; wherein (i) the extracellular domain of the IL2Rα polypeptide has at least one fewer glycosylation compared to the extracellular domain of native IL2Rα (SEQ ID NO:7); and/or (ii) the IL2 polypeptide has at least one fewer glycosylation compared to native IL2 (SEQ ID NO:2); and wherein the fusion protein has IL2 activity.

The present disclosure also describes a nucleotide encoding the fusion protein disclosed herein, a vector comprising the nucleotide, a host cell comprising the nucleotide, and a composition comprising the fusion protein, the nucleotide, the vector, or the host cell. The disclosure is also directed to methods of making the fusion protein, the nucleotide, the vector, the host cell, or the composition or methods of using the fusion protein, the nucleotide, the vector, the host cell, or the composition.

7.2 Definitions

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. Thus, "about 10-20" means "about 10 to about 20." In general, the term "about" can modify a numerical value above and below the stated value by a variance of, e.g., 10 percent, up or down (higher or lower).

As used herein, "Interleukin-2", "IL2", or "IL-2" refers to any native or recombinant IL2 from any vertebrate source, including mammals such as primates (e.g., humans) and rodents (e.g., mice and rats), and domesticated or agricultural mammals unless otherwise indicated. The term encompasses unprocessed IL2, as well as, any form of IL2 that results from processing in the cell (i.e., the mature form of IL2). The term also encompasses naturally occurring variants and fragments of IL2, e.g. splice variants or allelic variants, and non-naturally occurring variants that have IL2 activity of the naturally occurring IL2.

Additional nucleic acid and amino acid sequences for IL2 are known. See, for example, GenBank Accession Nos: Q7JFM2 (*Aotus lemurinus* (Gray-bellied night monkey)); Q7JFM5 (*Aotus nancymaae* (Ma's night monkey)); P05016 (*Bas taurus* (Bovine)); Q29416 (*Canis familiaris* (Dog) (*Canis lupus familiaris*)); P36835 (*Capra hircus* (Goat)); and, P37997 (*Equus caballus* (Horse)).

Biologically active fragments and variants of IL2 retain IL2 activity. The phrase "biological activity of IL2" or "IL2 activity" refers to one or more of the biological activities of IL2, including but not limited to, the ability to stimulate IL2 receptor bearing lymphocytes. Such activity can be measured both in vitro and in vivo. IL2 is a global regulator of immune activity and the effects seen here are the sum of such activities. For example, it regulates survival activity (Bcl-2), induces T effector activity (IFN-gamma, Granzyme B, and Perforin), and/or promotes T regulatory activity (FoxP3).

Biologically active variants of IL2 are known. See, for example, US Application Publications 20060269515 and 20060160187 and WO 99/60128.

The term "CD25," "IL2 receptor α," "IL2Rα," or "IL2Ra" as used herein, refers to any native or recombinant IL2Rα from any vertebrate source, including mammals such as primates (e.g. humans) and rodents (e.g., mice and rats) and domesticated or agricultural mammals unless otherwise indicated. The term also encompasses naturally occurring variants of IL2Rα, e.g., splice variants or allelic variants, or non-naturally occurring variants that have IL2Rα activity. Human IL2 exerts its biological effects via signaling through its receptor system, IL2R. IL2 and its receptor (IL2R) are required for T-cell proliferation and other fundamental functions which are crucial for the immune response. IL2R consists of 3 non-covalently linked type I transmembrane proteins, which are the alpha (p55), beta (p75), and gamma (p65) chains. The human IL2R alpha chain contains an extracellular domain of 219 amino acids, a transmembrane domain of 19 amino acids, and an intracellular domain of 13 amino acids. The secreted extracellular domain of IL2R alpha (IL2R-α) can be employed in the fusion proteins describe herein.

Nucleic acid and amino acid sequences for IL2Rα are known. See, for example, GenBank Accession Nos: NP_001030597.1 (*Pan troglodytes*); NP_001028089.1 (*Macaca mulatta*); NM_001003211.1 (*Canis lupus*); NP_776783.1 (*Bos taurus*); NP_032393.3 (*Mus musculus*); and, NP_037295.1 (*Rattus norvegicus*).

Biologically active fragments and variants of the extracellular domain of IL2Rα are also provided. Such IL2Rα extracellular domain active variants or fragments will retain the IL2Rα extracellular domain activity. The phrase "biological activity of the IL2Rα extracellular domain" refers to one or more of the biological activities of extracellular domain of IL2Rα, including but not limited to, the ability to bind to IL2 and/or enhance intracellular signaling in IL2 receptor responsive cells. Non-limiting examples of biologically active fragments and variants of the IL2Rα are disclosed, for example, in Robb et al., *Proc. Natl. Acad. Sci. USA*, 85:5654-5658, 1988. In some embodiments, the biologically active fragments and variants of the IL2Rα disclosed herein comprise at least one fewer glycosylation compared to the extracellular domain of native IL2Rα.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" or "fusion protein" can comprise one or more polypeptides.

Also included in the present disclosure are fragments or variants of polypeptides, and any combination thereof. The term "fragment" or "variant" when referring to polypeptide binding domains or binding molecules of the present disclosure include any polypeptides which retain at least some of the properties (e.g., IL2 binding activity for IL2Rα) of the reference polypeptide. Fragments of polypeptides include proteolytic fragments, as well as deletion fragments, but do not include the naturally occurring full-length polypeptide (or mature polypeptide). Variants of polypeptide binding domains or binding molecules of the present disclosure include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010)), proteolytic processing, phosphorylation, prenylation, racemization, selenoylation, sulfation, transfer-RNA mediated addition of amino acids to proteins such as arginylation, and ubiquitination.

As used herein, an "corresponding to," "amino acid corresponding to," "site corresponding to," or "equivalent amino acid" in a protein or nucleotide sequence is identified by alignment to maximize the identity or similarity between a first protein sequence, e.g., an IL2 sequence, and a second protein sequence, e.g., a second IL2 sequence. The number used to identify an equivalent amino acid in a second protein sequence is based on the number used to identify the corresponding amino acid in the first protein sequence. In some embodiments, the term "corresponding to" refers to the relationship of a mutation at one or more amino acids in a polypeptide or one or more nucleotides in a polynucleotide. By way of a non-limiting example, a specific amino acid (e.g., S50) of a polynucleotide (e.g., SEQ ID NO:7) as disclosed herein refers to the 50$^{th}$ amino acid—a serine—in SEQ ID NO: 7.

As used herein the term "associated with" refers to a covalent or non-covalent bond formed between a first amino acid chain and a second amino acid chain. In one embodiment, the term "associated with" means a covalent, non-peptide bond or a non-covalent bond. This association can be indicated by a colon, i.e., (:). In another embodiment, it means a covalent bond except a peptide bond. For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

The term "comparable" as used herein means a compared rate or level resulted from using, e.g., the fusion protein is equal to, substantially equal to, or similar to the reference rate or level. The term "similar" as used herein means a compared rate or level has a difference of no more than 10% or no more than 15% from the reference rate or level. The term "substantially equal" means a compared rate or level has a difference of no more than 0.01%, 0.5% or 1% from the reference rate or level.

The term "expression" as used herein refers to a process by which a polynucleotide produces a gene product, for example, an RNA or a polypeptide.

A "fusion" or "fusion" protein comprises a first amino acid sequence linked in frame to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of an IL2 protein with an IL2-Rα protein. A fusion protein is created, for example, by chemical synthesis, or by creating and translating a polynucleotide in which the peptide regions are encoded in the desired relationship. A fusion protein can further comprise a second amino acid sequence associated with the first amino acid sequence by a covalent, non-peptide bond or a non-covalent bond. Upon transcription/translation, a single protein is made. In this way, multiple proteins, or fragments thereof can be incorporated into a single polypeptide. "Operably linked" is intended to mean a functional linkage between two or more elements. For example, an operable linkage between two polypeptides fuses both polypeptides together in frame to produce a single polypeptide fusion protein. In a particular aspect, the fusion protein further comprises a third polypeptide which, as discussed in further detail below, can comprise a linker sequence.

An "Fc region" (fragment crystallizable region), "Fc domain," or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. The IgG isotype is divided in subclasses in certain species: IgG1, IgG2, IgG3 and IgG4 in humans, and IgG1, IgG2a, IgG2b and IgG3 in mice. For IgG, the Fc region comprises immunoglobulin domains CH2 and CH3 and the hinge between CH1 and CH2 domains. Although the definition of the boundaries of the Fc region of an immunoglobulin heavy chain might vary, as defined herein, the human IgG heavy chain Fc region is defined to stretch from an amino acid residue D221 for IgG1, V222 for IgG2, L221 for IgG3 and P224 for IgG4 to the carboxy-terminus of the heavy chain, wherein the numbering is according to the EU index as in Kabat. The CH2 domain of a human IgG Fc region extends from amino acid 237 to amino acid 340, and the CH3 domain is positioned on C-terminal side of a CH2 domain in an Fc region, i.e., it extends from amino acid 341 to amino acid 447 or 446 (if the C-terminal lysine residue is absent) or 445 (if the C-terminal glycine and lysine residues are absent) of an IgG. As used herein, the Fc region can be a native sequence Fc, including any allotypic variant, or a variant Fc (e.g., a non-naturally-occurring Fc).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Various properties of human FcγRs are known in the art. The majority of innate effector cell types co-express one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

The terms "inserted," "is inserted," "inserted into," or grammatically related terms, as used herein refers to the position of a heterologous moiety (e.g., a half-life extending moiety) in a fusion polypeptide relative to the analogous position in specified protein. As used herein the terms refer to the characteristics of the recombinant polypeptide disclosed herein, and do not indicate, imply or infer any methods or process by which the fusion polypeptide was made.

"Heterologous" and "heterologous moiety" in reference to a polypeptide or polynucleotide is a polypeptide or polynucleotide that originates from a different protein or polynucleotide. The additional components of the fusion protein can originate from the same organism as the other polypeptide components of the fusion protein, or the additional components can be from a different organism than the other polypeptide components of the fusion protein. For instance, a heterologous polypeptide can be synthetic, or derived from a different species, different cell type of an individual, or the same or different type of cell of distinct individuals. In one aspect, a heterologous moiety is a polypeptide fused to another polypeptide to produce a fusion polypeptide or protein. In another aspect, a heterologous moiety is a non-polypeptide such as PEG conjugated to a polypeptide or protein. Non-limiting examples of heterologous moieties disclosed herein are glycine/serine linkers (e.g., GGGSGGGSGGGS (SEQ ID NO:71) (also noted as $(Gly_3Ser)_3)$).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally-occurring variants thereof. Native sequence Fc include the various allotypes of Fcs (see, e.g., Jefferis et al. (2009) *mAbs* 1:1).

The term "$EC_{50}$" in the context of an in vitro or in vivo assay using fusion protein refers to the concentration of a fusion protein that induces a response that is 50% of the maximal response, i.e., halfway between the maximal response and the baseline.

"Conservative amino acid substitutions" refer to substitutions of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some embodiments, a predicted nonessential amino acid residue in IL2/IL2Rα fusion protein is replaced with another amino acid residue from the same side chain family. Methods of identifying nucleotide and amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

The term "nucleic acid molecule," as used herein, is intended to include DNA molecules and RNA molecules. A nucleic acid molecule can be single-stranded or double-stranded, and can be cDNA.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide, which encodes a gene product, e.g., a polypeptide, can include a promoter and/or other transcription or translation control elements operably associated with one or more coding regions. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions, which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "percent sequence identity," "percent identity," "sequence identity," or "identity" are used interchangeably and refers to the number of identical matched positions shared between two polynucleotide or polypeptide sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The comparison of sequences and determination of percent identity between two sequences can be accomplished using a mathematical algorithm, as described in the non-limiting examples below.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS*, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to the nucleic acid molecules described herein. BLAST protein searches can be performed with the XBLAST program, score=50, word length=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See worldwideweb.ncbi.nlm.nih.gov.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "in vitro host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein. Exemplary host cells include, but are not limited to, prokaryotic cells (e.g., *E. coli*), or alternatively, eukaryotic cells, for example, fungal cells (e.g., yeast cells such as *Saccharomyces cerevisiae, Pichia pastoris*, or *Schizosaccharomyces pombe*), and various animal cells, such as insect cells (e.g., Sf-9) or mammalian cells (e.g., HEK293F, CHO, COS-7, NIH-3T3).

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid. Therefore, the phrase "between two amino acids of an insertion site" as used herein refers to a position in which a heterologous moiety (e.g., a half-life extending moiety) is inserted between two adjacent amino acids.

As used herein, "administering" refers to the physical introduction of a composition comprising a therapeutic agent to a subject, using any of the various methods and delivery systems known to those skilled in the art. Different routes of administration for the IL2/IL2Rα fusion protein described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

An "immune response" is as understood in the art, and generally refers to a biological response within a vertebrate against foreign agents or abnormal, e.g., cancerous cells, which response protects the organism against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a CD4$^+$ cell, a CD8$^+$ T cell, or a Treg cell, or activation or inhibition of any other cell of the immune system, e.g., NK cell.

An "immunomodulator" or "immunoregulator" refers to an agent, e.g., an agent targeting a component of a signaling pathway that can be involved in modulating, regulating, or modifying an immune response. "Modulating," "regulating," or "modifying" an immune response refers to any alteration in a cell of the immune system or in the activity of such cell (e.g., an effector T cell, such as a Th1 cell). More particularly, as used herein, the term "modulating" includes inducing, inhibiting, potentiating, elevating, increasing, or decreasing a given activity or response. Such modulation includes stimulation or suppression of the immune system which can be manifested by an increase or decrease in the number of various cell types, an increase or decrease in the activity of these cells, or any other changes which can occur within the immune system. Both inhibitory and stimulatory immunomodulators have been identified, some of which can have enhanced function in a tumor microenvironment. In some embodiments, the immunomodulator targets a molecule on the surface of a T cell. An "immunomodulatory target" or "immunoregulatory target" is a molecule, e.g., a cell surface molecule, that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with, or at risk of contracting or suffering a recurrence of, a disease by a method comprising inducing, enhancing, suppressing or otherwise modifying the immune system or an immune response.

"Immuno stimulating therapy" or "immuno stimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject. This increase in effectiveness and potency can be achieved, for example, by overcoming mechanisms that suppress the endogenous host immune response or by stimulating mechanisms that enhance the endogenous host immune response.

"T effector" ("T$_{eff}$") cells refers to T cells (e.g., CD4$^+$ and CD8$^+$ T cells) with cytolytic activities as well as T helper (Th) cells, e.g., Th1 cells, which cells secrete cytokines and activate and direct other immune cells, but does not include regulatory T cells (Treg cells). Certain IL2/IL2Rα fusion proteins described herein activate T$_{eff}$ cells, e.g., CD4$^+$ and CD8$^+$ T$_{eff}$ cells and Th1 cells.

An increased ability to stimulate an immune response or the immune system, can result from an enhanced agonist activity of T cell co-stimulatory receptors and/or an enhanced antagonist activity of inhibitory receptors. An increased ability to stimulate an immune response or the immune system can be reflected by a fold increase of the EC$_{50}$ or maximal level of activity in an assay that measures an immune response, e.g., an assay that measures changes in cytokine or chemokine release, cytolytic activity (determined directly on target cells or indirectly via detecting CD107a or granzymes) and proliferation. The ability to stimulate an immune response or the immune system activity can be enhanced by at least 10%, 30%, 50%, 75%, 2 fold, 3 fold, 5 fold or more.

The terms "linked" and "fused" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence is linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The term "linked" is also indicated by a hyphen (-).

As used herein, the term "T cell-mediated response" refers to a response mediated by T cells, including effector T cells (e.g., CD8$^+$ cells) and helper T cells (e.g., CD4$^+$ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by CD8$^+$ T cells.

As used herein, the terms "inhibits" or "blocks" (e.g., referring to inhibition/blocking of binding of IL2 to IL2Rα on cells) are used interchangeably and encompass both partial and complete inhibition/blocking. In some embodiments, the IL2/IL2Rα fusion protein inhibits binding of IL2 to IL2Rα by at least about 50%, for example, about 60%, 70%, 80%, 90%, 95%, 99%, or 100%, determined, e.g., as further described herein. In some embodiments, the IL2/IL2Rα fusion protein inhibits binding of IL2 to IL2Rα by no more than 50%, for example, by about 40%, 30%, 20%, 10%, 5% or 1%, determined, e.g., as further described herein.

As used herein, the phrase "inhibits growth of a tumor" includes any measurable decrease in the growth of a tumor, e.g., the inhibition of growth of a tumor by at least about 10%, for example, at least about 20%, at least about 30%, at least about 40%, at least about 50%, at least about 60%, at least about 70%, at least about 80%, at least about 90%, at least about 99%, or 100%.

As used herein, "cancer" refers a broad group of diseases characterized by the uncontrolled growth of abnormal cells in the body. Unregulated cell division can result in the formation of malignant tumors or cells that invade neighboring tissues and can metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease or enhancing overall survival. Treatment can be of a subject having a disease or a subject who does not have a disease (e.g., for prophylaxis). When provided prophylactically, the fusion protein disclosed herein is provided in advance of any symptom. The prophylactic administration of the substance serves to prevent or attenuate any subsequent symptom.

By "enhancing the efficacy" or "enhancing the immunogenicity" with regard to a fusion protein, pharmaceutical composition, or vaccine is intended improving an outcome, for example, as measured by a change in a specific value, such as an increase or a decrease in a particular parameter of an activity of a fusion protein, pharmaceutical composition, or vaccine associated with protective immunity. In one embodiment, enhancement refers to at least a 5%, 10%, 25%, 50%, 100% or greater than 100% increase in a particular parameter. In another embodiment, enhancement refers to at least a 5%, 10%, 25%, 50%, 100% or greater than 100% decrease in a particular parameter. In one example, enhancement of the efficacy/immunogenicity of a vaccine refers to an increase in the ability of the vaccine to inhibit or treat disease progression, such as at least a 5%, 10%, 25%, 50%, 100%, or greater than 100% increase in the effectiveness of the vaccine for that purpose. In a further example, enhancement of the efficacy/immunogenicity of a vaccine refers to an increase in the ability of the vaccine to recruit the subject's natural defenses against cancers that have already developed, such as at least a 5%, 10%, 25%, 50%, 100%, or greater than 100% increase in the effectiveness of the fusion protein, pharmaceutical composition, or vaccine for that purpose.

Similarly, by "overcoming a suppressed immune response" with regard to a fusion protein, pharmaceutical composition, or vaccine is intended improving an outcome, for example, as measured by a change in a specific value, such as a return to a formerly positive value in a particular parameter of an activity of a vaccine associated with protective immunity. In one embodiment, overcoming refers to at least a 5%, 10%, 25%, 50%, 100% or greater than 100% increase in a particular parameter. In one example, overcoming a suppressed immune response to a fusion protein, pharmaceutical composition, or vaccine refers to a renewed ability of the fusion protein, pharmaceutical composition, or vaccine to inhibit or treat disease progression, such as at least a 5%, 10%, 25%, 50%, 100%, or greater than 100% renewal in the effectiveness of the vaccine for that purpose.

A "therapeutically effective amount," "therapeutic dose," "dose," "effective dose," "effective dosage," or "dosing amount" as used (interchangeably) herein, means a dose that achieves a therapeutic goal, as described herein. In some embodiments, a "therapeutic dose" means a dose that induces an immune tolerance in a subject. In certain embodiments, a "therapeutic dose" means a dose that induces an immune tolerance in a subject within a specified time to tolerance period, e.g., within 12 weeks of administration of the first dose. A "therapeutically effective amount" of an IL2/IL2Rα fusion protein refers to the amount of the IL2/IL2Rα fusion protein sufficient to elicit a desired biological response. As will be appreciated by one of ordinary skill in the art, the absolute amount of a particular IL2/IL2Rα fusion protein that is effective can vary depending on such factors as the desired biological endpoint, the IL2/IL2Rα fusion protein to be delivered, the target cell or tissue, and the like. One of ordinary skill in the art will further understand that an effective amount can be administered in a single dose, or can be achieved by administration of multiple doses (i.e., 1, 2, 3, 4, 5, 6, 7, 8, 9, 10 or more doses). The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

"Treat," "treatment," or "treating," as used herein refers to, e.g., the reduction in severity of a disease or condition; the reduction in the duration of a condition course; the amelioration or elimination of one or more symptoms associated with a disease or condition; the provision of beneficial effects to a subject with a disease or condition, without necessarily curing the disease or condition.

By way of example, an anti-cancer agent is a drug that promotes cancer regression in a subject. In some embodiments, a therapeutically effective amount of the drug promotes cancer regression to the point of eliminating the cancer. "Promoting cancer regression" means that administering an effective amount of the drug, alone or in combination with an antineoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount or dosage of the drug inhibits cell growth or tumor growth by at least about 20%, by at least about 40%, by at least about 60%, or by at least about 80% relative to untreated subjects. In some embodiments, a therapeutically effective amount or dosage of the drug completely inhibits cell growth or tumor growth, i.e., inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In some embodiments described herein, tumor regression can be observed and continue for a period of at least about 20 days, at least about 40 days, or at least about 60 days.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

The term "weight based" dose or dosing as referred to herein means that a dose that is administered to a patient is calculated based on the weight of the patient. For example, when a patient with 60 kg body weight requires 3 mg/kg of an anti-IL2 antibody, one can calculate and use the appropriate amount of the IL2/IL2Rα fusion protein (i.e., 180 mg) for administration.

The use of the term "flat dose" with regard to the methods and dosages described herein means a dose that is administered to a patient without regard for the weight or body surface area (BSA) of the patient. The flat dose is therefore not provided as a mg/kg dose, but rather as an absolute amount of the agent (e.g., the IL2/IL2Rα fusion protein). For example, a 60 kg person and a 100 kg person would receive the same dose of an antibody (e.g., 480 mg of an IL2/IL2Rα fusion protein).

As used herein, the terms "ug" and "uM" are used interchangeably with "µg" and "µM," respectively.

Various aspects described herein are described in further detail in the following subsections.

References made to amino acid numbering of immunoglobulins or immunoglobulin fragments, or regions, are all based on Kabat et al. 1991, Sequences of Proteins of Immunological Interest, U.S. Department of Public Health, Bethesda; MD. (The FcRn receptor has been isolated from several mammalian species including humans. The sequences of the human FcRn, rat FcRn, and mouse FcRn are known (Story et al., *J. Exp. Med.* 180: 2377 (1994).) An Fc can comprise the CH2 and CH3 domains of an immunoglobulin with or without the hinge region of the immunoglobulin. Exemplary Fc variants are provided in WO 2004/101740 and WO 2006/074199.

7.3 Interleukin-2/Interleukin-2 Receptor Alpha Fusion Proteins

Disclosed herein is a fusion protein comprising at least two components: (a) a first polypeptide comprising an Interleukin-2 (IL2) polypeptide; and (b) a second polypeptide comprising an extracellular domain of an Interleukin-2 Receptor alpha (IL2Rα) polypeptide. In some embodiments, the extracellular domain of the IL2Rα polypeptide has at least one fewer glycosylation compared to the extracellular domain of native IL2Rα (SEQ ID NO:7); and/or (ii) the IL2 polypeptide has at least one fewer glycosylation compared to native IL2 (SEQ ID NO:2). In some embodiments, the fusion protein has IL2 activity.

7.3.1 Interleukin-2

In some embodiments, a fusion protein is provided which comprises a first polypeptide comprising interleukin-2 (IL2) fused in frame to a second polypeptide comprising or consisting of the extracellular domain of the Interleukin-2 Receptor Alpha (IL2Rα) polypeptide. In some embodiments the fusion protein comprises a first polypeptide comprising IL2 having SEQ ID NO:2. In some embodiments, the first polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO:2.

In one embodiment, the IL2 polypeptide is a native or recombinant IL2 from any vertebrate source, including mammals such as primates (e.g., humans) and rodents (e.g., mice and rats), and domesticated or agricultural mammals unless otherwise indicated.

IL2 polypeptides useful for this disclosure are expressed in a fusion protein. Fusion proteins described herein specifically bind human IL2R, and more specifically, a particular domain (e.g., a functional domain) within the extracellular domain of human IL2Rα. In some embodiments, the fusion protein comprising IL2 is an antagonist. In some embodiments, the fusion protein comprising IL2 binds to human IL2Rα with high affinity.

The term IL2 encompasses unprocessed IL2, as well as, any form of IL2 that results from processing in the cell (i.e., the mature form of IL2). The term also encompasses naturally occurring variants and fragments of IL2, e.g., splice variants or allelic variants, and non-naturally occurring variants. The amino acid sequence of an exemplary mature form of human IL2 (having the 20 amino acid signal sequence) is shown in SEQ ID NO:2. Unprocessed human IL2 additionally comprises an N-terminal 20 amino acid signal peptide (SEQ ID NO:1), which is absent in the mature IL2 molecule. The amino acid sequence of an exemplary mature form of mouse IL2 (having the 20 amino acid signal sequence) is shown in SEQ ID NO:4. Unprocessed mouse IL2 additionally comprises an N-terminal 20 amino acid signal peptide (SEQ ID NO:3), which is absent in the mature IL2 molecule. By a "native IL2", also termed "wild-type IL2", is meant a naturally occurring or recombinant IL2.

Additional nucleic acid and amino acid sequences for IL2 are known. See, for example, GenBank Accession Nos: Q7JFM2 (*Aotus lemurinus* (Gray-bellied night monkey)); Q7JFM5 (*Aotus nancymaae* (Ma's night monkey)); P05016 (*Bas taurus* (Bovine)); Q29416 (*Canis familiaris* (Dog) (*Canis lupus familiaris*)); P36835 (*Capra hircus* (Goat)); and, P37997 (*Equus caballus* (Horse).

Biologically active fragments and variants of IL2 are also provided. Such IL2 active variants or fragments will retain IL2 activity. Biological activity of IL2 can refer to the ability to stimulate IL2 receptor bearing lymphocytes. Such activity can be measured both in vitro and in vivo. IL2 is a global regulator of immune activity and the effects seen here are the sum of such activities. For example, it is regulates survival activity (Bcl-2), induces T effector activity (IFN-gamma, Granzyme B, and Perforin), and promotes T regulatory activity (FoxP3). See, for example, Malek et al. (2010) Immunity 33(2):153-65.

Biologically active variants of IL2 are known. See, for example, US Application Publications 2006/0269515 and 2006/0160187 and WO 99/60128.

Biologically active fragments and variants of IL2 can be employed in the fusion proteins disclosed herein. Such a functional fragment can comprise at least 10, 11, 12, 13, 14, 15, 16, 17, 18, 19, 20, 30, 40, 50, 75, 100, 125, 150 or more continuous amino acids of SEQ ID NO:2. Alternatively, a functional variant can comprise at least 75%, 80%, 85%, 90%, 91%, 92%, 93%, 94%, 95%, 96%, 97%, 98%, or 99% sequence identity to the sequence set forth in SEQ ID NO:2.

Active variants and fragments of polynucleotides encoding the IL2 proteins are further provided. Such polynucleotide can comprise at least 100, 200, 300, 400, 500, 600, 700 continuous nucleotides of polypeptide encoding SEQ ID NO:2, and continue to encode a protein having IL2 activity.

Alternatively, a functional polynucleotide can comprise at least 75%, 80%, 85%, 90%, 91%, 92%, 93%, 94%, 95%, 96%, 97%, 98%, or 99% sequence identity to the polypeptide encoding the amino acid sequence set forth in SEQ ID NO:2 and continue to encode a functional IL2 polypeptide.

Exemplary polypeptide sequences of IL2 are recited in Table 1, below.

TABLE 1

| SEQ ID NO | Description | Sequence |
|---|---|---|
| 1 | IL2 (human, un-processed) | MYRMQLLSCIALSLALVTNSAPTSSSTKKTQLQL EHLLLDLQMILNGINNYKNPKLTRMLTFKFYMPK KATELKHLQCLEEELKPLEEVLNLAQSKNFHLRP RDLISNINVIVLELKGSETTFMCEYADETATIVE FLNRWITFCQSIISTLT |
| 2 | IL2 (human, mature form) | APTSSSTKKTQLQLEHLLLDLQMILNGINNYKNP KLTRMLTFKFYMPKKATELKHLQCLEEELKPLEE VLNLAQSKNFHLRPRDLISNINVIVLELKGSETT FMCEYADETATIVEFLNRWITFCQSIISTLT |
| 3 | IL2 (mouse, un-processed) | MYSMQLASCVTLTLVLLVNSAPTSSSTSSSTAEA QQQQQQQQQQQHLEQLLMDLQELLSRMENYRNL KLPRMLTFKFYLPKQATELKDLQCLEDELGPLRH VLDLTQSKSFQLEDAENFISNIRVTVVKLKGSDN TFECQFDDESATVVDFLRRWIAFCQSIISTSPQ |
| 4 | IL2 (mouse, mature form) | APTSSSTSSSTAEAQQQQQQQQQQQQHLEQLLMD LQELLSRMENYRNLKLPRMLTFKFYLPKQATELK DLQCLEDELGPLRHVLDLTQSKSFQLEDAENFIS NIRVTVVKLKGSDNTFECQFDDESATVVDFLRRW IAFCQSIISTSPQ |

In some embodiments, the fusion proteins provided herein can comprise at least one mutation within the extracellular domain of IL2Rα. In some embodiments, the IL2 polypeptide has at least one fewer glycosylation site compared to native IL2 (SEQ ID NO:2). In some embodiments, the at least one fewer glycosylation sites is due to one or more mutations that removes a glycosylation.

In other embodiments, the fusion protein comprises a mutation that is a substitution of an amino acid having a glycosylation site with an amino acid not having a glycosylation site. In some embodiments, the mutation removes an O-glycosylation and/or an N-glycosylation. In one embodiment, the mutation removes an O-glycosylation, e.g., threonine at amino acid 3 of SEQ ID NO: 2. In another embodiment, the mutation removes an N-glycosylation.

In some embodiments, the mutation is one or more substitutions of an amino acid of IL2 that is glycosylated with an amino acid that is not glycosylated. In some embodiments, the mutation is one or more substitutions of an amino acid of IL2 that allows glycosylation at a nearby amino acid with an amino acid that does not allow glycosylation at the nearby amino acid.

In some embodiments, the one or more substitutions of an amino acid of IL2 are from an alanine to an amino acid selected from the group consisting of arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In some embodiments, the one or more substitutions of an amino acid of IL2 are from a threonine to an amino acid selected from the group consisting of alanine, arginine, asparagine, aspartic acid, cysteine, glutamine, glutamic acid, glycine, histidine, isoleucine, leucine, lysine, methionine, phenylalanine, proline, tryptophan, tyrosine, and valine.

In some embodiments, the one or more substitutions of an amino acid of IL2 are from a reactive amino acid, e.g., a cysteine, to an amino acid selected from the group consisting of alanine, arginine, asparagine, aspartic acid, glutamine, glutamic acid, glycine, histidine, isoleucine, leucine, lysine, methionine, phenylalanine, proline, serine, threonine, tryptophan, tyrosine, and valine. In some embodiments, the one or more substitutions are from a cysteine to a serine. In some embodiments, the one or more substitutions are from a cysteine to an alanine. In some embodiments, the one or more substitutions are from a cysteine to a valine.

In some embodiments, the one or more substitutions are at amino acid T3 of IL2 compared to corresponding to SEQ ID NO:2.

In some embodiments, the one of the substitutions is at amino acid C125 of SEQ ID NO:2. In a particular embodiment, the substitution at amino acid C125 is selected from the group consisting of C125S, C125A, and C125V.

In some embodiments, the mutation is a deletion. In particular embodiments, the deletion is at amino acid A1 of SEQ ID NO:2.

The present disclosure also includes any other mutations to the IL2 polypeptide. In other embodiments, the mutations also include one or more substitutions that improve the properties of IL2, e.g., improve IL2 activity, improve a half-life of IL2, improve stability, etc.

As disclosed below in this section, the mutations recited herein are mutations relative to amino acid positions of SEQ ID NO:2. According to the present invention, any of the mutations below alone or in combination with the other disclosed mutations or any known in the art could be used in one or more of the IL2 fusion proteins as described herein.

In some embodiments, IL2 comprises one or more mutations disclosed in Carmenate et al., *J Immunol*, 200 (10) 3475-3484 (2018) and/or in U.S. Pat. No. 8,759,486: for example, at amino acid residue Q22, Q126, I129, S130, or any combination thereof, e.g., Q22V, Q126A, I129D, S130G, or any combination thereof. In some embodiments, IL2 comprises one or more mutations of L18N, Q126Y, and S130R as disclosed in U.S. Pat. No. 8,759,486 B2. In some embodiments, IL2 comprises one or more mutations of Q13Y, Q126Y, I129D, and S130R as disclosed in U.S. Pat. No. 8,759,486 B2. In some embodiments, IL2 comprises one or more mutations of K35E, K35D, and K35Q as disclosed in WO 2018/091003 A1.

In some embodiments, IL2 comprises one or more mutations disclosed in Epstein et al. *Blood*, 101(12):4853-61] (2003) and/or in U.S. Pat. No. 7,371,371: for example, at amino acid residue R38, e.g., R38W. In some embodiments, IL2 comprises the mutation of R38W and one or more mutations outside of amino acid positions 22 to 58 of IL2 as disclosed in U.S. Pat. No. 7,371,371 B2.

In some embodiments, IL2 comprises one or more mutations disclosed in Wittrup et al. *J Immunother.* 32(9):887-94 (2009) and/or in U.S. Pat. No. 8,906,356: for example, amino acid residue 91, 126, or both, e.g., V91R, Q126T, or both. In some embodiments, IL2 comprises the mutation of E15W as disclosed in Wittrup et al. *J Immunother.* 32(9): 887-94 (2009) and also in U.S. Pat. No. 8,906,356. In some embodiments, IL2 comprises one or both mutations of N88R and V91R as disclosed in Wittrup et al. *J Immunother.* 32(9):887-94 (2009) and also in U.S. Pat. No. 8,906,356. In some embodiments, IL2 comprises the mutation of Q126T or Q126I as disclosed in Wittrup et al. *J Immunother.* 32(9):887-94 (2009) and/or in U.S. Pat. No. 8,906,356.

In some embodiments, IL2 comprises one or more mutations disclosed in U.S. Pat. No. 8,906,356 B2: for example at amino acid 69, 74, 91, 126, or any combination thereof. In some embodiments, the mutation is V91R, Q126T, Q126L, Q127T, or any combination thereof as disclosed in U.S. Pat. No. 8,906,356 B2.

In some embodiments, IL2 comprises one or more mutations disclosed in Wittrup et al. *J Immunother.* 32(9):887-94 (2009) and/or in U.S. Pat. No. 7,569,215 B2: for example, at amino acid residue E15, N30, E68, V69, N71, S75, N90, or any combination thereof, e.g., N30S, E68D, V69A, N71A, S75P, N90H, or any combination thereof. In some embodiments, IL2 comprises the mutation of E15W as disclosed in Wittrup et al. *Biochemistry*, Vol. 44, No. 31 (2005). In some embodiments, the mutation is V69A as disclosed in U.S. Pat. No. 7,569,215 B2.

In some embodiments, IL2 comprises one or more mutations disclosed in Wittrup et al. *J Immunother.* 32(9):887-94 (2009) and/or in U.S. Pat. No. 7,951,360 B2: for example, at amino acid residue N29, Y31, K35, T37, K48, V69, N71, N88, or any combination thereof, e.g., N29S, Y31H, K35R, T37A, K48E, V69A, N71R, N88D, or any combination thereof. In some embodiments, IL2 comprises the mutation of E15W as disclosed in Wittrup et al. *Biochemistry*, Vol. 44, No. 31 (2005).

In some embodiments, IL2 comprises one or more mutations disclosed in Wittrup et al. *J Immunother.* 32(9):887-94 (2009) and/or in U.S. Pat. No. 8,349,311 B2: for example, at amino acid 69, 74, 128, or any combination thereof, e.g., V69A, I128P, or any combination thereof.

In some embodiments, IL2 comprises one or more mutations disclosed in Wittrup et al. *J Immunother.* 32(9):887-94 (2009): for example, at amino acid residue S4, T10, Q11, V69, N88, T133, or any combination thereof, e.g., S4P, T10A, Q11R, V69A, N88D, T133A, or any combination thereof.

In some embodiments, IL2 comprises one or more mutations disclosed in Wittrup et al. *J Immunother.* 32(9):887-94 (2009): for example, at amino acid residue N30, V69, I128, or any combination thereof, e.g., N30S, V69A, I128T, or any combination thereof.

In some embodiments, IL2 comprises one or more mutations disclosed in Wittrup et al. *J Immunother.* 32(9):887-94 (2009): for example, at amino acid residue K8, Q13, N26, N30, K35, T37, V69, or any combination thereof, e.g., K8R, Q13R, N26D, N30T, K35R, T37R, V69A, or any combination thereof.

In some embodiments, IL2 comprises one or more mutations disclosed in Shanafelt et al., *Nat Biotechnol.*, 18(11): 1197-202 (2000) for example, at amino acid residue N88, e.g., N88R.

In some embodiments, IL2 comprises one or more mutations disclosed in U.S. Pat. No. 9,616,105 B2: for example, amino acids 20, 88, 126, or any combination thereof, e.g., N88R, N88G, or N88I. In some embodiments, IL2 comprises a mutation of N88R, N88G, or N88I as disclosed in U.S. Pat. No. 9,616,105 B2. In some embodiments, IL2 comprises a mutation of D20H, D20I, or D20Y as disclosed in U.S. Pat. No. 9,616,105 B2. In some embodiments, IL2 comprises the mutation of Q126L as disclosed in U.S. Pat. No. 9,616,105 B2.

In some embodiments, IL2 comprises one or more mutations disclosed in US 2018/0125941 A1: for example, D20H, N88I, N88G, N88R, Q126L, Q126F, or any combination thereof. In some embodiments, IL2 comprises one or more mutations of T3A, N88G, N88R, D20H, C125S, Q126L, and Q126F as disclosed in US 2018/0037624 A1.

In some embodiments, IL2 comprises one or more mutations disclosed in US 2017/0327555 A1: for example, at amino acid residue N88, D20, C125, Q126, or any combination thereof, e.g., N88G, N88R, D20H, C125S, Q126L, Q126F, or any combination thereof.

In some embodiments, IL2 comprises one or more mutations disclosed in WO 2016/025385 A1: for example, at amino acid residue D109, C125, or both, e.g., D109C, C125S, or both. In some embodiments, IL2 comprises one or more mutations disclosed in WO 2016/025385 A1: for example; at amino acid residue D20, N88, Q126, C125, Q126, or any combination thereof, e.g., D20H, N88I, N88G, N88R, Q126L, C125S, Q126F, or any combination thereof.

In some embodiments, IL2 comprises one or more mutations disclosed in WO 2016/164937 A1: for example, at amino acid residue L12, Q13, E15, H16, L19, D20, M23, D84, S87, N88, V91, E95, or any combination thereof, e.g., L12G, L12K, L12Q, L12S, Q13G, E15A, E15G, E15S, H16A, H16D, H16G, H16K, H16M, H16N, H16R, H16S, H16T, H16V, H16Y, L19A, L19D, L19E, L19G, L19N, L19S, L19T, L19V, D20A, D20E, D20F, D20G, D20T, D20W, M23R, D84A, D84E, D84G, D841, D84M, D84Q, D84R, D84S, D84T, S87E, N88A, N88D, N88E, N88F, N88G, N88M, N88R, N88S, N88V, N88W, V91D, V91E, V91G, V91S, E95G, or any combination thereof.

In some embodiments, IL2 comprises one or more mutations disclosed in U.S. Pat. No. 9,932,380 B2 or U.S. Pat. No. 9,580,486: for example, at amino acid residue V91, e.g., V91K. In some embodiments, IL2 further comprises a mutation of C125A or C125S. In some embodiments, IL2 further comprises a mutation at T3. In some embodiments, the mutation at T3 is one of T3A or T3N. In some embodiments, IL2 comprises a mutation at S5. In some embodiments, the mutation is S5T.

In some embodiments, IL2 comprises one or more mutations disclosed in U.S. Pat. No. 9,732,134 B2: for example, E15, H16, Q22, D84, N88, E95, or any combination thereof.

In some embodiments, IL2 comprises one or more mutations disclosed in US 2015/0218260 A1: for example, N88D. In some embodiments, IL2 comprises a mutation disclosed in U.S. Pat. No. 9,266,938 B2: for example, at amino acid 42, 45, 72, or any combination thereof, e.g., L72G, L72A, L72S, L72T, L72Q, L72E, L72N, L72D, L72R, or L72K. In some embodiments, IL2 comprises a mutation of F42A, F42G, F42S, F42T, F42Q, F42E, F42N, F42D, F42R, and F42K. In some embodiments, IL2 comprises a mutation of Y45A, Y45G, Y45S, Y45T, Y45Q, Y45E, Y45N, Y45D, Y45R, and Y45K.

In some embodiments, IL2 comprises one to four mutations: the first mutation of L72G, L72A, L72S, L72T, L72Q, L72E, L72N, L72D, L72R, or L72K, the second mutation of F42A, F42G, F42S, F42T, F42Q, F42E, F42N, F42D, F42R, or F42K, Y45A, Y45G, Y45S, Y45T, Y45Q, Y45E, Y45N, Y45D, Y45R, or Y45K, the third mutation of T3A, T3G, T3Q, T3E, T3N, T3D, T3R, T3K, or T3P, and/or the fourth mutation of C125A, C125S, C125T or C125V. The mutations listed herein or disclosed in the patents, patent publications or any other references cited herein are incorporated herein by reference in their entireties.

7.3.2 Interleukin-2 Receptor Alpha

The fusion protein comprises a second polypeptide comprising the extracellular domain of the Interleukin-2 Receptor Alpha (IL2Rα). In some embodiments, the extracellular domain of IL2Rα comprises the amino acid sequence set forth as SEQ ID NO:7. In some embodiments, the second polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO:7.

The term "CD25" or "IL2 receptor a," "IL2Rα," "IL2Ra," "IL2-Rα," and "IL2-Ra" as used herein, refers to any native or recombinant IL2Rα from any vertebrate source, including mammals such as primates (e.g., humans) and rodents (e.g., mice and rats) and domesticated or agricultural mammals unless otherwise indicated. The term also encompasses naturally occurring variants of IL2Rα, e.g., splice variants or allelic variants, or non-naturally occurring variants. Human IL2 exerts its biological effects via signaling through its receptor system, IL2R. IL2 and its receptor (IL2R) are required for T-cell proliferation and other fundamental functions which are crucial of the immune response. IL2R consists of 3 non-covalently linked type I transmembrane proteins which are the alpha (p55), beta (p75), and gamma (p65) chains. The human IL2R alpha chain contains an extracellular domain of 219 amino acids, a transmembrane domain of 19 amino acids, and an intracellular domain of 13 amino acids. The secreted extracellular domain of IL2R alpha (IL2Rα) can be employed in the fusion proteins describe herein.

The amino acid sequence of an exemplary mature form of human IL2Rα is shown in SEQ ID NO:6. Unprocessed human IL2Rα is shown in SEQ ID NO:5. The extracellular domain of SEQ ID NO:5 and/or SEQ ID NO:6 is set forth in SEQ ID NO:7. The amino acid sequence of an exemplary mature form of mouse IL2Rα is shown in SEQ ID NO:9. Unprocessed mouse IL2Rα is shown in SEQ ID NO:8. The extracellular domain of SEQ ID NO:8 and/or SEQ ID NO:9 is set forth in SEQ ID NO:10. By a "native IL2Rα", also termed "wild-type IL2Rα", is meant a naturally occurring or recombinant IL2Rα.

Nucleic acid and amino acid sequences for IL2Rα are known. See, for example, GenBank Accession Nos: NP_001030597.1 (*P. troglodytes*); NP_001028089.1 (*M. mulatta*); NM_001003211.1 (*C. lupus*); NP_776783.1 (*B. taurus*); NP_032393.3 (*M. musculus*); and, NP_037295.1 (*R. norvegicus*).

The extracellular domain of IL2Rα as used herein means a functional IL2Rα extracellular domain in its normal role in binding to IL2, unless otherwise specified. The term a IL2Rα EC domain includes a functional fragment, variant, analog, or derivative thereof that retains the function of full-length wild-type IL2Rα EC in IL2 binding. The IL2Rα EC domain can be the human, porcine, canine, rat, or murine IL2Rα EC domain. The phrase "biological activity of the IL2Rα EC domain" refers to one or more of the biological activities of EC domain of IL2Rα, including but not limited to, the ability to enhance intracellular signaling in IL2 receptor responsive cells. Non-limiting examples of biologically active fragments and variants of the IL2Rα EC domain are disclosed, for example, in Robb et al., Proc. Natl. Acad. Sci. USA, 85:5654-5658, 1988. In some embodiments, the biologically active fragments and variants of the IL2Rα EC domain disclosed herein comprise at least one fewer glycosylation compared to the extracellular domain of native IL2Rα.

Biologically active fragments and variants of the extracellular domain of IL2Rα can be employed in the fusion proteins disclosed herein. Such a functional fragment can comprise at least 10, 11, 12, 13, 14, 15, 16, 17, 18, 19, 20, 30, 40, 50, 75, 100, 125, 150, 175, 200, 215 or greater continuous amino acids of the extracellular domain of any one of SEQ ID NO:7. Alternatively, a functional variant can comprise at least 75%, 80%, 85%, 90%, 91%, 92%, 93%, 94%, 95%, 96%, 97%, 98%, or 99% sequence identity to the sequence set forth in SEQ ID NO:7.

Active variants and fragments of polynucleotides encoding the extracellular domain of IL2Rα are further provided. Such polynucleotide can comprise at least 100, 200, 300, 400, 500, 600 or greater continuous nucleotides of polypeptide encoding SEQ ID NO:7 and continue to encode a protein having the extracellular domain activity of IL2Rα. Alternatively, a functional polynucleotide can comprise at least 80%, 85%, 90%, 91%, 92%, 93%, 94%, 95%, 96%, 97%, 98%, or 99% sequence identity to the polypeptide encoding the amino sequence set forth in SEQ ID NO:7 and continue to encode a protein having the extracellular domain activity of IL2Rα.

Polypeptide sequences of IL2Rα are recited in Table 2.

TABLE 2

| SEQ ID NO | Description | Sequence |
|---|---|---|
| 5 | IL2Rα (human, unprocessed form) | MDSYLLMWGLLTFIMVPGCQAELCDDDPPEIPHAT FKAMAYKEGTMLNCECKRGFRRIKSGSLYMLCTGN SSHSSWDNQCQCTSSATRNTTKQVTPQPEEQKERK TTEMQSPMQPVDQASLPGHCREPPPWENEATERIY HFVVGQMVYYQCVQGYRALHRGPAESVCKMTHGKT RWTQPQLICTGEMETSQFPGEEKPQASPEGRPESE TSCLVTTTDFQIQTEMAATMETSIFTTEYQVAVAG CVFLLISVLLLSGLTWQRRQRKSRRTI |
| 6 | IL2Rα (human, mature form) | ELCDDDPPEIPHATFKAMAYKEGTMLNCECKRGFR RIKSGSLYMLCTGNSSHSSWDNQCQCTSSATRNTT KQVTPQPEEQKERKTTEMQSPMQPVDQASLPGHCR EPPPWENEATERIYHFVVGQMVYYQCVQGYRALHR GPAESVCKMTHGKTRWTQPQLICTGEMETSQFPGE EKPQASPEGRPESETSCLVTTTDFQIQTEMAATME TSIFTTEYQVAVAGCVFLLISVLLLSGLTWQRRQR KSRRTI |
| 7 | IL2Rα (human, mature form of IL2Rα extracellular domain) | ELCDDDPPEIPHATFKAMAYKEGTMLNCECKRGFR RIKSGSLYMLCTGNSSHSSWDNQCQCTSSATRNTT KQVTPQPEEQKERKTTEMQSPMQPVDQASLPGHCR EPPPWENEATERIYHFVVGQMVYYQCVQGYRALHR GPAESVCKMTHGKTRWTQPQLICTGEMETSQFPGE EKPQASPEGRPESETSCLVTTTDFQIQTEMAATME TSIFTTEYQ |
| 8 | IL2Rα (mouse, unprocessed form) | MEPRLLMLGFLSLTIVPSCRAELCLYDPPEVPNAT FKALSYKNGTILNCECKRGFRRLKELVYMRCLGNS WSSNCQCTSNSHDKSRKQVTAQLEHQKEQQTTTDM QKPTQSMHQENLTGHCREPPPWKHEDSKRIYHFVE GQSVHYECIPGYKALQRGPAISICKMKCGKTGWTQ PQLTCVDEREHHRFLASEESQGSRNSSPESETSCP ITTTDFPQPTETTAMTETFVLTMEYKVAVASCLFL LISILLLSGLTWQHRWRKSRRTI |
| 9 | IL2Rα (mouse, mature form) | ELCLYDPPEVPNATFKALSYKNGTILNCECKRGFR RLKELVYMRCLGNSWSSNCQCTSNSHDKSRKQVTA QLEHQKEQQTTTDMQKPTQSMHQENLTGHCREPPP WKHEDSKRIYHFVEGQSVHYECIPGYKALQRGPAI SICKMKCGKTGWTQPQLTCVDEREHHRFLASEESQ GSRNSSPESETSCPITTTDFPQPTETTAMTETFVL TMEYKVAVASCLFLLISILLLSGLTWQHRWRKSRR TI |
| 10 | IL2Rα (mouse, mature form of IL2Rα extracellular domain) | ELCLYDPPEVPNATFKALSYKNGTILNCECKRGFR RLKELVYMRCLGNSWSSNCQCTSNILRASHDKSRK QVTAQLEHQKEQQTTTDMQKPTQSMHQENLTGHCR EPPPWKHEDSKRIYHFVEGQSVHYECIPGYKALQR GPAISICKMKCGKTGWTQPQLTCVDEREHHRFLAS EESQGSRNSSPESETSCPITTTDFPQPTETTAMTE TFVLTMEYK |

TABLE 2-continued

| SEQ ID NO | Description | Sequence |
|---|---|---|
| 11 | IL2Rα (human, mature form of IL2Rα extracellular domain) - full-truncated | ELCDDDPPEIPHATFKAMAYKEGTMLNCECKRGFR RIKSGSLYMLCTGNSSHSSWDNQCQCTSSATRNTT KQVTPQPEEQKERKTTEMQSPMQPVDQASLPGHCR EPPPWENEATERIYHFVVGQMVYYQCVQGYRALHR GPAESVCKMTHGKTRWTQPQLICTGE |
| 12 | IL2Rα (human, mature form of IL2Rα extracellular domain) - half-truncated | ELCDDDPPEIPHATFKAMAYKEGTMLNCECKRGFR RIKSGSLYMLCTGNSSHSSWDNQCQCTSSATRNTT KQVTPQPEEQKERKTTEMQSPMQPVDQASLPGHCR EPPPWENEATERIYHFVVGQMVYYQCVQGYRALHR GPAESVCKMTHGKTRWTQPQLICTGEMETSQFPGE EKPQASPEGRPESETS |

In some embodiments, the fusion proteins provided herein can comprise at least one mutation within the EC domain of IL2Rα.

In some embodiments, the EC domain of the IL2Rα polypeptide has at least one fewer glycosylation, at least two fewer glycosylations, at least three fewer glycosylations, at least four fewer glycosylations, at least five fewer glycosylations, at least six fewer glycosylations, at least seven fewer glycosylations, at least eight fewer glycosylations, or at least nine fewer glycosylations compared to the extracellular domain of native IL2Rα (SEQ ID NO:7).

In some embodiments, the EC domain of the IL2Rα polypeptide having at least one fewer glycosylation comprises a mutation that removes a glycosylation. In other embodiments, the fusion protein comprises a mutation that is a substitution of an amino acid having a glycosylation site with an amino acid not having a glycosylation site. In some embodiments, the mutation removes an O-glycosylation and/or an N-glycosylation. In one embodiment, the mutation removes an O-glycosylation. In another embodiment, the mutation removes an N-glycosylation.

In some embodiments, the mutation in the fusion protein comprises a deletion of the C-terminal end of IL2Rα. In some embodiments, the mutation is a deletion of amino acids 167 to 219 of SEQ ID NO:7. In some embodiments, the mutation is a deletion of amino acids 168 to 219 of SEQ ID NO:7. In some embodiments, the mutation is a deletion of amino acids 169 to 219 of SEQ ID NO:7. In some embodiments, the mutation is a deletion of amino acids 170 to 219 of SEQ ID NO:7. In some embodiments, the mutation is a deletion of amino acids 171 to 219 of SEQ ID NO:7. In some embodiments, the mutation is a deletion of amino acids 172 to 219 of SEQ ID NO:7. In some embodiments, the mutation is a deletion of amino acids 173 to 219 of SEQ ID NO:7. In some embodiments, the mutation is a deletion of amino acids 174 to 219 of SEQ ID NO:7. In some embodiments, the mutation is a deletion of amino acids 175 to 219 of SEQ ID NO:7. In some embodiments, the mutation is a deletion of amino acids 176 to 219 of SEQ ID NO:7. In some embodiments, the mutation is a deletion of amino acids 177 to 219 of SEQ ID NO:7. In some embodiments, the mutation is a deletion of amino acids 178 to 219 of SEQ ID NO:7. In some embodiments, the mutation is a deletion of amino acids 179 to 219 of SEQ ID NO:7. In some embodiments, the mutation is a deletion of amino acids 180 to 219 of SEQ ID NO:7. In some embodiments, the mutation is a deletion of amino acids 181 to 219 of SEQ ID NO:7. In some embodiments, the mutation is a deletion of amino acids 182 to 219 of SEQ ID NO:7. In some embodiments, the mutation is a deletion of amino acids 183 to 219 of SEQ ID NO:7. In some embodiments, the mutation is a deletion of amino acids 184 to 219 of SEQ ID NO:7. In some embodiments, the mutation is a deletion of amino acids 185 to 219 of SEQ ID NO:7. In some embodiments, the mutation is a deletion of amino acids 186 to 219 of SEQ ID NO:7. In some embodiments, the mutation is a deletion of amino acids 187 to 219 of SEQ ID NO:7. In some embodiments, the mutation is a deletion of amino acids 188 to 219 of SEQ ID NO:7. In some embodiments, the mutation is a deletion of amino acids 189 to 219 of SEQ ID NO:7. In some embodiments, the mutation is a deletion of amino acids 190 to 219 of SEQ ID NO:7. In some embodiments, the mutation is a deletion of amino acids 191 to 219 of SEQ ID NO:7. In some embodiments, the mutation is a deletion of amino acids 192 to 219 of SEQ ID NO:7.

In some embodiments, the mutation is a deletion of amino acids from 167, 168, 169 or 171 through 192 to 219, corresponding to SEQ ID NO:7. In some embodiments, the mutation does not include a deletion of 170 to 219, corresponding to SEQ ID NO:7.

In some embodiments, the second polypeptide comprises, consists essentially of, or consists of an amino acid sequence at least about 80%, at least about 85%, at least about 90%, at least about 95%, at least about 96%, at least about 97%, at least about 98%, at least about 99%, or about 100% identical to the amino acid sequence set forth in SEQ ID NO:11. In other embodiments, the second polypeptide comprises, consists essentially of, or consists of SEQ ID NO: 11 and +1, +2, +3, +4, +5, +6, +7, +8, +9, +10, +11, +12, +13, +14, +15, +16, +17, +18, +19, +20, +21, +22, +23, +24, or +25 amino acids. In some embodiments, the second polypeptide comprises, consists essentially of, or consists of SEQ ID NO: 11 with no more than 25, 24, 23, 22, 21, 20, 19, 18, 17, 16, 15, 14, 13, 12, 11, 10, 9, 8, 7, 6, 5, 4, 3, 2, or 1 amino acids. In some embodiments, the second polypeptide comprises, consists essentially of, or consists of an amino acid sequence at least about 80%, at least about 85%, at least about 90%, at least about 95%, at least about 96%, at least about 97%, at least about 98%, at least about 99%, or about 100% identical to the amino acid sequence set forth in SEQ ID NO:12.

In some embodiments, the fusion protein comprises one or more mutations. In some embodiments, the one or more mutations are one or more substitutions of an amino acid of IL2Rα that is glycosylated with an amino acid that is not glycosylated.

In some embodiments, the one or more substitutions amino acids of IL2Rα are at amino acid N49, amino acid N68, amino acid T74, amino acid T85, amino acid T197, amino acid T203, amino acid T208, and amino acid T216, or any combination thereof, wherein the amino acid locations correspond to SEQ ID NO:7.

In some embodiments, the one or more substitutions are from asparagine to another amino acid. In some embodiments, the one or more substitutions is from asparagine to an amino acid selected from the group consisting of alanine, threonine, serine, arginine, aspartic acid, glutamine, glutamic acid, glycine, histidine, isoleucine, leucine, lysine, methionine, phenylalanine, proline, tryptophan, tyrosine, and valine.

In some embodiments, the one or more substitutions are from threonine to another amino acid. In some embodiments, the one or more substitutions is from threonine to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the substitution is amino acid N49 of SEQ ID NO:7. In some embodiments, amino acid N49 of SEQ ID NO:7 is mutated to an amino acid selected from the group consisting of alanine, threonine, serine, arginine, aspartic acid, glutamine, glutamic acid, glycine, histidine, isoleucine, leucine, lysine, methionine, phenylalanine, proline, tryptophan, tyrosine, and valine.

In some embodiments, the substitution is amino acid N68 of SEQ ID NO:7. In some embodiments, amino acid N68 of SEQ ID NO:7 is mutated to an amino acid selected from the group consisting of alanine, threonine, serine, arginine, aspartic acid, glutamine, glutamic acid, glycine, histidine, isoleucine, leucine, lysine, methionine, phenylalanine, proline, tryptophan, tyrosine, and valine.

In some embodiments, the substitution is amino acid T74 of SEQ ID NO:7. In some embodiments, amino acid T74 of SEQ ID NO:7 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the substitution is amino acid T85 of SEQ ID NO:7. In some embodiments, amino acid T85 of SEQ ID NO:7 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the substitution is amino acid T197 of SEQ ID NO:7. In some embodiments, amino acid T197 of SEQ ID NO:7 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the substitution is amino acid T203 of SEQ ID NO:7. In some embodiments, amino acid T203 of SEQ ID NO:7 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the substitution is amino acid T208 of SEQ ID NO:7. In some embodiments, amino acid T208 of SEQ ID NO:7 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the substitution is amino acid T216 of SEQ ID NO:7. In some embodiments, amino acid T216 of SEQ ID NO:7 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the fusion protein comprises one or more mutations. In some embodiments, the one or more mutations is one or more substitutions of an amino acid of IL2Rα that allows glycosylation at a nearby amino acid with an amino acid that does not allow glycosylation at the nearby amino acid.

In some embodiments, the substitution is at amino acid S50, amino acid S51, amino acid T69, amino acid T70, amino acid C192, or any combination thereof, wherein the amino acid locations correspond to SEQ ID NO:7.

In some embodiments, the substitution is amino acid S50 corresponding to SEQ ID NO:7. In some embodiments, amino acid S50 corresponding to SEQ ID NO:7 is mutated to proline.

In some embodiments, the substitution is amino acid S51 corresponding to SEQ ID NO:7. In some embodiments, amino acid S51 corresponding to SEQ ID NO:7 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

In some embodiments, the substitution is amino acid T69 corresponding to SEQ ID NO:7. In some embodiments, amino acid T69 corresponding to SEQ ID NO:7 is mutated to proline.

In some embodiments, the substitution is amino acid T70 corresponding to SEQ ID NO:7. In some embodiments, amino acid T70 corresponding to SEQ ID NO:7 is mutated to an amino acid selected from the group consisting of alanine, arginine, asparagine, aspartic acid, cysteine, glutamine, glutamic acid, glycine, histidine, isoleucine, leucine, lysine, methionine, phenylalanine, proline, threonine, tryptophan, tyrosine, and valine.

In some embodiments, the substitution is amino acid C192 corresponding to SEQ ID NO:7. In some embodiments, amino acid C192 corresponding to SEQ ID NO:7 is mutated to an amino acid selected from the group consisting of alanine, arginine, asparagine, aspartic acid, glutamine, glutamic acid, glycine, histidine, isoleucine, leucine, lysine, methionine, phenylalanine, proline, serine, threonine, tryptophan, tyrosine, and valine.

7.3.3 Linker

The fusion protein of the present disclosure can further comprise a linker. In some embodiments, the linker can link the first polypeptide to the second polypeptide from N-terminus to C-terminus, e.g., N-IL2-linker-IL2Rα EC-C. In other embodiments, the linker can link the second polypeptide to the first polypeptide from N-terminus to C-terminus, e.g., N-IL2Rα EC-linker-IL2-C.

In one embodiment, the IL2/IL2Rα fusion protein comprises a linker sequence located between the IL2 polypeptide and the IL2Rα polypeptide. The linker can be of any length and can comprise at least 1, 2, 3, 4, 5, 6, 7, 8, 9, 10, 11, 12, 13, 14, 15, 16, 17, 18, 19, 20, 25, 30, 31, 32, 33, 34, 35, 36, 37, 38, 39, 40, 50, or 60 or more amino acids. In other embodiments, a linker useful for the present disclosure has at least one amino acid and less than 100 amino acids, less than 90 amino acids, less than 80 amino acids, less than 70 amino acids, less than 60 amino acids, less than 50 amino acids, less than 40 amino acids, less than 30 amino acids, less than 20 amino acids, less than 19 amino acids, less than 18 amino acids, less than 17 amino acids, less than 16 amino acids, less than 15 amino acids, less than 14 amino acids, less than 13 amino acids, or less than 12 amino acids. In one embodiment, the linker sequence comprises glycine amino acid residues. In other instances, the linker sequence comprises a combination of glycine and serine amino acid residues.

In some embodiments, the fusion protein comprises a linker fused in frame between the first polypeptide and the second polypeptide. In some embodiments, the fusion protein comprises a linker is a glycine/serine linker. Such glycine/serine linkers can comprises any combination of the amino acid residues, including, but not limited to, the peptide GGGS (SEQ ID NO: 174) or GGGGS (SEQ ID NO: 72) or repeats of the same, including 1, 2, 3, 4, 5, 6, 7, 8, 9, 10 or more repeats of these given peptides. The glycine/serine linkers disclosed herein comprises an amino acid sequence of $(GS)_n$, $(GGS)_n$, $(GGGS)_n$, $(GGGGS)_n$, or $(GGGGS)_n$, wherein n is an integer of 1, 2, 3, 4, 5, 6, 7, 8, 9, or 10. In a particular embodiment, the linker sequence comprises GGGSGGGSGGGS (SEQ ID NO:71) (also noted as $(Gly_3Ser)_3$). In another embodiment, the linker sequence comprises GGGSGGGSGGGSGGGS (SEQ ID NO: 74) (also noted as $(Gly_3Ser)_4$). In other embodiments, the linker sequence comprises one of $(Gly_3Ser)_5$ (GGGSGGGSGGGSGGGSGGGS) (SEQ ID NO: 75), $(Gly_3Ser)_6$ (GGGSGGGSGGGSGGGSGGGSGGGS) (SEQ ID NO: 76), or $(Gly_3Ser)_7$ (GGGSGGGSGGGSGGGSGGGSGGGSGGGS) (SEQ ID NO: 77). In other embodiments, the linker sequence comprises $(Gly_4Ser)_3$ (GGGGSGGGGSGGGGS) as set forth in SEQ ID NO: 78. In additional embodiments, the linker sequence comprises GGGGSGGGGSGGGGSGGGGS (SEQ ID NO: 79) (also noted as $(Gly_4Ser)_4$); GGGGSGGGGSGGGGSGGGGSGGGGS (SEQ ID NO: 80) (also noted as $(Gly_4Ser)_5$); $(Gly_4Ser)_2$ (GGGGSGGGGS) (SEQ ID NO: 81), $(Gly_4Ser)_1$ (GGGGS) (SEQ ID NO: 82), $(Gly_4Ser)_6$ (GGGGSGGGGSGGGGSGGGGSGGGGSGGGGS) (SEQ ID NO: 83); $(Gly_4Ser)_7$ (GGGGSGGGGSGGGGSGGGGSGGGGSGGGGSGGGGS) (SEQ ID NO: 97); or $(Gly_4Ser)_5$ (GGGGSGGGGSGGGGSGGGGSGGGGS) (SEQ ID NO: 84).

7.3.4 Heterologous Moiety

The fusion protein of the present disclosure can further comprise an additional element, e.g., heterologous moiety. Such elements can aid in the expression of the fusion protein, aid in the secretion of the fusion protein, improve the stability of the fusion protein, allow for more efficient purification of the protein, and/or modulate the activity of the fusion protein. In some embodiment, the heterologous moiety is a polypeptide moiety. In other embodiments, the heterologous moiety is a non-polypeptide moiety.

In some embodiments, the fusion protein comprises a heterologous moiety fused to the first polypeptide. In some embodiments, the fusion protein comprises a heterologous moiety fused to the second polypeptide. In some embodiments, the fusion protein comprises a heterologous moiety fused to the first polypeptide and the second polypeptide.

In some embodiments, the fusion proteins disclosed herein comprise one or more additional heterologous moieties. In some embodiments, the heterologous moieties are half-life extending moieties. In some embodiments, the heterologous moiety comprises albumin, an immunoglobulin constant region or a portion thereof, an immunoglobulin-binding polypeptide, an immunoglobulin G (IgG), albumin-binding polypeptide (ABP), a PASylation moiety, a HESylation moiety, XTEN, a PEGylation moiety, an Fc region, and any combination thereof.

1) Immunoglobulin Constant Region or Portion Thereof

An immunoglobulin constant region is comprised of domains denoted CH (constant heavy) domains (CH1, CH2, etc.). Depending on the isotype, (i.e. IgG, IgM, IgA IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An immunoglobulin constant region or a portion thereof for producing the fusion protein of the present disclosure may be obtained from a number of different sources. In preferred embodiments, An immunoglobulin constant region or a portion thereof is derived from a human immunoglobulin. It is understood, however, that the immunoglobulin constant region or a portion thereof may be derived from an immunoglobulin of another mammalian species, including for example, a rodent (e.g. a mouse, rat, rabbit, guinea pig) or non-human primate (e.g. chimpanzee, macaque) species. Moreover, the immunoglobulin constant region or a portion thereof may be derived from any immunoglobulin class, including IgM, IgG, IgD, IgA and IgE, and any immunoglobulin isotype, including IgG1, IgG2, IgG3 and IgG4. In one embodiment, the human isotype IgG1 is used.

A variety of the immunoglobulin constant region gene sequences (e.g. human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g. hinge, CH2, and/or CH3 sequences, or portions thereof) can be derived from these sequences using art recognized techniques. The genetic material obtained using any of the foregoing methods may then be altered or synthesized to obtain polypeptides of the present disclosure. It will further be appreciated that the scope of this disclosure encompasses alleles, variants and mutations of constant region DNA sequences.

The sequences of the immunoglobulin constant region or a portion thereof can be cloned, e.g., using the polymerase chain reaction and primers which are selected to amplify the domain of interest. To clone a sequence of the immunoglobulin constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995.

An immunoglobulin constant region used herein can include all domains and the hinge region or portions thereof. In one embodiment, the immunoglobulin constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native immunoglobulin, i.e., as formed by the dimeric association of the respective Fc domains of its two heavy chains. A native Fc region forms a homodimer with another Fc region.

In one embodiment, the "Fc region" refers to the portion of a single immunoglobulin heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an immunoglobulin constant region, depending on the immunoglobulin isotype can include the CH2, CH3, and CH4 domains, as well as the hinge region. Fusion proteins comprising an Fc region of an immunoglobulin bestow several desirable properties on a fusion protein including increased stability, increased serum half-life (see Capon et al., 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1).

In some embodiments, the "Fc region" includes an amino acid sequence of an Fc domain or derived from an Fc domain. In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

The Fc domains denoted as F, F1, or F2 herein may be obtained from a number of different sources. In one embodiment, an Fc region of the polypeptide is derived from a human immunoglobulin. It is understood, however, that an Fc region may be derived from an immunoglobulin of another mammalian species, including for example, a rodent (e.g. a mouse, rat, rabbit, guinea pig) or non-human primate (e.g. chimpanzee, macaque) species. Moreover, the polypeptide of the Fc domains or portions thereof may be derived from any immunoglobulin class, including IgM, IgG, IgD, IgA and IgE, and any immunoglobulin isotype, including IgG1, IgG2, IgG3 and IgG4. In another embodiment, the human isotype IgG1 is used.

In certain embodiments, the Fc variant confers a change in at least one effector function imparted by an Fc region comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The Fc regions of the disclosure may employ art-recognized Fc variants which are known to impart a change (e.g., an enhancement or reduction) in effector function and/or FcR binding. Specifically, a binding molecule of the disclosure may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO005/040217A2, WO004/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

The Fc region of IgG can be modified according to well recognized procedures such as site directed mutagenesis and the like to yield modified IgG or Fc fragments or portions thereof that will be bound by Fc receptors. Such modifications include modifications remote from the Fc receptor contact sites as well as modifications within the contact sites that preserve or even enhance binding to the Fc receptors. For example, the following single amino acid residues in human IgG1 Fc (Fc γ1) can be substituted without significant loss of Fc binding affinity for Fc receptors: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids may be substituted for the wild type amino acids at the positions specified above. Mutations may be introduced into Fc giving rise to more than one hundred Fc regions distinct from the native Fc. Additionally, combinations of two, three, or more of these individual mutations may be introduced together, giving rise to hundreds more Fc regions. Moreover, one of the Fc region of a construct of the disclosure may be mutated and the other Fc region of the construct not mutated at all, or they both may be mutated but with different mutations.

Certain of the above mutations may confer new functionality upon the Fc region. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for Fc receptors may be increased beyond that of wild type in some instances. This increased affinity may reflect an increased "on" rate, a decreased "off" rate or both an increased "on" rate and a decreased "off" rate. Examples of mutations believed to impart an increased affinity for Fc receptors include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In one embodiment, the immunoglobulin constant region or a portion thereof, e.g., an Fc region, is a polypeptide including the sequence PKNSSMISNTP (SEQ ID NO: 98) and optionally further including a sequence selected from HQSLGTQ (SEQ ID NO: 93), HQNLSDGK (SEQ ID NO: 94), HQNISDGK (SEQ ID NO: 95), or VISSHLGQ (SEQ ID NO: 96) (U.S. Pat. No. 5,739,277).

In certain embodiments, the immunoglobulin constant region or a portion thereof is hemi-glycosylated. For example, the fusion protein comprising two Fc regions or FcRn binding partners may contain a first, glycosylated, Fc region (e.g., a glycosylated CH2 region) and a second, aglycosylated, Fc region (e.g., an aglycosylated CH2 region). In one embodiment, a linker may be interposed between the glycosylated and aglycosylated Fc regions. In another embodiment, the Fc region or FcRn binding partner is fully glycosylated, i.e., all of the Fc regions are glycosylated. In other embodiments, the Fc region may be aglycosylated, i.e., none of the Fc moieties are glycosylated.

In certain embodiments, a fusion protein of the disclosure comprises an amino acid substitution to an immunoglobulin constant region or a portion thereof (e.g., Fc variants), which alters the antigen-independent effector functions of the Ig constant region, in particular the circulating half-life of the protein.

Such proteins exhibit either increased or decreased binding to an Fc receptor when compared to proteins lacking these substitutions and, therefore, have an increased or decreased half-life in serum, respectively. Fc variants with improved affinity for an Fc receptor are anticipated to have longer serum half-lives, and such molecules have useful applications in methods of treating mammals where long half-life of the administered polypeptide is desired, e.g., to treat a chronic disease or disorder (see, e.g., U.S. Pat. Nos. 7,348,004, 7,404,956, and 7,862,820). In contrast, Fc variants with decreased Fc receptor binding affinity are expected to have shorter half-lives, and such molecules are also useful, for example, for administration to a mammal where a shortened circulation time may be advantageous, e.g., for in vivo diagnostic imaging or in situations where the starting polypeptide has toxic side effects when present in the circulation for prolonged periods. Fc variants with decreased Fc receptor binding affinity are also less likely to cross the placenta and, thus, are also useful in the treatment of diseases or disorders in pregnant women. In addition, other applications in which reduced Fc receptor binding affinity may be desired include those applications in which localization the brain, kidney, and/or liver is desired. In one exemplary embodiment, the fusion protein of the disclosure exhibit reduced transport across the epithelium of kidney glomeruli from the vasculature. In another embodiment, the fusion protein of the disclosure exhibit reduced transport across the blood brain barrier (BBB) from the brain, into the vascular space. In one embodiment, a protein with altered Fc receptor binding comprises at least one Fc region (e.g., one or two Fc regions) having one or more amino acid substitutions within the "Fc receptor binding loop" of an Ig constant region. The Fc receptor binding loop is comprised of amino acid residues 280-299 (according to EU numbering) of a wild-type, full-length, Fc region. In other embodiments, an Ig constant region or a portion thereof of the disclosure having altered Fc receptor binding affinity comprises at least one Fc region having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered Fc receptor binding activity are disclosed in International PCT Publication No. WO05/047327.

2) Albumin or Fragment, or Variant Thereof

In certain embodiments, the heterologous moiety linked to the IL2 polypeptide and/or the IL2Rα EC domain is albumin or a functional fragment thereof.

Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof.

In one embodiment, the fusion protein comprises the IL2 polypeptide and the IL2Rα EC domain described herein and albumin, fragment, or variant thereof, wherein the IL2 polypeptide is linked to albumin or a fragment or variant thereof. In another embodiment, the fusion protein comprises the IL2 polypeptide and the IL2Rα EC domain described herein and albumin, fragment, or variant thereof, wherein the IL2Rα EC is linked to albumin or a fragment or variant thereof.

In other embodiments, the heterologous moiety linked to the IL2 polypeptide and the IL2Rα EC domain is albumin or a fragment or variant thereof, which extends (or is capable of extending) the half-life of the IL2 polypeptide and the IL2Rα EC domain. Further examples of albumin or the fragments or variants thereof are disclosed in US Pat. Publ. Nos. 2008/0194481 A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2.

3) Albumin Binding Moiety

In certain embodiments, the heterologous moiety linked to the IL2 polypeptide and the IL2Rα EC domain is an albumin binding moiety, which comprises an albumin binding peptide, a bacterial albumin binding domain, an albumin-binding antibody fragment, or any combinations thereof. For example, the albumin binding protein can be a bacterial albumin binding protein, an antibody or an antibody fragment including domain antibodies (see U.S. Pat. No. 6,696,245). An albumin binding protein, for example, can be a bacterial albumin binding domain, such as the one of streptococcal protein G (Konig, T. and Skerra, A. (1998) *J. Immunol. Methods* 218, 73-83). Other examples of albumin binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, H is, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395 or Dennis et al. (Dennis et al. (2002) *J. Biol. Chem.* 277, 35035-35043).

4) PAS Sequence

In other embodiments, the heterologous moiety linked the IL2 polypeptide and the IL2Rα EC domain is a PAS sequence. In one embodiment, the fusion protein comprises the IL2 polypeptide and the IL2Rα EC domain described herein and a PAS sequence, wherein the IL2 polypeptide and/or the IL2Rα EC domain is linked to the PAS sequence.

A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the fusion protein. Yet, the skilled person is aware that an amino acid polymer also may form random coil conformation when residues other than alanine, serine, and proline are added as a minor constituent in the PAS sequence. The term "minor constituent" as used herein means that amino acids other than alanine, serine, and proline may be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline may be selected from the group consisting of Arg, Asn, Asp, Cys, Gin, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to the IL2 polypeptide. Since the random coil domain does not adopt a stable structure or function by itself, the biological activity mediated by the IL2 polypeptide and the IL2Rα EC domain to which it is fused is essentially preserved. In other embodiments, the PAS sequences that form random coil domain are biologically inert, especially with respect to proteolysis in blood plasma, immunogenicity, isoelectric point/electrostatic behavior, binding to cell surface receptors or internalization, but are still biodegradable, which provides clear advantages over synthetic polymers such as PEG.

Non-limiting examples of the PAS sequences forming random coil conformation comprise an amino acid sequence selected from the group consisting of ASPAAPAPASPAA-PAPSAPA (SEQ ID NO: 85), AAPASPAPAAPSAPAPAAPS (SEQ ID NO: 86), APSSPSPSAPSSPSPASPSS (SEQ ID NO: 87), APSSPSPSAPSSPSPASPS (SEQ ID NO: 88), SSPSAPSPSSPASPSPSSPA (SEQ ID NO: 89), AASPAAPSAPPAAASPAAPSAPPA (SEQ ID NO: 90) and ASAAAPAAASAAASAPSAAA (SEQ ID NO: 91) or any combinations thereof. Additional examples of PAS sequences are known from, e.g., US Pat. Publ. No. 2010/0292130 A1 and PCT Appl. Publ. No. WO 2008/155134 A1.

5) HAP Sequence

In certain embodiments, the heterologous moiety linked to the IL2 polypeptide and the IL2Rα EC domain is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to $(Gly)_n$, $(Gly_4Ser)_n$ or $S(Gly_4Ser)_n$, wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200.

6) Transferrin or Fragment Thereof

In certain embodiments, the heterologous moiety linked to the IL2 polypeptide and the IL2Rα EC domain is transferrin or a fragment thereof. Any transferrin may be used to make the fusion proteins of the disclosure. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov/). Transferrin comprises two domains, N domain and C domain. N domain comprises two subdomains, N1 domain and N2 domain, and C domain comprises two subdomains, C1 domain and C2 domain.

In one embodiment, the transferrin portion of the fusion protein includes a transferrin splice variant. In one example, a transferrin splice variant can be a splice variant of human transferrin, e.g., Genbank Accession AAA61140. In another embodiment, the transferrin portion of the fusion protein includes one or more domains of the transferrin sequence, e.g., N domain, C domain, N1 domain, N2 domain, C1 domain, C2 domain or any combinations thereof.

7) Polymer, e.g., Polyethylene Glycol (PEG)

In other embodiments, the heterologous moiety attached to the IL2 polypeptide and the IL2Rα EC domain is a soluble polymer known in the art, including, but not limited to, polyethylene glycol, ethylene glycol/propylene glycol copolymers, carboxymethylcellulose, dextran, or polyvinyl alcohol. The heterologous moiety such as soluble polymer can be attached to any positions within the IL2 polypeptide or the IL2Rα EC domain or the N- or C-terminus.

Also provided by the disclosure are chemically modified derivatives of the fusion protein of the disclosure which may provide additional advantages such as increased solubility, stability and circulating time of the polypeptide, or decreased immunogenicity (see U.S. Pat. No. 4,179,337). The chemical moieties for modification can be selected from the group consisting of water soluble polymers including, but not limited to, polyethylene glycol, ethylene glycol/propylene glycol copolymers, carboxymethylcellulose, dextran, and polyvinyl alcohol. The fusion protein may be modified at random positions within the molecule or at the N- or C-terminus, or at predetermined positions within the molecule and may include one, two, three or more attached chemical moieties.

The polymer can be of any molecular weight, and can be branched or unbranched. For polyethylene glycol, in one embodiment, the molecular weight is between about 1 kDa and about 100 kDa for ease in handling and manufacturing. Other sizes may be used, depending on the desired profile (e.g., the duration of sustained release desired, the effects, if any on biological activity, the ease in handling, the degree or lack of antigenicity and other known effects of the polyethylene glycol to a protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

In some embodiments, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999).

The number of polyethylene glycol moieties attached to each fusion protein, the IL2 polypeptide, or the IL2Rα EC domain of the disclosure (i.e., the degree of substitution) may also vary. For example, the pegylated proteins of the disclosure may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

In other embodiments, the IL2 polypeptide and the IL2Rα EC domain used in the disclosure is conjugated to one or more polymers. The polymer can be water-soluble and covalently or non-covalently attached to the IL2 polypeptide, the IL2Rα EC domain or other moieties conjugated to the IL2 polypeptide or the IL2Rα EC domain. Non-limiting examples of the polymer can be poly(alkylene oxide), poly (vinyl pyrrolidone), poly(vinyl alcohol), polyoxazoline, or poly(acryloylmorpholine).

8) Hydroxyethyl Starch (HES)

In certain embodiments, the heterologous moiety linked to the IL2 polypeptide and the IL2Rα EC domain is a polymer, e.g., hydroxyethyl starch (HES) or a derivative thereof. In one embodiment, a fusion protein comprises an IL2 polypeptide described herein and HES, wherein the IL2 polypeptide and the IL2Rα EC domain is linked to HES.

Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., *Krankenhauspharmazie*, 8(8), 271-278 (1987); and Weidler et al., *Arzneim.-Forschung/Drug Res.*, 41, 494-498 (1991)).

Amylopectin contains glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. The degree of substitution, denoted as DS, relates to the molar substitution, is known to the skilled people. See Sommermeyer et al., *Krankenhauspharmazie*, 8(8), 271-278 (1987), as cited above, in particular p. 273.

In one embodiment, hydroxyethyl starch has a mean molecular weight (weight mean) of from 1 to 300 kD, from 2 to 200 kD, from 3 to 100 kD, or from 4 to 70 kD. hydroxyethyl starch can further exhibit a molar degree of substitution of from 0.1 to 3, preferably 0.1 to 2, more preferred, 0.1 to 0.9, preferably 0.1 to 0.8, and a ratio between C2:C6 substitution in the range of from 2 to 20 with respect to the hydroxyethyl groups. A non-limiting example of HES having a mean molecular weight of about 130 kD is a HES with a degree of substitution of 0.2 to 0.8 such as 0.2, 0.3, 0.4, 0.5, 0.6, 0.7, or 0.8, preferably of 0.4 to 0.7 such as 0.4, 0.5, 0.6, or 0.7. In a specific embodiment, HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolaemia. The characteristics of VOLUVEN® are a mean molecular weight of 130,000+/−20,000 D, a molar substitution of 0.4 and a C2:C6 ratio of about 9:1. In other embodiments, ranges of the mean molecular weight of hydroxyethyl starch are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD. In still other embodiments, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD) or from 12 to 13 kD or from 11 to 13 kD, or about 18 kD, or in the range of from 17 to 18 kD or from 18 to 19 kD or from 17 to 19 kD, or about 30 kD, or in the range of from 29 to 30, or from 30 to 31 kD, or about 50 kD, or in the range of from 49 to 50 kD or from 50 to 51 kD or from 49 to 51 kD.

In certain embodiments, the heterologous moiety can be mixtures of hydroxyethyl starches having different mean molecular weights and/or different degrees of substitution and/or different ratios of C2:C6 substitution. Therefore, mixtures of hydroxyethyl starches may be employed having different mean molecular weights and different degrees of substitution and different ratios of C2:C6 substitution, or having different mean molecular weights and different degrees of substitution and the same or about the same ratio of C2:C6 substitution, or having different mean molecular weights and the same or about the same degree of substitution and different ratios of C2:C6 substitution, or having the same or about the same mean molecular weight and different degrees of substitution and different ratios of C2:C6 substitution, or having different mean molecular weights and the same or about the same degree of substitution and the same or about the same ratio of C2:C6 substitution, or having the same or about the same mean molecular weights and different degrees of substitution and the same or about the same ratio of C2:C6 substitution, or having the same or about the same mean molecular weight and the same or about the same degree of substitution and different ratios of C2:C6 substitution, or having about the same mean molecular weight and about the same degree of substitution and about the same ratio of C2:C6 substitution.

9) Polysialic Acids (PSA)

In certain embodiments, the non-polypeptide heterologous moiety linked to the IL2 polypeptide and/or the IL2Rα EC domain is a polymer, e.g., polysialic acids (PSAs) or a derivative thereof. Polysialic acids (PSAs) are naturally occurring unbranched polymers of sialic acid produced by certain bacterial strains and in mammals in certain cells Roth J., et al. (1993) in *Polysialic Acid: From Microbes to Man*, eds Roth J., Rutishauser U., Troy F. A. (Birkhauser Verlag, Basel, Switzerland), pp 335-348. They can be produced in various degrees of polymerisation from n=about 80 or more sialic acid residues down to n=2 by limited acid hydrolysis or by digestion with neuraminidases, or by fractionation of the natural, bacterially derived forms of the polymer. The composition of different polysialic acids also varies such that there are homopolymeric forms i.e. the alpha-2,8-linked polysialic acid comprising the capsular polysaccharide of *E. coli* strain K1 and the group-B meningococci, which is also found on the embryonic form of the neuronal cell adhesion molecule (N-CAM). Heteropolymeric forms also exist—such as the alternating alpha-2,8 alpha-2,9 polysialic acid of *E. coli* strain K92 and group C polysaccharides of *N. meningitidis*. Sialic acid may also be found in alternating copolymers with monomers other than sialic acid such as group W135 or group Y of *N. meningitidis*. Polysialic acids have important biological functions including the evasion of the immune and complement systems by pathogenic bacteria and the regulation of glial adhesiveness of immature neurons during foetal development (wherein the polymer has an anti-adhesive function) Cho and Troy, *P.N.A.S., USA*, 91 (1994) 11427-11431, although there are no known receptors for polysialic acids in mammals. The alpha-2,8-linked polysialic acid of *E. coli* strain K1 is also known as 'colominic acid' and is used (in various lengths) to exemplify the present disclosure. Various methods of attaching or conjugating polysialic acids to a polypeptide have been described (for example, see U.S. Pat. No. 5,846,951; WO-A-0187922, and US 2007/0191597 A1).

10) XTEN Sequences

As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a fusion protein partner, XTENs can serve as a carrier, conferring certain desirable pharmacokinetic, physicochemical and pharmaceutical properties when linked to the IL2 polypeptide and/or the IL2Rα EC domain of the disclosure to create a fusion protein. Such desirable properties include but are not limited to enhanced pharmacokinetic parameters and solubility characteristics.

In some embodiments, the XTEN sequence of the disclosure is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain embodiments, XTEN is a peptide or a polypeptide having greater than about 20 to about 3000 amino acid residues, greater than 30 to about 2500 residues, greater than 40 to about 2000 residues, greater than 50 to about 1500 residues, greater than 60 to about 1000 residues, greater than 70 to about 900 residues, greater than 80 to about 800 residues, greater than 90 to about 700 residues, greater than 100 to about 600 residues, greater than 110 to about 500 residues, or greater than 120 to about 400 residues.

The XTEN sequence of the disclosure can comprise one or more sequence motif of 9 to 14 amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids selected from the group consisting of glycine (G), alanine (A), serine (S), threonine (T), glutamate (E) and proline (P). See US 2010-0239554 A1.

In some embodiments, an XTEN sequence comprises multiple units of non-overlapping sequence motifs of the AD motif family, or of the AE motif family, or of the AF motif family, or of the AG motif family, or of the AM motif family, or of the AQ motif family, or of the BC family, or of the BD family, with the resulting XTEN exhibiting the range of homology. In other embodiments, the XTEN comprises multiple units of motif sequences from two or more of the motif families. These sequences can be selected to achieve desired physical/chemical characteristics, including such properties as net charge, hydrophilicity, lack of secondary structure, or lack of repetitiveness that are conferred by the amino acid composition of the motifs, described more fully below. In other embodiments, the motifs incorporated into the XTEN can be selected and assembled using the methods described herein to achieve an XTEN of about 36 to about 3000 amino acid residues.

In further embodiments, the XTEN sequence used in the disclosure affects the physical or chemical property, e.g., pharmacokinetics, of the fusion protein of the present disclosure. The XTEN sequence used in the present disclosure can exhibit one or more of the following advantageous properties: conformational flexibility, enhanced aqueous solubility, high degree of protease resistance, low immunogenicity, low binding to mammalian receptors, or increased hydrodynamic (or Stokes) radii. In a specific embodiment, the XTEN sequence linked to the IL2 polypeptide and/or the IL2Rα EC domain in this disclosure increases pharmacokinetic properties such as longer terminal half-life or increased area under the curve (AUC), so that the fusion protein described herein stays in vivo for an increased period of time compared to wild type the IL2 polypeptide. In further embodiments, the XTEN sequence used in this disclosure increases pharmacokinetic properties such as longer terminal half-life or increased area under the curve (AUC), so that the IL2 polypeptide stays in vivo for an increased period of time compared to wild type IL2.

A variety of methods and assays can be employed to determine the physical/chemical properties of proteins comprising the XTEN sequence. Such methods include, but are not limited to analytical centrifugation, EPR, HPLC-ion exchange, HPLC-size exclusion, HPLC-reverse phase, light scattering, capillary electrophoresis, circular dichroism, differential scanning calorimetry, fluorescence, HPLC-ion exchange, HPLC-size exclusion, IR, NMR, Raman spectroscopy, refractometry, and UV/Visible spectroscopy. Additional methods are disclosed in Amau et al., *Prot Expr and Purif* 48, 1-13 (2006).

Additional examples of XTEN sequences that can be used according to the present disclosure and are disclosed in US Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2.

11) Immunoglobulin Binding Peptide (or Polypeptide)

In certain embodiments, the non-heterologous moiety linked to the IL2 polypeptide and/or the IL2Rα EC domain is an immunoglobulin binding peptide. The immunoglobulin binding peptides can bind to an Fc region and can improve a half-life of the fusion protein described herein.

In some embodiments, the immunoglobulin binding peptide useful for the disclosure is a peptide or a polypeptide having greater than about 5, 6, 7, 8, 9, 10, 11, 12, 13, 14, 15, 16, 17, 18, 19, 20, 30, 40, 50, 60, 70, 80, 90, 100, 150, 200, 250, 300, 350, 400, 450, or 500 amino acid residues.

In some embodiments, the immunoglobulin binding peptide useful for the disclosure comprises a 13-mer IgG-Fc domain binding peptide (IgGBP). DeLano W L, et al. (2000) Science 287:1279-1283. In other embodiments, the immunoglobulin binding peptide useful for the disclosure comprises the peptides disclosed in US Patent Publication No. 20170334954, US Patent Publication No. 20170210777, or PCT Publication No. WO/2017/069158.

7.3.5 Fusion Protein

In some embodiments, the fusion proteins comprise any one of SEQ ID NO:13 to SEQ ID NO:70 and SEQ ID NO:202 to SEQ ID NO:204 as recited in Table 3.

TABLE 3

| SEQ ID NO: | Construct | Sequence |
|---|---|---|
| 204 | IL2(21-153)-(G3S)3-CD25(22-240) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSCLVTTTDFQIQTEMAATMETSIFTTEYQ |
| 13 | IL2(C145S)-CD25(22-240) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSCLVTTTDFQIQTEMAATMETSIFTTEYQ |
| 14 | IL2(C145A)-CD25(22-240) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFAQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSCLVTTTDFQIQTEMAATMETSIFTTEYQ |
| 15 | IL2(C145V)-CD25(22-240) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFVQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSCLVTTTDFQIQTEMAATMETSIFTTEYQ |
| 16 | IL2-CD25(22-212) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |

TABLE 3-continued

| SEQ ID NO: Construct | Sequence |
|---|---|
| 17 IL2-CD25(22-187) | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFCQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGE |
| 18 IL2(C145A)-CD25(C213S, 22-240) | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFAQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGEMETSQFPGEEKPQASPEGR PESETSSLVTTTDFQIQTEMAATMETSIFTTEYQ |
| 19 HSA-(G4S)3-IL2-CD25(22-187) | DAHKSEVAHRFKDLGEENFKALVLIAFAQYLQQAPFEDHVKLVNEVTEFAKTCVA DESAENCDKSLHTLFGDKLCTVATLRETYGEMADCCAKQEPERNECFLQHKDDNP NLPRLVRPEVDVMCTAFHDNEETFLKKYLYEIARRHPYFYAPELLFFAKRYKAAF TECCQAADKAACLLPKLDELRDEGKASSAKQRLKCASLQKFGERAFKAWAVARLS QRFPKAEFAEVSKLVTDLTKVHTECCHGDLLECADDRADLAKYICENQDSISSKL KECCEKPLLEKSHCIAEVENDEMPADLPSLAADFVESKDVCKNYAEAKDVFLGMF LYEYARRHPDYSVVLLLRLAKTYETTLEKCCAAADPHECYAKVFDEFKPLVEEPQ NLIKQNCELFEQLGEYKFQNALLVRYTKKVPQVSTPTLVEVSRNLGKVGSKCCKH PEAKRMPCAEDYLSVVLNQLCVLHEKTPVSDRVTKCCTESLVNRRPCFSALEVDE TYVPKEFNAETFTFHADICTLSEKERQIKKQTALVELVKHKPKATKEQLKAVMDD FAAFVEKCCKADDKETCFAEEGKKLVAASQAALGLGGGGSGGGGSGGGGS APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFAQSIISTLTGGGSGGGSGGGS ELCDDDPPEIPHATFKAMAYKEGTMLNCECKRGFRRIKSGSLYMLCTGNSSHSSW DNQCQCTSSATRNTTKQVTPQPEEQKERKTTEMQSPMQPVDQASLPGHCREPPPW ENEATERIYHFVVGQMVYYQCVQGYRALHRGPAESVCKMTHGKTRWTQPQLICTG E |
| 20 IL2(C145A)-CD25(22-212)-GG-HSA | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFAQSIISTLTGGGSGGGSGGGS ELCDDDPPEIPHATFKAMAYKEGTMLNCECKRGFRRIKSGSLYMLCTGNSSHSSW DNQCQCTSSATRNTTKQVTPQPEEQKERKTTEMQSPMQPVDQASLPGHCREPPPW ENEATERIYHFVVGQMVYYQCVQGYRALHRGPAESVCKMTHGKTRWTQPQLICTG EMETSQFPGEEKPQASPEGRPESETSGGDAHKSEVAHRFKDLGEENFKALVLIAF AQYLQQAPFEDHVKLVNEVTEFAKTCVADESAENCDKSLHTLFGDKLCTVATLRE TYGEMADCCAKQEPERNECFLQHKDDNPNLPRLVRPEVDVMCTAFHDNEETFLKK YLYEIARRHPYFYAPELLFFAKRYKAAFTECCQAADKAACLLPKLDELRDEGKAS SAKQRLKCASLQKFGERAFKAWAVARLSQRFPKAEFAEVSKLVTDLTKVHTECCH GDLLECADDRADLAKYICENQDSISSKLKECCEKPLLEKSHCIAEVENDEMPADL PSLAADFVESKDVCKNYAEAKDVFLGMFLYEYARRHPDYSVVLLLRLAKTYETTL EKCCAAADPHECYAKVFDEFKPLVEEPQNLIKQNCELFEQLGEYKFQNALLVRYT KKVPQVSTPTLVEVSRNLGKVGSKCCKHPEAKRMPCAEDYLSVVLNQLCVLHEKT PVSDRVTKCCTESLVNRRPCFSALEVDETYVPKEFNAETFTFHADICTLSEKERQ IKKQTALVELVKHKPKATKEQLKAVMDDFAAFVEKCCKADDKETCFAEEGKKLVA ASQAALGL |
| 21 IL2(C145A)-CD25(22-192)-GGC | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFAQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGEMETSQGGC |
| 22 IL2(C145A)-CD25(22-213) | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFAQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGEMETSQFPGEEKPQASPEGR PESETSC |
| 23 IL2(C145A)-CD25(22-187, N70C) | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFAQSIISTLTGGGSGGGSGGGSELCDDDPPEIPHATFKAMAY KEGTMLNCECKRGFRRIKSGSLYMLCTGCSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGE |

TABLE 3-continued

| SEQ ID NO: | Construct | Sequence |
|---|---|---|
| 24 | IL2(C145A)-CD25(22-187, N89C) | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFAQSIISTLTGGGSGGGSGGGSELCDDDPPEIPHATFKAMAY KEGTMLNCECKRGFRRIKSGSLYMLCTGNSSHSSWDNQCQCTSSATRCTTKQVTP QPEEQKERKTTEMQSPMQPVDQASLPGHCREPPPWENEATERIYHFVVGQMVYYQ CVQGYRALHRGPAESVCKMTHGKTRWTQPQLICTGE |
| 25 | IL2(C145A)-CD25(22-187)-C | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFAQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGEC |
| 26 | Human Fc1.1(f)-AZ1-IL2(C145S)-CD25(22-187)-G first side of Fc to make as heterodimeric | DKTHTCPPCPAPEAEGAPSVFLFPPKPKDTLMISRTPEVTCVVVDVSHEDPEVKF NWYVDGVEVHNAKTKPREEQYNSTYRVVSVLTVLHQDWLNGKEYKCKVSNKALPS SIEKTISKAKGQPREPQVYVLPPSREEMTKNQVSLTCLVKGFYPSDIAVEWESNG QPENNYKTTPPVLDSDGSFALVSKLTVDKSRWQQGNVFSCSVMHEALHNHYTQKS LSLSPGAAPTSSSTKKTQLQLEHLLLDLQMILNGINNYKNPKLTRMLTFKFYMPK KATELKHLQCLEEELKPLEEVLNLAQSKNFHLRPRDLISNINVIVLELKGSETTF MCEYADETATIVEFLNRWITFSQSIISTLTGGGSGGGSGGGSELCDDDPPEIPHA TFKAMAYKEGTMLNCECKRGFRRIKSGSLYMLCTGNSSHSSWDNQCQCTSSATRN TTKQVTPQPEEQKERKTTEMQSPMQPVDQASLPGHCREPPPWENEATERIYHFVV GQMVYYQCVQGYRALHRGPAESVCKMTHGKTRWTQPQLICTGEG |
| 27 | IL2(C145S)-CD25(22-187)-HuFc1.1(f)-AZ1 first side of Fc to make as heterodimeric pair | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFSQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGEPKSSDKTHTCPPCPAPEAE GAPSVFLFPPKPKDTLMISRTPEVTCVVVDVSHEDPEVKFNWYVDGVEVHNAKTK PREEQYNSTYRVVSVLTVLHQDWLNGKEYKCKVSNKALPSSIEKTISKAKGQPRE PQVYVLPPSREEMTKNQVSLTCLVKGFYPSDIAVEWESNGQPENNYKTTPPVLDS DGSFALVSKLTVDKSRWQQGNVFSCSVMHEALHNHYTQKSLSLSPG |
| 29 | IL2-C145S-CD25(22-187) | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFSQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGE |
| 30 | IL2-T23A-C145S-CD25(22-187) | APASSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFSQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGE |
| 31 | IL2-CD25(22-240)-C213S | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFCQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGEMETSQFPGEEKPQASPEGR PESETSSLVTTTDFQIQTEMAATMETSIFTTEYQ |
| 32 | IL2-T23A-C145S-CD25(22-240)-C213S | APASSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFSQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGEMETSQFPGEEKPQASPEGR PESETSSLVTTTDFQIQTEMAATMETSIFTTEYQ |
| 33 | Native SigPep-IL2-CD25(22-187) | MYRMQLLSCIALSLALVTNSAPTSSSTKKTQLQLEHLLLDLQMILNGINNYKNPK LTRMLTFKFYMPKKATELKHLQCLEEELKPLEEVLNLAQSKNFHLRPRDLISNIN VIVLELKGSETTFMCEYADETATIVEFLNRWITFCQSIISTLTGGGSGGGSGGGS ELCDDDPPEIPHATFKAMAYKEGTMLNCECKRGFRRIKSGSLYMLCTGNSSHSSW DNQCQCTSSATRNTTKQVTPQPEEQKERKTTEMQSPMQPVDQASLPGHCREPPPW ENEATERIYHFVVGQMVYYQCVQGYRALHRGPAESVCKMTHGKTRWTQPQLICTG E |

TABLE 3-continued

| SEQ ID NO: | Construct | Sequence |
|---|---|---|
| 34 | Native SigPep-HuIL2-CD25(22-212)-PP | MYRMQLLSCIALSLALVTNSAPTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSPP |
| 35 | M-IL2(C145S)-CD25(C213S) | MAPTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSSLVTTTDFQIQTEMAATMETSIFTTEYQ |
| 36 | M-IL2(C145S)-CD25(C213S) | MAPTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSSLVTTTDFQIQTEMAATMETSIFTTEYQ |
| 37 | M-IL2-C145A-CD25(22-212) | MAPTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFAQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 38 | M-IL2-C145A-CD25(22-212) | MAPTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFAQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 39 | Del-A21-IL2-CD(22-212) | PTSSSTKKTQLQLEHLLLDLQMILNGINNYKNPKLTRMLTEKEYMPKKATELKHLQCLEEELKPLEEVLNLAQSKNFHLRPRDLISNINVIVLELKGSETTFMCEYADETATIVEFLNRWITFCQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 40 | IL2-T23A-L2-CD25(22-212) | APASSSTKKTQLQLEHLLLDLQMILNGINNYKNPKLTRMLTEKEYMPKKATELKHLQCLEEELKPLEEVLNLAQSKNFHLRPRDLISNINVIVLELKGSETTFMCEYADETATIVEFLNRWITFCQSIISTLTGGSSGGAGGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 41 | IL2-T3A-L3-CD(22-212) | APASSSTKKTQLQLEHLLLDLQMILNGINNYKNPKLTRMLTEKEYMPKKATELKHLQCLEEELKPLEEVLNLAQSKNFHLRPRDLISNINVIVLELKGSETTFMCEYADETATIVEFLNRWITFCQSIISTLTGGGSGGGSGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 43 | IL2-T23A-C145S-CD25(22-187) | APASSSTKKTQLQLEHLLLDLQMILNGINNYKNPKLTRMLTEKEYMPKKATELKHLQCLEEELKPLEEVLNLAQSKNFHLRPRDLISNINVIVLELKGSETTFMCEYADETATIVEFLNRWITFSQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGE |
| 44 | IL2-T23A-C145S-CD25(22-240)-C213S | APASSSTKKTQLQLEHLLLDLQMILNGINNYKNPKLTRMLTEKEYMPKKATELKHLQCLEEELKPLEEVLNLAQSKNFHLRPRDLISNINVIVLELKGSETTFMCEYADETATIVEFLNRWITFSQSIISTLTGGGSGGGSGGGSELCDDDPPEIPHATFKAMAYKEGTMLNCECKRGFRRIKSGSLYMLCTGNSSHSSWDNQCQCTSSATRNTTKQVTP |

TABLE 3-continued

| SEQ ID NO: | Construct | Sequence |
|---|---|---|
| | | QPEEQKERKTTEMQSPMQPVDQASLPGHCREPPPWENEATERIYHFVVGQMVYYQ<br>CVQGYRALHRGPAESVCKMTHGKTRWTQPQLICTGEMETSQFPGEEKPQASPEGR<br>PESETSSLVTTTDFQIQTEMAATMETSIFTTEYQ |
| 45 | IL2-T23A-CD25(22-187) | APASSSTKKTQLQLEHLLLDLQMILNGINNYKNPKLTRMLTEKEYMPKKATELKH<br>LQCLEEELKPLEEVLNLAQSKNFHLRPRDLISNINVIVLELKGSETTFMCEYADE<br>TATIVEFLNRWITFCQSIISTLTGGGSGGGSGGGSELCDDDPPEIPHATFKAMAY<br>KEGTMLNCECKRGFRRIKSGSLYMLCTGNSSHSSWDNQCQCTSSATRNTTKQVTP<br>QPEEQKERKTTEMQSPMQPVDQASLPGHCREPPPWENEATERIYHFVVGQMVYYQ<br>CVQGYRALHRGPAESVCKMTHGKTRWTQPQLICTGE |
| 46 | IL2-T23A-CD25(22-212)-T106A | APASSSTKKTQLQLEHLLLDLQMILNGINNYKNPKLTRMLTEKEYMPKKATELKH<br>LQCLEEELKPLEEVLNLAQSKNFHLRPRDLISNINVIVLELKGSETTFMCEYADE<br>TATIVEFLNRWITFCQSIISTLTGGGSGGGSGGGSELCDDDPPEIPHATFKAMAY<br>KEGTMLNCECKRGFRRIKSGSLYMLCTGNSSHSSWDNQCQCTSSATRNTTKQVTP<br>QPEEQKERKATEMQSPMQPVDQASLPGHCREPPPWENEATERIYHFVVGQMVYYQ<br>CVQGYRALHRGPAESVCKMTHGKTRWTQPQLICTGEMETSQFPGEEKPQASPEGR<br>PESETS |
| 47 | IL2-T23A-CD25(22-212)-T95A | APASSSTKKTQLQLEHLLLDLQMILNGINNYKNPKLTRMLTEKEYMPKKATELKH<br>LQCLEEELKPLEEVLNLAQSKNFHLRPRDLISNINVIVLELKGSETTFMCEYADE<br>TATIVEFLNRWITFCQSIISTLTGGGSGGGSGGGSELCDDDPPEIPHATFKAMAY<br>KEGTMLNCECKRGFRRIKSGSLYMLCTGNSSHSSWDNQCQCTSSATRNTTKQVAP<br>QPEEQKERKTTEMQSPMQPVDQASLPGHCREPPPWENEATERIYHFVVGQMVYYQ<br>CVQGYRALHRGPAESVCKMTHGKTRWTQPQLICTGEMETSQFPGEEKPQASPEGR<br>PESETS |
| 49 | IL2-T23A-CD25(22-212) | APASSSTKKTQLQLEHLLLDLQMILNGINNYKNPKLTRMLTEKEYMPKKATELKH<br>LQCLEEELKPLEEVLNLAQSKNFHLRPRDLISNINVIVLELKGSETTFMCEYADE<br>TATIVEFLNRWITFCQSIISTLTGGGSGGGSGGGSELCDDDPPEIPHATFKAMAY<br>KEGTMLNCECKRGFRRIKSGSLYMLCTGNSSHSSWDNQCQCTSSATRNTTKQVTP<br>QPEEQKERKTTEMQSPMQPVDQASLPGHCREPPPWENEATERIYHFVVGQMVYYQ<br>CVQGYRALHRGPAESVCKMTHGKTRWTQPQLICTGEMETSQFPGEEKPQASPEGR<br>PESETS |
| 50 | IL2-T23A-C145S-CD25(22-212) | APASSSTKKTQLQLEHLLLDLQMILNGINNYKNPKLTRMLTEKEYMPKKATELKH<br>LQCLEEELKPLEEVLNLAQSKNFHLRPRDLISNINVIVLELKGSETTFMCEYADE<br>TATIVEFLNRWITFSQSIISTLTGGGSGGGSGGGSELCDDDPPEIPHATFKAMAY<br>KEGTMLNCECKRGFRRIKSGSLYMLCTGNSSHSSWDNQCQCTSSATRNTTKQVTP<br>QPEEQKERKTTEMQSPMQPVDQASLPGHCREPPPWENEATERIYHFVVGQMVYYQ<br>CVQGYRALHRGPAESVCKMTHGKTRWTQPQLICTGEMETSQFPGEEKPQASPEGR<br>PESETS |
| 51 | IL2-C145S-CD25(22-212) | APTSSSTKKTQLQLEHLLLDLQMILNGINNYKNPKLTRMLTEKEYMPKKATELKH<br>LQCLEEELKPLEEVLNLAQSKNFHLRPRDLISNINVIVLELKGSETTFMCEYADE<br>TATIVEFLNRWITFSQSIISTLTGGGSGGGSGGGSELCDDDPPEIPHATFKAMAY<br>KEGTMLNCECKRGFRRIKSGSLYMLCTGNSSHSSWDNQCQCTSSATRNTTKQVTP<br>QPEEQKERKTTEMQSPMQPVDQASLPGHCREPPPWENEATERIYHFVVGQMVYYQ<br>CVQGYRALHRGPAESVCKMTHGKTRWTQPQLICTGEMETSQFPGEEKPQASPEGR<br>PESETS |
| 52 | IL2-T23A-CD25(22-212, T95A-T105A) | APASSSTKKTQLQLEHLLLDLQMILNGINNYKNPKLTRMLTEKEYMPKKATELKH<br>LQCLEEELKPLEEVLNLAQSKNFHLRPRDLISNINVIVLELKGSETTFMCEYADE<br>TATIVEFLNRWITFCQSIISTLTGGGSGGGSGGGSELCDDDPPEIPHATFKAMAY<br>KEGTMLNCECKRGFRRIKSGSLYMLCTGNSSHSSWDNQCQCTSSATRNTTKQVAP<br>QPEEQKERKATEMQSPMQPVDQASLPGHCREPPPWENEATERIYHFVVGQMVYYQ<br>CVQGYRALHRGPAESVCKMTHGKTRWTQPQLICTGEMETSQFPGEEKPQASPEGR<br>PESETS |
| 53 | IL2-T23A-CD25(22-212)-PG | APASSSTKKTQLQLEHLLLDLQMILNGINNYKNPKLTRMLTEKEYMPKKATELKH<br>LQCLEEELKPLEEVLNLAQSKNFHLRPRDLISNINVIVLELKGSETTFMCEYADE<br>TATIVEFLNRWITFCQSIISTLTGGGSGGGSGGGSELCDDDPPEIPHATFKAMAY<br>KEGTMLNCECKRGFRRIKSGSLYMLCTGNSSHSSWDNQCQCTSSATRNTTKQVTP<br>QPEEQKERKTTEMQSPMQPVDQASLPGHCREPPPWENEATERIYHFVVGQMVYYQ<br>CVQGYRALHRGPAESVCKMTHGKTRWTQPQLICTGEMETSQFPGEEKPQASPEGR<br>PESETSPG |
| 54 | IL2-CD25(22-187) | APTSSSTKKTQLQLEHLLLDLQMILNGINNYKNPKLTRMLTEKEYMPKKATELKH<br>LQCLEEELKPLEEVLNLAQSKNFHLRPRDLISNINVIVLELKGSETTFMCEYADE<br>TATIVEFLNRWITFCQSIISTLTGGGSGGGSGGGSELCDDDPPEIPHATFKAMAY<br>KEGTMLNCECKRGFRRIKSGSLYMLCTGNSSHSSWDNQCQCTSSATRNTTKQVTP<br>QPEEQKERKTTEMQSPMQPVDQASLPGHCREPPPWENEATERIYHFVVGQMVYYQ<br>CVQGYRALHRGPAESVCKMTHGKTRWTQPQLICTGE |
| 55 | IL2-T23A-C145S- | APASSSTKKTQLQLEHLLLDLQMILNGINNYKNPKLTRMLTEKEYMPKKATELKH<br>LQCLEEELKPLEEVLNLAQSKNFHLRPRDLISNINVIVLELKGSETTFMCEYADE |

TABLE 3-continued

| SEQ ID NO: | Construct | Sequence |
|---|---|---|
| | CD25(22-187) | TATIVEFLNRWITFSQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGE |
| 56 | IL2-CD25(22-240, C213S) | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFCQSIISTLTGGGSGGGSGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGEMETSQFPGEEKPQASPEGR PESETSSLVTTTDFQIQTEMAATMETSIFTTEYQ |
| 57 | Del-A21-IL2-CD(22-212) | PTSSSTKKTQLQLEHLLLDLQMILNGINNYKNPKLTRMLTFKFYMPKKATELKHL QCLEEELKPLEEVLNLAQSKNFHLRPRDLISNINVIVLELKGSETTFMCEYADET ATIVEFLNRWITFCQSIISTLTGGGSGGGSGGGSELCDDDPPEIPHATFKAMAYK EGTMLNCECKRGFRRIKSGSLYMLCTGNSSHSSWDNQCQCTSSATRNTTKQVTPQ PEEQKERKTTEMQSPMQPVDQASLPGHCREPPPWENEATERIYHFVVGQMVYYQC VQGYRALHRGPAESVCKMTHGKTRWTQPQLICTGEMETSQFPGEEKPQASPEGRP ESETS |
| 58 | IL2-T23A-L2-CD25(22-212) | APASSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFCQSIISTLTGGSSGGAGGGGSELCDDDPPEIPHATFKAMAY KEGTMLNCECKRGFRRIKSGSLYMLCTGNSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGEMETSQFPGEEKPQASPEGR PESETS |
| 59 | IL2-T23A-L3-CD25(22-212) | APASSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFCQSIISTLTGGGSGGGSGGGSGGGSGGGSELCDDDPPEIPH ATFKAMAYKEGTMLNCECKRGFRRIKSGSLYMLCTGNSSHSSWDNQCQCTSSATR NTTKQVTPQPEEQKERKTTEMQSPMQPVDQASLPGHCREPPPWENEATERIYHFV VGQMVYYQCVQGYRALHRGPAESVCKMTHGKTRWTQPQLICTGEMETSQFPGEEK PQASPEGRPESETS |
| 60 | IL2-T23A-C145S-CD25(22-187)-N70Q-N89Q | APASSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFSQSIISTLTGGGSGGGSGGGSELCDDDPPEIPHATFKAMAY KEGTMLNCECKRGFRRIKSGSLYMLCTGQSSHSSWDNQCQCTSSATRQTTKQVTP QPEEQKERKTTEMQSPMQPVDQASLPGHCREPPPWENEATERIYHFVVGQMVYYQ CVQGYRALHRGPAESVCKMTHGKTRWTQPQLICTGE |
| 61 | IL2-C145S-CD25(22-187)-N70Q-N89Q | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFSQSIISTLTGGGSGGGSGGGSELCDDDPPEIPHATFKAMAY KEGTMLNCECKRGFRRIKSGSLYMLCTGQSSHSSWDNQCQCTSSATRQTTKQVTP QPEEQKERKTTEMQSPMQPVDQASLPGHCREPPPWENEATERIYHFVVGQMVYYQ CVQGYRALHRGPAESVCKMTHGKTRWTQPQLICTGE |
| 62 | IL2-T23A-C145S-CD25(22-187)-N89Q | APASSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFSQSIISTLTGGGSGGGSGGGSELCDDDPPEIPHATFKAMAY KEGTMLNCECKRGFRRIKSGSLYMLCTGNSSHSSWDNQCQCTSSATRQTTKQVTP QPEEQKERKTTEMQSPMQPVDQASLPGHCREPPPWENEATERIYHFVVGQMVYYQ CVQGYRALHRGPAESVCKMTHGKTRWTQPQLICTGE |
| 63 | IL2-T23A-C145S-CD25(22-187)-N70Q | APASSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFSQSIISTLTGGGSGGGSGGGSELCDDDPPEIPHATFKAMAY KEGTMLNCECKRGFRRIKSGSLYMLCTGQSSHSSWDNQCQCTSSATRNTTKQVTP QPEEQKERKTTEMQSPMQPVDQASLPGHCREPPPWENEATERIYHFVVGQMVYYQ CVQGYRALHRGPAESVCKMTHGKTRWTQPQLICTGE |
| 64 | IL2-C145S-CD25(22-187)-N89Q | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFSQSIISTLTGGGSGGGSGGGSELCDDDPPEIPHATFKAMAY KEGTMLNCECKRGFRRIKSGSLYMLCTGNSSHSSWDNQCQCTSSATRQTTKQVTP QPEEQKERKTTEMQSPMQPVDQASLPGHCREPPPWENEATERIYHFVVGQMVYYQ CVQGYRALHRGPAESVCKMTHGKTRWTQPQLICTGE |
| 65 | IL2-C145S-CD25(22-187)-N70Q | APTSSSTKKTQLQLEHLLLDLQMILNGINNYKNPKLTRMLTFKFYMPKKATELKH LQCLEEELKPLEEVLNLAQSKNFHLRPRDLISNINVIVLELKGSETTFMCEYADE TATIVEFLNRWITFSQSIISTLTGGGSGGGSGGGSELCDDDPPEIPHATFKAMAY KEGTMLNCECKRGFRRIKSGSLYMLCTGQSSHSSWDNQCQCTSSATRNTTKQVTP |

TABLE 3-continued

| SEQ ID NO: | Construct | Sequence |
|---|---|---|
| | | QPEEQKERKTTEMQSPMQPVDQASLPGHCREPPPWENEATERIYHFVVGQMVYYQCVQGYRALHRGPAESVCKMTHGKTRWTQPQLICTGE |
| 66 | IL2-T23A-C145S-CD25(22-187) | APASSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGE |
| 67 | Fc1.1-7linker-IL2-CD25(22-212) Generates Fc homodimer | DKTHTCPPCPAPEAEGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPSSIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGGSGGSGGAPTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 68 | IL2-CD25(22-212)-Fc1.1 Generates Fc homodimer | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSDKTHTCPPCPAPEAEGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPSSIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 69 | IL2(V111K)-CD25(22-212) | APTSSSTKKTQLQLEHLLLDLQMILNGINNYKNPKLTRMLTFKFYMPKKATELKHLQCLEEELKPLEEVLNLAQSKNFHLRPRDLISNINKIVLELKGSETTFMCEYADETATIVEFLNRWITFCQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 70 | IL2(D40T)-CD25(22-212) | APTSSSTKKTQLQLEHLLLTLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 202 | IL2-T3A-CD25(22-187)-N89Q-T95A-T106A | APASSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLTGGGSGGGSGGGSELCDDDPPEIPHATFKAMAYKEGTMLNCECKRGFRRIKSGSLYMLCTGNSSHSSWDNQCQCTSSATRQTTKQVAPQPEEQKERKATEMQSPMQPVDQASLPGHCREPPPWENEATERIYHFVVGQMVYYQCVQGYRALHRGPAESVCKMTHGKTRWTQPQLICTGE |
| 203 | Fc-(IL2(V91K)CD25)2 bivalent | DKTHTCPPCPAPELLGGKSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGGSGGSGGAPTSSSTKKTQLQLEHLLLDLQMILNGINNYKNPKLTRMLTFKFYMPKKATELKHLQCLEEELKPLEEVLNLAQSKNFHLRPRDLISNINKIVLELKGSETTFMCEYADETATIVEFLNRWITFCQSIISTLTGGGSGGGSGGGSELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |

IL2 is mature (IL2(21-153)) unless noted otherwise. Linker between IL2 and CD25 is (G3S)3 unless otherwise noted.

In some embodiments, the fusion protein of the present disclosure comprises an amino acid sequence at least about 80%, at least about 85%, at least about 90%, at least about 95%, at least about 96%, at least about 97%, at least about 98%, at least about 99%, or about 100% identical to any one of SEQ ID NO:13 to SEQ ID NO:70 and SEQ ID NO:202 to SEQ ID NO:204.

The IL2-IL2Rα fusion protein of the present disclosure can have one or more the following properties/activities: (1) increasing activity of regulatory T cells (Tregs) and/or increasing immune tolerance in low dose IL2 based therapies; (2) increasing immune response and memory in higher dose therapies; (3) increasing IL2 availability when compared to recombinant IL2; and/or (4) increasing persistent IL2 stimulation of IL2R bearing lymphocytes in vivo.

In one embodiment, the fusion proteins disclosed herein comprises one or more pharmacokinetic properties selected from the group consisting of an increased half-life, increased $C_{max}$, increased AUC, increased $C_{min}$, decreased clearance, improved bioavailability, and any combination thereof, compared to the pharmacokinetic property of the polypeptide consisting of IL2 (SEQ ID NO:2) or SEQ ID NO:204 (wt IL2-CD25 sequence with the 12mer linker without truncation).

In one embodiment, the fusion proteins disclosed herein have an extended half-life compared to IL2 (SEQ ID NO:2) or SEQ ID NO:204 (wt IL2-CD25 sequence with the 12mer linker without truncation). In some embodiments, the extended half-life is at least about 1.5 fold, at least about 2 fold, at least about 3 fold, at least about 4 fold, at least about 5 fold, at least about 6 fold, at least about 7 fold, at least about 8 fold, at least about 9 fold, at least about 10 fold, at least about 11 fold, at least about 12 fold, at least about 13 fold, at least about 14 fold, at least about 15 fold, at least about 16 fold, at least about 17 fold, at least about 18 fold, at least about 19 fold, at least about 20 fold, at least about 21 fold, or at least about 22 fold compared to the half-life of a polypeptide consisting of IL2 (SEQ ID NO:2) or SEQ ID NO: 204 (wt IL2-CD25 sequence with the 12mer linker without any truncation).

In some embodiments, an increased activity of Tregs that results from the IL2/IL2Rα fusion protein can be assayed in a variety of ways including, for example, (1) an increased representation and number of Tregs in the CD4+ T cell compartment; (2) upregulation of IL2-dependent CD25; (3) increased proliferation as assessed by expression of the proliferative marker Ki67; and (4) an increased fraction of IL2-dependent terminally differentiated Klrg1+ Treg subset. Such effects on Tregs can be seen in, for example, in the spleen and/or the inflamed pancreas.

In some embodiments, the IL2/IL2Rα fusion protein of the present disclosure increases tolerogenic and immune suppressive Tregs and immunity through increasing T effector/memory responses and, in further embodiments, it exhibits improved pharmacokinetics by delivering such responses at (1) lower effective levels of IL2 activity compared to native or recombinant IL2; and/or (2) displays more persistent biological responses than native or recombinant IL2.

In specific embodiments, the fusion protein has an improved activity over the native or recombinant IL2. For example, the effect of the IL2/IL-2Rα fusion protein can increase tolerogenic Tregs at about 2 fold, 5 fold, 10 fold, 20 fold, 30 fold, 40 fold, 50 fold, 60 fold, 70 fold, 80 fold, 90 fold, 100 fold 150 fold, 200 fold or lower level IL2 activity in comparison to native or recombinant IL2. In other embodiments, the IL2/IL2Rα fusion protein is more effective than native or recombinant IL2 in inducing persistent augmentation of Tregs and related properties.

Various IL2 and IL2Rα fragments and variants from a variety of organism can be used to generate the IL2/IL2Rα extracellular domain fusion proteins provided herein. Such components are discussed in further detailed elsewhere herein. Examples of non-limiting unprocessed or mature IL2/IL2Rα extracellular domain fusion proteins are set forth in SEQ ID NOs: SEQ ID NO:13 to SEQ ID NO:70 and SEQ ID NO:202 to SEQ ID NO:204.

The term "secretory signal sequence" denotes a polynucleotide sequence that encodes a polypeptide (a "secretory peptide") that, as a component of a larger polypeptide, directs the larger polypeptide through a secretory pathway of the cell in which it is synthesized. The larger polypeptide is commonly cleaved to remove the secretory peptide during the transit through the secretory pathway. As used herein, a "mature" form of a fusion protein or polypeptide comprises the processed form of the polypeptide that has had the secretory peptide removed. As used herein, the "unprocessed" form of the fusion protein retains the secretory peptide sequence.

Biologically active fragments and variants of the mature and unprocessed form of the IL2/IL-Ra EC domain fusion proteins, and the polynucleotide encoding the same, are also provided. Such a functional polypeptide fragment can comprise at least 5, 6, 7, 8, 9, 10, 11, 12, 13, 14, 15, 16, 17, 18, 19, 20, 30, 40, 50, 75, 100, 150, 200, 250, 300, 350, 400, 450, 500 or more continuous amino acids of any one of SEQ ID NOs: SEQ ID NO:13 to SEQ ID NO:70 and SEQ ID NO:202 to SEQ ID NO:204. Alternatively, a functional polypeptide variant can comprise at least 75%, 80%, 85%, 90%, 91%, 92%, 93%, 94%, 95%, 96%, 97%, 98%, or 99% sequence identity to the sequence set forth in SEQ ID NOs: SEQ ID NO:13 to SEQ ID NO:70 and SEQ ID NO:202 to SEQ ID NO:204.

Active variants and fragments of polynucleotides encoding the IL2/IL-Ra extracellular domain fusion proteins are further provided. Such polynucleotide can comprise at least 100, 200, 300, 400, 500, 600, 700, 800, 1000, 1100, 1200, 1300, 1500, 1800,2000 continuous nucleotides encoding the polypeptides set forth in SEQ ID NOs: SEQ ID NO:13 to SEQ ID NO:70 and SEQ ID NO:202 to SEQ ID NO:204 and continue to encode a functional IL2/IL-Ra extracellular domain fusion protein.

It is further recognized that the components of the IL2/IL2Rα fusion protein can be found any order. In one embodiment, the IL2 polypeptide is at the N-terminus and the extracellular domain of IL2Rα is at the C-terminus of the fusion protein.

In some embodiments, the fusion protein forms a dimer. In other embodiments, the fusion protein is a monomer. Still, in some embodiments, the dimer comprises two monomers, and the monomers are associated with each other via covalent bonds. In some embodiments, the dimer comprises two monomers, and the monomers are associated via non-covalent bonds.

In some embodiment of the disclosure, the fusion protein is more stable than the polypeptide consisting of IL2 (SEQ ID NO: 2) or SEQ ID NO: 204 (wt IL2-CD25 sequence with the 12mer linker without truncation). In some embodiments, the fusion protein has one or more properties selected from the group consisting of (i) increased thermodynamic stability compared to a reference protein; (ii) increased TM compared to a reference protein; (iii) increased resistant to degradation compared to a reference protein; (iv) increased resistance to modifications compared to a reference protein; (v) increased stability in vivo compared to a reference protein; and (vi) any combination thereof, wherein the reference protein comprises (i) a first polypeptide comprising an Interleukin-2 (IL2) polypeptide; and (b) a second polypeptide comprising an extracellular domain of an Interleukin-2 Receptor alpha (IL2Rα) polypeptide; and has at least one more glycosylation compared to the fusion protein.

Any of the glycosylation sites of the fusion proteins disclosed herein can be removed by other mechanisms. In some embodiments, the fusion protein is deglycosylated enzymatically or chemically. In some embodiments, the fusion protein is deglycosylated by alkali, hydrazinolysis, Peptide-N-Glycosidase F (PNGase F), Endo-β-N-acetylglucosaminidase H (Endo H), O-glycosidase, or any combination thereof.

In some embodiments, removal of one or more glycosylation sites of the fusion protein is achieved by treatment of the fusion protein with an alkali. In some embodiments, the glycans are removed from the glycosylated polypeptides by alkali borohydride treatment. In other embodiments, glycosylation sites of the fusion proteins disclosed herein can be removed using alkaline metal carbonates such as sodium carbonate and potassium carbonate. In some embodiments, the alkali is used for β-elimination treatment.

In some embodiments, removal of one or more glycosylation sites of the fusion protein is achieved by chemical treatment of the fusion protein by means of hydrazinolysis. In one embodiment, glycosylations are released from a fusion protein disclosed herein by subjecting the fusion protein to hydrazinolysis, and the released sugar chain is subjected to fluorescence labeling with 2-aminopyridine. See Hase et al. *J. Biochem.*, 95, 197 (1984). In some embodiments, hydrazinolysis is carried out using an instrument supplied by Oxford GlycoSystems (the GlycoPrep 1000).

In another embodiment, removal of one or more glycosylation sites of the fusion protein is achieved by subjecting the fusion protein to trifluoromethanesulfonic acid (TFMS).

In some embodiments, removal of one or more glycosylation sites of the fusion protein is achieved by treatment of the fusion protein with an enzyme. In some embodiments, the enzyme is a glycosidase. In some embodiments, removal of one or more glycosylation sites of the fusion protein is achieved using Peptide-N-Glycosidase F (PNGase F). The concentration of PNGase F can vary and is to be determined empirically. In some embodiments, the glycosidase is PNGase F. PNGase F is a commercially available enzyme (e.g., New England Biolabs, Ipswich Mass., Cat. #P0704 or #P0710). In some embodiments, the PNGase F is a fusion protein. For example, the PNGase F can be PNGase F tagged with a chitin binding domain (CBD) or a PNGase F-SNAP fusion protein. In some embodiments, the glycosidase is lyophilized. In some embodiments, the glycosidase is a lyophilized PNGase F. In some embodiments, the glycosidase is substantially free of animal-derived reagents.

In some embodiments, removal of one or more glycosylation sites of the fusion protein is achieved by treatment of the fusion protein with Endo-β-N-acetylglucosaminidase H (Endo H). Endo-H is a glycohydrolase that is secreted by *Streptomyces plicatus* and a few other *Streptomyces* species (Tarentino et al., 1976). It cleaves the β-1, 4-glycosidic bond of the N-acetyl glucosamine core of oligosaccharides and leaves one N-acetylchitobiose attached to the asparagine residue of the glycoprotein (Trimble et al., 1978; Muramatsu 1971). The Endo H gene of *S. plicatus* is 939 bp (GenBank accession AAA26738.1) encodes a 28.9-kDa protein. Endo H from *S. plicatus* was recently expressed in *Pichia pastoris* and deglycosylated activity of *P. pastoris* produced Endo H was demonstrated in vitro, through both co-fermentation and post-fermentation treatments (Wang et al., 2015).

In some embodiments, removal of one or more glycosylation sites of the fusion protein is achieved by treatment of the fusion protein with O-glycosidase (New England Biolabs, Ipswich Mass.). O-glycosides, also called endo-alpha-N-acetylgalactosaminidase, catalyzes the removal of Core 1 and Core 3 O-linked disaccharides from glycoproteins. In some embodiments, it releases unsubstituted Ser- and Thr-linked from glycoproteins.

The removal of one or more glycosylation sites of the fusion protein can be achieved after the IL2/IL2Rα fusion protein is produced in a cell culture (e.g., bioreactor), while the IL2/IL2Rα fusion protein is produced in a cell culture, after the fusion protein is harvested, and/or while the fusion protein is being purified. In some embodiments, the removal of one or more glycosylation sites can be achieved by adding one or more removal agents during the cell culture while the fusion protein is expressed. In other embodiments, the removal of one or more glycosylation sites can be achieved by selecting a particular cell type as a host cell that eliminates glycosylation or has reduced glycosylation (e.g., *E. coli* or *Streptomyces* species). In certain embodiments, the removal of one or more glycosylation sites is achieved by co-expressing a gene encoding the fusion protein with a gene encoding an enzyme that removes one or more glycosylation.

Table 4 below recites various IL-2 amino acid sequences. In some embodiments, the fusion proteins described herein comprises any one of SEQ ID NO:101 to SEQ ID NO:115 as recited in Table 4.

TABLE 4

| SEQ ID NO: | Construct | Sequence |
|---|---|---|
| 101 | IL2 (21-153) | APTSSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMC EYADETATIVEFLNRWITFCQSIISTLT |
| 102 | IL2 (21-153) (C145S) | APTSSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMC EYADETATIVEFLNRWITFSQSIISTLT |
| 103 | IL2 (21-153) (C145A) | APTSSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMC EYADETATIVEFLNRWITFAQSIISTLT |
| 104 | IL2 (21-153) (C145V) | APTSSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMC EYADETATIVEFLNRWITFVQSIISTLT |
| 105 | IL2 (21-153) (T23A) | APASSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMC EYADETATIVEFLNRWITESQSIISTLT |
| 106 | IL2 (21-153) (T23A + C145S) | APASSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMC EYADETATIVEFLNRWITFSQSIISTLT |
| 107 | IL2 (21-153) (T23A + C145A) | APASSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMC EYADETATIVEFLNRWITFAQSIISTLT |
| 108 | Native SigPep-IL2 (1-153) | MYRMQLLSCIALSLALVTNSAPTSSSTKKTQLE HLLLDLQMILNGINNYKNPKLTRMLTFKFYMPKKA TELKHLQCLEEELKPLEEVLNLAQSKNFHLRPRDL ISNINVIVLELKGSETTFMCEYADETATIVEFLNR WITFCQSIISTLT |
| 109 | M-IL2 (C145S) | MAPTSSSTKKTQLQLEHLLLDLQMILNGINNYKNP KLTRMLTFKFYMPKKATELKHLQCLEEELKPLEEV |

TABLE 4-continued

| SEQ ID NO: | Construct | Sequence |
|---|---|---|
| | | LNLAQSKNFHLRPRDLISNINVIVLELKGSETTFMCEYADETATIVEFLNRWITFSQSIISTLT |
| 110 | M-IL2 (C145A) | MAPTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFAQSIISTLT |
| 111 | Del-A21-IL2 | PTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLT |
| 112 | Del-A21-IL2 (C145S) | PTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT |
| 113 | Del-A21-IL2 (C145A) | PTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFAQSIISTLT |
| 114 | IL2 (V111K) | APTSSSTKKTQLQLEHLLLDLQMILNGINNYKNPKLTRMLTFKFYMPKKATELKHLQCLEEELKPLEEVLNLAQSKNFHLRPRDLISNINKIVLELKGSETTFMCEYADETATIVEFLNRWITFCQSIISTLT |
| 115 | IL2 (D40T) | APTSSSTKKTQLQLEHLLLTLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLT |

Table 5 below recites various linker amino acid sequences. In some embodiments, a fusion protein disclosed herein includes multiple concatenated sequences selected from any one of SEQ ID NO:116 to SEQ ID NO:127 as recited in Table 5.

TABLE 5

| SEQ ID NO: | Construct | Sequence |
|---|---|---|
| 116 | L1-(G3S)3 | GGGSGGGSGGGS |
| 117 | L2-G2S2 | GGSSGGAGGGGS |
| 118 | L3-(G3S)5 | GGGSGGGSGGGSGGGSGGGS |
| 119 | L4-(G2S)3 | GGSGGSGGS |
| 120 | L5-(G2S)5 | GGSGGSGGSGGSGGS |
| 121 | L6-GGEEE | GGEEEGGEEEGS |
| 122 | L7-12mer_Stiff | ESPEPETPEDES |
| 123 | L8-22mer_Helix | GRGGEEKKKEKEKEEQEERETK |
| 124 | L9-G | G |
| 125 | L10-GG | GG |
| 126 | L11-S | S |
| 127 | L12-GS | GS |

Table 6 below recites various CD25 amino acid sequences. In some embodiments, the fusion proteins described herein comprises any one of SEQ ID NO:128 to SEQ ID NO:169 as recited in Table 6.

TABLE 6

| SEQ ID NO: | Construct | Sequence |
|---|---|---|
| 128 | CD25(22-240) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSCLVTTTDFQIQTEMAATMETSIFTTEYQ |
| 129 | CD25(22-212) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 130 | CD25(22-187) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGE |
| 131 | CD25(22-240) (C213S) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSSLVTTTDFQIQTEMAATMETSIFTTEYQ |
| 132 | CD25(22-192)-GGC | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQGGC |
| 133 | CD25(22-213) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSC |
| 134 | CD25(22-187) (N70C) | ELCDDDPPEIPHATFKAMAYKEGTMLNCECKRGFRRIKSGSLYMLCTGCSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGE |

TABLE 6-continued

| SEQ ID NO: | Construct | Sequence |
|---|---|---|
| 135 | CD25(22-187) (N89C) | ELCDDDPPEIPHATFKAMAYKEGTMLNCECKRGFRRIKSGSLYMLCTGNSSHSSWDNQCQCTSSATRCTTKQVTPQPEEQKERKTTEMQSPMQPVDQASLPGHCREPPPWENEATERIYHFVVGQMVYYQCVQGYRALHRGPAESVCKMTHGKTRWTQPQLICTGE |
| 136 | CD25(22-187)-C | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEC |
| 137 | CD25(22-187)-G | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEG |
| 138 | CD25(22-212)-PP | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSPP |
| 139 | CD25(22-212) (T106A) | ELCDDDPPEIPHATFKAMAYKEGTMLNCECKRGFRRIKSGSLYMLCTGNSSHSSWDNQCQCTSSATRNTTKQVTPQPEEQKERKATEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 140 | CD25(22-212) (T95A) | ELCDDDPPEIPHATFKAMAYKEGTMLNCECKRGFRRIKSGSLYMLCTGNSSHSSWDNQCQCTSSATRNTTKQVAPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 141 | CD25(22-212) (T95A + T106A) | ELCDDDPPEIPHATFKAMAYKEGTMLNCECKRGFRRIKSGSLYMLCTGNSSHSSWDNQCQCTSSATRNTTKQVAPQPEEQKERKATEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETS |
| 142 | CD25(22-212)-PG | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSPG |
| 143 | CD25(22-187) (N70Q + N89Q) | ELCDDDPPEIPHATFKAMAYKEGTMLNCECKRGFRRIKSGSLYMLCTGQSSHSSWDNQCQCTSSATRQTTKQVTPQPEEQKERKTTEMQSPMQPVDQASLPGHCREPPPWENEATERIYHFVVGQMVYYQCVQGYRALHRGPAESVCKMTHGKTRWTQPQLICTGE |
| 144 | CD25(22-187) (N89Q) | ELCDDDPPEIPHATFKAMAYKEGTMLNCECKRGFRRIKSGSLYMLCTGNSSHSSWDNQCQCTSSATRQTTKQVTPQPEEQKERKTTEMQSPMQPVDQASLPGHCREPPPWENEATERIYHFVVGQMVYYQCVQGYRALHRGPAESVCKMTHGKTRWTQPQLICTGE |
| 145 | CD25(22-187) (N70Q) | ELCDDDPPEIPHATFKAMAYKEGTMLNCECKRGFRRIKSGSLYMLCTGQSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGE |
| 146 | CD25(22-211) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESET |
| 147 | CD25(22-210) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESE |
| 148 | CD25(22-209) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPES |
| 149 | CD25(22-208) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPE |
| 150 | CD25(22-207) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRP |

TABLE 6-continued

| SEQ ID NO: | Construct | Sequence |
|---|---|---|
| 151 | CD25(22-206) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGR |
| 152 | CD25(22-205) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEG |
| 153 | CD25(22-204) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPE |
| 154 | CD25(22-203) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASP |
| 155 | CD25(22-202) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQAS |
| 156 | CD25(22-201) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQA |
| 157 | CD25(22-200) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQ |
| 158 | CD25(22-199) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKP |
| 159 | CD25(22-198) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEK |
| 160 | CD25(22-197) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEE |
| 161 | CD25(22-196) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGE |
| 162 | CD25(22-195) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPG |
| 163 | CD25(22-194) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFP |
| 164 | CD25(22-193) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQF |
| 165 | CD25(22-192) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQ |
| 166 | CD25(22-191) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETS |

TABLE 6-continued

| SEQ ID NO: | Construct | Sequence |
|---|---|---|
| 167 | CD25(22-190) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMET |
| 168 | CD25(22-189) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEME |
| 169 | CD25(22-188) | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEM |

Table 7 below recites various linker amino acid sequences. In some embodiments, the fusion proteins described herein comprises any one of SEQ ID NO:170 to SEQ ID NO:186 as recited in Table 7. In some embodiments, there is no linker sequences (i.e., "TL0" as recited in Table 7).

TABLE 7

| SEQ ID NO: | Construct | Sequence |
|---|---|---|
|  | TL0 | — |
| 170 | TL1 | G |
| 171 | TL2 | GG |
| 172 | TL3 | GS |
| 173 | TL4 | GGS |
| 174 | TL5 | GGGS |
| 175 | TL6 | GGSGG |
| 176 | TL7 | GGGSGG |
| 177 | TL8 | GGSGGSG |
| 178 | TL9 | GGSGGGSG |
| 179 | TL10 | GGGSGGGSG |
| 180 | TL11 | GGGGSGGGGS |
| 181 | TL12 | GGGGSGGGGSG |
| 182 | TL13 | EPKSS |
| 183 | TL14 | PKSS |
| 184 | TL15 | KSS |
| 185 | TL16 | SS |
| 186 | TL17 | S |

Table 8 below recites various enhancer amino acid sequences. In some embodiments, the fusion proteins described herein comprises any one of SEQ ID NO:187 to SEQ ID NO:201 as recited in Table 8.

TABLE 8

| SEQ ID NO: | Construct | Sequence |
|---|---|---|
| 187 | IgG1-Fc | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 188 | IgG1.1-Fc | DKTHTCPPCPAPEAEGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPSSIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 189 | IgG1.3-Fc | DKTHTCPPCPAPEAEGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 190 | IgG1-Fc (P238K) | DKTHTCPPCPAPELLGGKSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 191 | IgG4-Fc | ESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 192 | IgG4.1-Fc | ESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 193 | IgG1.3-Fc-knob | DKTHTCPPCPAPEAEGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPG |

TABLE 8-continued

| SEQ ID NO: | Construct | Sequence |
|---|---|---|
| 194 | IgG1.3-Fc-hole | DKTHTCPPCPAPEAEGAPSVFLFPPKPKDTLMI SRTPEVTCVVVDVSHEDPEVKFNWYVDGVEVHN AKTKPREEQYNSTYRVVSVLTVLHQDWLNGKEY KCKVSNKALPAPIEKTISKAKGQPREPQVYTLP PSREEMTKNQVSLSCAVKGFYPSDIAVEWESNG QPENNYKTTPPVLDSDGSFFLVSKLTVDKSRWQ QGNVFSCSVMHEALHNHYTQKSLSLSPG |
| 195 | IgG1-Fc (P238K)-knob | DKTHTCPPCPAPELLGGKSVFLFPPKPKDTLMI SRTPEVTCVVVDVSHEDPEVKFNWYVDGVEVHN AKTKPREEQYNSTYRVVSVLTVLHQDWLNGKEY KCKVSNKALPAPIEKTISKAKGQPREPQVYTLP PSREEMTKNQVSLWCLVKGFYPSDIAVEWESNG QPENNYKTTPPVLDSDGSFFLYSKLTVDKSRWQ QGNVFSCSVMHEALHNHYTQKSLSLSPG |
| 196 | IgG1-Fc (P238K)-hole | DKTHTCPPCPAPELLGGKSVFLFPPKPKDTLMI SRTPEVTCVVVDVSHEDPEVKFNWYVDGVEVHN AKTKPREEQYNSTYRVVSVLTVLHQDWLNGKEY KCKVSNKALPAPIEKTISKAKGQPREPQVYTLP PSREEMTKNQVSLSCAVKGFYPSDIAVEWESNG QPENNYKTTPPVLDSDGSFFLVSKLTVDKSRWQ QGNVFSCSVMHEALHNHYTQKSLSLSPG |
| 197 | IgG1.1-Fc (AZ1) | DKTHTCPPCPAPEAEGAPSVFLFPPKPKDTLMI SRTPEVTCVVVDVSHEDPEVKFNWYVDGVEVHN AKTKPREEQYNSTYRVVSVLTVLHQDWLNGKEY KCKVSNKALPSSIEKTISKAKGQPREPQVYVYP PSREEMTKNQVSLTCLVKGFYPSDIAVEWESNG QPENNYKTTPPVLDSDGSFALVSKLTVDKSRWQ QGNVFSCSVMHEALHNHYTQKSLSLSPG |
| 198 | IgG1.1-Fc (AZ2) | DKTHTCPPCPAPEAEGAPSVFLFPPKPKDTLMI SRTPEVTCVVVDVSHEDPEVKFNWYVDGVEVHN AKTKPREEQYNSTYRVVSVLTVLHQDWLNGKEY KCKVSNKALPSSIEKTISKAKGQPREPQVYVLP PSREEMTKNQVSLLCLVKGFYPSDIAVEWESNG QPENNYLTWPPVLDSDGSFFLYSKLTVDKSRWQ QGNVFSCSVMHEALHNHYTQKSLSLSPG |
| 199 | HSA | DAHKSEVAHRFKDLGEENFKALVLIAFAQYLQQ CPFEDHVKLVNEVTEFAKTCVADESAENCDKSL HTLFGDKLCTVATLRETYGEMADCCAKQEPERN ECFLQHKDDNPNLPRLVRPEVDVMCTAFHDNEE TFLKKYLYEIARRHPYFYAPELLFFAKRYKAAF TECCQAADKAACLLPKLDELRDEGKASSAKQRL KCASLQKFGERAFKAWAVARLSQRFPKAEFAEV SKLVTDLTKVHTECCHGDLLECADDRADLAKYI CENQDSISSKLKECCEKPLLEKSHCIAEVENDE MPADLPSLAADFVESKDVCKNYAEAKDVFLGMF LYEYARRHPDYSVVLLLRLAKTYETTLEKCCAA ADPHECYAKVFDEFKPLVEEPQNLIKQNCELFE QLGEYKFQNALLVRYTKKVPQVSTPTLVEVSRN LGKVGSKCCKHPEAKRMPCAEDYLSVVLNQLCV LHEKTPVSDRVTKCCTESLVNRRPCFSALEVDE TYVPKEFNAETFTFHADICTLSEKERQIKKQTA LVELVKHKPKATKEQLKAVMDDFAAFVEKCCKA DDKETCFAEEGKKLVAASQAALGL |
| 200 | HSA (C34S) | DAHKSEVAHRFKDLGEENFKALVLIAFAQYLQQ SPFEDHVKLVNEVTEFAKTCVADESAENCDKSL HTLFGDKLCTVATLRETYGEMADCCAKQEPERN ECFLQHKDDNPNLPRLVRPEVDVMCTAFHDNEE TFLKKYLYEIARRHPYFYAPELLFFAKRYKAAF TECCQAADKAACLLPKLDELRDEGKASSAKQRL KCASLQKFGERAFKAWAVARLSQRFPKAEFAEV SKLVTDLTKVHTECCHGDLLECADDRADLAKYI CENQDSISSKLKECCEKPLLEKSHCIAEVENDE MPADLPSLAADFVESKDVCKNYAEAKDVFLGMF LYEYARRHPDYSVVLLLRLAKTYETTLEKCCAA ADPHECYAKVFDEFKPLVEEPQNLIKQNCELFE QLGEYKFQNALLVRYTKKVPQVSTPTLVEVSRN LGKVGSKCCKHPEAKRMPCAEDYLSVVLNQLCV LHEKTPVSDRVTKCCTESLVNRRPCFSALEVDE TYVPKEFNAETFTFHADICTLSEKERQIKKQTA LVELVKHKPKATKEQLKAVMDDFAAFVEKCCKA DDKETCFAEEGKKLVAASQAALGL |
| 201 | HSA (C35A) | DAHKSEVAHREKDLGEENFKALVLIAFAQYLQQ APFEDHVKLVNEVTEFAKTCVADESAENCDKSL HTLFGDKLCTVATLRETYGEMADCCAKQEPERN ECFLQHKDDNPNLPRLVRPEVDVMCTAFHDNEE TFLKKYLYEIARRHPYFYAPELLFFAKRYKAAF TECCQAADKAACLLPKLDELRDEGKASSAKQRL KCASLQKFGERAFKAWAVARLSQRFPKAEFAEV SKLVTDLTKVHTECCHGDLLECADDRADLAKYI CENQDSISSKLKECCEKPLLEKSHCIAEVENDE MPADLPSLAADFVESKDVCKNYAEAKDVFLGMF LYEYARRHPDYSVVLLLRLAKTYETTLEKCCAA ADPHECYAKVFDEFKPLVEEPQNLIKQNCELFE QLGEYKFQNALLVRYTKKVPQVSTPTLVEVSRN LGKVGSKCCKHPEAKRMPCAEDYLSVVLNQLCV LHEKTPVSDRVTKCCTESLVNRRPCFSALEVDE TYVPKEFNAETFTFHADICTLSEKERQIKKQTA LVELVKHKPKATKEQLKAVMDDFAAFVEKCCKA DDKETCFAEEGKKLVAASQAALGL |

In some embodiments, a fusion protein disclosed herein comprises an IL-2 sequence selected from Table 4 (i.e., one of SEQ ID NO:101 to SEQ ID NO:115) and a CD25 sequence from Table 6 (i.e., one of SEQ ID NO:128 to SEQ ID NO:169). In some embodiments, a fusion protein also comprises a sequence, or multiple concatenated sequences, chosen from Table 5 (i.e., one or more of SEQ ID NO:116 to SEQ ID NO:127).

In some embodiments, a fusion protein disclosed herein comprises an IL-2 sequence selected from Table 4 (i.e., one of SEQ ID NO:101 to SEQ ID NO:115) above and a CD25 sequence from Table 6 (i.e., one of SEQ ID NO:128 to SEQ ID NO:169), a sequence, or multiple concatenated sequences, chosen from Table 5 (i.e., one or more of SEQ ID NO:116 to SEQ ID NO:127), and an optional linker comprising a sequence, or multiple concatenated sequences, from Table 7 (i.e., one or more of SEQ ID NO:170 to SEQ ID NO:186).

In some embodiments, a fusion protein disclosed herein comprises an IL-2 sequence selected from Table 4 (i.e., one of SEQ ID NO:101 to SEQ ID NO:115) above and a CD25 sequence from Table 6 (i.e., one of SEQ ID NO:128 to SEQ ID NO:169), a sequence, or multiple concatenated sequences, chosen from Table 5, and an optional linker comprising a sequence, or multiple concatenated sequences, from Table 8 (i.e., one of SEQ ID NO:187 to SEQ ID NO:201).

In some embodiments, a fusion protein disclosed herein comprises, in order, an enhancer sequence from Table 8 (i.e., one of SEQ ID NO:187 to SEQ ID NO:201), a sequence, or multiple concatenated sequences, chosen from Table 7 (i.e., one or more of SEQ ID NO:170 to SEQ ID NO:186), an IL-2 sequence selected from Table 4 (i.e., one of SEQ ID NO:101 to SEQ ID NO:115), and a CD25 sequence from Table 6 (i.e., one of SEQ ID NO:128 to SEQ ID NO:169). In some embodiments, the fusion protein comprises a sequence, or multiple concatenated sequences, chosen from Table 7 (i.e., one or more of SEQ ID NO:170 to SEQ ID NO:186). In some embodiments, the fusion protein comprises a sequence, or multiple concatenated sequences, chosen from Table 5 (i.e., one or more of SEQ ID NO:116 to SEQ ID NO:127).

7.4 Polynucleotides

In certain aspects, provided herein are polynucleotides, e.g., DNA or RNA, comprising a nucleotide sequence encoding a fusion protein described herein that has IL2 activity, as well as vectors comprising such polynucleotide sequences, e.g., expression vectors for their efficient expression in host cells, e.g., mammalian cells. In some embodiments, provided herein are polynucleotide sequences that encode polypeptide sequences of SEQ ID NO: 1 to SEQ ID NO:70 and SEQ ID NO: 202 to SEQ ID NO: 204.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding a fusion protein described herein is isolated or purified.

The polynucleotides can be obtained, and the nucleotide sequence of the polynucleotides determined, by any method known in the art. Nucleotide sequences encoding fusion proteins described herein, e.g., the fusion proteins described in Table 3, and modified versions of these fusion proteins can be determined using methods well known in the art, i.e., nucleotide codons known to encode particular amino acids are assembled in such a way to generate a nucleic acid that encodes the fusion protein. Such a polynucleotide encoding the fusion protein can be assembled from chemically synthesized oligonucleotides (e.g., as described in Kutmeier G et al., (1994), BioTechniques 17: 242-6), which, briefly, involves the synthesis of overlapping oligonucleotides containing portions of the sequence encoding the fusion protein, annealing and ligating of those oligonucleotides, and then amplification of the ligated oligonucleotides by PCR.

Alternatively, a polynucleotide encoding a fusion protein described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the fusion protein of interest. Such PCR amplification methods can be used to obtain nucleic acids comprising the sequence encoding e.g., IL2, a linker sequence, or IL2-Rα. The amplified nucleic acids can be cloned into vectors for expression in host cells and for further cloning, for example, to generate fusion proteins.

If a clone containing a nucleic acid encoding a particular fusion protein is not available, but the sequence of the fusion protein molecule is known, a nucleic acid encoding the fusion protein can be chemically synthesized or obtained from a suitable source (e.g., a cDNA library or a cDNA library generated from, or nucleic acid, preferably poly A+ RNA, isolated from, any tissue or cells expressing the proteins of interest, such as hybridoma cells selected to express a fusion protein described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the fusion proteins. Amplified nucleic acids generated by PCR can then be cloned into replicable cloning vectors using any method well known in the art.

DNA encoding fusion proteins described herein can be readily isolated and sequenced using conventional procedures (e.g., by using oligonucleotide probes that are capable of binding specifically to genes encoding the fusion proteins disclosed herein). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of fusion proteins in the recombinant host cells.

It is further recognized that the polynucleotide encoding the IL2/IL2Rα fusion protein can comprise additional elements that aid in the translation of the fusion protein. Such sequences include, for example, Kozak sequences attached to the 5' end of the polynucleotide encoding the fusion protein. The Kozak consensus sequence is a sequence which occurs on eukaryotic mRNA that plays a role in the initiation of the translation process and has the consensus (gee) gccRccAUGG (SEQ ID NO:92); wherein (1) a lower case letter denotes the most common base at a position where the base can nevertheless vary; (2) upper case letters indicate highly-conserved bases, i.e. the 'AUGG' sequence is constant or rarely, if ever, changes, with the exception being the IUPAC ambiguity code 'R' which indicates that a purine (adenine or guanine) is normally observed at this position; and (3) the sequence in brackets ((gee)) is of uncertain significance.

In one non-limiting embodiment, the IL2/IL2Rα fusion protein comprises an IL2 leader optimized Kozak sequence as set forth in SEQ ID NO: 92 (gccaccATGGACAGGAT-GCAACTCCTGTCTTGCATTGCACTAAGTCTTG-CACTTGTCACAAACAGT) or a functional variant or fragment thereof. A functional variant or fragment of a Kozak sequence will retain the ability to increase translation of the protein when compared to the level of translation from a sequence lacking the leader. Such a functional fragment can comprise at least 5, 6, 7, 8, 9, 10, 11, 12, 13, 14, 15, 16, 17, 18, 19, 20, 30, 40 continuous nucleotides of a Kozak sequence or the sequence set forth in SEQ ID NO:92 or SEQ ID NO:99 (gccaccATGG). Alternatively, a functional variant can comprise at least 80%, 85%, 90%, 91%, 92%, 93%, 94%, 95%, 96%, 97%, 98%, or 99% sequence identity to the Kozak sequence or the sequence set forth in SEQ ID NO:92 or SEQ ID NO:99.

7.5 Cells and Vectors

In certain aspects, provided herein are cells (e.g., host cells) expressing (e.g., recombinantly) fusion proteins described herein and expression vectors comprising nucleotides that encode fusion proteins described herein. Provided herein are vectors (e.g., expression vectors) comprising polynucleotides comprising nucleotide sequences encoding a fusion protein for recombinant expression in host cells.

In some embodiments, the host cell comprises the nucleic acids described herein.

In some embodiments, the host cell is a eukaryotic cell. In some embodiments, the host cell is selected from the group consisting of a mammalian cell, an insect cell, a yeast cell, a transgenic mammalian cell, and a plant cell. In some embodiments, the host cell is a prokaryotic cell. In some embodiments, the prokaryotic cell is a bacterial cell.

In some embodiments, the host cell is a mammalian cell. Such mammalian host cells include but are not limited to CHO, VERO, BHK, HeLa, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the disclosure also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

For the purposes of this disclosure, numerous expression vector systems can be employed. These expression vectors are typically replicable in the host organisms either as episomes or as an integral part of the host chromosomal DNA. Expression vectors can include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors can also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

An example of a vector useful for optimized expression of the fusion proteins used in the methods of the present disclosure is NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. Vector systems are also taught in U.S. Pat. Nos. 5,736,137 and 5,658,570. This system provides for high expression levels, e.g., >30 pg/cell/day. Other exemplary vector systems are disclosed e.g., in U.S. Pat. No. 6,413,777.

In other embodiments the polypeptides of the instant disclosure are expressed using polycistronic constructs. In these expression systems, multiple gene products of interest such as multiple polypeptides of multimer binding protein can be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980.

More generally, once the vector or DNA sequence encoding a polypeptide has been prepared, the expression vector can be introduced into an appropriate host cell. That is, the host cells can be transformed. Introduction of the plasmid into the host cell can be accomplished by various techniques well known to those of skill in the art, as discussed above. The transformed cells are grown under conditions appropriate for the production of the fusion protein, and assayed for fusion protein synthesis. Exemplary assay techniques include enzyme-linked immunosorbent assay (ELISA), radioimmunoassay (RIA), or fluorescence-activated cell sorter analysis (FACS), immunohistochemistry, and the like.

7.6 Pharmaceutical Compositions

The various IL2/IL2Rα fusion proteins disclosed herein (also referred to herein as "active compounds") can be incorporated into pharmaceutical compositions suitable for administration. Such compositions typically comprise the fusion protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In some embodiments, disclosed is a pharmaceutical composition comprising (a) a IL2/IL2Rα fusion protein as described herein and (b) a pharmaceutically acceptable excipient.

In some embodiments, disclosed is a pharmaceutical composition comprising (a) a composition comprising a IL2/IL2Rα fusion protein as described herein and (b) a pharmaceutically acceptable excipient.

In some embodiments, disclosed is a pharmaceutical composition comprising (a) a nucleic acid as described herein and (b) a pharmaceutically acceptable excipient.

In some embodiments, disclosed is a pharmaceutical composition comprising (a) a vector as described herein and (b) a pharmaceutically acceptable excipient.

In some embodiments, disclosed is a pharmaceutical composition comprising (a) a host cell as described herein and (b) a pharmaceutically acceptable excipient.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal. In addition, it may be desirable to administer a therapeutically effective amount of the pharmaceutical composition locally to an area in need of treatment. This can be achieved by, for example, local or regional infusion or perfusion during surgery, topical application, injection, catheter, suppository, or implant (for example, implants formed from porous, non-porous, or gelatinous materials, including membranes, such as sialastic membranes or fibers), and the like. In another embodiment, the therapeutically effective amount of the pharmaceutical composition is delivered in a vesicle, such as liposomes (see, e.g., Langer, Science 249:1527-33, 1990 and Treat et al., in Liposomes in the Therapy of Infectious Disease and Cancer, Lopez Berestein and Fidler (eds.), Liss, N.Y., pp. 353-65, 1989).

In yet another embodiment, the therapeutically effective amount of the pharmaceutical composition can be delivered in a controlled release system. In one example, a pump can be used (see, e.g., Langer, Science 249:1527-33, 1990; Sefton, Crit. Rev. Biomed. Eng. 14:201-40, 1987; Buchwald et al., Surgery 88:507-16, 1980; Saudek et al., N Engl. J Med. 321:574-79, 1989). In another example, polymeric materials can be used (see, e.g., Levy et al., Science 228: 190-92, 1985; During et al., Ann. Neural. 25:351-56, 1989; Howard et al., J Neurosurg. 71:105-12, 1989). Other controlled release systems, such as those discussed by Langer (Science 249:1527-33, 1990), can also be used.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor ELS (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

For administration by inhalation, the compounds are delivered in the form of an aerosol spray from a pressurized container or dispenser that contains a suitable propellant, e.g., a gas such as carbon dioxide, or a nebulizer. Systemic administration can also be by transmucosal or transdermal means.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such a functional compound for the treatment of individuals. The pharmaceutical compositions can be included in a container, pack, or dispenser together with instructions for administration.

The effective amount of an IL2/IL2Rα fusion protein useful for modulating such functions will depend on the subject being treated, the severity of the affliction, and the manner of administration of the IL2/IL2Rα fusion protein. Exemplary doses include about 104 to about 107 IU of IL2 activity per adult, about 104 to 105 IU of IL2 activity per adult, about 105 to about 106 IU of IL2 activity per adult, about 106 to about 107 IU of IL2 activity per adult. In other instances, the therapeutically effective dose of the IL2/IL2Rα fusion protein is about 105 IU of IL2 activity±100-fold, is about 105 IU of IL2 activity±10-fold, about 105 IU of IL2 activity±2-fold, about 105 IU of IL2 activity±20-fold, about 105 IU of IL2 activity±30-fold, about 105 IU of IL2 activity±40-fold, about 105 IU of IL2 activity±50-fold, about 105 IU of IL2 activity±60-fold, about 105 IU of IL2 activity±70-fold, about 105 IU of IL2 activity±80-fold, or about 105 IU of IL2 activity±90-fold. In a specific non-limiting embodiment, a human IL2 fusion protein is administered at this dosage.

7.7 Uses and Methods

7.7.1 Methods of Making Compositions Disclosed Herein

As discussed above, the IL2/IL2Rα fusion proteins disclosed herein can be used to create new IL2/IL2Rα fusion proteins by modifying IL2, IL2Rα, or any heterologous moiety sequence described herein. Thus, in another aspect described herein, the structural features of an IL2/IL2Rα fusion protein described herein are used to create structurally related IL2/IL2Rα fusion proteins that retain at least one functional property of the IL2/IL2Rα fusion protein described herein, such as binding to human IL2Rα and cynomolgus IL2Rα. For example, one or more of IL2, IL2Rα, or any heterologous moiety sequence described herein can be combined recombinantly with known framework regions and/or other proteins to create additional, recombinantly-engineered, fusion protein described herein, as discussed above.

In some embodiments, disclosed herein are methods of producing an IL2/IL2Rα fusion protein comprising culturing a host cell comprising the fusion protein under suitable conditions and recovering the fusion protein. In some embodiments, the host cell is a eukaryotic cell or a prokaryotic cell. In some embodiments, the host cell is a mammalian cell, an insect cell, a fungal cell, a plant cell, a transgenic mammalian cell, or a bacterial cell. In some embodiments, the host cell is selected from the group consisting of a CHO cell, a HEK 293 cell, a NS0 cell, a Per C6 cell, a BHK cell, and a COS cell. In one embodiment, the host cell is a bacterial cell. In a particular embodiment, the bacterial cell is *Escherichia coli*.

Other types of modifications include those described in the previous section. The starting material for the engineering method is one or more of the IL2 or IL2Rα sequences provided herein. To create the engineered fusion protein, it is not necessary to actually prepare (i.e., express as a protein) a fusion protein having one or more of the IL2 or IL2Rα sequences provided herein. Rather, the information contained in the sequence(s) is used as the starting material to create a "second generation" sequence(s) derived from the original sequence(s) and then the "second generation" sequence(s) is prepared and expressed as a protein.

Accordingly, provided herein are methods for preparing a fusion protein comprising: (a) providing IL2 and IL2Rα; (b) altering at least one amino acid residue within IL2 and IL2Rα to create at least one altered fusion protein sequence; and (c) expressing the altered fusion protein sequence as a protein.

Also provided herein are methods for preparing a fusion protein comprising: (a) providing IL2 and IL2Rα; (b) altering at least one glycosylation within IL2 and IL2Rα to create at least one altered glycosylation site; and (c) expressing the altered fusion protein sequence as a protein.

The altered antibody can exhibit one or more, two or more, three or more, four or more, five or more, six or more, seven or more, eight or more, nine or more, or all of the functional properties set forth as (1) through (10) above. The functional properties of the altered antibodies can be assessed using standard assays available in the art.

In some embodiments of the methods of engineering the IL2/IL2Rα fusion proteins described herein, mutations can be introduced randomly or selectively along all or part of an IL2/IL2Rα fusion protein coding sequence and the resulting modified IL2/IL2Rα fusion proteins can be screened for binding activity and/or other functional properties as described herein. Mutational methods have been described in the art. For example, PCT Publication WO 02/092780 by Short describes methods for creating and screening mutations using saturation mutagenesis, synthetic ligation assembly, or a combination thereof. Alternatively, PCT Publication WO 03/074679 by Lazar et al. describes methods of using computational screening methods to optimize physiochemical properties of proteins.

Compositions further include isolated polynucleotides that encode the various fusion proteins described herein above, and variants and fragments thereof. Vectors and expression cassettes comprising the polynucleotides described herein are further disclosed. Expression cassettes will generally include a promoter operably linked to a polynucleotide and a transcriptional and translational termination region.

The use of the term "polynucleotide" is not intended to limit the present disclosure to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues.

In constructs that include more than one processing or cleavage site, it will be understood that such sites can be the same or different.

An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

A protein that is substantially free of cellular material includes preparations of protein having less than about 30%, 20%, 10%, 5%, or 1% (by dry weight) of contaminating protein. When the protein of the disclosure or biologically active portion thereof is recombinantly produced, optimally culture medium represents less than about 30%, 20%, 10%, 5%, or 1% (by dry weight) of chemical precursors or non-protein-of-interest chemicals.

Conventional molecular biology, microbiology, and recombinant DNA techniques within the skill of the art may be employed herein. Such techniques are explained fully in the literature. See, e.g., Sambrook et al., "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gaited. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

A vector which comprises the above-described polynucleotides operably linked to a promoter is also provided herein. A nucleotide sequence is "operably linked" to an expression control sequence (e.g., a promoter) when the expression control sequence controls and regulates the transcription and translation of that sequence. The term "operably linked" when referring to a nucleotide sequence includes having an appropriate start signal (e.g., ATG) in front of the nucleotide sequence to be expressed and maintaining the correct reading frame to permit expression of the sequence under the control of the expression control sequence and production of the desired product encoded by the sequence. If a gene that one desires to insert into a recombinant nucleic acid molecule does not contain an appropriate start signal, such a start signal can be inserted in front of the gene. A "vector" is a replicon, such as plasmid, phage or cosmid, to which another nucleic acid segment may be attached so as to bring about the replication of the attached segment. The promoter may be, or is identical to, a bacterial, yeast, insect or mammalian promoter. Further, the vector may be a plasmid, cosmid, yeast artificial chromosome (YAC), bacteriophage or eukaryotic viral DNA. Other numerous vector backbones known in the art as useful for expressing protein may be employed. Such vectors include, but are not limited to: adenovirus, simian virus 40 (SV40), cytomegalovirus (CMV), mouse mammary tumor virus (MMTV), Moloney murine leukemia virus, DNA delivery systems, i.e. liposomes, and expression plasmid delivery systems. Further, one class of vectors comprises DNA elements derived from viruses such as bovine papilloma virus, polyoma virus, baculovirus, retroviruses or Semliki Forest virus. Such vectors may be obtained commercially or assembled from the sequences described by methods well-known in the art.

A host vector system for the production of a polypeptide which comprises the vector of a suitable host cell is provided herein. Suitable host cells include, but are not limited to, prokaryotic or eukaryotic cells, e.g. bacterial cells (including gram positive cells), yeast cells, fungal cells, insect cells, and animal cells. Numerous mammalian cells may be used as hosts, including, but not limited to, the mouse fibroblast cell NIH 3T3, CHO cells, HeLa cells, Ltk cells, etc. Additional animal cells, such as R1.1, B-W and L-M cells, African Green Monkey kidney cells (e.g., COS 1, COS 7, BSC1, BSC40, and BMT10), insect cells (e.g., Sf9), and human cells and plant cells in tissue culture can also be used.

A wide variety of host/expression vector combinations may be employed in expressing the polynucleotide sequences presented herein. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage A, e.g., NM989, and other phage DNA, e.g., M13 and filamentous single stranded phage DNA; yeast plasmids such as the 2!l plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences (sequences that control the expression of a nucleotide sequence operably linked to it) may be used in these vectors to express the polynucleotide sequences provided herein. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage A, the control regions of fd coat protein, the promoter for 3-phosphoglycerate kinase or other glycolytic enzymes, the promoters of acid phosphatase (e.g., Pho5), the promoters of the yeast a-mating factors, and other sequences known to control the expression of genes of prokaryotic or eukaryotic cells or their viruses, and various combinations thereof.

It will be understood that not all vectors, expression control sequences and hosts will function equally well to express the polynucleotide sequences provided herein. Neither will all hosts function equally well with the same expression system. However, one skilled in the art will be able to select the proper vectors, expression control sequences, and hosts without undue experimentation to accomplish the desired expression without departing from the scope of this disclosure. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular nucleotide sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the nucleotide sequences to be expressed, and the ease of purification of the expression products.

In preparing the expression cassette, the various polynucleotides may be manipulated, so as to provide for the polynucleotide sequences in the proper orientation and, as appropriate, in the proper reading frame. Toward this end, adapters or linkers may be employed to join the polynucleotides or other manipulations may be involved to provide for convenient restriction sites, removal of superfluous DNA, removal of restriction sites, or the like. For example, linkers such as two glycines may be added between polypeptides. Methionine residues encoded by ATG nucleotide sequences may be added to allow initiation of gene transcription. For this purpose, in vitro mutagenesis, primer repair, restriction, annealing, resubstitutions, e.g., transitions and transversions, may be involved.

Further provided is a method of producing a polypeptide which comprises expressing a polynucleotide encoding a fusion protein disclosed herein in a host cell under suitable conditions permitting the production of the polypeptide and recovering the polypeptide so produced.

7.7.2 Therapeutic Uses and Methods

The fusion proteins and methods described herein have numerous in vitro and in vivo utilities involving, for example, enhancement of immune response, such as by inhibiting (or antagonizing) IL2Rα (e.g., signaling), or detection of IL2. For example, the IL2/IL2Rα fusion proteins described herein can be administered to cells in culture, in vitro or ex vivo, or to human subjects, e.g., in vivo, to enhance immunity in a variety of diseases. Accordingly, provided herein are method of treating a disease or disorder a subject in need thereof, comprising administering to the subject an IL2/IL2Rα fusion protein described herein such that the immune response in the subject is modified. In some embodiments, the response is enhanced, stimulated or up-regulated.

Subjects suitable for the present methods include human patients in whom enhancement of an immune response would be desirable. The methods are particularly suitable for treating human patients having a disorder that can be treated by augmenting an immune response (e.g., a T-cell mediated immune response, e.g., an antigen specific T cell response). In some embodiments, the methods are particularly suitable for treatment of cancer in vivo. To achieve antigen-specific enhancement of immunity, IL2/IL2Rα fusion proteins described herein can be administered together with an antigen of interest or the antigen can already be present in the subject to be treated (e.g., a tumor-bearing or virus-bearing subject). When the IL2/IL2Rα fusion proteins described herein are administered together with another agent, the two can be administered separately or simultaneously.

Also encompassed are methods for detecting the presence of human IL2 or human IL2Rα in a sample, or measuring the amount of human IL2 antigen, comprising contacting the sample, and a control sample, with a fusion protein or monoclonal antibody, e.g., a human monoclonal antibody, or an antigen binding portion thereof, which specifically binds to human IL2 or IL2Rα, under conditions that allow for formation of a complex between the IL2/IL2Rα fusion proteins described herein and human IL2Rα. The formation of a complex is then detected, wherein a difference complex formation between the sample compared to the control sample is indicative the presence of human IL2 or IL2Rα in the sample. Moreover, the IL2/IL2Rα fusion proteins described herein can be used to purify human IL2 or IL2Rα via immunoaffinity purification.

Given the ability of IL2/IL2Rα fusion proteins described herein to stimulate or co-stimulate T cell responses, e.g., antigen-specific T cell responses, such as by inhibiting negative effects of IL2 or IL2Rα, provided herein are in vitro and in vivo methods of using the IL2/IL2Rα fusion proteins described herein to stimulate, enhance or upregulate antigen-specific T cell responses, e.g., anti-tumor T cell responses. In some embodiments, CD3 stimulation is also provided (e.g., by coincubation with a cell expressing membrane CD3), which stimulation can be provided at the same time, before, or after stimulation with an IL2/IL2Rα fusion proteins described herein. For example, provided herein are methods of stimulating an antigen-specific T cell response comprising contacting said T cell with an IL2/IL2Rα fusion proteins described herein, and optionally with an anti-CD3 antibody, such that an antigen-specific T cell response is stimulated.

Any suitable indicator of an antigen-specific T cell response can be used to measure the antigen-specific T cell response. Non-limiting examples of such suitable indicators include increased T cell proliferation in the presence of the antibody and/or increase cytokine production in the presence of the antibody. In some embodiments, interleukin-2 and/or interferon-γ production by the antigen-specific T cell is stimulated.

T cells that can be enhanced or co-stimulated with IL2/IL2Rα fusion proteins described herein include CD4$^+$ T cells and CD8$^+$ T cells. The T cells can be Teff cells, e.g., CD4$^+$ Teff cells, CD8$^+$ Teff cells, Thelper (Th) cells (e.g., Th1 cells) or T cytotoxic (Tc) cells.

Further encompassed are methods of stimulating an immune response (e.g., an antigen-specific T cell response) in a subject comprising administering an IL2/IL2Rα fusion protein described herein to the subject such that an immune response (e.g., an antigen-specific T cell response) in the subject is stimulated. In some embodiments, the subject is a tumor-bearing subject and an immune response against the tumor is stimulated. A tumor can be a solid tumor or a liquid tumor, e.g., a hematological malignancy. In some embodiments, a tumor is an immunogenic tumor. In some embodiments, a tumor is non-immunogenic. In some embodiments, a tumor is PD-L1 positive. In some embodiments a tumor is PD-L1 negative. A subject can also be a virus-bearing subject and an immune response against the virus is stimulated.

Further provided are methods for inhibiting growth of tumor cells in a subject comprising administering to the subject an IL2/IL2Rα fusion protein described herein such that growth of the tumor is inhibited in the subject. Also provided are methods of treating a viral infection in a subject comprising administering to the subject an IL2/IL2Rα fusion protein described herein such that the viral infection is treated in the subject.

In some embodiments, an IL2/IL2Rα fusion protein described herein is given to a subject as an adjunctive therapy. Treatments of subjects having cancer with an IL2/IL2Rα fusion protein described herein can lead to prolonged survival, e.g., long-term durable response relative to the current standard of care; long term survival of at least 3 months, 6 months, 9 months, 1, 2, 3, 4, 5, 10 or more years, or recurrence-free survival of at least 3 months, 6 months, 9 months, 1, 2, 3, 4, 5, or 10 or more years. In some embodiments, treatment of a subject having cancer with an IL2/IL2Rα fusion proteins described herein prevents recurrence of cancer or delays recurrence of cancer by, e.g., 3 months, 6 months, 9 months, 1, 2, 3, 4, 5, or 10 or more years. An IL2/IL2Rα fusion protein treatment can be used as a first-, second-, or third-line treatment.

Treatment of a subject having cancer with an IL2/IL2Rα fusion protein described herein can result in, e.g., stable disease, partial response, increased overall survival, increased disease free survival, or enhanced progression free survival.

In some embodiments, an IL2/IL2Rα fusion protein described herein is not significantly toxic. For example, an IL2/IL2Rα fusion protein described herein is not significantly toxic to an organ of a human, e.g., one or more of the liver, kidney, brain, lungs, and heart, as determined, e.g., in clinical trials. In some embodiments, an IL2/IL2Rα fusion protein described herein does not significantly trigger an undesirable immune response, e.g., autoimmunity or inflammation.

In some embodiments, treatment of a subject with an IL2/IL2Rα fusion protein described herein does not result in overstimulation of the immune system to the extent that the subject's immune system then attacks the subject itself (e.g., autoimmune response) or results in, e.g., anaphylaxis. Thus, in some embodiments, the IL2/IL2Rα fusion proteins described herein do not cause anaphylaxis.

In some embodiments, treatment of a subject with an IL2/IL2Rα fusion protein described herein does not cause significant inflammatory reactions, e.g., immune-mediated pneumonitis, immune-mediated colitis, immune mediated hepatitis, immune-mediated nephritis or renal dysfunction, immune-mediated hypophysitis, immune-mediated hypothyroidism and hyperthyroidism, or other immune-mediated adverse reactions. In some embodiments, treatment of a subject with the IL2/IL2Rα fusion proteins described herein does not cause significant cardiac disorders, e.g., ventricular arrhythmia; eye disorders, e.g., iridocyclitis; infusion-related reactions; increased amylase, increased lipase; nervous system disorders, e.g., dizziness, peripheral and sensory neuropathy; skin and subcutaneous tissue disorders, e.g., rash, pruritus, exfoliative dermatitis, erythema multiforme, vitiligo or psoriasis; respiratory, thoracic and mediastinal disorders, e.g., cough; fatigue; nausea; decreased appetite; constipation; arthralgia; or diarrhea.

In some embodiments, the IL2/IL2Rα fusion proteins described herein provide synergistic anti-tumor effects in combination with another cancer therapy, such as a compound that stimulates the immune system (e.g., an immuno-oncology agent), e.g., a compound described herein or a compound modulating a target described herein.

In some embodiments, the IL2/IL2Rα fusion proteins described herein is administered via a topical, epidermal mucosal, intranasal, oral, vaginal, rectal, sublingual, topical, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural or intrasternal route.

Various methods are provided for increasing the immune response in a subject. Such methods comprise administering to a subject in need of an increase in the immune response a therapeutically effective amount of an IL2/IL2Rα fusion protein. As such, in specific embodiments, transient application of higher doses of IL2 are employed to boosted immune effector and memory responses.

Various methods are provided for decreasing the immune response in a subject. Such methods comprise administering to a subject in need of a decrease in the immune response a therapeutically effective amount of an IL2/IL2Rα fusion protein. There is much interest to harness the suppressive power of Tregs to inhibit unwanted immune responses. Data in mouse and man shows that enhancing IL2R signaling with a low dose of IL2 selectively boosts Tregs and enhances immune tolerogenic mechanisms. IL2/IL2Rα fusion proteins provided herein represent a new and improved form of IL2 that more potentially enhances Tregs. Thus, the IL2/IL2Rα fusion proteins can be administered to patients with autoimmune diseases, chronic graft versus host disease, transplant rejection reactions, and other conditions where the goal is to suppress self-reactivity.

These and other methods described herein are discussed in further detail below.

7.7.2.1 Cancer

In some embodiments, disclosed herein are methods of treating cancer. Inhibition of IL2Rα by an IL2/IL2Rα fusion protein can enhance the immune response to cancerous cells in a patient having cancer. Provided herein are methods for treating a subject having cancer, comprising administering to the subject an IL2/IL2Rα fusion protein described herein, such that the subject is treated, e.g., such that growth of cancerous tumors is inhibited or reduced and/or that the tumors regress and/or that prolonged survival is achieved. An IL2/IL2Rα fusion protein can be used alone to inhibit the growth of cancerous tumors. Alternatively, an IL2/IL2Rα fusion protein can be used in conjunction with another agent, e.g., another immunogenic agent, a standard cancer treatment, or another antibody, as described below.

Accordingly, provided herein are methods of treating cancer, e.g., by inhibiting growth of tumor cells, in a subject, comprising administering to the subject a therapeutically effective amount of an IL2/IL2Rα fusion protein disclosed herein. Cancers whose growth can be inhibited using the antibodies of the disclosure include cancers typically responsive to immunotherapy and those that are not typically responsive to immunotherapy. Cancers can be cancers with solid tumors or blood malignancies (liquid tumors). In some embodiments, the cancer is a bladder cancer, breast cancer, uterine cancer, endometrial carcinoma, ovarian cancer, colorectal cancer, colon cancer, head and neck cancer, lung cancer, stomach cancer, germ cell cancer, bone cancer, squamous cell cancer, skin cancer, neoplasm of the central nervous system, lymphoma, leukemia, sarcoma, virus-related cancer, small-cell lung cancer, non-small cell lung cancer, gastrointestinal cancer, Hodgkin's or non-Hodgkin's lymphoma, pancreatic cancer, glioblastoma, glioma, cervical cancer, ovarian cancer, liver cancer, myeloma, salivary gland carcinoma, kidney cancer, basal cell carcinoma, melanoma, prostate cancer, vulval cancer, thyroid cancer, testicular cancer, esophageal cancer, or head or neck cancer, and any combinations thereof.

Other non-limiting examples of cancers for treatment include squamous cell carcinoma, small-cell lung cancer, non-small cell lung cancer, squamous non-small cell lung cancer (NSCLC), nonsquamous NSCLC, glioma, gastrointestinal cancer, renal cancer (e.g., clear cell carcinoma), ovarian cancer, liver cancer, colorectal cancer, endometrial cancer, kidney cancer (e.g., renal cell carcinoma (RCC)), prostate cancer (e.g., hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, T-cell lymphoma, environmentally-induced cancers including those induced by asbestos, virus-related cancers or cancers of viral origin (e.g., human papilloma virus (HPV-related or -originating tumors)), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, B cell lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein can also be used for treatment of metastatic cancers, unresectable, refractory cancers (e.g., cancers refractory to previous immunotherapy, e.g., with a blocking CTLA-4 or PD-1 antibody), and/or recurrent cancers.

In some embodiments, an IL2/IL2Rα fusion protein disclosed herein is administered to patients having a cancer that exhibited an inadequate response to, or progressed on, a prior treatment, e.g., a prior treatment with an immuno-oncology or immunotherapy drug, or patients having a cancer that is refractory or resistant, either intrinsically refractory or resistant (e.g., refractory to a PD-1 pathway antagonist), or a wherein the resistance or refractory state is acquired. For example, subjects who are not responsive or not sufficiently responsive to a first therapy or who see disease progression following treatment, e.g., anti-PD-1 treatment, can be treated by administration of an IL2/IL2Rα fusion protein disclosed herein alone or in combination with another therapy (e.g., with an anti-PD-1 therapy).

In some embodiments, an IL2/IL2Rα fusion protein disclosed herein is administered to patients who have not previously received (i.e., been treated with) an immuno-oncology agent, e.g., a PD-1 pathway antagonist.

A method of treating a subject having cancer with an IL2/IL2Rα fusion protein disclosed herein can comprise administering to a subject who has cancer cells that express IL2 or IL2Rα, a therapeutically effective amount of the IL2/IL2Rα fusion protein disclosed herein. Also provided herein are methods for predicting whether a subject will respond to treatment with an IL2/IL2Rα fusion protein disclosed herein, wherein the methods comprise determining the level of IL2 or IL2Rα in a patient, and if the subject is positive for IL2 or IL2Rα, then the subject is likely to respond to a treatment with an IL2/IL2Rα fusion protein disclosed herein.

In some embodiments, a method of treating cancer in a subject comprises first determining whether the subject is PD-L1 or PD-1 positive, e.g., has tumor cells or TILs that express PD-L1 or PD-1, and if the subject has PD-L1 or PD-1 positive cancer or TIL cells, then administering to the subject an IL2/IL2Rα fusion protein disclosed herein (and optionally a PD-1 or PD-L1 antagonist). A method of treating a subject having cancer with an IL2/IL2Rα fusion protein disclosed herein (and optionally a PD-1 or PD-L1 antagonist) can comprise administering to a subject who has cancer cells or TIL cells that express PD-L1 or PD-1, a therapeutically effective amount of an IL2/IL2Rα fusion protein disclosed herein (and optionally a PD-1 or PD-L1 antagonist). Also provided herein are methods for predicting whether a subject will respond to treatment with an IL2/IL2Rα fusion protein disclosed herein (and optionally a PD-1 or PD-L1 antagonist), wherein the methods comprise determining the level of PD-L1 or PD-1 in cancer or TIL cells of the patient, and if cancer or TIL cells of the subject are PD-L1 or PD-1 positive, then the subject is likely to respond to a treatment with an IL2/IL2Rα fusion protein disclosed herein (and optionally a PD-1 or PD-L1 antagonist).

In some embodiments, an IL2/IL2Rα fusion protein disclosed herein is administered with a standard of care treatment. In some embodiments, an IL2/IL2Rα fusion protein disclosed herein is administered as a maintenance therapy, e.g., a therapy that is intended to prevent the occurrence or recurrence of tumors.

In some embodiments, an IL2/IL2Rα fusion protein disclosed herein is administered with another treatment, e.g., radiation, surgery, or chemotherapy. For example, in some embodiments, adjunctive therapy using an IL2/IL2Rα fusion protein disclosed herein is administered when there is a risk that micrometastases can be present and/or in order to reduce the risk of a relapse.

In some embodiments, an IL2/IL2Rα fusion protein disclosed herein is administered as a monotherapy, or as the only immuno stimulating therapy. Antibodies to IL2Rα can also be combined with an immunogenic agent, such as cancerous cells, purified tumor antigens (including recombinant proteins, peptides, and carbohydrate molecules), cells, and cells transfected with genes encoding immune stimulating cytokines (He et al., (2004) *J. Immunol.* 173: 4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In some embodiments, an IL2/IL2Rα fusion protein disclosed herein is combined with a vaccination protocol. Many experimental strategies for vaccination against tumors have been devised (see Rosenberg, S., 2000, Development of Cancer Vaccines, ASCO Educational Book Spring: 60-62; Logothetis, C, 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. In some embodiments, the IL2/IL2Rα fusion protein disclosed herein is used in conjunction with a collection of recombinant proteins and/or peptides expressed in a tumor in order to generate an immune response to these proteins. These proteins are normally viewed by the immune system as self-antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). Tumor antigen can also be "neoantigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with the fusion protein of the present disclosure is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269: 1585-1588; Tamura et al. (1997) *Science* 278: 117-120).

Dendritic cells (DC) are potent antigen presenting cells that can be used to prime antigen-specific responses. DCs can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with an IL2/IL2Rα fusion protein disclosed herein to activate more potent anti-tumor responses.

In some embodiments, methods of treatment of cancer using an IL2/IL2Rα fusion protein disclosed herein are combined with standard cancer treatments (e.g., surgery, radiation, and chemotherapy). An example of such a combination is an anti-TIM3 antibody in combination with an IL2/IL2Rα fusion protein disclosed herein for the treatment of melanoma. The scientific rationale behind the combined use of an IL2/IL2Rα fusion protein disclosed herein and chemotherapy is that cell death, that is a consequence of the cytotoxic action of most chemotherapeutic compounds, should result in increased levels of tumor antigen in the antigen presentation pathway. Other combination therapies that can result in synergy with an IL2/IL2Rα fusion protein disclosed herein through cell death are radiation, surgery, and hormone deprivation. Each of these protocols creates a source of tumor antigen in the host. Angiogenesis inhibitors can also be combined with an IL2/IL2Rα fusion protein disclosed herein. Inhibition of angiogenesis leads to tumor cell death which can feed tumor antigen into host antigen presentation pathways.

The IL2/IL2Rα fusion protein disclosed herein described herein can also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example anti-Fc receptor/anti-tumor antigen (e.g., Her-2/neu) bispecific antibodies have been used to target macrophages to sites of tumor. This targeting can more effectively activate tumor specific responses. Alternatively, antigen can be delivered directly to DCs by the use of bispecific antibodies which bind to tumor antigen and a dendritic cell specific cell surface marker.

Tumors evade host immune surveillance by a large variety of mechanisms. Many of these mechanisms can be overcome by the inactivation of proteins which are expressed by the tumors and which are immunosuppressive. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with an IL2/IL2Rα fusion protein disclosed herein to counteract the effects of the immunosuppressive agent and favor tumor immune responses by the host.

Other antibodies which activate host immune responsiveness can be used in combination with an IL2/IL2Rα fusion protein disclosed herein. These include molecules on the surface of dendritic cells which activate DC function and antigen presentation. Anti-CD40 antibodies are able to substitute effectively for T cell helper activity (Ridge et al. (1998) *Nature* 393: 474-478) and can be used in conjunction with an IL2/IL2Rα fusion protein disclosed herein. Activating antibodies to T cell costimulatory molecules such as CTLA-4 (e.g., U.S. Pat. No. 5,811,097), OX-40 (Weinberg et al. (2000) *Immunol* 164: 2160-2169), 4-1BB (Melero et al. (1997) *Nature Medicine* 3: 682-685 (1997), and ICOS (Hutloff et al. (1999) *Nature* 397: 262-266) can also provide for increased levels of T cell activation. Inhibitors of PD1 or PD-L1 can also be used in conjunction with an IL2/IL2Rα fusion protein disclosed herein. Other combinations are provided elsewhere herein.

Bone marrow transplantation is currently being used to treat a variety of tumors of hematopoietic origin. While graft versus host disease is a consequence of this treatment, therapeutic benefit can be obtained from graft vs. tumor responses. In some embodiments, an IL2/IL2Rα fusion protein disclosed herein is used to increase the effectiveness of the donor engrafted tumor specific T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. In some embodiments, ex vivo activation in the presence of an IL2/IL2Rα fusion protein disclosed herein can increase the frequency and activity of the adoptively transferred T cells.

7.7.2.2 Inflammatory Disease or Autoimmune Disease

In some embodiments, disclosed herein are methods of treating a disease or disorder a subject in need thereof, wherein the disease or disorder is an inflammatory disease or an autoimmune disease. In some embodiments, the methods comprise administering to the subject a therapeutically effective amount of an IL2/IL2Rα fusion protein disclosed herein.

In some embodiments, an IL2/IL2Rα fusion protein disclosed herein is administered to patients having an inflammatory disease or an autoimmune disease that exhibited an inadequate response to, or progressed on, a prior treatment. In some embodiments, an IL2/IL2Rα fusion protein disclosed herein is administered to patients who have not previously received (i.e., been treated with) treatment for the an inflammatory disease or an autoimmune disease.

In some embodiments, an IL2/IL2Rα fusion protein disclosed herein is administered with a standard of care treatment for an inflammatory disease or an autoimmune disease. In some embodiments, an IL2/IL2Rα fusion protein disclosed herein is administered as a maintenance therapy for an inflammatory disease or an autoimmune disease, e.g., a therapy that is intended to prevent the occurrence or recurrence of inflammation.

In some embodiments, an IL2/IL2Rα fusion protein disclosed herein is administered as a monotherapy for treatment of an inflammatory disease or an autoimmune disease, or as the only immuno stimulating therapy for treatment of an inflammatory disease or an autoimmune disease. In some embodiments, an IL2/IL2Rα fusion protein disclosed herein is combined with a vaccination protocol for treatment of an inflammatory disease or an autoimmune disease. In some embodiments, an IL2/IL2Rα fusion protein disclosed herein is combined with an antibody used for treatment of an inflammatory disease or an autoimmune disease.

In some embodiments, the inflammatory disease or an autoimmune disease is selected from the group consisting of type 1 diabetes, multiple sclerosis, rheumatoid arthritis, celiac disease, systemic lupus erythematous, lupus nephritis, cutaneous lupus, juvenile idiopathic arthritis, Crohn's disease, ulcerative colitis or systemic sclerosis, graft versus host disease, psoriasis, alopecia areata, HCV-induced vasculitis, Sjogren's syndrome, Pemphigus, Ankylosing Spondylitis, Behcet's Disease, Wegener's Granulomatosis, Takayasu's Disease, Autoimmune Hepatitis, Sclerosing Cholangitis, Gougerot-sjögren, and Macrophage Activation Syndrome.

7.7.2.3 Infectious Disease

Methods described herein can also be used to treat patients that have been exposed to particular toxins or pathogens. Accordingly, in some embodiments, disclosed herein are methods of treating a disease or disorder a subject in need thereof, wherein the disease or disorder is an infectious disease. In some embodiments, the methods comprise administering to the subject a therapeutically effective amount of an IL2/IL2Rα fusion protein disclosed herein to treat the infectious disease.

Similar to its application to tumors as discussed above, methods comprising treatment with an IL2/IL2Rα fusion protein disclosed herein are used alone, or as an adjuvant, in combination with vaccines, to stimulate the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas aeruginosa.*

Some examples of pathogenic viruses causing infections treatable by methods described herein include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods described herein include *Chlamydia*, rickettsial bacteria, mycobacteria, staphylococci, streptococci, pneumonococci, meningococci and gonococci, *Klebsiella, Proteus, Serratia, Pseudomonas, Legionella, Diphtheria, Salmonella*, bacilli, cholera, tetanus, botulism, anthrax, plague, leptospirosis, and Lymes disease bacteria.

Some examples of pathogenic fungi causing infections treatable by methods described herein include *Candida (albicans, krusei, glabrata, tropicalis*, etc.), *Cryptococcus neoformans, Aspergillus (fumigatus, niger*, etc.), Genus *Mucorales (mucor, absidia, rhizopus), Sporothrix schenkii, Blastomyces dermatitidis, Paracoccidioides brasiliensis, Coccidioides immitis* and *Histoplasma capsulatum*.

Some examples of pathogenic parasites causing infections treatable by methods described herein include *Entamoeba histolytica, Balantidium coli*, Naegleriafowleri, *Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii*, and *Nippostrongylus brasiliensis*.

In all of the above methods, treatment with an IL2/IL2Rα fusion protein disclosed herein can be combined with other forms of immunotherapy, those described herein, such as cytokine treatment (e.g., interferons, GM-CSF, G-CSF, IL2), or bispecific antibody therapy, which provides for enhanced presentation of tumor antigens (see, e.g, Holliger (1993) *Proc. Natl. Acad. Sci. USA* 90:6444-6448; Poljak (1994) *Structure* 2: 1121-1123).

7.7.2.4 Vaccines

The IL2/IL2Rα fusion proteins disclosed herein can be used to stimulate antigen-specific immune responses by co-administration of an IL2/IL2Rα fusion protein disclosed herein with an antigen of interest (e.g., a vaccine). Accordingly, provided herein are methods of enhancing an immune response to an antigen in a subject, comprising administering to the subject: (i) the antigen; and (ii) an IL2/IL2Rα fusion protein disclosed herein, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

In some embodiments, a peptide or fusion protein comprising the epitope to which an IL2/IL2Rα fusion protein disclosed herein binds is used as a vaccine instead of, or in addition to, an IL2/IL2Rα fusion protein disclosed herein.

Suitable routes of administering the antibody compositions (e.g., human monoclonal antibodies, multispecific and bispecific molecules and immunoconjugates) described herein in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

7.7.2.5 Co-Administration with a Second Agent

As previously described, an IL2/IL2Rα fusion protein disclosed herein can be co-administered with one or other more therapeutic agents, e.g., a cytotoxic agent, a radiotoxic agent or an immunosuppressive agent. The IL2/IL2Rα fusion protein disclosed herein can be linked to the agent (as an immuno-complex) or can be administered separate from the agent. In the latter case (separate administration), the IL2/IL2Rα fusion protein disclosed herein can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Co-administration of an IL2/IL2Rα fusion protein disclosed herein with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Provided herein are methods of combination therapy in which an IL2/IL2Rα fusion protein disclosed herein is co-administered with one or more additional agents (a second therapeutic agent), e.g., small molecule drugs, antibodies or antigen binding portions thereof, that are effective in stimulating immune responses to thereby further enhance, stimulate or upregulate immune responses in a subject.

Generally, an IL2/IL2Rα fusion protein disclosed herein can be combined with (i) an agonist of a stimulatory (e.g., co-stimulatory) molecule (e.g., receptor or ligand) and/or (ii) an antagonist of an inhibitory signal or molecule (e.g., receptor or ligand) on immune cells, such as T cells, both of which result in amplifying immune responses, such as antigen-specific T cell responses. In some aspects, an immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on cells, e.g., those inhibiting T cell activation or those involved in innate immunity, e.g., NK cells, and wherein the immuno-oncology agent enhances innate immunity. Such immuno-oncology agents are often referred to as immune checkpoint regulators, e.g., immune checkpoint inhibitor or immune checkpoint stimulator.

In some embodiments, an IL2/IL2Rα fusion protein disclosed herein is administered with an agent that targets a stimulatory or inhibitory molecule that is a member of the immunoglobulin super family (IgSF). For example, an IL2/IL2Rα fusion protein disclosed herein can be administered to a subject with an agent that targets a member of the IgSF family to increase an immune response. For example, an IL2/IL2Rα fusion protein disclosed herein can be administered with an agent that targets (or binds specifically to) a member of the B7 family of membrane-bound ligands that includes B7-1, B7-2, B7-H1 (PD-L1), B7-DC (PD-L2), B7-H2 (ICOS-L), B7-H3, B7-H4, B7-H5 (VISTA), and B7-H6 or a co-stimulatory or co-inhibitory receptor or ligand binding specifically to a B7 family member.

An IL2/IL2Rα fusion protein disclosed herein can also be administered with an agent that targets a member of the TNF and TNFR family of molecules (ligands or receptors), such as CD40 and CD40L, OX-40, OX-40L, CD70, CD27L, CD30, CD30L, 4-1BBL, CD137, TRAIL/Apo2-L, TRAILR1/DR4, TRAILR2/DR5, TRAILR3, TRAILR4, OPG, RANK, RANKL, TWEAKR/Fn 14, TWEAK, BAFFR, EDAR, XEDAR, TACI, APRIL, BCMA, LTβR, LIGHT, DcR3, HVEM, VEGI/TL1A, TRAMP/DR3, EDA1, EDA2, TNFR1, Lymphotoxin a/TNFp, TNFR2, TNFa, LTpR, Lymphotoxin a 1β2, FAS, FASL, RELT, DR6, TROY, and NGFR (see, e.g., Tansey (2009) *Drug Discovery Today* 00:1).

In some embodiments, an IL2/IL2Rα fusion protein disclosed herein is administered with an agent comprising an anti-PD-1 antibody. The anti-PD-1 antibody can be any antibody that binds PD-1 and inhibits the interaction of PD-1 and PD-L1. In some embodiments, the anti-PD-1 antibody is any anti-PD-1 antibody known in the art. In some embodiments, the second therapeutic agent comprises nivolumab. In some embodiments, the second therapeutic agent comprises pembrolizumab.

In some embodiments, wherein the second therapeutic agent comprises an anti-PD-L1 antibody. The anti-PD-L1 antibody can be any antibody that binds PD-L1 and inhibits the interaction of PD-1 and PD-L1. In some embodiments, the anti-PD-L1 antibody is any anti-PD-L1 antibody known in the art. In some embodiments, the second therapeutic agent comprises atezolizumab. In some embodiments, the second therapeutic agent comprises durvalumab. In some embodiments, the second therapeutic agent comprises avelumab.

In some embodiments, wherein the second therapeutic agent comprises an anti-CTLA-4 antibody. The anti-CTLA-4 antibody can be any antibody that binds CTLA-4 and inhibits its activity. In some embodiments, the anti-CTLA-4 antibody is any anti-CTLA-4 antibody known in the art. In some embodiments, the second therapeutic agent comprises tremelimumab. In some embodiments, the second therapeutic agent comprises ipilimumab.

In some embodiments, wherein the second therapeutic agent comprises an anti-LAG3 antibody. The anti-LAG3 antibody can be any antibody that binds LAG-3 and inhibits its activity. In some embodiments, the anti-LAG3 antibody is any anti-LAG3 antibody known in the art. In some embodiments, the second therapeutic agent comprises 25F7.

In some embodiments, wherein the second therapeutic agent comprises an anti-CD137 antibody. The anti-CD137 antibody can be any antibody that binds CD137 and inhibits its activity. In some embodiments, the anti-CD137 antibody is any anti-CD137 antibody known in the art. In some embodiments, the second therapeutic agent comprises urelumab.

In some embodiments, wherein the second therapeutic agent comprises an anti-KIR antibody. The anti-KIR antibody can be any antibody that binds KIR and inhibits its activity. In some embodiments, the anti-KIR antibody is any anti-KIR antibody known in the art. In some embodiments, the second therapeutic agent comprises lirilumab.

In some embodiments, wherein the second therapeutic agent comprises an anti-GITR antibody. The anti-GITR antibody can be any antibody that binds GITR and inhibits its activity. In some embodiments, the anti-GITR antibody is any anti-GITR antibody known in the art. In some embodiments, the second therapeutic agent comprises MK4166. In some embodiments, the second therapeutic agent comprises TRX518.

In other embodiments, the second therapy comprises administering an anti-TIM3 antibody. The anti-TIM3 antibody can be any antibody that binds TIM3 and inhibits its activity. In some embodiments, the anti-TIM3 antibody is any anti-TIM3 antibody known in the art.

In certain embodiments, the second therapy comprises administering a chemotherapeutic agent. In some embodiments, the chemotherapeutic agent is selected from a proteasome inhibitor, an immunomodulatory drug (IMiD), a Bet inhibitor, and any combination thereof. In some embodiments, the proteasome inhibitor is selected from bortezomib, ixazomib, carfilzomib, oprozomib and marizomib. In certain embodiments, the proteasome inhibitor comprises bortezomib.

In some embodiments, the second therapy comprises a radiotherapy. Any radiotherapy known in the art can be used as the second therapy.

In some embodiments, the second therapy comprises administering an agent that activates innate immune cells. In some embodiments, the agent that activates innate immune cells comprises an NLRP3 agonist. In some embodiments, the NLRP3 agonist comprises monosodium urate monohydrate (MSU) and/or the vaccine adjuvant alum. In some embodiments, the agent that activates innate immune cells is a toll like receptor 7 (TLR7) agonist. In some embodiments, the TLR7 agonist comprises imiquimod (R837), GS-9620 (see Tsai et al., J. Virology doi:10.1128/JVI.02166-16 (Feb. 8, 2017)), ORN R-2336 (Miltenyl Biotec), or any combination thereof.

In some embodiments, the second therapy comprises administering an agent that enhances the survival of natural killer (NK) cells, CD8$^+$ T cells, or both.

In certain embodiments, the second therapy comprises administering an agent selected from the group consisting of doxorubicin (ADRIAMYCIN®), cisplatin, carboplatin, bleomycin sulfate, carmustine, chlorambucil (LEUK- ERAN®), cyclophosphamide (CYTOXAN®; NEOSAR®), lenalidomide (REVLIMID®), bortezomib (VELCADE®), dexamethasone, mitoxantrone, etoposide, cytarabine, bendamustine (TREANDA®), rituximab (RITUXAN®), ifosfamide, vincristine (ONCOVIN®), fludarabine (FLUDARA®), thalidomide (THALOMID®), alemtuzumab (CAMPATH®), ofatumumab (ARZERRA®), everolimus (AFINITOR®, ZORTRESS®), carfilzomib (KYPROLIS™), and any combination thereof.

Exemplary agents that modulate one of the above proteins and can be combined with the fusion protein described herein, for treating cancer, include: YERVOY® (ipilimumab) or Tremelimumab (to CTLA-4), galiximab (to B7.1), BMS-936558 (to PD-1), MK-3475 (to PD-1), atezolizumab (TECENTRIQ®), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3); anti-GITR antibodies MK4166, TRX518, Medi1873, INBRX-110, LK2-145, GWN-323, GITRL-Fc, or any combination thereof.

Other molecules that can be combined with the fusion protein for the treatment of a disease or disorder include antagonists of inhibitory receptors on NK cells or agonists of activating receptors on NK cells. For example, the fusion proteins described herein can be combined with antagonists of KIR (e.g., lirilumab).

T cell activation is also regulated by soluble cytokines, and the fusion proteins described herein can be administered to a subject, e.g., having cancer, with antagonists of cytokines that inhibit T cell activation or agonists of cytokines that stimulate T cell activation.

In some embodiments, the fusion proteins described herein can be used in combination with (i) antagonists (or inhibitors or blocking agents) of proteins of the IgSF family or B7 family or the TNF family that inhibit T cell activation or antagonists of cytokines that inhibit T cell activation (e.g., IL-6, IL-10, TGF-β, VEGF; "immunosuppressive cytokines") and/or (ii) agonists of stimulatory receptors of the IgSF family, B7 family or the TNF family or of cytokines that stimulate T cell activation, for stimulating an immune response, e.g., for treating proliferative diseases, such as cancer.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, W013/87699, W013/119716, WO13/132044) or FPA-008 (WO11/140249; W013169264; WO14/036357).

The fusion protein of the present disclosure can also be administered with agents that inhibit TGF-β signaling.

Additional agents that can be combined with a fusion protein described herein include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Another therapy that can be combined with the fusion protein described herein is a therapy that inhibits a metabolic enzyme such as indoleamine dioxigenase (IDO), dioxigenase, arginase, or nitric oxide synthetase.

Another class of agents that can be used with the fusion protein described herein includes agents that inhibit the formation of adenosine, e.g., CD73 inhibitors, or inhibit the adenosine A2A receptor.

Other therapies that can be combined with the fusion protein described herein for treating a disease or disorder, e.g., cancer, include therapies that reverse/prevent T cell anergy or exhaustion and therapies that trigger an innate immune activation and/or inflammation at a tumor site.

Other therapies that can be combined with the fusion protein described herein for treating a disease or disorder, e.g., cancer, include therapies that block IL-8, e.g., with HuMax-IL8.

A fusion protein described herein can be combined with more than one immuno-oncology agent, and can be, e.g., combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells; a therapy that stimulates positive immune regulation, e.g., with agonists that stimulate the CD-137, OX-40, and/or CD40 or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immuno repressive cytokines.

Fusion proteins described herein can be used together with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In some embodiments, the fusion protein of the present disclosure is administered to a subject together with a BRAF inhibitor if the subject is BRAF V600 mutation positive.

For example, the fusion protein of the present disclosure and combination therapies described herein can be used in combination (e.g., simultaneously or separately) with an additional treatment, such as irradiation and/or chemotherapy, e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxorubicin, or camptothecin+apo21/TRAIL (a 6× combo)), one or more proteasome inhibitors (e.g., bortezomib or MG132), one or more Bcl-2 inhibitors (e.g., BH3I-2' (bcl-xl inhibitor), indoleamine dioxygenase-1 inhibitor (e.g., INCB24360, indoximod, NLG-919, or F001287), AT-101 (R-(-)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., *Nat Med* 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., Avastin), synthetic triterpenoids (see Hyer et al, *Cancer Research* 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), Trastuzumab, Cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK3β inhibitors, IAP inhibitors and/or genotoxic drugs.

The fusion protein of the present disclosure and combination therapies described herein can further be used in combination with one or more anti-proliferative cytotoxic agents. Classes of compounds that can be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN®) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Suitable anti-proliferative agents for combining with the fusion protein of the present disclosure, without limitation, taxanes, paclitaxel (paclitaxel is commercially available as TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone BIO, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment with the fusion protein of the present disclosure described herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX®, can also be administered to the patient. When employing the methods or compositions described herein, other agents used in the modulation of tumor growth or metastasis in a clinical setting, such as antimimetics, can also be administered as desired.

In some embodiments, the combination of the fusion protein of the present disclosure and a second agent discussed herein can be administered concurrently as a single composition in a pharmaceutically acceptable carrier, or concurrently as separate compositions with the fusion protein of the present disclosure and the second agent in a pharmaceutically acceptable carrier. In some embodiments, the combination of the fusion protein of the present disclosure and the second agent can be administered sequentially. The administration of the two agents can start at times that are, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks apart, or administration of the second agent can start, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks after the first agent has been administered.

In some embodiments, an anti-neoplastic antibody that can be combined with a fusion protein of the present disclosure and/or a second agent includes RITUXAN® (rituximab), HERCEPTIN® (trastuzumab), BEXXAR® (tositumomab), ZEVALIN® (ibritumomab), CAMPATH® (alemtuzumab), LYMPHOCIDE® (eprtuzumab), AVASTIN® (bevacizumab), and TARCEVA® (erlotinib), or any combination thereof. In some embodiments, the second antibody useful for the combination therapy with a fusion protein of the present disclosure can be an antibody drug conjugate.

In some embodiments, a fusion protein of the present disclosure alone or in combination with another agent is used concurrently or sequentially with bone marrow transplantation to treat a variety of tumors of hematopoietic origin.

Provided herein are methods for altering an adverse event associated with treatment of a hyperproliferative disease (e.g., cancer) with an immuno stimulatory agent, comprising administering a fusion protein of the present disclosure with or without a second agent, to a subject. For example, the methods described herein provide for a method of reducing the incidence of immuno stimulatory therapeutic antibody-induced colitis or diarrhea by administering a non-absorbable steroid to the patient. As used herein, a "non-absorbable steroid" is a glucocorticoid that exhibits extensive first pass metabolism such that, following metabolism in the liver, the bioavailability of the steroid is low, i.e., less than about 20%. In some embodiments described herein, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. In some embodiments, a fusion protein of the present disclosure in conjunction with a non-absorbable steroid can be further combined with a salicylate. Salicylates include 5-ASA agents such as, for example: sulfasalazine (AZULFIDINE®, Pharmacia & Up John); olsalazine (DJ-PENTUM®, Pharmacia & Up John); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

7.8 Kits

As used herein, a kit comprises an IL2/IL2Rα fusion protein for use in modulating the immune response, as described elsewhere herein. The terms "kit" and "system," as used herein are intended to refer to at least one or more IL2/IL2Rα fusion protein which, in specific embodiments, are in combination with one or more other types of elements or components (e.g., other types of biochemical reagents, containers, packages, such as packaging intended for commercial sale, instructions of use, and the like).

In some embodiments, disclosed is a kit comprising (a) one or more of an IL2/IL2Rα fusion protein as described herein, a composition comprising an IL2/IL2Rα fusion protein as described herein, a nucleic acid encoding for an IL2/IL2Rα fusion protein as described herein, a vector, and/or a host cell; and (b) and instructions for administering the fusion protein to a subject in need thereof. In some embodiments, disclosed is a kit comprising (a) an IL2/IL2Rα fusion protein as described herein and (b) and instructions for administering the fusion protein to a subject in need thereof. In some embodiments, disclosed is a kit comprising (a) a composition comprising an IL2/IL2Rα fusion protein as described herein and (b) and instructions for administering the composition to a subject in need thereof. In some embodiments, disclosed is a kit comprising (a) a nucleic acid encoding for an IL2/IL2Rα fusion protein as described herein and (b) and instructions for administering the nucleic to a subject in need thereof. In some embodiments, disclosed is a kit comprising (a) a vector as described herein and (b) and instructions for administering the vector to a subject in need thereof. In some embodiments, disclosed is a kit comprising (a) a host cell as described herein and (b) and instructions for administering the host cell to a subject in need thereof.

In a specific embodiment, provided herein is a pharmaceutical pack or kit comprising one or more containers filled with one or more of the ingredients of the pharmaceutical compositions described herein, such as one or more fusion proteins provided herein. In some embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits that can be used in the above methods. In one embodiment, a kit comprises a fusion protein described herein, preferably a purified fusion protein, in one or more containers. In a specific embodiment, kits described herein contain a substantially isolated fusion protein as a control. In another specific embodiment, the kits described herein further comprise a control antibody or fusion protein which does not react with an IL2 and/or IL2-Rα antigen. In another specific embodiment, kits described herein contain one or more elements for detecting the binding of the fusion protein to an IL2 and/or IL2-Rα antigen (e.g., the fusion protein can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized fusion protein. The antigen to a fusion protein disclosed herein as provided in the kit can also be attached to a solid support. In a more specific embodiment, the detecting means of the above described kit includes a solid support to which an antigen of the fusion protein is attached. Such a kit can also include a non-attached reporter-labeled anti-human antibody or anti-mouse/rat antibody. In this embodiment, binding of the fusion protein to an antigen can be detected by binding of the said reporter-labeled antibody.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986)); Crooks, Antisense drug Technology: Principles, strategies and applications, $2^{nd}$ Ed. CRC Press (2007) and in Ausubel et al. (1989) Current Protocols in Molecular Biology (John Wiley and Sons, Baltimore, Md.).

All of the references cited above, as well as all references cited herein and the amino acid or nucleotide sequences (e.g., GenBank numbers and/or Uniprot numbers), are incorporated herein by reference in their entireties.

The following examples are offered by way of illustration and not by way of limitation.

8. EXAMPLES

Example 1. IL2-CD25 Fusion Protein Forms a Stable, Homogeneous Homo-Dimer

The size and oligomeric state of the fusion proteins were studied by size-exclusion chromatography coupled to an in-line multi-angle light scattering detector (SEC-MALS). Samples were prepared by injecting 30 μg of stock protein sample. Isocratic separations were performed on a GE Healthcare Superdex 200 Increase 10/300 GL column (10 mm×300 mm) connected to a Prominence Shimadzu UFLC system consisting of a degasser, isocratic pump, chilled sample holder with injector, UV/vis detector, and column oven in buffer containing 40 mM Tris, 200 mM NaCl (pH 7.5), with 0.02% Na azide added and 0.1 um filtered running at a flow rate of 0.75 mL/min. Samples were injected onto the column using an Shimadzu autosampler, and data were obtained from three online detectors connected in series: a Shimadzu SPD-20 dual wavelength UV/vis spectrophotometer set for collection at 280 nm, followed by a Wyatt Technologies mini-Dawn TREOS three angle laser light scattering detector and then a Wyatt Optilab T-rEX interferometric refractometer. Data were collected and analyzed using Astra 6 (Wyatt) and LabSolutions Lite (Shimadzu) software.

The data in FIG. 1 show typical absolute mass versus elution time from analytical size exclusion chromatography. The sample analyzed in FIG. 1 is for IL2-CD25(22-212) (SEQ ID NO: 16) fused to a His tag (GGHHHHHH (SEQ ID NO: 100), which has a theoretical molecular mass of 37,812 (reduced) for the polypeptide chain. The data indicate that IL2-CD25(22-212) forms a homogeneous species across the elution profile having a measured absolute mass of 93 kDa. The elution peak shows no evidence of monomeric species nor of oligomeric species of higher order than the main peak. The mass value of 93 kDa indicates the molecule forms a homodimer and is also glycosylated (about 18% mass from known N- and O-linked glycosylation sites on IL2 and CD25).

Example 2: IL2-CD25 Fusion Proteins Bind Equivalently to sCD25 and sIL2Rβ/IL2Rγ Heteroreceptors with Attenuated Observed Affinity Surface plasmon resonance (SPR) studies were performed on a Biacore T100 and/or T200 instrument (GE Healthcare) at 25° C. The binding of the fusion protein analytes were tested in phosphate buffered saline (PBS-T) (pH 7.1) on surfaces consisting of a low density (~300RU) of biot-hCD25-BioP-TVMV-His which had been His cleaved (hCD25) and captured on a streptavidin, SA sensor chip or hCD122(27-241)-hFc-D/hCD 132(23-263)-hFc-K heterodimeric Fc fusion (hIL2-Rb/g) that had been captured via Protein A immobilized CM5 sensorchip surface using standard ethyl(dimethylaminopropyl) carbodiimide/N-hydroxysuccinimide (NHS) chemistry, with ethanolamine blocking. The protein analytes were injected in a titration series and regeneration back to baseline was performed by 2×8s injections of low pH buffer. The data were analyzed using the Biacore T-200 Evaluation software.

Figure 2:
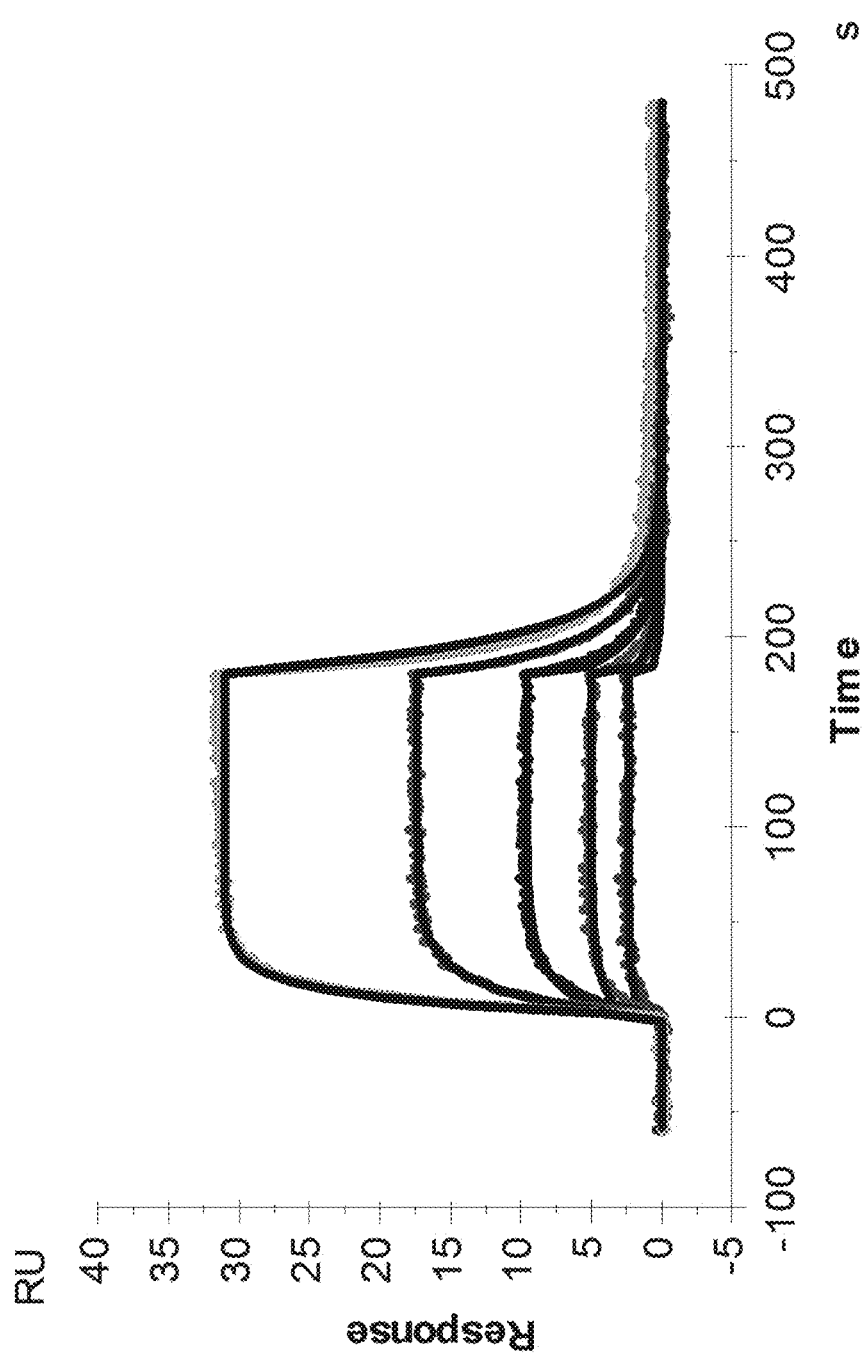
Figure 3:
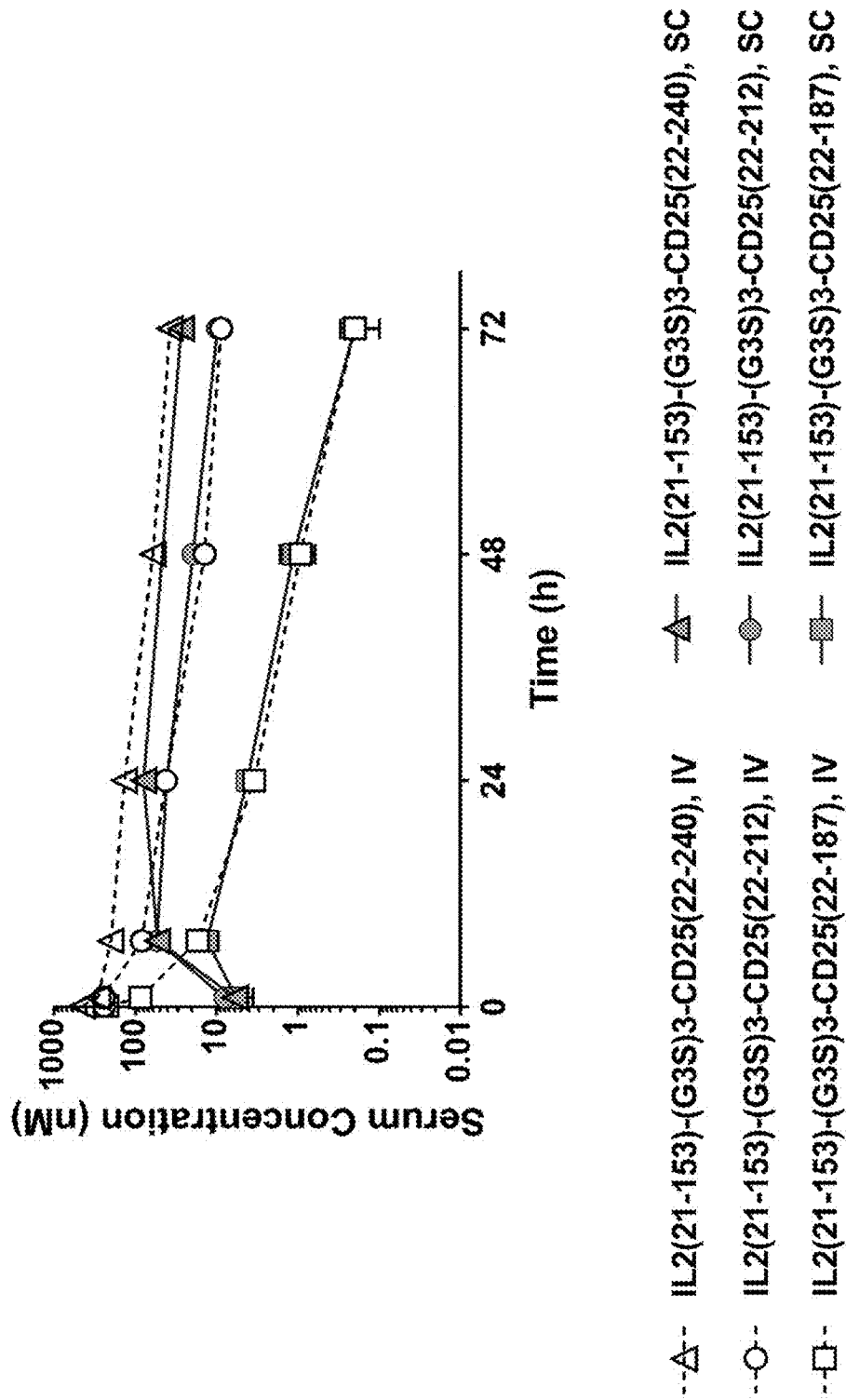
Figure 4:
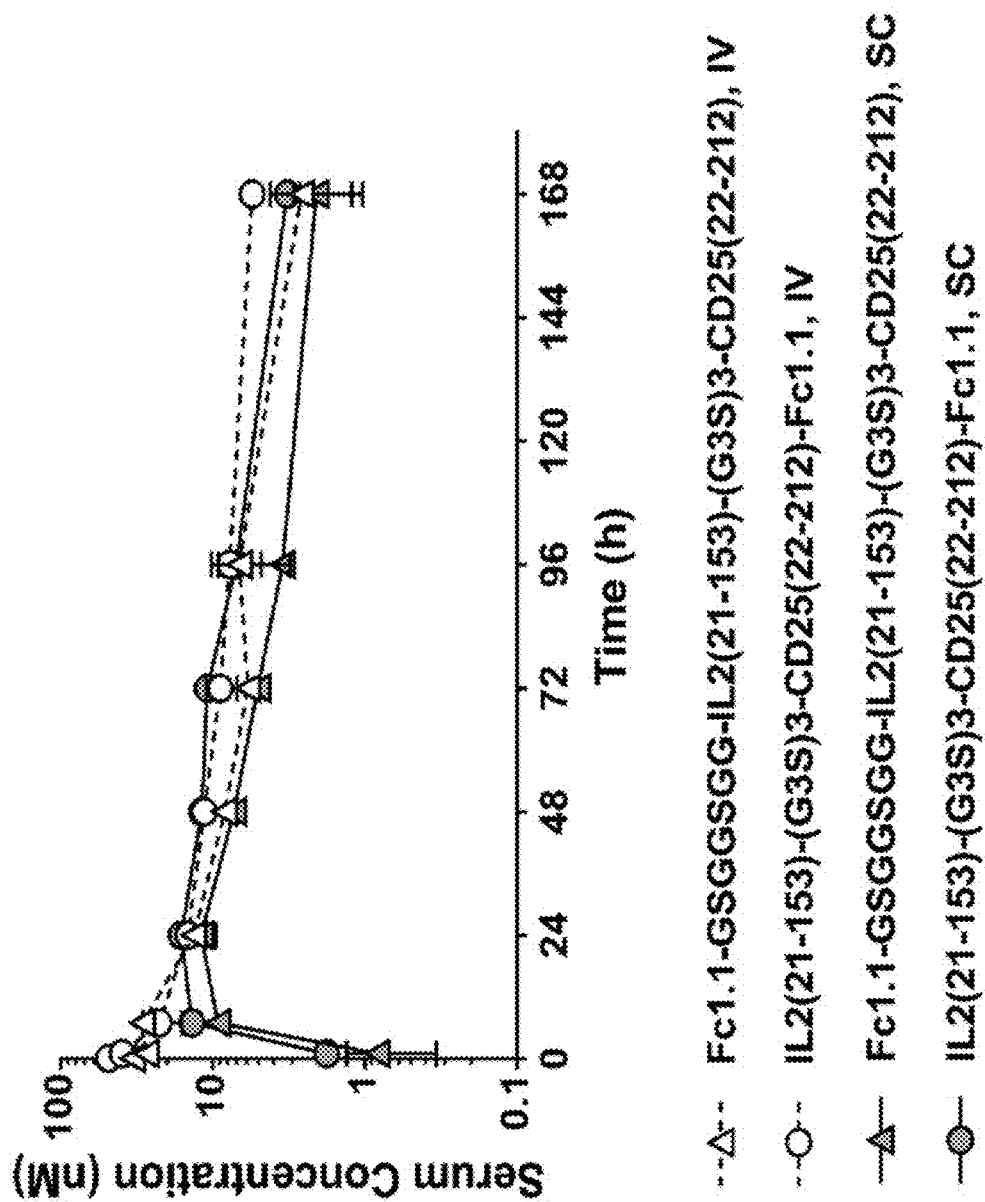
Figure 5:
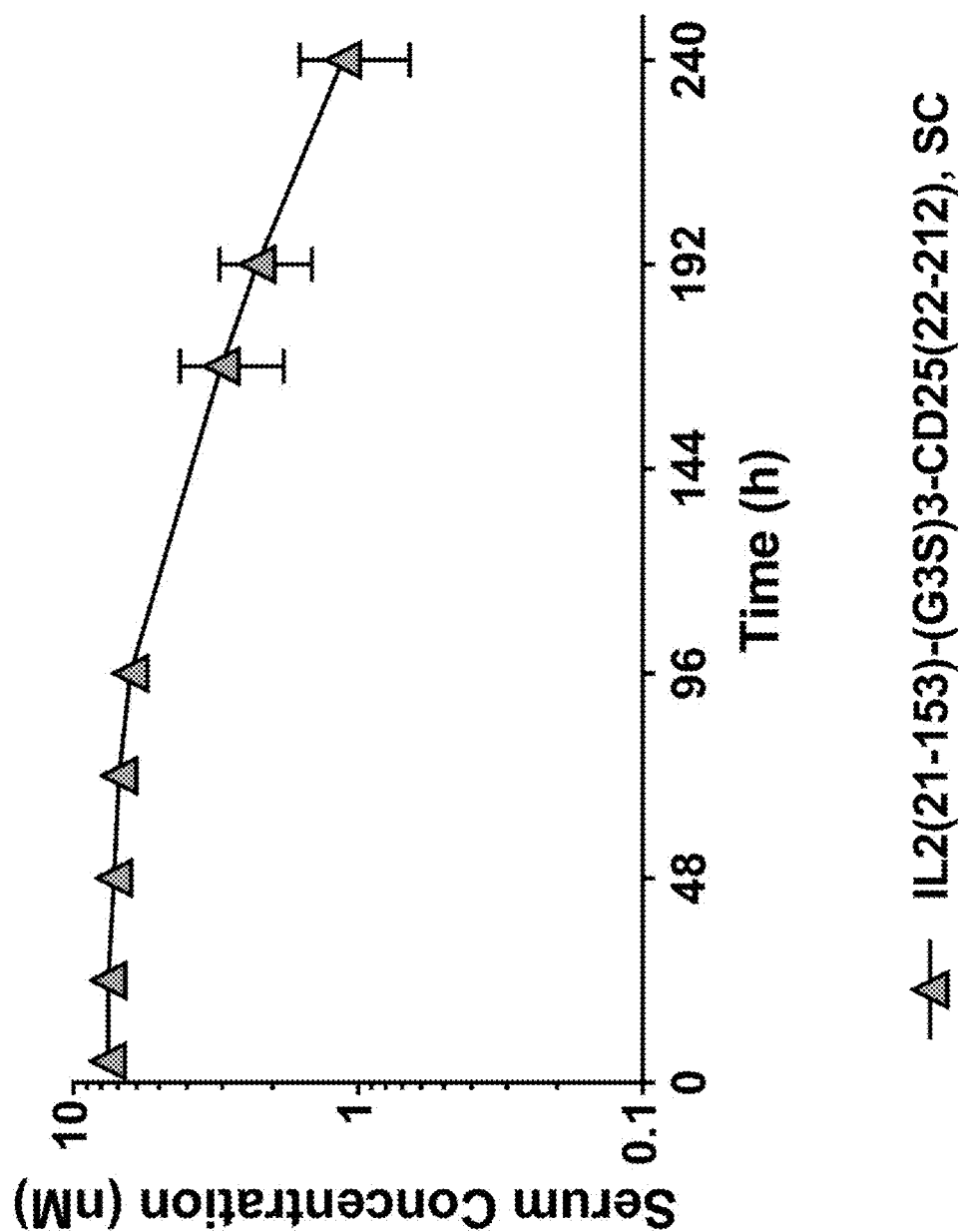
Figure 6:
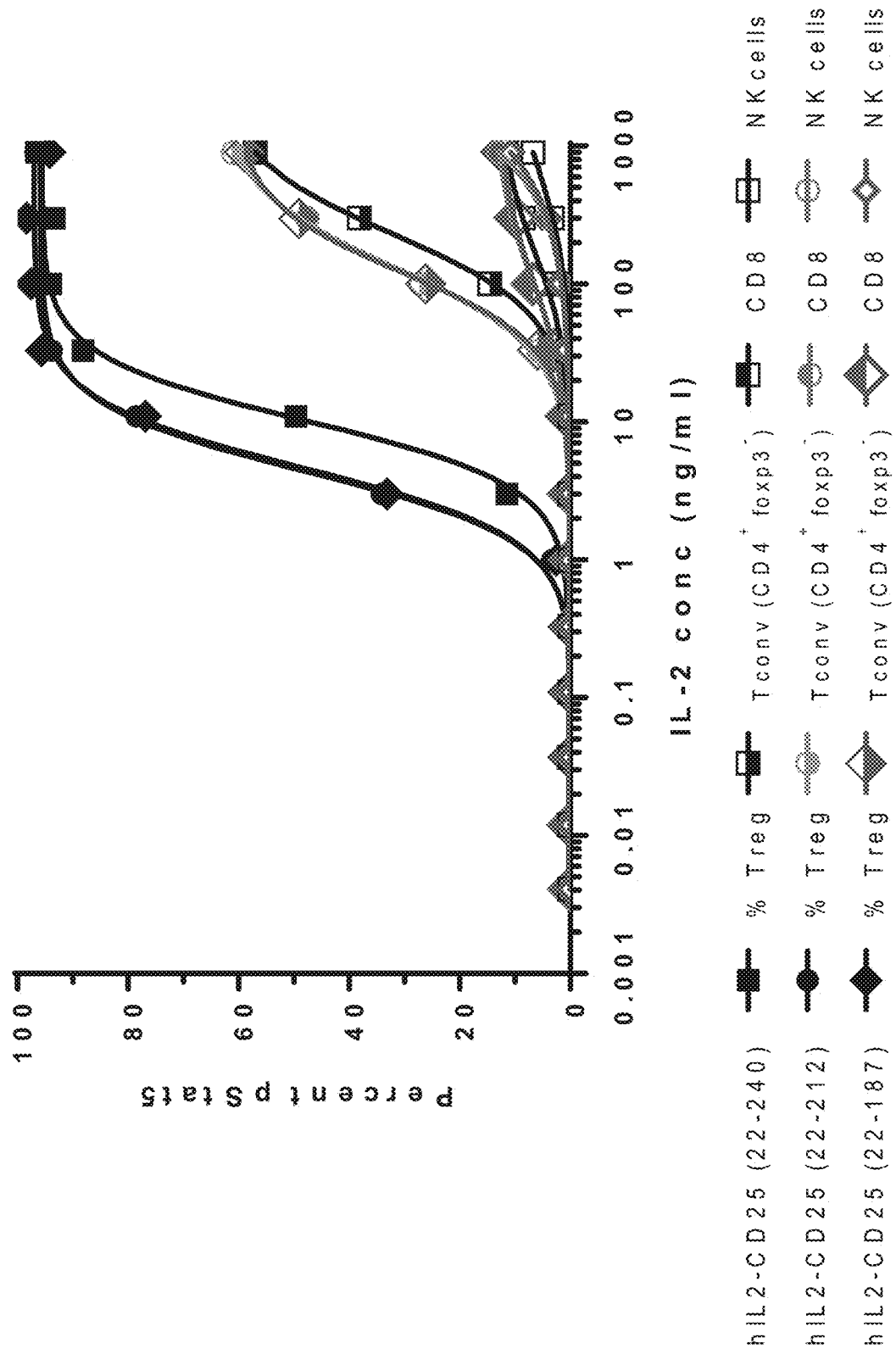
Figure 7:
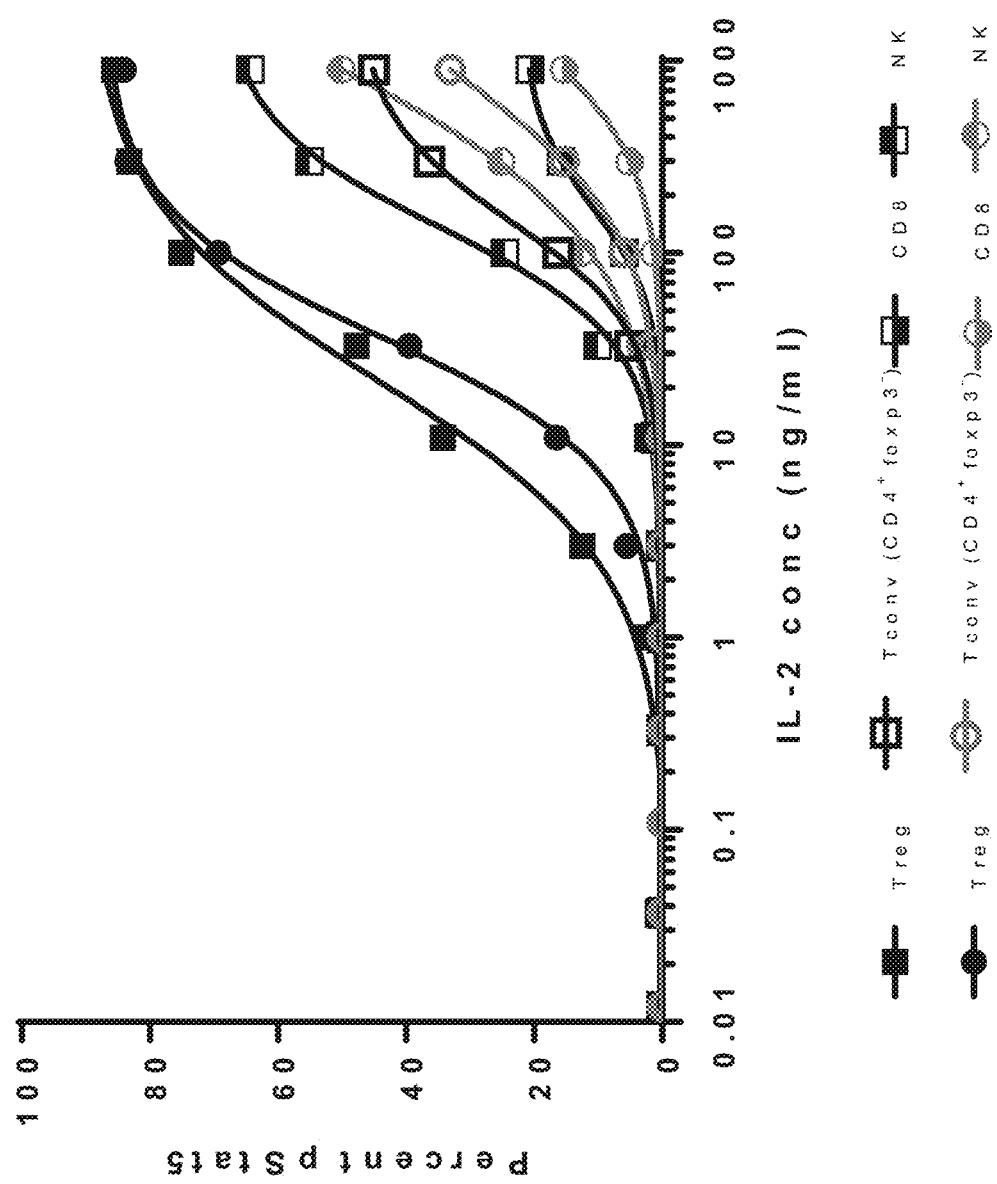
Figures 8A, 8B, 8C:
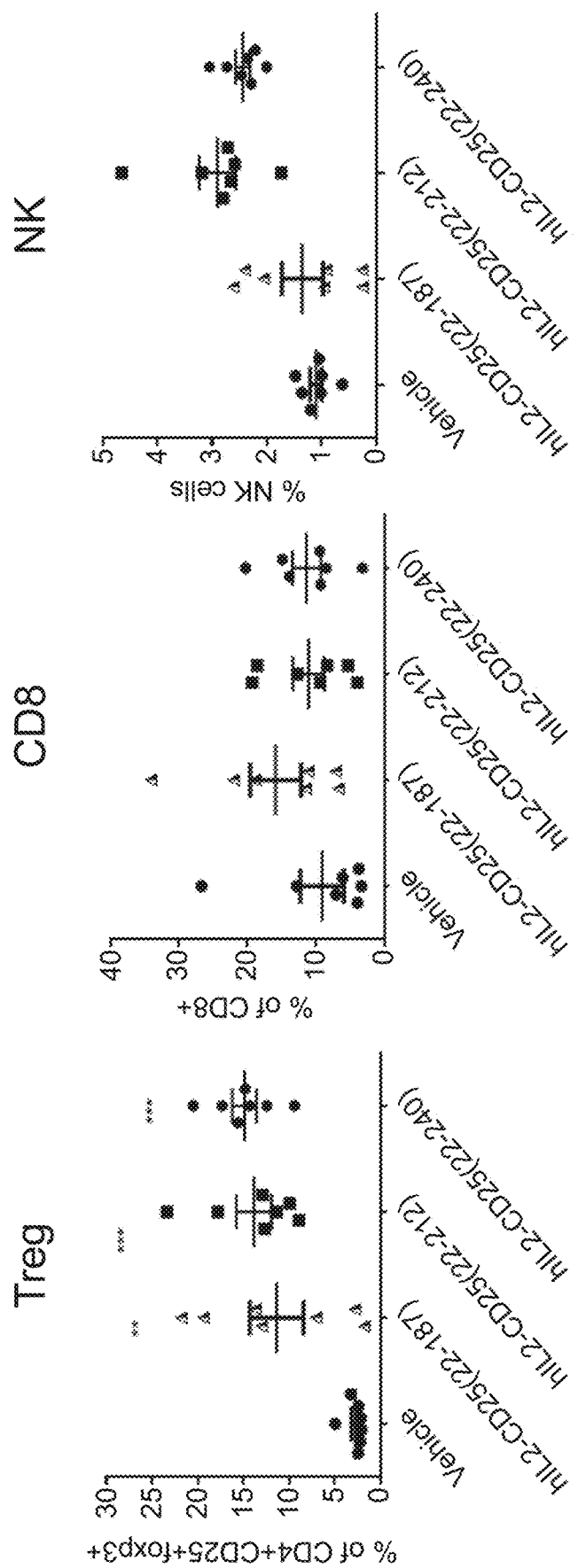

FIG. 2 shows prototypical binding of the IL2-CD25 fusion protein (SEQ ID NO: 16) to human sCD25. The observed apparent equilibrium dissociation constant of 4.2 micromolar is approximately 150-fold weaker than the affinity of isolated IL2 to sCD25 as measured by surface plasmon resonance (Liparoto, S. F., Myszka, D. G., Wu, Z., Goldstein, B., Laue, T. M., and Ciardelli, T. L. (2002) Biochemistry 41, 2543-51).

TABLE 9

Pharmacokinetics of binding of the IL2-CD25 fusion protein (SEQ ID NO: 16) to human sCD25.

| ka (1/Ms) | kd (1/s) | KD (M) |
|---|---|---|
| 1.29E+4 | 0.054 | 4.2E−6 |

Table 10 below shows prototypical binding observed equilibrium $K_D$ values for short and long versions of IL2-CD25 to human sCD25 and sIL2Rβ/IL2Rγ heterodimer. The observed apparent equilibrium dissociation constants for the various IL2-CD25 fusion proteins are markedly attenuated compared to IL2. Binding to sCD25 is approximately 100-fold weaker for the IL2-CD25 fusions compared to IL2. Likewise binding of the IL2-CD25 fusions is about 150-fold weaker to the beta-gamma heterodimer than is IL2.

TABLE 10

Observed equilibrium $K_D$ values for binding IL2 and IL2-CD25 constructs to sCD25 or sIL2Rβ/IL2Rγ heterodimer as measured by surface plasmon resonance.

| Receptor | $K_D$ to sCD25, μM | $K_D$ to sIL2Rβ/IL2Rγ heterodimer, μM |
|---|---|---|
| IL2 | 0.025 | 0.0004 |
| IL2-CD25(22-187) | 1.6 | 0.054 |
| IL2-CD25(22-212) | 2.3 | 0.065 |
| IL2-CV-CD25(22-240) | 2.1 | 0.063 |
| IL2-CD25(22-240) | 2.4 | 0.044 |
| Fc1.1-7linker-IL2-CD25(22-212) Bivalent SEQ ID NO: 67 | 5.6 | N.D. |
| IL2-CD25(22-212)-Fc1.1 SEQ ID NO: 68 | 2.5 | 0.1 |
| IL2-T3A-CD25(22-187)-N89Q-T95A-T106A (SEQ ID NO: 202) | 1.9 | N.D. |
| Fc-(IL2(V91K)CD25)2 bivalent SEQ ID NO: 203 | 3.0 | |
| HSA-(G4S)3-IL2-CD25(22-187) SEQ ID NO: 19 | 4.0 | 0.03 |
| IL2(C145 A)-CD25(22-212)-GG-HSA SEQ ID NO: 20 | 2.1 | 0.03 |
| Human Fc1.1(f)-AZ1-IL2(C145S)-CD25(22-187)-G SEQ ID NO: 26 | 3.0 | 0.15 |
| IL2(C145S)-CD25(22-187)-HuFc1.1(f)-AZ1 SEQ ID NO: 27 | 2.0 | 0.15 |
| IL2(V111K)-CD25 SEQ ID NO: 69 | 1.9 | |
| IL2(D40T)-CD25 SEQ ID NO: 70 | 2.8 | |

Example 3: Truncated Versions of IL2-CD25 have Improved Stability Against Aggregation: Accelerated Stability Testing The stability of the fusion proteins were tested by incubating at 40° C. in buffers of pH range 4-8. Fusion proteins were concentrated to about 15 mg/ml and dialyzed at 4° C. into the following buffers: 1) 20 mM Acetate, 250 mM Sucrose, pH 4, 2) 20 mM Citrate, 250 mM Sucrose, pH 5, 3) 20 mM Histidine, 250 mM Sucrose, pH 6, 4) 20 mM Phosphate, 250 mM Sucrose, pH 7 and 5) 20 mM Tris, 250 mM Sucrose, pH 8.4 (room temperature). After recovery from dialysis, the concentration of the fusion proteins were normalized to 10 mg/ml by dilution with dialysis buffer, and placed in an incubator monitored at 40° C. for four weeks, with aliquots removed just prior to incubation (t0), after one week (1w) and after four weeks (4w) of 40° C. incubation. Each time point was analyzed by Size Exclusion Chromatography on a Shodex KW403-4F column, connected to an Agilent 1260 HPLC system in buffer containing 100 mM Sodium Phosphate, 150 mM Sodium Chloride, pH7.3 (0.2 µm filtered) running at a flow rate of 0.30 mL/min.

As seen in Tables 11 and 12, the truncated versions of IL2-CD25 display much better high molecular weight and low molecular weight profiles after accelerated stability studies than the longer versions. This is especially true for pH values 4, 5, 6 and 7. Samples were held at different pH conditions for four weeks and forty degrees Celsius. The results shown as percent of high molecular weight and low molecular weight fractions of each construct indicate greatly improved stability of the short constructs compared to the long ones. The results shown as percent of main peak fractions of each construct indicate greatly improved stability of the short constructs compared to the long ones.

Example 4: Pharmacokinetic Studies in Non-Human Animals

Pharmacokinetic Studies

All animal protocols were approved by Central New Jersey Institutional Animal Care and Use Committee and animals were housed according to guidelines. Female Balb/C mice weighing 19-20 grams were purchased from Charles-River (Wilmington, Mass.). Non-fasted Balb/C mice were administered a single 0.5 mg/kg dose of the indicated molecule, either by intravenous (IV) route via tail-vein or subcutaneous (SC) route. IL2(21-153)-(G3S)3-CD25(22-240) used in pharmacokinetic studies has a His6-tag. Blood was collected from tail vein at following time-points after dose: 5 minutes (IV only), 1h, 7h, 24h, 48h, 72h, 96h and 168h. For monkey PK study, male cynomolgus monkeys were obtained from Buckshire Corporation (Perkasie, Pa.). Monkeys (N=3, average body weight 7.8 kg) were administered a single 0.075 mg/kg subcutaneous dose of hIL2-CD25 (22-212). Serial blood samples were collected from a femoral artery from conscious and chaired monkeys at 5h, 24h, 48h, 72h, 96h, 168h, 192h, and 240h following dosing. Blood samples were allowed to coagulate and centrifuged at 4° C. (1500-2000×g) to obtain serum. Serum samples were stored at −80° C. until further analysis.

Detection of Fusion Protein in Serum:

A ligand binding assay was used to detect levels of the fusion protein in mouse or monkey serum samples. Briefly, 96-well Nunc MaxdiSorp flat bottom plates (Thermo Fisher Scientific, Denmark) were coated with capture reagent (rat anti-human IL2 antibody, monoclonal clone: MQ1-17H12; Thermo Fisher Scientific, San Diego, Calif.), at 2 µg/mL in

TABLE 11

Accelerated stability profiles of IL2-CD25 fusion proteins.

| pH | IL2-CD25(22-187) HMW (%) | IL2-CD25(22-187) LMW (%) | IL2-CD25(22-212) HMW (%) | IL2-CD25(22-212) LMW (%) | IL2-C145V-CD25(22-240) HMW (%) | IL2-C145V-CD25(22-240) LMW (%) | IL2-CD25(22-240) HMW (%) | IL2-CD25(22-240) LMW (%) |
|---|---|---|---|---|---|---|---|---|
| 4 | 2.3 | 6.3 | 5.3 | 3.4 | 19.4 | 5.7 | 13.0 | 13.4 |
| 5 | 1.9 | 3.9 | 1.8 | 1.9 | 12.5 | 0.3 | 14.3 | 2.6 |
| 6 | 1.3 | 2.2 | 1.9 | 1.2 | 13.3 | 0.0 | 15.9 | 0.0 |
| 7 | 5.1 | 3.8 | 2.6 | 2.5 | 9.4 | 2.3 | 10.5 | 2.5 |
| 8 | 5.5 | 4.2 | 2.6 | 2.7 | 6.2 | 2.3 | 7.8 | 2.7 |

The IL2-CD25 fusion proteins herein contain a His tag (GGHHHHHH, SEQ ID NO: 100) for purpose of easy purification.

TABLE 12

Accelerated stability profiles of IL2-CD25 fusion proteins.

| pH | IL2-CD25 (22-187) | IL2-CD25 (22-212) | IL2-C145V-CD25 (22-240) | IL2-CD25 (22-240) |
|---|---|---|---|---|
| 4 | 91.4 | 91.3 | 74.9 | 73.6 |
| 5 | 94.2 | 96.4 | 87.2 | 83.1 |
| 6 | 96.6 | 97.0 | 86.7 | 84.1 |
| 7 | 91.1 | 94.9 | 88.3 | 87.0 |
| 8 | 90.3 | 94.7 | 91.6 | 89.5 |

PBS overnight at 4° C. Plates were blocked with blocking buffer (5% BSA in PBS) and incubated at 25° C. for one hour. The standards, QCs and samples were diluted 20-fold with assay buffer (PBS with 1% BSA and 0.05% Tween 20) and added to the washed plates in duplicate, and incubated at 4° C. overnight. Washed plates were incubated with detection reagent (human CD25 biotinylated antibody, R&D Systems, Minneapolis, Minn. at 250 ng/mL in assay buffer) and incubated for 2 hours at 25° C. To the washed plates were added sequentially, at 25° C., NeutrAvidin-HRP (Thermo Scientific, Rockford, Ill.) 100 ng/mL in assay buffer for 45 minutes followed by chemiluminescent substrate mix (Thermo Scientific, Rockford, Ill.) for one minute before reading in SpectraMax plate reader at luminescence mode. Concentration of the analyte in serum samples was calculated using the standard curve made by the Log-Log linear curve fit algorithm of softmax analysis program (Molecular Devices).

TABLE 13

Pharmacokinetic parameters of indicated molecules in Balb/C mice.

| | Dose mg/kg | Route | CL ml/h/kg | Vss ml/kg | AUC (0-last) nM*h | Cmax nM | Tmax h | T½ h | Bioavailability % |
|---|---|---|---|---|---|---|---|---|---|
| IL2(21-153)-(G3S)3-CD25(22-240) | 0.5 | IV | 1.3 | 46.3 | 8046.3 | NA | NA | 19.4 | NA |
| | 0.5 | SC | NA | NA | 3639.6 | 79 | 24 | 31 | 45% |
| IL2(21-153)-(G3S)3-CD25(22-212) | 0.5 | IV | 4 | 94.2 | 3053.1 | NA | NA | 19.4 | NA |
| | 0.5 | SC | NA | NA | 2033.1 | 54.6 | 7 | 23 | 67% |
| IL2(21-153)-(G3S)3-CD25(22-187) | 0.5 | IV | 23.1 | 200.4 | 610.4 | NA | NA | 11.6 | NA |
| | 0.5 | SC | NA | NA | 261.3 | 13.2 | 7 | 10.9 | 43% |
| Fc1.1-GSGGSGG-IL2(21-153)-(G3S)3-CD25(22-212) | 0.5 | IV | 1.96 | 167.6 | 1442 | NA | NA | 66.6 | NA |
| | 0.5 | SC | NA | NA | 886.5 | 12.02 | 24 | 68.8 | 61% |
| IL2(21-153)-(G3S)3-CD25(22-212)-Fc1.1 | 0.5 | IV | 1.2 | 194.4 | 1771.3 | NA | NA | 120 | NA |
| | 0.5 | SC | NA | NA | 1478.6 | 16.2 | 24 | 61.3 | 83% |

NA = not applicable, ND = not determined.

TABLE 14

Pharmacokinetic parameters of hIL2-CD25 (22-212) in cynomolgus monkeys.

| | Dose mg/kg | Route | AUC (0-last) nM*h | Cmax nM | Tmax h | $T_{1/2}$ day |
|---|---|---|---|---|---|---|
| IL2(21-153)-(G3S)3-CD25(22-212) | 0.075 | SC | 1200 | 7.6 | 24 | 2.1 |

Example 5: Activity of IL2-CD25 Fusion Protein on Kit225 Cells

The biological activity of the modified fusion proteins was determined by measuring the ability to stimulate IL2R endogenously expressed on the T cell line, Kit225 (an IL2 dependent human T cell line from a patient with T cell chronic lymphocytic leukemia with OKT3+, -T4+, -T8- phenotype). Activity was measured by the use of a reporter system sensitive to the signaling cascade of IL2R. Kit225 human T cells stably integrated with the firefly luciferase reporter gene under the control of the IFNγ activation sequence (IRF1-GAS-Luc) were grown in medium containing RPMI+Glutamax, 10% heat-inactivated FBS, 20 ng/mL recombinant IL2 (Invitrogen PHC0023), 1% Pen/Strep and 0.7 mg/mL Geneticin. A day prior to the assay, reporter cells were washed and re-suspended in assay medium (Phenol-red-free RPMI+L-glutamine, 10% heat-inactivated FBS, 1% Pen/Strep) to remove IL2 present in the growth medium, then incubated overnight at 37° C. On the day of the assay, IL2 molecules were serially diluted in the assay buffer for a 3-fold, 11-point concentration response curve, various concentrations of IL2 molecules were added to a CulturPlate-384 assay plate (Perkin Elmer cat. no. 6007688) followed by the addition of 70,000 cells/well. Assay plates were incubated for 5 hours in a 37° C. $CO_2$ incubator then equilibrated to room temperature for 20 minutes before adding ONE-GLO™ substrate (Promega E6120). Plates were sealed and luminescent signals were measured on a Perkin Elmer Envision. 11 points of IL2 dose response luminescent signals were plotted using GraphPad Priam. The EC50 is defined as the concentration of test IL2 fusion proteins corresponding to 50% activation derived from the 11-point fitted curve as determined using a four-parameter logistic regression model. The potency of the fusion proteins on IL2R signaling in primary cells was determined by stimulation of either human peripheral blood mononuclear cells (PBMCs) or whole blood with fusion proteins. Tyrosine phosphorylation of pSTAT5 is an immediate consequence of IL2R signaling and was detected in various cell populations in either whole blood or PBMCs by flow cytometry. Blood samples or PBMCs were treated with serial dilutions of hIL2-CD25 fusion proteins for 15 min at 37° C. After incubation, cells were fixed and blood lysed with Lyse/Fix buffer for 10 min (BD Phosflow). Cells were washed twice and then permeabilized in ice-cold methanol on ice for 30 min, further washed twice. Samples were then treated with Human Fc Block (ebioscience), followed by staining with labeled antibodies for CD3, CD4, CD8, CD25, pSTAT5, Foxp3, and CD56. All samples were then analyzed by flow cytometry.

In in vitro cell based assays, the fusion protein exhibited potency of IL2 receptor activation which was significantly right shifted (poorer potency) relative to wt IL2. This is consistent with the reduced apparent affinity of the fusion protein in the non-covalent dimeric form. Addition of an Fc tail to the fusion protein did produce a further shift to poorer potency by 20-30 fold. Removal of the His-tag or truncation of the C terminus had minimal effect on the potency of the fusion proteins. Similar relative potency results were obtained in whole blood.

TABLE 15A

Activity of IL2-CD25 fusion protein on Kit225 cells.

| Fusion Protein | $EC_{50}$ (ng/ml) | |
|---|---|---|
| IL2 WT | 0.41 | N = 9 |
| hIL2-CD25 (22-240)-His | 138 | n = 2 |
| hIL2-C145V-CD25 (22-240)-His | 166 | n = 2 |
| hIL2-CD25(22-212)-His | 210 | n = 2 |
| hIL2-CD25(22-212) | 139 | n = 12 |
| hIL2-CD25(22-187)-His | 145 | n = 2 |
| hIL2-CD25(22-187) | 49 | n = 2 |
| Fc1.1-7linker-IL2-CD25(22-212) (bivalent) | 3414 | n = 2 |
| hIL2-CD25(22-212)-Fc1.1 (bivalent) | 3413 | n = 2 |

TABLE 15B

Activity of IL2-CD25 fusion protein on Kit225 cells.

| Protein | SEQ | Potency EC50 ng/ml | STDEV | n | Ymax (%) % of wt IL2 response |
|---|---|---|---|---|---|
| wt-hIL2 | | 0.42 | 0.23 | 9 | N/A |
| hIL2-CD25(22-212) | 16 | 139 | 112 | 12 | 103% |
| HSA-hIL2-CD25(22-187) | 19 | 972 | 856 | 4 | 104% |
| hIL2-CD25(22-187)-HSA | 20 | 205 | 78 | 4 | 95% |
| Fc-hIL2-CD25(22-187) | 26 | 327 | 90 | 3 | 91% |
| hIL2-CD25(22-187)-Fc | 27 | 257 | 95 | 3 | 93% |
| Fc-(hIL2-CD25(22-187))2 bivalent | 67 | 737 | 264 | 4 | 97% |
| hIL2-CD25 (quad aglycosylated) | 202 | 39.4 | 3.1 | 3 | 85% |

Figures 9A, 9B:
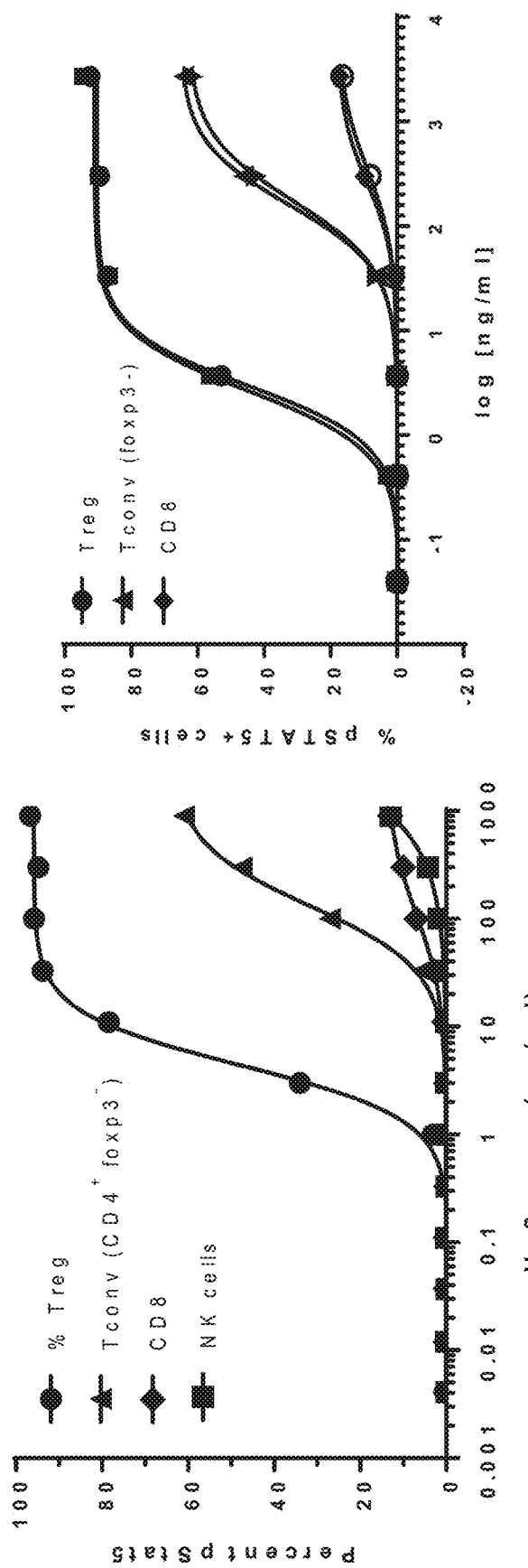
FIG. 9A and FIG. 9B show phosphorylation of STAT5 after 15 min in a mixed cell population including in PBMCs (FIG. 9A) or whole blood concentration (FIG. 9B) with hIL2-CD25(22-212) (SEQ ID NO:16).

The selectivity of hIL2-CD25 proteins including hIL2-CD25 (22-212) (SEQ ID NO:16) signaling on Treg over other cell types can be measured by monitored phosphorylation of STAT5 after 15 min in a mixed cell population including in PBMCs or whole blood (FIGS. 9A and 9B, respectively). Freshly acquired blood samples were treated with serial dilutions of hIL2-CD25 (22-212) (SEQ ID NO:16) for 15 min at 37° C. After incubation, cells were processed (fixed and permeabilized), stained with labeled antibodies for CD3, CD4, CD8, CD25, pSTAT5, Foxp3, and CD56, and analyzed by flow cytometry. Treg are very sensitive to IL2R stimulation by hIL2-CD25 (22-212) (SEQ ID NO:16) with maximal efficacy of 90% of Treg responding to stimulation by upregulation of pSTAT5 and with a potency of 7+/−11 ng/ml. In contrast to the robust activation observed on Treg, CD4 non-Treg (foxp3−), CD8 and NK cells were less effectively stimulated by hIL2-CD25 (22-212) (SEQ ID NO:16); below 50% of these cells upregulated pSTAT5 even at concentrations up to 2700 ng/ml on average across all other cell types (Table 16). Overall the selectivity of IL2R on Treg over other cell types is maintained or increased for hIL2-CD25 (22-212) (SEQ ID NO: 16) relative to rhIL2. Fc- or HSA-fusion proteins with IL2-CD25 maintained high Treg selectivity in whole blood albeit with lower potency (Table 16).

TABLE 16

Potency and efficacy of stimulation of various cell types in human whole blood. Data is the average for 2-10 donors on freshly drawn blood from normal donors. The maximal % pSTAT5 positive cells was determines at concentrations ~200-400x greater than the Treg potency.

| % pSTAT5 positive cells | Treg EC50 ng/ml | Treg Max @ highest conc. tested | CD4 foxp3-Non-Treg Max @ highest conc. tested | CD8 T cells Max @ highest conc. tested | NK cells Max @ highest conc. tested |
|---|---|---|---|---|---|
| hIL2-CD25 (22-212) (SEQ 16) | 7.2 (±10.4, n = 10) | 90% (+/−8, n = 10) | 48% (+/−14, n = 10) @2.7 µg/ml | 27% (+/−11, n = 10) @2.7 µg/ml | 22% (+/−19, n = 8) @2.7 µg/ml |
| Fc-(IL2-CD25)2 (SEQ 67) bivalent | 88 (±74, n = 4) | 95% (+/−2, n = 4) | 50% (n = 3) @24 µg/ml | 33% (n = 3) @24 µg/ml | 8% (n = 2) @24 µg/ml |
| Fc-(IL2-CD25) (SEQ 26) monovalent | 25 (±12, n = 3) | 94% (+/−1, n = 3) | 60% (n = 3) @8.1 µg/ml | 36% (n = 3) @8.1 µg/ml | 6% (n = 3) @8.1 µg/ml |
| HSA-(G4S)3-IL2-CD25-FT (SEQ 19) | 83 (±53, n = 3) | 95% (+/−3, n = 3) | 59% (n = 2) @24 µg/ml | 38% (n = 2) @24 µg/ml | 6% (n = 2) @24 µg/ml |
| IL2-CD25 FT-GG-HSA (SEQ 20) | 43 (±35, n = 2) | 92% (+/−5, n = 2) | 60% (n = 2) @8.1 µg/ml | 39% (n = 2) @8.1 g/ml | 10% (n = 2) @8.1 µg/ml |
| (IL2-CD25)-Fc (SEQ 27) monovalent | 11.4 (±1.6, n = 2) | 94% (+/−5, n = 2) | 67% n = 2 @8.1 µg/ml | 49% n = 2 @8.1 µg/ml | 25% n = 2 @8.1 µg/ml |

Example 6: In Vivo Activity of Increasing Leukocytes by Truncated IL2-CD25 Fusion Proteins The ability of fusion proteins to increase leukocytes in vivo was tested in mice with a humanized immune system. 16-20 weeks old female NSG-huCD34 engrafted mice (NOD.Cg-Prkdc$^{scid}$ IL2rg$^{tm1Wjl}$/SzJ, which are reconstituted with human CD34+ hematopoietic stem cells) were purchased from Jackson Laboratory. Each humanized mouse was examined for the presence of hCD45+ cells and murine CD45+ cells (mCD45+) in peripheral blood by flow cytometry 14 weeks post engraftment. Mice were selected with at least 25% human CD45 engraftments. The engrafted human hematopoietic stem cells have been tested to be free of HIV, HBV, HCV and LCMV (lymphocytic choriomeningitis virus). Animals were provided standard rodent chow and purified water ad libitum and acclimated for a minimum of 1 week prior to use. All procedures using animals were reviewed and approved by the BMS Institutional Animal Care and Use Committee. Every third day, 16-20 weeks old NSG-huCD34 engrafted mice were dose subcutaneously either with PBS or with fusion protein huIL2-CD25(22-187), huIL2-CD25(22-212) and HuIL2-CD25(22-240) at 10 µg/mouse in a volume of 200 µl via the sub-cutaneous while the animals were under anesthesia. Total of three subcutaneous doses were administered on Day 0, 3 and 6. 24 hrs following the last dose, all treated groups were anesthetized, spleen was harvested in HBSS for FACS analysis of Treg, CD8 T, or NK cells. All three fusion proteins showed similar ability to increase spleen cell numbers.

Example 7: Stability of the (G3S)3 Peptide Linker in IL2(21-153)-(G3S)3-CD25(22-212) in Human or Mouse Serum Liquid chromatography with tandem mass spectrometry (LC-MS/MS)-based bioanalytical method was developed to support the evaluation of stability of the (G3S)3 linker in in vitro serum stability studies and in vivo monkey PK study. Following capture of IL2(21-153)-(G3S)3-CD25(22-212) (i.e., SEQ ID NO:16) using rat anti-IL-2 antibody, the peak area ratio of two signature peptides, DLISNINVIVLELK (from the IL-2 domain of IL2(21-153)-(G3S)3-CD25(22-212)) and EPPPWENEATER (from the CD25 domain of IL2(21-153)-(G3S)3-CD25(22-212)), was used to evaluate the linker stability between IL-2 and CD25. Linker-cleavage and resulting circulating cleaved product in serum would result in a systematic increase in the IL2/CD25 area ratio >1.

To test the linker-cleavage liability of IL2(21-153)-(G3S)3-CD25(22-212) in vitro, 0.5 μM of IL2(21-153)-(G3S)3-CD25(22-212) was incubated in human serum (Bioreclamation Cat# HMSRM-M; Lot# BRH1332647) or mouse serum (Bioreclamation Cat# MSESRM-BALB-M; Lot# MSE264349) in a total volume of 1.5 ml for up to 72 hours at 37° C. Samples (200 μL serum) were collected at 0, 4, 24, 48, and 72 hours and stored at −80° C. until analysis of peak area ratio by LC-MS/MS. To identify presence of circulating cleavage product due to linker-cleavage in vivo after a single dose of IL2(21-153)-(G3S)3-CD25(22-212) in monkey, serum samples collected at 5, 24, 48, 72, 96, and 168 hours after dose were analyzed for peak area ratio by LC-MS/MS.

Figure 10:
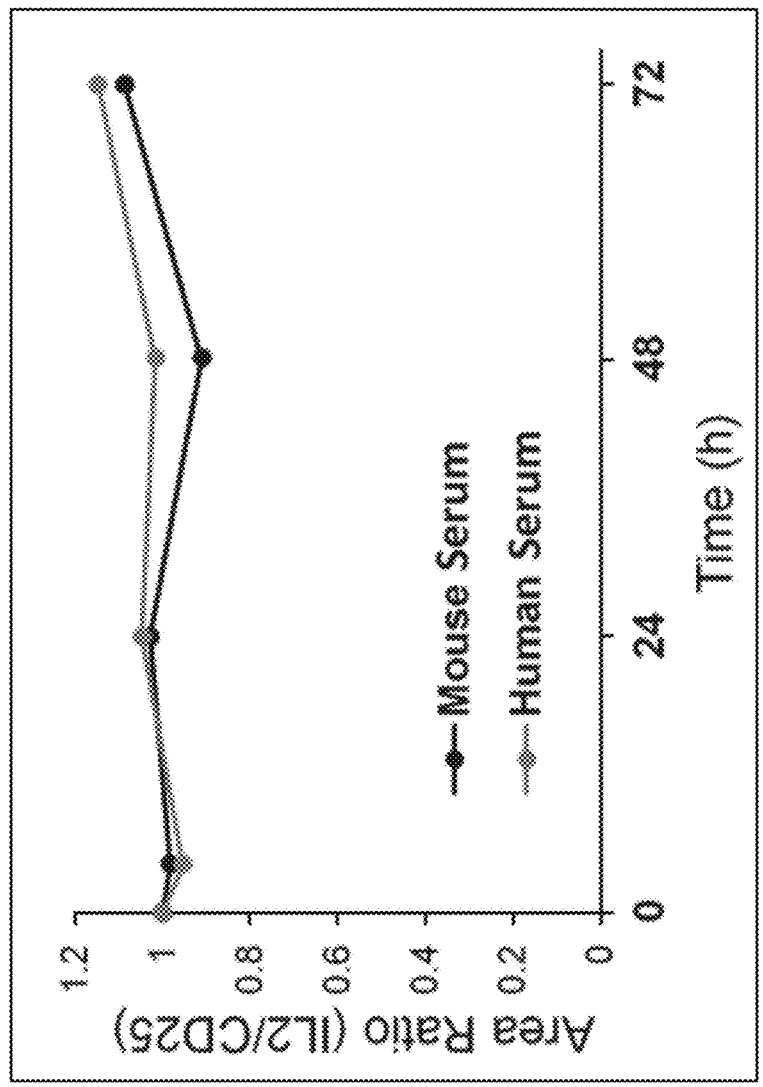
FIG. 10 shows LC-MS/MS based analysis of (G3S)3 linker stability in IL2(21-153)-(G3S)3-CD25(22-212) in human or mouse serum in vitro. Peak area ratio of IL2 and CD25 using LC-MS/MS is reported after capture using anti-IL2 antibody.

As shown in FIG. 10, the peak area ratio of signature peptides in IL2 and CD25 domains of IL2(21-153)-(G3S)3-CD25(22-212) remained close to unity over 72 hours of in vitro incubation in human or mouse serum at 37° C., therefore indicating negligible linker-cleavage in IL2(21-153)-(G3S)3-CD25(22-212) both in human serum and in mouse serum.

Figure 11:
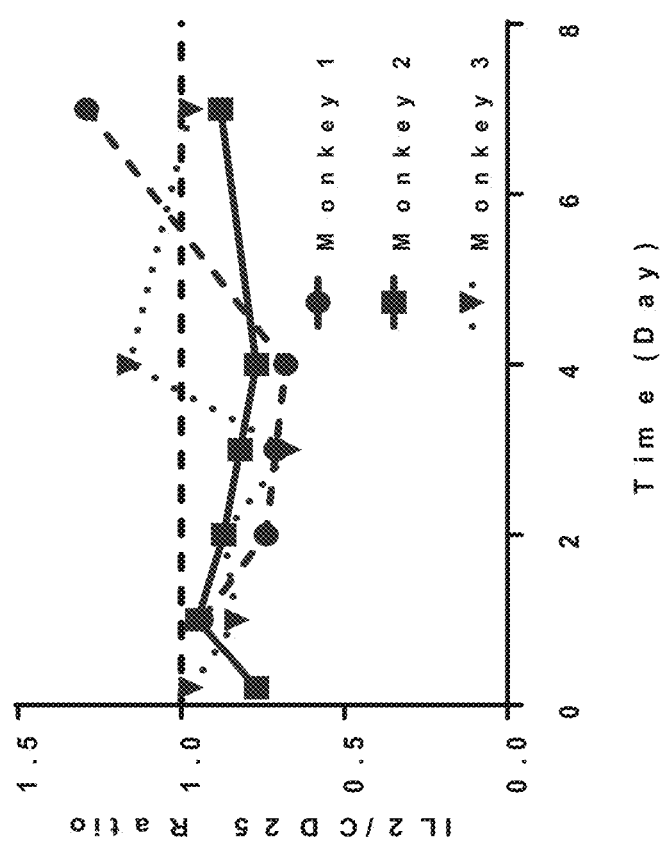
FIG. 11 shows LC-MS/MS based analysis of (G3S)3 linker stability in IL2(21-153)-(G3S)3-CD25(22-212) in serum of monkeys after a single subcutaneous dose of 0.075 mg/kg. Peak area ratio of IL2 and CD25 using LC-MS/MS is reported after capture using anti-IL2 antibody.

In addition, as shown in FIG. 11, in serum samples collected from the monkey after a single subcutaneous dose of 0.075 mg/kg IL2(21-153)-(G3S)3-CD25(22-212), ratio of IL2 and CD25 surrogate peptides after immuno-capture using anti-IL2, remained close to unity. The data suggest absence of linker-cleavage in serum of monkeys dosed with IL2(21-153)-(G3S)3-CD25(22-212) (i.e., SEQ ID NO:16).

What is claimed is:

1. A fusion protein:
   consisting of the amino acid sequence as set forth in SEQ ID NO: 16.

2. The fusion protein of claim 1, wherein the fusion protein is deglycoslyated enzymatically.

3. The fusion protein of claim 1, wherein the fusion protein is deglycoslyated chemically.

4. The fusion protein of claim 1, which is a monomer or a dimer.

5. The fusion protein of claim 1, which is a dimer.

6. A pharmaceutical composition comprising (a) the fusion protein of claim 1; and (b) a pharmaceutically acceptable excipient.

7. A kit comprising the fusion protein of claim 1 and instructions for administering the fusion protein to a subject in need thereof.

8. A nucleic acid that encodes the fusion protein of claim 1.

* * * * *

```
                          SEQUENCE LISTING

<160> NUMBER OF SEQ ID NOS: 204

<210> SEQ ID NO 1
<211> LENGTH: 153
<212> TYPE: PRT
<213> ORGANISM: Artificial Sequence
<220> FEATURE:
<223> OTHER INFORMATION: IL2 (human, unprocessed)

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 2
<211> LENGTH: 133
<212> TYPE: PRT
<213> ORGANISM: Artificial Sequence
<220> FEATURE:
<223> OTHER INFORMATION: IL2 (human, mature form)

<400> SEQUENCE: 2

Ala Pro Thr Ser Ser Ser Thr Lys Lys Thr Gln Leu Gln Leu Glu His
1               5                   10                  15
```

```
Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                    100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 3
<211> LENGTH: 169
<212> TYPE: PRT
<213> ORGANISM: Artificial Sequence
<220> FEATURE:
<223> OTHER INFORMATION: IL2 (mouse, unprocessed)

<400> SEQUENCE: 3

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
                20                  25                  30

Glu Ala Gln Gln Gln Gln Gln Gln Gln Gln Gln Gln His Leu
            35                  40                  45

Glu Gln Leu Leu Met Asp Leu Gln Glu Leu Leu Ser Arg Met Glu Asn
 50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
                    100                 105                 110

Gln Leu Glu Asp Ala Glu Asn Phe Ile Ser Asn Ile Arg Val Thr Val
            115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165

<210> SEQ ID NO 4
<211> LENGTH: 149
<212> TYPE: PRT
<213> ORGANISM: Artificial Sequence
<220> FEATURE:
<223> OTHER INFORMATION: IL2 (mouse, mature form)

<400> SEQUENCE: 4

Ala Pro Thr Ser Ser Ser Thr Ser Ser Ser Thr Ala Glu Ala Gln Gln
```

```
                1               5                  10                 15
              Gln Gln Gln Gln Gln Gln Gln Gln Gln His Leu Glu Gln Leu Leu
                          20                 25                 30

Met Asp Leu Gln Glu Leu Leu Ser Arg Met Glu Asn Tyr Arg Asn Leu
                          35                 40                 45

Lys Leu Pro Arg Met Leu Thr Phe Lys Phe Tyr Leu Pro Lys Gln Ala
                          50                 55                 60

Thr Glu Leu Lys Asp Leu Gln Cys Leu Glu Asp Glu Leu Gly Pro Leu
               65                 70                 75                 80

Arg His Val Leu Asp Leu Thr Gln Ser Lys Ser Phe Gln Leu Glu Asp
                                 85                 90                 95

Ala Glu Asn Phe Ile Ser Asn Ile Arg Val Thr Val Val Lys Leu Lys
                             100                105                110

Gly Ser Asp Asn Thr Phe Glu Cys Gln Phe Asp Asp Glu Ser Ala Thr
                             115                120                125

Val Val Asp Phe Leu Arg Arg Trp Ile Ala Phe Cys Gln Ser Ile Ile
                         130                135                140

Ser Thr Ser Pro Gln
              145

<210> SEQ ID NO 5
<211> LENGTH: 272
<212> TYPE: PRT
<213> ORGANISM: Artificial Sequence
<220> FEATURE:
<223> OTHER INFORMATION: IL2R? (human, unprocessed form)

<400> SEQUENCE: 5

Met Asp Ser Tyr Leu Leu Met Trp Gly Leu Leu Thr Phe Ile Met Val
               1               5                  10                 15

Pro Gly Cys Gln Ala Glu Leu Cys Asp Asp Asp Pro Pro Glu Ile Pro
                          20                 25                 30

His Ala Thr Phe Lys Ala Met Ala Tyr Lys Glu Gly Thr Met Leu Asn
                          35                 40                 45

Cys Glu Cys Lys Arg Gly Phe Arg Arg Ile Lys Ser Gly Ser Leu Tyr
                          50                 55                 60

Met Leu Cys Thr Gly Asn Ser Ser His Ser Ser Trp Asp Asn Gln Cys
               65                 70                 75                 80

Gln Cys Thr Ser Ser Ala Thr Arg Asn Thr Thr Lys Gln Val Thr Pro
                             85                 90                 95

Gln Pro Glu Glu Gln Lys Glu Arg Lys Thr Thr Glu Met Gln Ser Pro
                             100                105                110

Met Gln Pro Val Asp Gln Ala Ser Leu Pro Gly His Cys Arg Glu Pro
                             115                120                125

Pro Pro Trp Glu Asn Glu Ala Thr Glu Arg Ile Tyr His Phe Val Val
                         130                135                140

Gly Gln Met Val Tyr Tyr Gln Cys Val Gln Gly Tyr Arg Ala Leu His
              145                150                155                160

Arg Gly Pro Ala Glu Ser Val Cys Lys Met Thr His Gly Lys Thr Arg
                             165                170                175

Trp Thr Gln Pro Gln Leu Ile Cys Thr Gly Glu Met Glu Thr Ser Gln
                             180                185                190

Phe Pro Gly Glu Glu Lys Pro Gln Ala Ser Pro Glu Gly Arg Pro Glu
                             195                200                205

Ser Glu Thr Ser Cys Leu Val Thr Thr Thr Asp Phe Gln Ile Gln Thr
```

```
                    210                 215                 220
Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
                260                 265                 270

<210> SEQ ID NO 6
<211> LENGTH: 251
<212> TYPE: PRT
<213> ORGANISM: Artificial Sequence
<220> FEATURE:
<223> OTHER INFORMATION: IL2R? (human, mature form)

<400> SEQUENCE: 6

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln Val Ala Val Ala Gly
    210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
                245                 250

<210> SEQ ID NO 7
<211> LENGTH: 219
<212> TYPE: PRT
<213> ORGANISM: Artificial Sequence
<220> FEATURE:
<223> OTHER INFORMATION: IL2R? (human, mature form of IL2R?
      extracellular domain)

<400> SEQUENCE: 7
```

```
Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
        50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
            195                 200                 205

Met Glu Thr Ser Ile Phe Thr Thr Glu Tyr Gln
            210                 215

<210> SEQ ID NO 8
<211> LENGTH: 268
<212> TYPE: PRT
<213> ORGANISM: Artificial Sequence
<220> FEATURE:
<223> OTHER INFORMATION: IL2R? (mouse, unprocessed form)

<400> SEQUENCE: 8

Met Glu Pro Arg Leu Leu Met Leu Gly Phe Leu Ser Leu Thr Ile Val
1               5                   10                  15

Pro Ser Cys Arg Ala Glu Leu Cys Leu Tyr Asp Pro Pro Glu Val Pro
            20                  25                  30

Asn Ala Thr Phe Lys Ala Leu Ser Tyr Lys Asn Gly Thr Ile Leu Asn
            35                  40                  45

Cys Glu Cys Lys Arg Gly Phe Arg Arg Leu Lys Glu Leu Val Tyr Met
        50                  55                  60

Arg Cys Leu Gly Asn Ser Trp Ser Ser Asn Cys Gln Cys Thr Ser Asn
65                  70                  75                  80

Ser His Asp Lys Ser Arg Lys Gln Val Thr Ala Gln Leu Glu His Gln
                85                  90                  95

Lys Glu Gln Gln Thr Thr Thr Asp Met Gln Lys Pro Thr Gln Ser Met
            100                 105                 110

His Gln Glu Asn Leu Thr Gly His Cys Arg Glu Pro Pro Pro Trp Lys
            115                 120                 125

His Glu Asp Ser Lys Arg Ile Tyr His Phe Val Glu Gly Gln Ser Val
            130                 135                 140
```

His Tyr Glu Cys Ile Pro Gly Tyr Lys Ala Leu Gln Arg Gly Pro Ala
145                 150                 155                 160

Ile Ser Ile Cys Lys Met Lys Cys Gly Lys Thr Gly Trp Thr Gln Pro
            165                 170                 175

Gln Leu Thr Cys Val Asp Glu Arg Glu His His Arg Phe Leu Ala Ser
            180                 185                 190

Glu Glu Ser Gln Gly Ser Arg Asn Ser Ser Pro Glu Ser Glu Thr Ser
        195                 200                 205

Cys Pro Ile Thr Thr Thr Asp Phe Pro Gln Pro Thr Glu Thr Thr Ala
        210                 215                 220

Met Thr Glu Thr Phe Val Leu Thr Met Glu Tyr Lys Val Ala Val Ala
225                 230                 235                 240

Ser Cys Leu Phe Leu Leu Ile Ser Ile Leu Leu Ser Gly Leu Thr
            245                 250                 255

Trp Gln His Arg Trp Arg Lys Ser Arg Arg Thr Ile
            260                 265

<210> SEQ ID NO 9
<211> LENGTH: 247
<212> TYPE: PRT
<213> ORGANISM: Artificial Sequence
<220> FEATURE:
<223> OTHER INFORMATION: IL2R? (mouse, mature form)

<400> SEQUENCE: 9

Glu Leu Cys Leu Tyr Asp Pro Pro Glu Val Pro Asn Ala Thr Phe Lys
1               5                   10                  15

Ala Leu Ser Tyr Lys Asn Gly Thr Ile Leu Asn Cys Glu Cys Lys Arg
            20                  25                  30

Gly Phe Arg Arg Leu Lys Glu Leu Val Tyr Met Arg Cys Leu Gly Asn
        35                  40                  45

Ser Trp Ser Ser Asn Cys Gln Cys Thr Ser Asn Ser His Asp Lys Ser
    50                  55                  60

Arg Lys Gln Val Thr Ala Gln Leu Glu His Gln Lys Glu Gln Gln Thr
65                  70                  75                  80

Thr Thr Asp Met Gln Lys Pro Thr Gln Ser Met His Gln Glu Asn Leu
                85                  90                  95

Thr Gly His Cys Arg Glu Pro Pro Pro Trp Lys His Glu Asp Ser Lys
            100                 105                 110

Arg Ile Tyr His Phe Val Glu Gly Gln Ser Val His Tyr Glu Cys Ile
        115                 120                 125

Pro Gly Tyr Lys Ala Leu Gln Arg Gly Pro Ala Ile Ser Ile Cys Lys
    130                 135                 140

Met Lys Cys Gly Lys Thr Gly Trp Thr Gln Pro Gln Leu Thr Cys Val
145                 150                 155                 160

Asp Glu Arg Glu His His Arg Phe Leu Ala Ser Glu Glu Ser Gln Gly
                165                 170                 175

Ser Arg Asn Ser Ser Pro Glu Ser Glu Thr Ser Cys Pro Ile Thr Thr
            180                 185                 190

Thr Asp Phe Pro Gln Pro Thr Glu Thr Thr Ala Met Thr Glu Thr Phe
        195                 200                 205

Val Leu Thr Met Glu Tyr Lys Val Ala Val Ala Ser Cys Leu Phe Leu
    210                 215                 220

Leu Ile Ser Ile Leu Leu Ser Gly Leu Thr Trp Gln His Arg Trp
225                 230                 235                 240

```
Arg Lys Ser Arg Arg Thr Ile
            245

<210> SEQ ID NO 10
<211> LENGTH: 219
<212> TYPE: PRT
<213> ORGANISM: Artificial Sequence
<220> FEATURE:
<223> OTHER INFORMATION: IL2R? (mouse, mature form of IL2R?
      extracellular domain)

<400> SEQUENCE: 10

Glu Leu Cys Leu Tyr Asp Pro Pro Glu Val Pro Asn Ala Thr Phe Lys
1               5                   10                  15

Ala Leu Ser Tyr Lys Asn Gly Thr Ile Leu Asn Cys Glu Cys Lys Arg
            20                  25                  30

Gly Phe Arg Arg Leu Lys Glu Leu Val Tyr Met Arg Cys Leu Gly Asn
        35                  40                  45

Ser Trp Ser Ser Asn Cys Gln Cys Thr Ser Asn Ile Leu Arg Ala Ser
50                  55                  60

His Asp Lys Ser Arg Lys Gln Val Thr Ala Gln Leu Glu His Gln Lys
65                  70                  75                  80

Glu Gln Gln Thr Thr Thr Asp Met Gln Lys Pro Thr Gln Ser Met His
                85                  90                  95

Gln Glu Asn Leu Thr Gly His Cys Arg Glu Pro Pro Trp Lys His
            100                 105                 110

Glu Asp Ser Lys Arg Ile Tyr His Phe Val Glu Gly Gln Ser Val His
        115                 120                 125

Tyr Glu Cys Ile Pro Gly Tyr Lys Ala Leu Gln Arg Gly Pro Ala Ile
130                 135                 140

Ser Ile Cys Lys Met Lys Cys Gly Lys Thr Gly Trp Thr Gln Pro Gln
145                 150                 155                 160

Leu Thr Cys Val Asp Glu Arg Glu His His Arg Phe Leu Ala Ser Glu
                165                 170                 175

Glu Ser Gln Gly Ser Arg Asn Ser Ser Pro Glu Ser Glu Thr Ser Cys
            180                 185                 190

Pro Ile Thr Thr Thr Asp Phe Pro Gln Pro Thr Glu Thr Thr Ala Met
        195                 200                 205

Thr Glu Thr Phe Val Leu Thr Met Glu Tyr Lys
    210                 215

<210> SEQ ID NO 11
<211> LENGTH: 166
<212> TYPE: PRT
<213> ORGANISM: Artificial Sequence
<220> FEATURE:
<223> OTHER INFORMATION: IL2R? (human, mature form of IL2R?
      extracellular domain) - full-truncated

<400> SEQUENCE: 11

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
50                  55                  60
```

```
Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                 85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu
                165

<210> SEQ ID NO 12
<211> LENGTH: 191
<212> TYPE: PRT
<213> ORGANISM: Artificial Sequence
<220> FEATURE:
<223> OTHER INFORMATION: IL2R? (human, mature form of IL2R?
      extracellular domain) - half-truncated

<400> SEQUENCE: 12

Glu Leu Cys Asp Asp Asp Pro Pro Glu Ile Pro His Ala Thr Phe Lys
 1               5                  10                  15

Ala Met Ala Tyr Lys Glu Gly Thr Met Leu Asn Cys Glu Cys Lys Arg
                 20                  25                  30

Gly Phe Arg Arg Ile Lys Ser Gly Ser Leu Tyr Met Leu Cys Thr Gly
             35                  40                  45

Asn Ser Ser His Ser Ser Trp Asp Asn Gln Cys Gln Cys Thr Ser Ser
 50                  55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                 85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser
            180                 185                 190

<210> SEQ ID NO 13
<211> LENGTH: 364
<212> TYPE: PRT
<213> ORGANISM: Artificial Sequence
<220> FEATURE:
<223> OTHER INFORMATION: IL2(C145S)-CD25(22-240)

<400> SEQUENCE: 13
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Ser Gly Gly Gly Gly
    130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

Cys Leu Val Thr Thr Thr Asp Phe Gln Ile Gln Thr Glu Met Ala Ala
            340                 345                 350

Thr Met Glu Thr Ser Ile Phe Thr Thr Glu Tyr Gln
        355                 360

<210> SEQ ID NO 14
<211> LENGTH: 364
<212> TYPE: PRT
<213> ORGANISM: Artificial Sequence
<220> FEATURE:
<223> OTHER INFORMATION: IL2(C145A)-CD25(22-240)

<400> SEQUENCE: 14

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ala Gln Ser Ile
        115                 120                 125
Ile Ser Thr Leu Thr Gly Gly Gly Ser Gly Gly Gly Ser Gly Gly Gly
    130                 135                 140
Ser Glu Leu Cys Asp Asp Asp Pro Pro Glu Ile Pro His Ala Thr Phe
145                 150                 155                 160
Lys Ala Met Ala Tyr Lys Glu Gly Thr Met Leu Asn Cys Glu Cys Lys
                165                 170                 175
Arg Gly Phe Arg Arg Ile Lys Ser Gly Ser Leu Tyr Met Leu Cys Thr
            180                 185                 190
Gly Asn Ser Ser His Ser Ser Trp Asp Asn Gln Cys Gln Cys Thr Ser
        195                 200                 205
Ser Ala Thr Arg Asn Thr Thr Lys Gln Val Thr Pro Gln Pro Glu Glu
    210                 215                 220
Gln Lys Glu Arg Lys Thr Thr Glu Met Gln Ser Pro Met Gln Pro Val
225                 230                 235                 240
Asp Gln Ala Ser Leu Pro Gly His Cys Arg Glu Pro Pro Pro Trp Glu
                245                 250                 255
Asn Glu Ala Thr Glu Arg Ile Tyr His Phe Val Val Gly Gln Met Val
            260                 265                 270
Tyr Tyr Gln Cys Val Gln Gly Tyr Arg Ala Leu His Arg Gly Pro Ala
        275                 280                 285
Glu Ser Val Cys Lys Met Thr His Gly Lys Thr Arg Trp Thr Gln Pro
    290                 295                 300
Gln Leu Ile Cys Thr Gly Glu Met Glu Thr Ser Gln Phe Pro Gly Glu
305                 310                 315                 320
Glu Lys Pro Gln Ala Ser Pro Glu Gly Arg Pro Glu Ser Glu Thr Ser
                325                 330                 335
Cys Leu Val Thr Thr Thr Asp Phe Gln Ile Gln Thr Glu Met Ala Ala
            340                 345                 350
Thr Met Glu Thr Ser Ile Phe Thr Thr Glu Tyr Gln
        355                 360
```

<210> SEQ ID NO 15
<211> LENGTH: 364
<212> TYPE: PRT
<213> ORGANISM: Artificial Sequence
<220> FEATURE:
<223> OTHER INFORMATION: IL2(C145V)-CD25(22-240)

<400> SEQUENCE: 15

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Val Gln Ser Ile
            115                 120                 125

Ile Ser Thr Leu Thr Gly Gly Gly Ser Gly Gly Gly Ser Gly Gly Gly
    130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
                180                 185                 190

Gly Asn Ser Ser His Ser Ser Trp Asp Asn Gln Cys Gln Cys Thr Ser
                195                 200                 205

Ser Ala Thr Arg Asn Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
                260                 265                 270

Tyr Tyr Gln Cys Val Gln Gly Tyr Arg Ala Leu His Arg Gly Pro Ala
                275                 280                 285

Glu Ser Val Cys Lys Met Thr His Gly Lys Thr Arg Trp Thr Gln Pro
                290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

Cys Leu Val Thr Thr Thr Asp Phe Gln Ile Gln Thr Glu Met Ala Ala
                340                 345                 350

Thr Met Glu Thr Ser Ile Phe Thr Thr Glu Tyr Gln
                355                 360

<210> SEQ ID NO 16
<211> LENGTH: 336
<212> TYPE: PRT
<213> ORGANISM: Artificial Sequence
<220> FEATURE:
<223> OTHER INFORMATION: IL2-CD25(22-212)

<400> SEQUENCE: 16

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr Gly Gly Gly Ser Gly Gly Gly Ser Gly Gly Gly
    130                 135                 140
Ser Glu Leu Cys Asp Asp Asp Pro Pro Glu Ile Pro His Ala Thr Phe
145                 150                 155                 160
Lys Ala Met Ala Tyr Lys Glu Gly Thr Met Leu Asn Cys Glu Cys Lys
                165                 170                 175
Arg Gly Phe Arg Arg Ile Lys Ser Gly Ser Leu Tyr Met Leu Cys Thr
            180                 185                 190
Gly Asn Ser Ser His Ser Ser Trp Asp Asn Gln Cys Gln Cys Thr Ser
        195                 200                 205
Ser Ala Thr Arg Asn Thr Thr Lys Gln Val Thr Pro Gln Pro Glu Glu
    210                 215                 220
Gln Lys Glu Arg Lys Thr Thr Glu Met Gln Ser Pro Met Gln Pro Val
225                 230                 235                 240
Asp Gln Ala Ser Leu Pro Gly His Cys Arg Glu Pro Pro Pro Trp Glu
                245                 250                 255
Asn Glu Ala Thr Glu Arg Ile Tyr His Phe Val Val Gly Gln Met Val
            260                 265                 270
Tyr Tyr Gln Cys Val Gln Gly Tyr Arg Ala Leu His Arg Gly Pro Ala
        275                 280                 285
Glu Ser Val Cys Lys Met Thr His Gly Lys Thr Arg Trp Thr Gln Pro
    290                 295                 300
Gln Leu Ile Cys Thr Gly Glu Met Glu Thr Ser Gln Phe Pro Gly Glu
305                 310                 315                 320
Glu Lys Pro Gln Ala Ser Pro Glu Gly Arg Pro Glu Ser Glu Thr Ser
                325                 330                 335
```

<210> SEQ ID NO 17
<211> LENGTH: 311
<212> TYPE: PRT
<213> ORGANISM: Artificial Sequence
<220> FEATURE:
<223> OTHER INFORMATION: IL2-CD25(22-187)

<400> SEQUENCE: 17

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
```

```
Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Ser Gly Gly Ser Gly Gly Gly
    130                 135                 140

Ser Glu Leu Cys Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300

Gln Leu Ile Cys Thr Gly Glu
305                 310

<210> SEQ ID NO 18
<211> LENGTH: 364
<212> TYPE: PRT
<213> ORGANISM: Artificial Sequence
<220> FEATURE:
<223> OTHER INFORMATION: IL2(C145A)-CD25(C213S, 22-240)

<400> SEQUENCE: 18

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Gly Ser Gly Gly Gly Gly Gly
130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

Ser Leu Val Thr Thr Thr Asp Phe Gln Ile Gln Thr Glu Met Ala Ala
            340                 345                 350

Thr Met Glu Thr Ser Ile Phe Thr Thr Glu Tyr Gln
        355                 360

<210> SEQ ID NO 19
<211> LENGTH: 911
<212> TYPE: PRT
<213> ORGANISM: Artificial Sequence
<220> FEATURE:
<223> OTHER INFORMATION: HSA-(G4S)3- IL2-CD25(22-187)

<400> SEQUENCE: 19

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80
```

-continued

Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp

```
                500             505             510
Ile Cys Thr Leu Ser Glu Lys Glu Arg Gln Ile Lys Lys Gln Thr Ala
            515             520             525
Leu Val Glu Leu Val Lys His Lys Pro Lys Ala Thr Lys Glu Gln Leu
            530             535             540
Lys Ala Val Met Asp Asp Phe Ala Ala Phe Val Glu Lys Cys Cys Lys
545             550             555             560
Ala Asp Asp Lys Glu Thr Cys Phe Ala Glu Glu Gly Lys Lys Leu Val
                565             570             575
Ala Ala Ser Gln Ala Ala Leu Gly Leu Gly Gly Gly Ser Gly Gly
            580             585             590
Gly Gly Ser Gly Gly Gly Ser Ala Pro Thr Ser Ser Ser Thr Lys
        595             600             605
Lys Thr Gln Leu Gln Leu Glu His Leu Leu Leu Asp Leu Gln Met Ile
        610             615             620
Leu Asn Gly Ile Asn Asn Tyr Lys Asn Pro Lys Leu Thr Arg Met Leu
625             630             635             640
Thr Phe Lys Phe Tyr Met Pro Lys Lys Ala Thr Glu Leu Lys His Leu
                645             650             655
Gln Cys Leu Glu Glu Glu Leu Lys Pro Leu Glu Glu Val Leu Asn Leu
            660             665             670
Ala Gln Ser Lys Asn Phe His Leu Arg Pro Arg Asp Leu Ile Ser Asn
            675             680             685
Ile Asn Val Ile Val Leu Glu Leu Lys Gly Ser Glu Thr Thr Phe Met
        690             695             700
Cys Glu Tyr Ala Asp Glu Thr Ala Thr Ile Val Glu Phe Leu Asn Arg
705             710             715             720
Trp Ile Thr Phe Ala Gln Ser Ile Ile Ser Thr Leu Thr Gly Gly Gly
                725             730             735
Ser Gly Gly Gly Ser Gly Gly Gly Ser Glu Leu Cys Asp Asp Asp Pro
            740             745             750
Pro Glu Ile Pro His Ala Thr Phe Lys Ala Met Ala Tyr Lys Glu Gly
            755             760             765
Thr Met Leu Asn Cys Glu Cys Lys Arg Gly Phe Arg Arg Ile Lys Ser
        770             775             780
Gly Ser Leu Tyr Met Leu Cys Thr Gly Asn Ser Ser His Ser Ser Trp
785             790             795             800
Asp Asn Gln Cys Gln Cys Thr Ser Ser Ala Thr Arg Asn Thr Thr Lys
                805             810             815
Gln Val Thr Pro Gln Pro Glu Glu Gln Lys Glu Arg Lys Thr Thr Glu
            820             825             830
Met Gln Ser Pro Met Gln Pro Val Asp Gln Ala Ser Leu Pro Gly His
            835             840             845
Cys Arg Glu Pro Pro Pro Trp Glu Asn Glu Ala Thr Glu Arg Ile Tyr
        850             855             860
His Phe Val Val Gly Gln Met Val Tyr Tyr Gln Cys Val Gln Gly Tyr
865             870             875             880
Arg Ala Leu His Arg Gly Pro Ala Glu Ser Val Cys Lys Met Thr His
                885             890             895
Gly Lys Thr Arg Trp Thr Gln Pro Gln Leu Ile Cys Thr Gly Glu
            900             905             910

<210> SEQ ID NO 20
```

<211> LENGTH: 923
<212> TYPE: PRT
<213> ORGANISM: Artificial Sequence
<220> FEATURE:
<223> OTHER INFORMATION: IL2(C145A)-CD25(22-212)-GG-HSA

<400> SEQUENCE: 20

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Ser Gly Gly Gly Ser Gly Gly Gly
    130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

Gly Gly Asp Ala His Lys Ser Glu Val Ala His Arg Phe Lys Asp Leu
            340                 345                 350

Gly Glu Glu Asn Phe Lys Ala Leu Val Leu Ile Ala Phe Ala Gln Tyr
        355                 360                 365

Leu Gln Gln Ala Pro Phe Glu Asp His Val Lys Leu Val Asn Glu Val
    370                 375                 380
```

```
Thr Glu Phe Ala Lys Thr Cys Val Ala Asp Glu Ser Ala Glu Asn Cys
385                 390                 395                 400

Asp Lys Ser Leu His Thr Leu Phe Gly Asp Lys Leu Cys Thr Val Ala
            405                 410                 415

Thr Leu Arg Glu Thr Tyr Gly Glu Met Ala Asp Cys Cys Ala Lys Gln
        420                 425                 430

Glu Pro Glu Arg Asn Glu Cys Phe Leu Gln His Lys Asp Asp Asn Pro
    435                 440                 445

Asn Leu Pro Arg Leu Val Arg Pro Glu Val Asp Val Met Cys Thr Ala
    450                 455                 460

Phe His Asp Asn Glu Glu Thr Phe Leu Lys Lys Tyr Leu Tyr Glu Ile
465                 470                 475                 480

Ala Arg Arg His Pro Tyr Phe Tyr Ala Pro Glu Leu Leu Phe Phe Ala
                485                 490                 495

Lys Arg Tyr Lys Ala Ala Phe Thr Glu Cys Cys Gln Ala Ala Asp Lys
            500                 505                 510

Ala Ala Cys Leu Leu Pro Lys Leu Asp Glu Leu Arg Asp Glu Gly Lys
        515                 520                 525

Ala Ser Ser Ala Lys Gln Arg Leu Lys Cys Ala Ser Leu Gln Lys Phe
    530                 535                 540

Gly Glu Arg Ala Phe Lys Ala Trp Ala Val Ala Arg Leu Ser Gln Arg
545                 550                 555                 560

Phe Pro Lys Ala Glu Phe Ala Glu Val Ser Lys Leu Val Thr Asp Leu
                565                 570                 575

Thr Lys Val His Thr Glu Cys Cys His Gly Asp Leu Leu Glu Cys Ala
            580                 585                 590

Asp Asp Arg Ala Asp Leu Ala Lys Tyr Ile Cys Glu Asn Gln Asp Ser
        595                 600                 605

Ile Ser Ser Lys Leu Lys Glu Cys Cys Glu Lys Pro Leu Leu Glu Lys
    610                 615                 620

Ser His Cys Ile Ala Glu Val Glu Asn Asp Glu Met Pro Ala Asp Leu
625                 630                 635                 640

Pro Ser Leu Ala Ala Asp Phe Val Glu Ser Lys Asp Val Cys Lys Asn
                645                 650                 655

Tyr Ala Glu Ala Lys Asp Val Phe Leu Gly Met Phe Leu Tyr Glu Tyr
            660                 665                 670

Ala Arg Arg His Pro Asp Tyr Ser Val Val Leu Leu Leu Arg Leu Ala
        675                 680                 685

Lys Thr Tyr Glu Thr Thr Leu Glu Lys Cys Cys Ala Ala Ala Asp Pro
    690                 695                 700

His Glu Cys Tyr Ala Lys Val Phe Asp Glu Phe Lys Pro Leu Val Glu
705                 710                 715                 720

Glu Pro Gln Asn Leu Ile Lys Gln Asn Cys Glu Leu Phe Glu Gln Leu
                725                 730                 735

Gly Glu Tyr Lys Phe Gln Asn Ala Leu Leu Val Arg Tyr Thr Lys Lys
            740                 745                 750

Val Pro Gln Val Ser Thr Pro Thr Leu Val Glu Val Ser Arg Asn Leu
        755                 760                 765

Gly Lys Val Gly Ser Lys Cys Cys Lys His Pro Glu Ala Lys Arg Met
    770                 775                 780

Pro Cys Ala Glu Asp Tyr Leu Ser Val Val Leu Asn Gln Leu Cys Val
785                 790                 795                 800
```

```
Leu His Glu Lys Thr Pro Val Ser Asp Arg Val Thr Lys Cys Cys Thr
                805                 810                 815
Glu Ser Leu Val Asn Arg Arg Pro Cys Phe Ser Ala Leu Glu Val Asp
                820                 825                 830
Glu Thr Tyr Val Pro Lys Glu Phe Asn Ala Glu Thr Phe Thr Phe His
                835                 840                 845
Ala Asp Ile Cys Thr Leu Ser Glu Lys Glu Arg Gln Ile Lys Lys Gln
        850                 855                 860
Thr Ala Leu Val Glu Leu Val Lys His Lys Pro Lys Ala Thr Lys Glu
865                 870                 875                 880
Gln Leu Lys Ala Val Met Asp Asp Phe Ala Ala Phe Val Glu Lys Cys
                885                 890                 895
Cys Lys Ala Asp Asp Lys Glu Thr Cys Phe Ala Glu Glu Gly Lys Lys
                900                 905                 910
Leu Val Ala Ala Ser Gln Ala Ala Leu Gly Leu
                915                 920

<210> SEQ ID NO 21
<211> LENGTH: 319
<212> TYPE: PRT
<213> ORGANISM: Artificial Sequence
<220> FEATURE:
<223> OTHER INFORMATION: IL2(C145A)-CD25(22-192)-GGC

<400> SEQUENCE: 21

Ala Pro Thr Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
                35                  40                  45
Lys Ala Thr Glu Leu Lys His Leu Gln Cys Leu Glu Glu Glu Leu Lys
        50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Ala Gln Ser Ile
        115                 120                 125
Ile Ser Thr Leu Thr Gly Gly Gly Ser Gly Gly Ser Gly Gly Gly
130                 135                 140
Ser Glu Leu Cys Asp Asp Asp Pro Pro Glu Ile Pro His Ala Thr Phe
145                 150                 155                 160
Lys Ala Met Ala Tyr Lys Glu Gly Thr Met Leu Asn Cys Glu Cys Lys
                165                 170                 175
Arg Gly Phe Arg Arg Ile Lys Ser Gly Ser Leu Tyr Met Leu Cys Thr
                180                 185                 190
Gly Asn Ser Ser His Ser Ser Trp Asp Asn Gln Cys Gln Cys Thr Ser
                195                 200                 205
Ser Ala Thr Arg Asn Thr Thr Lys Gln Val Thr Pro Gln Pro Glu Glu
        210                 215                 220
Gln Lys Glu Arg Lys Thr Thr Glu Met Gln Ser Pro Met Gln Pro Val
225                 230                 235                 240
```

Asp Gln Ala Ser Leu Pro Gly His Cys Arg Glu Pro Pro Trp Glu
            245                 250                 255

Asn Glu Ala Thr Glu Arg Ile Tyr His Phe Val Val Gly Gln Met Val
        260                 265                 270

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
        290                 295                 300

Gln Leu Ile Cys Thr Gly Glu Met Glu Thr Ser Gln Gly Gly Cys
305                 310                 315

<210> SEQ ID NO 22
<211> LENGTH: 337
<212> TYPE: PRT
<213> ORGANISM: Artificial Sequence
<220> FEATURE:
<223> OTHER INFORMATION: IL2(C145A)-CD25(22-213)

<400> SEQUENCE: 22

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Ser Gly Gly Gly Ser Gly Gly Gly
    130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

```
Glu Ser Val Cys Lys Met Thr His Gly Lys Thr Arg Trp Thr Gln Pro
            290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

Cys

<210> SEQ ID NO 23
<211> LENGTH: 311
<212> TYPE: PRT
<213> ORGANISM: Artificial Sequence
<220> FEATURE:
<223> OTHER INFORMATION: IL2(C145A)- CD25(22-187, N70C)

<400> SEQUENCE: 23

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Ser Gly Gly Gly Ser Gly Gly Gly
    130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Cys Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
290                 295                 300

Gln Leu Ile Cys Thr Gly Glu
```

<210> SEQ ID NO 24
<211> LENGTH: 311
<212> TYPE: PRT
<213> ORGANISM: Artificial Sequence
<220> FEATURE:
<223> OTHER INFORMATION: IL2(C145A)-CD25(22-187, N89C)

<400> SEQUENCE: 24

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Ser Gly Gly Gly Ser Gly Gly Gly
    130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Cys Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300

Gln Leu Ile Cys Thr Gly Glu
305                 310
```

<210> SEQ ID NO 25
<211> LENGTH: 312
<212> TYPE: PRT
<213> ORGANISM: Artificial Sequence
<220> FEATURE:
<223> OTHER INFORMATION: IL2(C145A)-CD25(22-187)-C

<400> SEQUENCE: 25

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
                115                 120                 125

Ile Ser Thr Leu Thr Gly Gly Gly Ser Gly Gly Gly Ser Gly Gly Gly
130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
            245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300

Gln Leu Ile Cys Thr Gly Glu Cys
305                 310

<210> SEQ ID NO 26
<211> LENGTH: 539
<212> TYPE: PRT
<213> ORGANISM: Artificial Sequence
<220> FEATURE:
<223> OTHER INFORMATION: Human Fc1.1(f)-AZ1-IL2(C145S)-CD25(22-187)-G

<400> SEQUENCE: 26

Asp Lys Thr His Thr Cys Pro Pro Cys Pro Ala Pro Glu Ala Glu Gly
1               5                   10                  15

Ala Pro Ser Val Phe Leu Phe Pro Pro Lys Pro Lys Asp Thr Leu Met
            20                  25                  30

```
Ile Ser Arg Thr Pro Glu Val Thr Cys Val Val Val Asp Val Ser His
 35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ser Ser Ile
            100                 105                 110
Glu Lys Thr Ile Ser Lys Ala Lys Gly Gln Pro Arg Glu Pro Gln Val
            115                 120                 125
Tyr Val Tyr Pro Pro Ser Arg Glu Glu Met Thr Lys Asn Gln Val Ser
            130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Ala Leu Val Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
            210                 215                 220
Pro Gly Ala Ala Pro Thr Ser Ser Ser Thr Lys Lys Thr Gln Leu Gln
225                 230                 235                 240
Leu Glu His Leu Leu Leu Asp Leu Gln Met Ile Leu Asn Gly Ile Asn
                245                 250                 255
Asn Tyr Lys Asn Pro Lys Leu Thr Arg Met Leu Thr Phe Lys Phe Tyr
            260                 265                 270
Met Pro Lys Lys Ala Thr Glu Leu Lys His Leu Gln Cys Leu Glu Glu
            275                 280                 285
Glu Leu Lys Pro Leu Glu Glu Val Leu Asn Leu Ala Gln Ser Lys Asn
            290                 295                 300
Phe His Leu Arg Pro Arg Asp Leu Ile Ser Asn Ile Asn Val Ile Val
305                 310                 315                 320
Leu Glu Leu Lys Gly Ser Glu Thr Thr Phe Met Cys Glu Tyr Ala Asp
                325                 330                 335
Glu Thr Ala Thr Ile Val Glu Phe Leu Asn Arg Trp Ile Thr Phe Ser
            340                 345                 350
Gln Ser Ile Ile Ser Thr Leu Thr Gly Gly Gly Ser Gly Gly Gly Ser
            355                 360                 365
Gly Gly Gly Ser Glu Leu Cys Asp Asp Pro Pro Glu Ile Pro His
            370                 375                 380
Ala Thr Phe Lys Ala Met Ala Tyr Lys Glu Gly Thr Met Leu Asn Cys
385                 390                 395                 400
Glu Cys Lys Arg Gly Phe Arg Arg Ile Lys Ser Gly Ser Leu Tyr Met
                405                 410                 415
Leu Cys Thr Gly Asn Ser Ser His Ser Ser Trp Asp Asn Gln Cys Gln
            420                 425                 430
Cys Thr Ser Ser Ala Thr Arg Asn Thr Thr Lys Gln Val Thr Pro Gln
            435                 440                 445
Pro Glu Glu Gln Lys Glu Arg Lys Thr Thr Glu Met Gln Ser Pro Met
```

```
                       450                 455                 460
Gln Pro Val Asp Gln Ala Ser Leu Pro Gly His Cys Arg Glu Pro Pro
465                 470                 475                 480

Pro Trp Glu Asn Glu Ala Thr Glu Arg Ile Tyr His Phe Val Val Gly
                485                 490                 495

Gln Met Val Tyr Tyr Gln Cys Val Gln Gly Tyr Arg Ala Leu His Arg
                500                 505                 510

Gly Pro Ala Glu Ser Val Cys Lys Met Thr His Gly Lys Thr Arg Trp
            515                 520                 525

Thr Gln Pro Gln Leu Ile Cys Thr Gly Glu Gly
        530                 535

<210> SEQ ID NO 27
<211> LENGTH: 541
<212> TYPE: PRT
<213> ORGANISM: Artificial Sequence
<220> FEATURE:
<223> OTHER INFORMATION: IL2(C145S)-CD25(22-187)- HuFc1.1(f)-AZ1

<400> SEQUENCE: 27

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Gly Ser Gly Gly Gly Ser Gly Gly
130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
```

```
                275                 280                 285
Glu Ser Val Cys Lys Met Thr His Gly Lys Thr Arg Trp Thr Gln Pro
290                 295                 300
Gln Leu Ile Cys Thr Gly Glu Pro Lys Ser Ser Asp Lys Thr His Thr
305                 310                 315                 320
Cys Pro Pro Cys Pro Ala Pro Glu Ala Glu Gly Ala Pro Ser Val Phe
                325                 330                 335
Leu Phe Pro Pro Lys Pro Lys Asp Thr Leu Met Ile Ser Arg Thr Pro
                340                 345                 350
Glu Val Thr Cys Val Val Val Asp Val Ser His Glu Asp Pro Glu Val
                355                 360                 365
Lys Phe Asn Trp Tyr Val Asp Gly Val Glu Val His Asn Ala Lys Thr
370                 375                 380
Lys Pro Arg Glu Glu Gln Tyr Asn Ser Thr Tyr Arg Val Val Ser Val
385                 390                 395                 400
Leu Thr Val Leu His Gln Asp Trp Leu Asn Gly Lys Glu Tyr Lys Cys
                405                 410                 415
Lys Val Ser Asn Lys Ala Leu Pro Ser Ser Ile Glu Lys Thr Ile Ser
                420                 425                 430
Lys Ala Lys Gly Gln Pro Arg Glu Pro Gln Val Tyr Val Tyr Pro Pro
                435                 440                 445
Ser Arg Glu Glu Met Thr Lys Asn Gln Val Ser Leu Thr Cys Leu Val
                450                 455                 460
Lys Gly Phe Tyr Pro Ser Asp Ile Ala Val Glu Trp Glu Ser Asn Gly
465                 470                 475                 480
Gln Pro Glu Asn Asn Tyr Lys Thr Thr Pro Pro Val Leu Asp Ser Asp
                485                 490                 495
Gly Ser Phe Ala Leu Val Ser Lys Leu Thr Val Asp Lys Ser Arg Trp
                500                 505                 510
Gln Gln Gly Asn Val Phe Ser Cys Ser Val Met His Glu Ala Leu His
                515                 520                 525
Asn His Tyr Thr Gln Lys Ser Leu Ser Leu Ser Pro Gly
                530                 535                 540

<210> SEQ ID NO 28

<400> SEQUENCE: 28

000

<210> SEQ ID NO 29
<211> LENGTH: 311
<212> TYPE: PRT
<213> ORGANISM: Artificial Sequence
<220> FEATURE:
<223> OTHER INFORMATION: IL2-C145S-CD25(22-187)

<400> SEQUENCE: 29

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
                35                  40                  45
Lys Ala Thr Glu Leu Lys His Leu Gln Cys Leu Glu Glu Glu Leu Lys
                50                  55                  60
```

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Gly Gly Ser Gly Gly Gly Ser Gly Gly Gly
130                 135                 140

Ser Glu Leu Cys Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
                180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
290                 295                 300

Gln Leu Ile Cys Thr Gly Glu
305                 310

<210> SEQ ID NO 30
<211> LENGTH: 311
<212> TYPE: PRT
<213> ORGANISM: Artificial Sequence
<220> FEATURE:
<223> OTHER INFORMATION: IL2-T23A-C145S-CD25(22-187)

<400> SEQUENCE: 30

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Leu Lys
                55                  60
    50

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

```
Thr Ile Val Glu Phe Leu Asn Arg Trp Ile Thr Phe Ser Gln Ser Ile
            115                 120                 125

Ile Ser Thr Leu Thr Gly Gly Ser Gly Gly Gly Ser Gly Gly Gly
        130                 135                 140

Ser Glu Leu Cys Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
            245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
            290                 295                 300

Gln Leu Ile Cys Thr Gly Glu
305                 310

<210> SEQ ID NO 31
<211> LENGTH: 364
<212> TYPE: PRT
<213> ORGANISM: Artificial Sequence
<220> FEATURE:
<223> OTHER INFORMATION: IL2-CD25(22-240)-C213S

<400> SEQUENCE: 31

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Gly Ser Gly Gly Gly Ser Gly Gly Gly
        130                 135                 140

Ser Glu Leu Cys Asp Asp Pro Pro Glu Ile Pro His Ala Thr Phe
145                 150                 155                 160
```

```
Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Trp Glu
                245                 250                 255

Asn Glu Ala Thr Glu Arg Ile Tyr His Phe Val Val Gly Gln Met Val
                260                 265                 270

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

Ser Leu Val Thr Thr Thr Asp Phe Gln Ile Gln Thr Glu Met Ala Ala
            340                 345                 350

Thr Met Glu Thr Ser Ile Phe Thr Thr Glu Tyr Gln
                355                 360

<210> SEQ ID NO 32
<211> LENGTH: 364
<212> TYPE: PRT
<213> ORGANISM: Artificial Sequence
<220> FEATURE:
<223> OTHER INFORMATION: IL2-T23A-C145S-CD25(22-240)-C213S

<400> SEQUENCE: 32

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Gly Gly Ser Gly Gly Gly Ser Gly Gly Gly
            130                 135                 140

Ser Glu Leu Cys Asp Asp Asp Pro Pro Glu Ile Pro His Ala Thr Phe
145                 150                 155                 160
```

```
Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
        210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

Ser Leu Val Thr Thr Thr Asp Phe Gln Ile Gln Thr Glu Met Ala Ala
            340                 345                 350

Thr Met Glu Thr Ser Ile Phe Thr Thr Glu Tyr Gln
            355                 360

<210> SEQ ID NO 33
<211> LENGTH: 331
<212> TYPE: PRT
<213> ORGANISM: Artificial Sequence
<220> FEATURE:
<223> OTHER INFORMATION: NativeSigPep-IL2-CD25(22-187)

<400> SEQUENCE: 33

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Gly Ser Gly Gly
145                 150                 155                 160
```

```
Ser Gly Gly Gly Ser Glu Leu Cys Asp Asp Asp Pro Glu Ile Pro
            165                 170                 175

His Ala Thr Phe Lys Ala Met Ala Tyr Lys Glu Gly Thr Met Leu Asn
            180                 185                 190

Cys Glu Cys Lys Arg Gly Phe Arg Arg Ile Lys Ser Gly Ser Leu Tyr
            195                 200                 205

Met Leu Cys Thr Gly Asn Ser Ser His Ser Ser Trp Asp Asn Gln Cys
            210                 215                 220

Gln Cys Thr Ser Ser Ala Thr Arg Asn Thr Thr Lys Gln Val Thr Pro
225                 230                 235                 240

Gln Pro Glu Glu Gln Lys Glu Arg Lys Thr Thr Glu Met Gln Ser Pro
            245                 250                 255

Met Gln Pro Val Asp Gln Ala Ser Leu Pro Gly His Cys Arg Glu Pro
            260                 265                 270

Pro Pro Trp Glu Asn Glu Ala Thr Glu Arg Ile Tyr His Phe Val Val
            275                 280                 285

Gly Gln Met Val Tyr Tyr Gln Cys Val Gln Gly Tyr Arg Ala Leu His
            290                 295                 300

Arg Gly Pro Ala Glu Ser Val Cys Lys Met Thr His Gly Lys Thr Arg
305                 310                 315                 320

Trp Thr Gln Pro Gln Leu Ile Cys Thr Gly Glu
            325                 330

<210> SEQ ID NO 34
<211> LENGTH: 358
<212> TYPE: PRT
<213> ORGANISM: Artificial Sequence
<220> FEATURE:
<223> OTHER INFORMATION: NativeSigPep-HuIL2-CD25(22-212)-PP

<400> SEQUENCE: 34

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
            85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr Gly Gly Gly Ser Gly Gly Gly
145                 150                 155                 160

Ser Gly Gly Gly Ser Glu Leu Cys Asp Asp Asp Pro Glu Ile Pro
            165                 170                 175

His Ala Thr Phe Lys Ala Met Ala Tyr Lys Glu Gly Thr Met Leu Asn
            180                 185                 190
```

```
Cys Glu Cys Lys Arg Gly Phe Arg Arg Ile Lys Ser Gly Ser Leu Tyr
            195                 200                 205
Met Leu Cys Thr Gly Asn Ser Ser His Ser Ser Trp Asp Asn Gln Cys
    210                 215                 220
Gln Cys Thr Ser Ser Ala Thr Arg Asn Thr Thr Lys Gln Val Thr Pro
225                 230                 235                 240
Gln Pro Glu Glu Gln Lys Glu Arg Lys Thr Thr Glu Met Gln Ser Pro
                245                 250                 255
Met Gln Pro Val Asp Gln Ala Ser Leu Pro Gly His Cys Arg Glu Pro
            260                 265                 270
Pro Pro Trp Glu Asn Glu Ala Thr Glu Arg Ile Tyr His Phe Val Val
        275                 280                 285
Gly Gln Met Val Tyr Tyr Gln Cys Val Gln Gly Tyr Arg Ala Leu His
    290                 295                 300
Arg Gly Pro Ala Glu Ser Val Cys Lys Met Thr His Gly Lys Thr Arg
305                 310                 315                 320
Trp Thr Gln Pro Gln Leu Ile Cys Thr Gly Glu Met Glu Thr Ser Gln
                325                 330                 335
Phe Pro Gly Glu Glu Lys Pro Gln Ala Ser Pro Glu Gly Arg Pro Glu
            340                 345                 350
Ser Glu Thr Ser Pro Pro
            355

<210> SEQ ID NO 35
<211> LENGTH: 365
<212> TYPE: PRT
<213> ORGANISM: Artificial Sequence
<220> FEATURE:
<223> OTHER INFORMATION: M-IL2(C145S)-CD25(C213S)

<400> SEQUENCE: 35

Met Ala Pro Thr Ser Ser Ser Thr Lys Lys Thr Gln Leu Gln Leu Glu
1               5                   10                  15
His Leu Leu Leu Asp Leu Gln Met Ile Leu Asn Gly Ile Asn Asn Tyr
            20                  25                  30
Lys Asn Pro Lys Leu Thr Arg Met Leu Thr Phe Lys Phe Tyr Met Pro
        35                  40                  45
Lys Lys Ala Thr Glu Leu Lys His Leu Gln Cys Leu Glu Glu Glu Leu
    50                  55                  60
Lys Pro Leu Glu Glu Val Leu Asn Leu Ala Gln Ser Lys Asn Phe His
65                  70                  75                  80
Leu Arg Pro Arg Asp Leu Ile Ser Asn Ile Asn Val Ile Val Leu Glu
                85                  90                  95
Leu Lys Gly Ser Glu Thr Thr Phe Met Cys Glu Tyr Ala Asp Glu Thr
            100                 105                 110
Ala Thr Ile Val Glu Phe Leu Asn Arg Trp Ile Thr Phe Ser Gln Ser
        115                 120                 125
Ile Ile Ser Thr Leu Thr Gly Gly Gly Ser Gly Gly Gly Ser Gly Gly
    130                 135                 140
Gly Ser Glu Leu Cys Asp Asp Asp Pro Pro Glu Ile Pro His Ala Thr
145                 150                 155                 160
Phe Lys Ala Met Ala Tyr Lys Glu Gly Thr Met Leu Asn Cys Glu Cys
                165                 170                 175
Lys Arg Gly Phe Arg Arg Ile Lys Ser Gly Ser Leu Tyr Met Leu Cys
            180                 185                 190
```

Thr Gly Asn Ser Ser His Ser Ser Trp Asp Asn Gln Cys Gln Cys Thr
            195                 200                 205

Ser Ser Ala Thr Arg Asn Thr Thr Lys Gln Val Thr Pro Gln Pro Glu
    210                 215                 220

Glu Gln Lys Glu Arg Lys Thr Thr Glu Met Gln Ser Pro Met Gln Pro
225                 230                 235                 240

Val Asp Gln Ala Ser Leu Pro Gly His Cys Arg Glu Pro Pro Pro Trp
                245                 250                 255

Glu Asn Glu Ala Thr Glu Arg Ile Tyr His Phe Val Val Gly Gln Met
                260                 265                 270

Val Tyr Tyr Gln Cys Val Gln Gly Tyr Arg Ala Leu His Arg Gly Pro
            275                 280                 285

Ala Glu Ser Val Cys Lys Met Thr His Gly Lys Thr Arg Trp Thr Gln
    290                 295                 300

Pro Gln Leu Ile Cys Thr Gly Glu Met Glu Thr Ser Gln Phe Pro Gly
305                 310                 315                 320

Glu Glu Lys Pro Gln Ala Ser Pro Glu Gly Arg Pro Glu Ser Glu Thr
                325                 330                 335

Ser Ser Leu Val Thr Thr Thr Asp Phe Gln Ile Gln Thr Glu Met Ala
            340                 345                 350

Ala Thr Met Glu Thr Ser Ile Phe Thr Thr Glu Tyr Gln
    355                 360                 365

<210> SEQ ID NO 36
<211> LENGTH: 365
<212> TYPE: PRT
<213> ORGANISM: Artificial Sequence
<220> FEATURE:
<223> OTHER INFORMATION: M-IL2(C145S)-CD25(C213S)

<400> SEQUENCE: 36

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ser Gln Ser
        115                 120                 125

Ile Ile Ser Thr Leu Thr Gly Gly Ser Gly Gly Gly Ser Gly Gly
    130                 135                 140

Gly Ser Glu Leu Cys Asp Asp Asp Pro Pro Glu Ile Pro His Ala Thr
145                 150                 155                 160

Phe Lys Ala Met Ala Tyr Lys Glu Gly Thr Met Leu Asn Cys Glu Cys
                165                 170                 175

Lys Arg Gly Phe Arg Arg Ile Lys Ser Gly Ser Leu Tyr Met Leu Cys
            180                 185                 190

Thr Gly Asn Ser Ser His Ser Ser Trp Asp Asn Gln Cys Gln Cys Thr
            195                 200                 205

Ser Ser Ala Thr Arg Asn Thr Thr Lys Gln Val Thr Pro Gln Pro Glu
    210                 215                 220

Glu Gln Lys Glu Arg Lys Thr Thr Glu Met Gln Ser Pro Met Gln Pro
225                 230                 235                 240

Val Asp Gln Ala Ser Leu Pro Gly His Cys Arg Glu Pro Pro Pro Trp
                245                 250                 255

Glu Asn Glu Ala Thr Glu Arg Ile Tyr His Phe Val Val Gly Gln Met
            260                 265                 270

Val Tyr Tyr Gln Cys Val Gln Gly Tyr Arg Ala Leu His Arg Gly Pro
    275                 280                 285

Ala Glu Ser Val Cys Lys Met Thr His Gly Lys Thr Arg Trp Thr Gln
290                 295                 300

Pro Gln Leu Ile Cys Thr Gly Glu Met Glu Thr Ser Gln Phe Pro Gly
305                 310                 315                 320

Glu Glu Lys Pro Gln Ala Ser Pro Glu Gly Arg Pro Glu Ser Glu Thr
                325                 330                 335

Ser Ser Leu Val Thr Thr Thr Asp Phe Gln Ile Gln Thr Glu Met Ala
            340                 345                 350

Ala Thr Met Glu Thr Ser Ile Phe Thr Thr Glu Tyr Gln
        355                 360                 365

<210> SEQ ID NO 37
<211> LENGTH: 337
<212> TYPE: PRT
<213> ORGANISM: Artificial Sequence
<220> FEATURE:
<223> OTHER INFORMATION: M-IL2-C145A-CD25(22-212)

<400> SEQUENCE: 37

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr Gly Gly Gly Gly Ser Gly Gly Ser Gly Gly
    130                 135                 140

Gly Ser Glu Leu Cys Asp Asp Asp Pro Pro Glu Ile Pro His Ala Thr
145                 150                 155                 160

Phe Lys Ala Met Ala Tyr Lys Glu Gly Thr Met Leu Asn Cys Glu Cys
                165                 170                 175

Lys Arg Gly Phe Arg Arg Ile Lys Ser Gly Ser Leu Tyr Met Leu Cys
            180                 185                 190

```
Thr Gly Asn Ser Ser His Ser Ser Trp Asp Asn Gln Cys Gln Cys Thr
            195                 200                 205

Ser Ser Ala Thr Arg Asn Thr Thr Lys Gln Val Thr Pro Gln Pro Glu
    210                 215                 220

Glu Gln Lys Glu Arg Lys Thr Thr Glu Met Gln Ser Pro Met Gln Pro
225                 230                 235                 240

Val Asp Gln Ala Ser Leu Pro Gly His Cys Arg Glu Pro Pro Pro Trp
                245                 250                 255

Glu Asn Glu Ala Thr Glu Arg Ile Tyr His Phe Val Val Gly Gln Met
                260                 265                 270

Val Tyr Tyr Gln Cys Val Gln Gly Tyr Arg Ala Leu His Arg Gly Pro
    275                 280                 285

Ala Glu Ser Val Cys Lys Met Thr His Gly Lys Thr Arg Trp Thr Gln
290                 295                 300

Pro Gln Leu Ile Cys Thr Gly Glu Met Glu Thr Ser Gln Phe Pro Gly
305                 310                 315                 320

Glu Glu Lys Pro Gln Ala Ser Pro Glu Gly Arg Pro Glu Ser Glu Thr
                325                 330                 335

Ser

<210> SEQ ID NO 38
<211> LENGTH: 337
<212> TYPE: PRT
<213> ORGANISM: Artificial Sequence
<220> FEATURE:
<223> OTHER INFORMATION: M-IL2-C145A-CD25(22-212)

<400> SEQUENCE: 38

Met Ala Pro Thr Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
                20                  25                  30

Lys Asn Pro Lys Leu Thr Arg Met Leu Thr Phe Lys Phe Tyr Met Pro
            35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
    115                 120                 125

Ile Ile Ser Thr Leu Thr Gly Gly Ser Gly Gly Ser Gly Gly
130                 135                 140

Gly Ser Glu Leu Cys Asp Asp Pro Pro Glu Ile Pro His Ala Thr
145                 150                 155                 160

Phe Lys Ala Met Ala Tyr Lys Glu Gly Thr Met Leu Asn Cys Glu Cys
                165                 170                 175

Lys Arg Gly Phe Arg Arg Ile Lys Ser Gly Ser Leu Tyr Met Leu Cys
            180                 185                 190

Thr Gly Asn Ser Ser His Ser Ser Trp Asp Asn Gln Cys Gln Cys Thr
    195                 200                 205

Ser Ser Ala Thr Arg Asn Thr Thr Lys Gln Val Thr Pro Gln Pro Glu
```

```
                    210                 215                 220
Glu Gln Lys Glu Arg Lys Thr Thr Glu Met Gln Ser Pro Met Gln Pro
225                 230                 235                 240

Val Asp Gln Ala Ser Leu Pro Gly His Cys Arg Glu Pro Pro Pro Trp
                    245                 250                 255

Glu Asn Glu Ala Thr Glu Arg Ile Tyr His Phe Val Val Gly Gln Met
                    260                 265                 270

Val Tyr Tyr Gln Cys Val Gln Gly Tyr Arg Ala Leu His Arg Gly Pro
                275                 280                 285

Ala Glu Ser Val Cys Lys Met Thr His Gly Lys Thr Arg Trp Thr Gln
            290                 295                 300

Pro Gln Leu Ile Cys Thr Gly Glu Met Glu Thr Ser Gln Phe Pro Gly
305                 310                 315                 320

Glu Glu Lys Pro Gln Ala Ser Pro Glu Gly Arg Pro Gly Ser Glu Thr
                325                 330                 335

Ser

<210> SEQ ID NO 39
<211> LENGTH: 335
<212> TYPE: PRT
<213> ORGANISM: Artificial Sequence
<220> FEATURE:
<223> OTHER INFORMATION: Del-A21-IL2-CD(22-212)

<400> SEQUENCE: 39

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr Gly Gly Gly Ser Gly Gly Gly Ser Gly Gly Gly Ser
130                 135                 140

Glu Leu Cys Asp Asp Asp Pro Pro Glu Ile Pro His Ala Thr Phe Lys
145                 150                 155                 160

Ala Met Ala Tyr Lys Glu Gly Thr Met Leu Asn Cys Glu Cys Lys Arg
                165                 170                 175

Gly Phe Arg Arg Ile Lys Ser Gly Ser Leu Tyr Met Leu Cys Thr Gly
            180                 185                 190

Asn Ser Ser His Ser Ser Trp Asp Asn Gln Cys Gln Cys Thr Ser Ser
        195                 200                 205

Ala Thr Arg Asn Thr Thr Lys Gln Val Thr Pro Gln Pro Glu Glu Gln
    210                 215                 220

Lys Glu Arg Lys Thr Thr Glu Met Gln Ser Pro Met Gln Pro Val Asp
225                 230                 235                 240
```

```
Gln Ala Ser Leu Pro Gly His Cys Arg Glu Pro Pro Trp Glu Asn
                245                 250                 255

Glu Ala Thr Glu Arg Ile Tyr His Phe Val Val Gly Gln Met Val Tyr
            260                 265                 270

Tyr Gln Cys Val Gln Gly Tyr Arg Ala Leu His Arg Gly Pro Ala Glu
        275                 280                 285

Ser Val Cys Lys Met Thr His Gly Lys Thr Arg Trp Thr Gln Pro Gln
    290                 295                 300

Leu Ile Cys Thr Gly Glu Met Glu Thr Ser Gln Phe Pro Gly Glu Glu
305                 310                 315                 320

Lys Pro Gln Ala Ser Pro Glu Gly Arg Pro Glu Ser Glu Thr Ser
                325                 330                 335

<210> SEQ ID NO 40
<211> LENGTH: 336
<212> TYPE: PRT
<213> ORGANISM: Artificial Sequence
<220> FEATURE:
<223> OTHER INFORMATION: IL2-T23A-L2-CD25(22-212)

<400> SEQUENCE: 40

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Ser Ser Gly Ala Gly Gly Gly Gly
    130                 135                 140

Ser Glu Leu Cys Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Trp Glu
                245                 250                 255

Asn Glu Ala Thr Glu Arg Ile Tyr His Phe Val Val Gly Gln Met Val
            260                 265                 270
```

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
            325                 330                 335

<210> SEQ ID NO 41
<211> LENGTH: 344
<212> TYPE: PRT
<213> ORGANISM: Artificial Sequence
<220> FEATURE:
<223> OTHER INFORMATION: IL2-T3A-L3-CD(22-212)

<400> SEQUENCE: 41

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Gly Gly
    130                 135                 140

Ser Gly Gly Gly Ser Gly Gly Gly Ser Glu Leu Cys Asp Asp Asp Pro
145                 150                 155                 160

Pro Glu Ile Pro His Ala Thr Phe Lys Ala Met Ala Tyr Lys Glu Gly
                165                 170                 175

Thr Met Leu Asn Cys Glu Cys Lys Arg Gly Phe Arg Arg Ile Lys Ser
            180                 185                 190

Gly Ser Leu Tyr Met Leu Cys Thr Gly Asn Ser Ser His Ser Ser Trp
        195                 200                 205

Asp Asn Gln Cys Gln Cys Thr Ser Ser Ala Thr Arg Asn Thr Thr Lys
    210                 215                 220

Gln Val Thr Pro Gln Pro Glu Glu Gln Lys Glu Arg Lys Thr Thr Glu
225                 230                 235                 240

Met Gln Ser Pro Met Gln Pro Val Asp Gln Ala Ser Leu Pro Gly His
                245                 250                 255

Cys Arg Glu Pro Pro Pro Trp Glu Asn Glu Ala Thr Glu Arg Ile Tyr
            260                 265                 270

His Phe Val Val Gly Gln Met Val Tyr Tyr Gln Cys Val Gln Gly Tyr
        275                 280                 285

Arg Ala Leu His Arg Gly Pro Ala Glu Ser Val Cys Lys Met Thr His
    290                 295                 300

Gly Lys Thr Arg Trp Thr Gln Pro Gln Leu Ile Cys Thr Gly Glu Met
305                 310                 315                 320

Glu Thr Ser Gln Phe Pro Gly Glu Glu Lys Pro Gln Ala Ser Pro Glu
            325                 330                 335

Gly Arg Pro Glu Ser Glu Thr Ser
            340

<210> SEQ ID NO 42

<400> SEQUENCE: 42

000

<210> SEQ ID NO 43
<211> LENGTH: 311
<212> TYPE: PRT
<213> ORGANISM: Artificial Sequence
<220> FEATURE:
<223> OTHER INFORMATION: IL2-T23A-C145S-CD25(22-187)

<400> SEQUENCE: 43

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Gly Ser Gly Gly Gly Gly
    130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala

```
            275                 280                 285
Glu Ser Val Cys Lys Met Thr His Gly Lys Thr Arg Trp Thr Gln Pro
        290                 295                 300

Gln Leu Ile Cys Thr Gly Glu
305                 310

<210> SEQ ID NO 44
<211> LENGTH: 364
<212> TYPE: PRT
<213> ORGANISM: Artificial Sequence
<220> FEATURE:
<223> OTHER INFORMATION: IL2-T23A-C145S-CD25(22-240)-C213S

<400> SEQUENCE: 44

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly Gly Gly
130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
        290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
```

```
                    325                 330                 335
Ser Leu Val Thr Thr Thr Asp Phe Gln Ile Gln Thr Glu Met Ala Ala
                340                 345                 350

Thr Met Glu Thr Ser Ile Phe Thr Thr Glu Tyr Gln
            355                 360

<210> SEQ ID NO 45
<211> LENGTH: 311
<212> TYPE: PRT
<213> ORGANISM: Artificial Sequence
<220> FEATURE:
<223> OTHER INFORMATION: IL2-T23A-CD25(22-187)

<400> SEQUENCE: 45

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly Gly Gly
130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300

Gln Leu Ile Cys Thr Gly Glu
305                 310
```

```
<210> SEQ ID NO 46
<211> LENGTH: 336
<212> TYPE: PRT
<213> ORGANISM: Artificial Sequence
<220> FEATURE:
<223> OTHER INFORMATION: IL2-T23A-CD25(22-212)-T106A

<400> SEQUENCE: 46
```

| | | | | | | | | | | | | | | | |
|---|---|---|---|---|---|---|---|---|---|---|---|---|---|---|---|
| Ala | Pro | Ala | Ser | Ser | Ser | Thr | Lys | Lys | Thr | Gln | Leu | Gln | Leu | Glu | His |
| 1 | | | | 5 | | | | | 10 | | | | | 15 | |
| Leu | Leu | Leu | Asp | Leu | Gln | Met | Ile | Leu | Asn | Gly | Ile | Asn | Asn | Tyr | Lys |
| | | | 20 | | | | | 25 | | | | | 30 | | |
| Asn | Pro | Lys | Leu | Thr | Arg | Met | Leu | Thr | Phe | Lys | Phe | Tyr | Met | Pro | Lys |
| | | 35 | | | | | 40 | | | | | 45 | | | |
| Lys | Ala | Thr | Glu | Leu | Lys | His | Leu | Gln | Cys | Leu | Glu | Glu | Glu | Leu | Lys |
| | 50 | | | | | 55 | | | | | 60 | | | | |
| Pro | Leu | Glu | Glu | Val | Leu | Asn | Leu | Ala | Gln | Ser | Lys | Asn | Phe | His | Leu |
| 65 | | | | | 70 | | | | | 75 | | | | | 80 |
| Arg | Pro | Arg | Asp | Leu | Ile | Ser | Asn | Ile | Asn | Val | Ile | Val | Leu | Glu | Leu |
| | | | | 85 | | | | | 90 | | | | | 95 | |
| Lys | Gly | Ser | Glu | Thr | Thr | Phe | Met | Cys | Glu | Tyr | Ala | Asp | Glu | Thr | Ala |
| | | | 100 | | | | | 105 | | | | | 110 | | |
| Thr | Ile | Val | Glu | Phe | Leu | Asn | Arg | Trp | Ile | Thr | Phe | Cys | Gln | Ser | Ile |
| | | 115 | | | | | 120 | | | | | 125 | | | |
| Ile | Ser | Thr | Leu | Thr | Gly | Gly | Gly | Gly | Ser | Gly | Gly | Gly | Gly | Ser | Gly |
| | 130 | | | | | 135 | | | | | 140 | | | | |
| Ser | Glu | Leu | Cys | Asp | Asp | Asp | Pro | Pro | Glu | Ile | Pro | His | Ala | Thr | Phe |
| 145 | | | | | 150 | | | | | 155 | | | | | 160 |
| Lys | Ala | Met | Ala | Tyr | Lys | Glu | Gly | Thr | Met | Leu | Asn | Cys | Glu | Cys | Lys |
| | | | | 165 | | | | | 170 | | | | | 175 | |
| Arg | Gly | Phe | Arg | Arg | Ile | Lys | Ser | Gly | Ser | Leu | Tyr | Met | Leu | Cys | Thr |
| | | | 180 | | | | | 185 | | | | | 190 | | |
| Gly | Asn | Ser | Ser | His | Ser | Ser | Trp | Asp | Asn | Gln | Cys | Gln | Cys | Thr | Ser |
| | | 195 | | | | | 200 | | | | | 205 | | | |
| Ser | Ala | Thr | Arg | Asn | Thr | Thr | Lys | Gln | Val | Thr | Pro | Gln | Pro | Glu | Glu |
| | 210 | | | | | 215 | | | | | 220 | | | | |
| Gln | Lys | Glu | Arg | Lys | Ala | Thr | Glu | Met | Gln | Ser | Pro | Met | Gln | Pro | Val |
| 225 | | | | | 230 | | | | | 235 | | | | | 240 |
| Asp | Gln | Ala | Ser | Leu | Pro | Gly | His | Cys | Arg | Glu | Pro | Pro | Pro | Trp | Glu |
| | | | | 245 | | | | | 250 | | | | | 255 | |
| Asn | Glu | Ala | Thr | Glu | Arg | Ile | Tyr | His | Phe | Val | Val | Gly | Gln | Met | Val |
| | | | 260 | | | | | 265 | | | | | 270 | | |
| Tyr | Tyr | Gln | Cys | Val | Gln | Gly | Tyr | Arg | Ala | Leu | His | Arg | Gly | Pro | Ala |
| | | 275 | | | | | 280 | | | | | 285 | | | |
| Glu | Ser | Val | Cys | Lys | Met | Thr | His | Gly | Lys | Thr | Arg | Trp | Thr | Gln | Pro |
| | 290 | | | | | 295 | | | | | 300 | | | | |
| Gln | Leu | Ile | Cys | Thr | Gly | Glu | Met | Glu | Thr | Ser | Gln | Phe | Pro | Gly | Glu |
| 305 | | | | | 310 | | | | | 315 | | | | | 320 |
| Glu | Lys | Pro | Gln | Ala | Ser | Pro | Glu | Gly | Arg | Pro | Glu | Ser | Glu | Thr | Ser |
| | | | | 325 | | | | | 330 | | | | | 335 | |

```
<210> SEQ ID NO 47
<211> LENGTH: 336
<212> TYPE: PRT
<213> ORGANISM: Artificial Sequence
<220> FEATURE:
<223> OTHER INFORMATION: IL2-T23A-CD25(22-212)-T95A
```

<400> SEQUENCE: 47

```
Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr Gly Gly Gly Ser Gly Gly Gly Ser Gly Gly Gly
130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Ala Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335
```

<210> SEQ ID NO 48

<400> SEQUENCE: 48

000

<210> SEQ ID NO 49
<211> LENGTH: 336
<212> TYPE: PRT
<213> ORGANISM: Artificial Sequence
<220> FEATURE:

<223> OTHER INFORMATION: IL2-T23A-CD25(22-212)

<400> SEQUENCE: 49

```
Ala Pro Ala Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr Gly Gly Gly Ser Gly Gly Gly Ser Gly Gly Gly
    130                 135                 140
Ser Glu Leu Cys Asp Asp Asp Pro Pro Glu Ile Pro His Ala Thr Phe
145                 150                 155                 160
Lys Ala Met Ala Tyr Lys Glu Gly Thr Met Leu Asn Cys Glu Cys Lys
                165                 170                 175
Arg Gly Phe Arg Arg Ile Lys Ser Gly Ser Leu Tyr Met Leu Cys Thr
            180                 185                 190
Gly Asn Ser Ser His Ser Ser Trp Asp Asn Gln Cys Gln Cys Thr Ser
        195                 200                 205
Ser Ala Thr Arg Asn Thr Thr Lys Gln Val Thr Pro Gln Pro Glu Glu
    210                 215                 220
Gln Lys Glu Arg Lys Thr Thr Glu Met Gln Ser Pro Met Gln Pro Val
225                 230                 235                 240
Asp Gln Ala Ser Leu Pro Gly His Cys Arg Glu Pro Pro Pro Trp Glu
                245                 250                 255
Asn Glu Ala Thr Glu Arg Ile Tyr His Phe Val Val Gly Gln Met Val
            260                 265                 270
Tyr Tyr Gln Cys Val Gln Gly Tyr Arg Ala Leu His Arg Gly Pro Ala
        275                 280                 285
Glu Ser Val Cys Lys Met Thr His Gly Lys Thr Arg Trp Thr Gln Pro
    290                 295                 300
Gln Leu Ile Cys Thr Gly Glu Met Glu Thr Ser Gln Phe Pro Gly Glu
305                 310                 315                 320
Glu Lys Pro Gln Ala Ser Pro Glu Gly Arg Pro Glu Ser Glu Thr Ser
                325                 330                 335
```

<210> SEQ ID NO 50
<211> LENGTH: 336
<212> TYPE: PRT
<213> ORGANISM: Artificial Sequence
<220> FEATURE:
<223> OTHER INFORMATION: IL2-T23A-C145S-CD25(22-212)

<400> SEQUENCE: 50

```
Ala Pro Ala Ser Ser Ser Thr Lys Lys Thr Gln Leu Gln Leu Glu His
1               5                   10                  15
```

```
Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly Gly Gly
130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

<210> SEQ ID NO 51
<211> LENGTH: 336
<212> TYPE: PRT
<213> ORGANISM: Artificial Sequence
<220> FEATURE:
<223> OTHER INFORMATION: IL2-C145S-CD25(22-212)

<400> SEQUENCE: 51

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45
```

```
Lys Ala Thr Glu Leu Lys His Leu Gln Cys Leu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly Gly Gly
130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

<210> SEQ ID NO 52
<211> LENGTH: 336
<212> TYPE: PRT
<213> ORGANISM: Artificial Sequence
<220> FEATURE:
<223> OTHER INFORMATION: IL2-C145S-CD25(22-212)

<400> SEQUENCE: 52

Ala Pro Ala Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Leu Lys
         50                  55                  60

Pro Leu Glu Glu Val Leu Asn Leu Ala Gln Ser Lys Asn Phe His Leu
 65                  70                  75                  80
```

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly
130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Ala Pro Gln Pro Glu Glu
210                 215                 220

Gln Lys Glu Arg Lys Ala Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

<210> SEQ ID NO 53
<211> LENGTH: 338
<212> TYPE: PRT
<213> ORGANISM: Artificial Sequence
<220> FEATURE:
<223> OTHER INFORMATION: IL2-T23A-CD25(22-212)-PG

<400> SEQUENCE: 53

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

```
Thr Ile Val Glu Phe Leu Asn Arg Trp Ile Thr Phe Cys Gln Ser Ile
            115                 120                 125

Ile Ser Thr Leu Thr Gly Gly Gly Ser Gly Gly Ser Gly Gly Gly
            130                 135                 140

Ser Glu Leu Cys Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
            290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

Pro Gly

<210> SEQ ID NO 54
<211> LENGTH: 311
<212> TYPE: PRT
<213> ORGANISM: Artificial Sequence
<220> FEATURE:
<223> OTHER INFORMATION: IL2-CD25(22-187)

<400> SEQUENCE: 54

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125
```

```
Ile Ser Thr Leu Thr Gly Gly Gly Ser Gly Gly Gly Ser Gly Gly Gly
        130                 135                 140

Ser Glu Leu Cys Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                    165                 170                 175

Arg Gly Phe Arg Arg Ile Lys Ser Gly Ser Leu Tyr Met Leu Cys Thr
                180                 185                 190

Gly Asn Ser Ser His Ser Ser Trp Asp Asn Gln Cys Gln Cys Thr Ser
                195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
                260                 265                 270

Tyr Tyr Gln Cys Val Gln Gly Tyr Arg Ala Leu His Arg Gly Pro Ala
                275                 280                 285

Glu Ser Val Cys Lys Met Thr His Gly Lys Thr Arg Trp Thr Gln Pro
290                 295                 300

Gln Leu Ile Cys Thr Gly Glu
305                 310

<210> SEQ ID NO 55
<211> LENGTH: 311
<212> TYPE: PRT
<213> ORGANISM: Artificial Sequence
<220> FEATURE:
<223> OTHER INFORMATION: IL2-T23A-C145S-CD25(22-187)

<400> SEQUENCE: 55

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr Gly Gly Gly Ser Gly Gly Gly Ser Gly Gly Gly
            130                 135                 140

Ser Glu Leu Cys Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                    165                 170                 175
```

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Trp Glu
            245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
            290                 295                 300

Gln Leu Ile Cys Thr Gly Glu
305                 310

<210> SEQ ID NO 56
<211> LENGTH: 364
<212> TYPE: PRT
<213> ORGANISM: Artificial Sequence
<220> FEATURE:
<223> OTHER INFORMATION: IL2-CD25(22-240, C213S)

<400> SEQUENCE: 56

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Ser Gly Gly Ser Gly Gly Gly
            130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Trp Glu
                245                 250                 255

Asn Glu Ala Thr Glu Arg Ile Tyr His Phe Val Val Gly Gln Met Val
                260                 265                 270

Tyr Tyr Gln Cys Val Gln Gly Tyr Arg Ala Leu His Arg Gly Pro Ala
                275                 280                 285

Glu Ser Val Cys Lys Met Thr His Gly Lys Thr Arg Trp Thr Gln Pro
                290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

Ser Leu Val Thr Thr Thr Asp Phe Gln Ile Gln Thr Glu Met Ala Ala
                340                 345                 350

Thr Met Glu Thr Ser Ile Phe Thr Thr Glu Tyr Gln
                355                 360

<210> SEQ ID NO 57
<211> LENGTH: 335
<212> TYPE: PRT
<213> ORGANISM: Artificial Sequence
<220> FEATURE:
<223> OTHER INFORMATION: Del-A21-IL2-CD(22-212)

<400> SEQUENCE: 57

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
                35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Cys Gln Ser Ile Ile
                115                 120                 125

Ser Thr Leu Thr Gly Gly Gly Ser Gly Gly Gly Ser Gly Gly Gly Ser
                130                 135                 140

Glu Leu Cys Asp Asp Asp Pro Pro Glu Ile Pro His Ala Thr Phe Lys
145                 150                 155                 160

Ala Met Ala Tyr Lys Glu Gly Thr Met Leu Asn Cys Glu Cys Lys Arg
                165                 170                 175

Gly Phe Arg Arg Ile Lys Ser Gly Ser Leu Tyr Met Leu Cys Thr Gly
                180                 185                 190

Asn Ser Ser His Ser Ser Trp Asp Asn Gln Cys Gln Cys Thr Ser Ser
                195                 200                 205

Ala Thr Arg Asn Thr Thr Lys Gln Val Thr Pro Gln Pro Glu Glu Gln
                210                 215                 220

```
Lys Glu Arg Lys Thr Thr Glu Met Gln Ser Pro Met Gln Pro Val Asp
225                 230                 235                 240

Gln Ala Ser Leu Pro Gly His Cys Arg Glu Pro Pro Trp Glu Asn
            245                 250                 255

Glu Ala Thr Glu Arg Ile Tyr His Phe Val Val Gly Gln Met Val Tyr
            260                 265                 270

Tyr Gln Cys Val Gln Gly Tyr Arg Ala Leu His Arg Gly Pro Ala Glu
            275                 280                 285

Ser Val Cys Lys Met Thr His Gly Lys Thr Arg Trp Thr Gln Pro Gln
            290                 295                 300

Leu Ile Cys Thr Gly Glu Met Glu Thr Ser Gln Phe Pro Gly Glu Glu
305                 310                 315                 320

Lys Pro Gln Ala Ser Pro Glu Gly Arg Pro Glu Ser Glu Thr Ser
            325                 330                 335

<210> SEQ ID NO 58
<211> LENGTH: 336
<212> TYPE: PRT
<213> ORGANISM: Artificial Sequence
<220> FEATURE:
<223> OTHER INFORMATION: IL2-T23A-L2-CD25(22-212)

<400> SEQUENCE: 58

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Gly Ser Gly Gly Ala Gly Gly Gly Gly
130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
            165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
            210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
            245                 250                 255
```

Asn Glu Ala Thr Glu Arg Ile Tyr His Phe Val Val Gly Gln Met Val
                260                 265                 270

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

<210> SEQ ID NO 59
<211> LENGTH: 344
<212> TYPE: PRT
<213> ORGANISM: Artificial Sequence
<220> FEATURE:
<223> OTHER INFORMATION: IL2-T23A-L3-CD25(22-212)

<400> SEQUENCE: 59

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Ser Gly Gly Gly
    130                 135                 140

Ser Gly Gly Gly Ser Gly Gly Gly Ser Glu Leu Cys Asp Asp Asp Pro
145                 150                 155                 160

Pro Glu Ile Pro His Ala Thr Phe Lys Ala Met Ala Tyr Lys Glu Gly
                165                 170                 175

Thr Met Leu Asn Cys Glu Cys Lys Arg Gly Phe Arg Arg Ile Lys Ser
            180                 185                 190

Gly Ser Leu Tyr Met Leu Cys Thr Gly Asn Ser Ser His Ser Ser Trp
        195                 200                 205

Asp Asn Gln Cys Gln Cys Thr Ser Ser Ala Thr Arg Asn Thr Thr Lys
    210                 215                 220

Gln Val Thr Pro Gln Pro Glu Glu Gln Lys Glu Arg Lys Thr Thr Glu
225                 230                 235                 240

Met Gln Ser Pro Met Gln Pro Val Asp Gln Ala Ser Leu Pro Gly His
                245                 250                 255

Cys Arg Glu Pro Pro Pro Trp Glu Asn Glu Ala Thr Glu Arg Ile Tyr
            260                 265                 270

His Phe Val Val Gly Gln Met Val Tyr Tyr Gln Cys Val Gln Gly Tyr
        275                 280                 285

Arg Ala Leu His Arg Gly Pro Ala Glu Ser Val Cys Lys Met Thr His
            290                 295                 300
Gly Lys Thr Arg Trp Thr Gln Pro Gln Leu Ile Cys Thr Gly Glu Met
305                 310                 315                 320
Glu Thr Ser Gln Phe Pro Gly Glu Glu Lys Pro Gln Ala Ser Pro Glu
                325                 330                 335
Gly Arg Pro Glu Ser Glu Thr Ser
            340

<210> SEQ ID NO 60
<211> LENGTH: 311
<212> TYPE: PRT
<213> ORGANISM: Artificial Sequence
<220> FEATURE:
<223> OTHER INFORMATION: IL2-T23A-C145S-CD25(22-187)-N70Q-N89Q

<400> SEQUENCE: 60

Ala Pro Ala Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
            35                  40                  45
Lys Ala Thr Glu Leu Lys His Leu Gln Cys Leu Glu Glu Glu Leu Lys
50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr Gly Gly Gly Ser Gly Gly Gly Ser Gly Gly Gly
130                 135                 140
Ser Glu Leu Cys Asp Asp Asp Pro Pro Glu Ile Pro His Ala Thr Phe
145                 150                 155                 160
Lys Ala Met Ala Tyr Lys Glu Gly Thr Met Leu Asn Cys Glu Cys Lys
                165                 170                 175
Arg Gly Phe Arg Arg Ile Lys Ser Gly Ser Leu Tyr Met Leu Cys Thr
            180                 185                 190
Gly Gln Ser Ser His Ser Ser Trp Asp Asn Gln Cys Gln Cys Thr Ser
        195                 200                 205
Ser Ala Thr Arg Gln Thr Thr Lys Gln Val Thr Pro Gln Pro Glu Glu
210                 215                 220
Gln Lys Glu Arg Lys Thr Thr Glu Met Gln Ser Pro Met Gln Pro Val
225                 230                 235                 240
Asp Gln Ala Ser Leu Pro Gly His Cys Arg Glu Pro Pro Pro Trp Glu
                245                 250                 255
Asn Glu Ala Thr Glu Arg Ile Tyr His Phe Val Val Gly Gln Met Val
            260                 265                 270
Tyr Tyr Gln Cys Val Gln Gly Tyr Arg Ala Leu His Arg Gly Pro Ala
        275                 280                 285
Glu Ser Val Cys Lys Met Thr His Gly Lys Thr Arg Trp Thr Gln Pro
290                 295                 300

Gln Leu Ile Cys Thr Gly Glu
305                 310

<210> SEQ ID NO 61
<211> LENGTH: 311
<212> TYPE: PRT
<213> ORGANISM: Artificial Sequence
<220> FEATURE:
<223> OTHER INFORMATION: IL2-C145S-CD25(22-187)-N70Q-N89Q

<400> SEQUENCE: 61

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Ser Gly Gly Gly Gly
    130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Gln Ser Ser His Ser Ser Trp Asp Asn Gln Cys Gln Cys Thr Ser
        195                 200                 205

Ser Ala Thr Arg Gln Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300

Gln Leu Ile Cys Thr Gly Glu
305                 310

<210> SEQ ID NO 62
<211> LENGTH: 311
<212> TYPE: PRT
<213> ORGANISM: Artificial Sequence
<220> FEATURE:

<223> OTHER INFORMATION: IL2-T23A -C145S-CD25(22-187)-N89Q

<400> SEQUENCE: 62

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Gly Gly Ser Gly Gly Gly Ser Gly Gly Gly
130                 135                 140

Ser Glu Leu Cys Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
            165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Gln Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
            245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
290                 295                 300

Gln Leu Ile Cys Thr Gly Glu
305                 310

<210> SEQ ID NO 63
<211> LENGTH: 311
<212> TYPE: PRT
<213> ORGANISM: Artificial Sequence
<220> FEATURE:
<223> OTHER INFORMATION: IL2-T23A -C145S-CD25(22-187)-N70Q

<400> SEQUENCE: 63

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly Gly Gly
        130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Gln Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300

Gln Leu Ile Cys Thr Gly Glu
305                 310

<210> SEQ ID NO 64
<211> LENGTH: 311
<212> TYPE: PRT
<213> ORGANISM: Artificial Sequence
<220> FEATURE:
<223> OTHER INFORMATION: IL2-C145S-CD25(22-187)-N89Q

<400> SEQUENCE: 64

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Gly Gly Ser Gly Gly Gly
130                 135                 140

Ser Glu Leu Cys Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Gln Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
290                 295                 300

Gln Leu Ile Cys Thr Gly Glu
305                 310

<210> SEQ ID NO 65
<211> LENGTH: 311
<212> TYPE: PRT
<213> ORGANISM: Artificial Sequence
<220> FEATURE:
<223> OTHER INFORMATION: IL2-C145S-CD25(22-187)-N70Q

<400> SEQUENCE: 65

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125
```

Ile Ser Thr Leu Thr Gly Gly Ser Gly Gly Gly Ser Gly Gly Gly
            130                 135                 140

Ser Glu Leu Cys Asp Asp Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
                180                 185                 190

Gly Gln Ser Ser His Ser Ser Trp Asp Asn Gln Cys Gln Cys Thr Ser
                195                 200                 205

Ser Ala Thr Arg Asn Thr Thr Lys Gln Val Thr Pro Gln Pro Glu Glu
            210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Trp Glu
                245                 250                 255

Asn Glu Ala Thr Glu Arg Ile Tyr His Phe Val Val Gly Gln Met Val
                260                 265                 270

Tyr Tyr Gln Cys Val Gln Gly Tyr Arg Ala Leu His Arg Gly Pro Ala
                275                 280                 285

Glu Ser Val Cys Lys Met Thr His Gly Lys Thr Arg Trp Thr Gln Pro
290                 295                 300

Gln Leu Ile Cys Thr Gly Glu
305                 310

<210> SEQ ID NO 66
<211> LENGTH: 311
<212> TYPE: PRT
<213> ORGANISM: Artificial Sequence
<220> FEATURE:
<223> OTHER INFORMATION: IL2-T23A -C145S-CD25(22-187)

<400> SEQUENCE: 66

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr Gly Gly Ser Gly Gly Gly Ser Gly Gly Gly
            130                 135                 140

Ser Glu Leu Cys Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

```
Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
            290                 295                 300

Gln Leu Ile Cys Thr Gly Glu
305                 310

<210> SEQ ID NO 67
<211> LENGTH: 569
<212> TYPE: PRT
<213> ORGANISM: Artificial Sequence
<220> FEATURE:
<223> OTHER INFORMATION: Fc1.1-7linker-IL2-CD25(22-212)

<400> SEQUENCE: 67

Asp Lys Thr His Thr Cys Pro Pro Cys Pro Ala Pro Glu Ala Glu Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ser Ser Ile
        100                 105                 110

Glu Lys Thr Ile Ser Lys Ala Lys Gly Gln Pro Arg Glu Pro Gln Val
    115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

```
Pro Gly Gly Ser Gly Gly Ser Gly Gly Ala Pro Thr Ser Ser Ser Thr
225                 230                 235                 240

Lys Lys Thr Gln Leu Gln Leu Glu His Leu Leu Asp Leu Gln Met
            245                 250                 255

Ile Leu Asn Gly Ile Asn Asn Tyr Lys Asn Pro Lys Leu Thr Arg Met
            260                 265                 270

Leu Thr Phe Lys Phe Tyr Met Pro Lys Lys Ala Thr Glu Leu Lys His
            275                 280                 285

Leu Gln Cys Leu Glu Glu Glu Leu Lys Pro Leu Glu Glu Val Leu Asn
            290                 295                 300

Leu Ala Gln Ser Lys Asn Phe His Leu Arg Pro Arg Asp Leu Ile Ser
305                 310                 315                 320

Asn Ile Asn Val Ile Val Leu Glu Leu Lys Gly Ser Glu Thr Thr Phe
                325                 330                 335

Met Cys Glu Tyr Ala Asp Glu Thr Ala Thr Ile Val Glu Phe Leu Asn
                340                 345                 350

Arg Trp Ile Thr Phe Cys Gln Ser Ile Ile Ser Thr Leu Thr Gly Gly
            355                 360                 365

Gly Ser Gly Gly Ser Gly Gly Ser Gly Leu Cys Asp Asp
            370                 375                 380

Pro Pro Glu Ile Pro His Ala Thr Phe Lys Ala Met Ala Tyr Lys Glu
385                 390                 395                 400

Gly Thr Met Leu Asn Cys Glu Cys Lys Arg Gly Phe Arg Arg Ile Lys
                405                 410                 415

Ser Gly Ser Leu Tyr Met Leu Cys Thr Gly Asn Ser Ser His Ser Ser
                420                 425                 430

Trp Asp Asn Gln Cys Gln Cys Thr Ser Ser Ala Thr Arg Asn Thr Thr
            435                 440                 445

Lys Gln Val Thr Pro Gln Pro Glu Glu Gln Lys Glu Arg Lys Thr Thr
            450                 455                 460

Glu Met Gln Ser Pro Met Gln Pro Val Asp Gln Ala Ser Leu Pro Gly
465                 470                 475                 480

His Cys Arg Glu Pro Pro Pro Trp Glu Asn Glu Ala Thr Glu Arg Ile
                485                 490                 495

Tyr His Phe Val Val Gly Gln Met Val Tyr Tyr Gln Cys Val Gln Gly
                500                 505                 510

Tyr Arg Ala Leu His Arg Gly Pro Ala Glu Ser Val Cys Lys Met Thr
            515                 520                 525

His Gly Lys Thr Arg Trp Thr Gln Pro Gln Leu Ile Cys Thr Gly Glu
            530                 535                 540

Met Glu Thr Ser Gln Phe Pro Gly Glu Glu Lys Pro Gln Ala Ser Pro
545                 550                 555                 560

Glu Gly Arg Pro Glu Ser Glu Thr Ser
                565
```

<210> SEQ ID NO 68
<211> LENGTH: 562
<212> TYPE: PRT
<213> ORGANISM: Artificial Sequence
<220> FEATURE:
<223> OTHER INFORMATION: IL2-CD25(22-212)-Fc1.1

<400> SEQUENCE: 68

```
Ala Pro Thr Ser Ser Ser Thr Lys Lys Thr Gln Leu Gln Leu Glu His
1               5                   10                  15
```

```
Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
             85                  90                  95

Lys Gly Ser Glu Thr Thr Phe Met Cys Glu Tyr Ala Asp Glu Thr Ala
             100                 105                 110

Thr Ile Val Glu Phe Leu Asn Arg Trp Ile Thr Phe Cys Gln Ser Ile
             115                 120                 125

Ile Ser Thr Leu Thr Gly Gly Ser Gly Gly Ser Gly Gly Gly
 130                 135                 140

Ser Glu Leu Cys Asp Asp Pro Pro Glu Ile Pro His Ala Thr Phe
 145                 150                 155                 160

Lys Ala Met Ala Tyr Lys Glu Gly Thr Met Leu Asn Cys Glu Cys Lys
             165                 170                 175

Arg Gly Phe Arg Arg Ile Lys Ser Gly Ser Leu Tyr Met Leu Cys Thr
             180                 185                 190

Gly Asn Ser Ser His Ser Ser Trp Asp Asn Gln Cys Gln Cys Thr Ser
             195                 200                 205

Ser Ala Thr Arg Asn Thr Thr Lys Gln Val Thr Pro Gln Pro Glu Glu
 210                 215                 220

Gln Lys Glu Arg Lys Thr Thr Glu Met Gln Ser Pro Met Gln Pro Val
225                  230                 235                 240

Asp Gln Ala Ser Leu Pro Gly His Cys Arg Glu Pro Pro Trp Glu
             245                 250                 255

Asn Glu Ala Thr Glu Arg Ile Tyr His Phe Val Val Gly Gln Met Val
             260                 265                 270

Tyr Tyr Gln Cys Val Gln Gly Tyr Arg Ala Leu His Arg Gly Pro Ala
             275                 280                 285

Glu Ser Val Cys Lys Met Thr His Gly Lys Thr Arg Trp Thr Gln Pro
 290                 295                 300

Gln Leu Ile Cys Thr Gly Glu Met Glu Thr Ser Gln Phe Pro Gly Glu
305                  310                 315                 320

Glu Lys Pro Gln Ala Ser Pro Glu Gly Arg Pro Glu Ser Glu Thr Ser
             325                 330                 335

Asp Lys His Thr Cys Pro Pro Cys Pro Ala Pro Glu Ala Glu Gly
             340                 345                 350

Ala Pro Ser Val Phe Leu Phe Pro Pro Lys Pro Lys Asp Thr Leu Met
             355                 360                 365

Ile Ser Arg Thr Pro Glu Val Thr Cys Val Val Val Asp Val Ser His
             370                 375                 380

Glu Asp Pro Glu Val Lys Phe Asn Trp Tyr Val Asp Gly Val Glu Val
385                  390                 395                 400

His Asn Ala Lys Thr Lys Pro Arg Glu Glu Gln Tyr Asn Ser Thr Tyr
             405                 410                 415

Arg Val Val Ser Val Leu Thr Val Leu His Gln Asp Trp Leu Asn Gly
             420                 425                 430
```

```
Lys Glu Tyr Lys Cys Lys Val Ser Asn Lys Ala Leu Pro Ser Ser Ile
            435                 440                 445
Glu Lys Thr Ile Ser Lys Ala Lys Gly Gln Pro Arg Glu Pro Gln Val
450                 455                 460
Tyr Thr Leu Pro Pro Ser Arg Glu Glu Met Thr Lys Asn Gln Val Ser
465                 470                 475                 480
Leu Thr Cys Leu Val Lys Gly Phe Tyr Pro Ser Asp Ile Ala Val Glu
            485                 490                 495
Trp Glu Ser Asn Gly Gln Pro Glu Asn Asn Tyr Lys Thr Thr Pro Pro
            500                 505                 510
Val Leu Asp Ser Asp Gly Ser Phe Phe Leu Tyr Ser Lys Leu Thr Val
            515                 520                 525
Asp Lys Ser Arg Trp Gln Gln Gly Asn Val Phe Ser Cys Ser Val Met
530                 535                 540
His Glu Ala Leu His Asn His Tyr Thr Gln Lys Ser Leu Ser Leu Ser
545                 550                 555                 560
Pro Gly
```

<210> SEQ ID NO 69
<211> LENGTH: 336
<212> TYPE: PRT
<213> ORGANISM: Artificial Sequence
<220> FEATURE:
<223> OTHER INFORMATION: IL2(V111K)-CD25(22-212)

<400> SEQUENCE: 69

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Lys Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr Gly Gly Gly Ser Gly Gly Gly Ser Gly Gly Gly
130                 135                 140
Ser Glu Leu Cys Asp Asp Asp Pro Pro Glu Ile Pro His Ala Thr Phe
145                 150                 155                 160
Lys Ala Met Ala Tyr Lys Glu Gly Thr Met Leu Asn Cys Glu Cys Lys
                165                 170                 175
Arg Gly Phe Arg Arg Ile Lys Ser Gly Ser Leu Tyr Met Leu Cys Thr
            180                 185                 190
Gly Asn Ser Ser His Ser Ser Trp Asp Asn Gln Cys Gln Cys Thr Ser
        195                 200                 205
Ser Ala Thr Arg Asn Thr Thr Lys Gln Val Thr Pro Gln Pro Glu Glu
210                 215                 220
Gln Lys Glu Arg Lys Thr Thr Glu Met Gln Ser Pro Met Gln Pro Val
```

```
225                 230                 235                 240

Asp Gln Ala Ser Leu Pro Gly His Cys Arg Glu Pro Pro Trp Glu
                245                 250                 255

Asn Glu Ala Thr Glu Arg Ile Tyr His Phe Val Val Gly Gln Met Val
                260                 265                 270

Tyr Tyr Gln Cys Val Gln Gly Tyr Arg Ala Leu His Arg Gly Pro Ala
                275                 280                 285

Glu Ser Val Cys Lys Met Thr His Gly Lys Thr Arg Trp Thr Gln Pro
        290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

<210> SEQ ID NO 70
<211> LENGTH: 336
<212> TYPE: PRT
<213> ORGANISM: Artificial Sequence
<220> FEATURE:
<223> OTHER INFORMATION: IL2(D40T)-CD25(22-212)

<400> SEQUENCE: 70

Ala Pro Thr Ser Ser Thr Lys Lys Thr Gln Leu Gln Leu Glu His
1               5                   10                  15

Leu Leu Leu Thr Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65              70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Ser Gly Gly Ser Gly Gly Gly
                130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
                180                 185                 190

Gly Asn Ser Ser His Ser Ser Trp Asp Asn Gln Cys Gln Cys Thr Ser
            195                 200                 205

Ser Ala Thr Arg Asn Thr Thr Lys Gln Val Thr Pro Gln Pro Glu Glu
        210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
```

```
                260             265             270
Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

<210> SEQ ID NO 71
<211> LENGTH: 12
<212> TYPE: PRT
<213> ORGANISM: Artificial Sequence
<220> FEATURE:
<223> OTHER INFORMATION: glycine linker

<400> SEQUENCE: 71

Gly Gly Gly Ser Gly Gly Gly Ser Gly Gly Gly Ser
1               5                   10

<210> SEQ ID NO 72
<211> LENGTH: 5
<212> TYPE: PRT
<213> ORGANISM: Artificial Sequence
<220> FEATURE:
<223> OTHER INFORMATION: glycine linker

<400> SEQUENCE: 72

Gly Gly Gly Gly Ser
1               5

<210> SEQ ID NO 73
<211> LENGTH: 8
<212> TYPE: PRT
<213> ORGANISM: Artificial Sequence
<220> FEATURE:
<223> OTHER INFORMATION: glycine linker

<400> SEQUENCE: 73

Gly Gly His His His His His His
1               5

<210> SEQ ID NO 74
<211> LENGTH: 16
<212> TYPE: PRT
<213> ORGANISM: Artificial Sequence
<220> FEATURE:
<223> OTHER INFORMATION: glycine linker

<400> SEQUENCE: 74

Gly Gly Gly Ser Gly Gly Gly Ser Gly Gly Gly Ser Gly Gly Gly Ser
1               5                   10                  15

<210> SEQ ID NO 75
<211> LENGTH: 20
<212> TYPE: PRT
<213> ORGANISM: Artificial Sequence
<220> FEATURE:
<223> OTHER INFORMATION: Glycine Linker

<400> SEQUENCE: 75

Gly Gly Gly Ser Gly Gly Gly Ser Gly Gly Gly Ser Gly Gly Gly Ser
1               5                   10                  15
```

Gly Gly Gly Ser
        20

<210> SEQ ID NO 76
<211> LENGTH: 24
<212> TYPE: PRT
<213> ORGANISM: Artificial Sequence
<220> FEATURE:
<223> OTHER INFORMATION: Glycine Linker

<400> SEQUENCE: 76

Gly Gly Gly Ser Gly Gly Gly Ser Gly Gly Gly Ser Gly Gly Gly Ser
1               5                   10                  15

Gly Gly Gly Ser Gly Gly Gly Ser
        20

<210> SEQ ID NO 77
<211> LENGTH: 28
<212> TYPE: PRT
<213> ORGANISM: Artificial Sequence
<220> FEATURE:
<223> OTHER INFORMATION: Glycine Linker

<400> SEQUENCE: 77

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser
        20                  25

<210> SEQ ID NO 78
<211> LENGTH: 15
<212> TYPE: PRT
<213> ORGANISM: Artificial Sequence
<220> FEATURE:
<223> OTHER INFORMATION: Glycine Linker

<400> SEQUENCE: 78

Gly Gly Gly Gly Ser Gly Gly Gly Gly Ser Gly Gly Gly Gly Ser
1               5                   10                  15

<210> SEQ ID NO 79
<211> LENGTH: 20
<212> TYPE: PRT
<213> ORGANISM: Artificial Sequence
<220> FEATURE:
<223> OTHER INFORMATION: Glycine Linker

<400> SEQUENCE: 79

Gly Gly Gly Gly Ser Gly Gly Gly Gly Ser Gly Gly Gly Gly Ser Gly
1               5                   10                  15

Gly Gly Gly Ser
        20

<210> SEQ ID NO 80
<211> LENGTH: 25
<212> TYPE: PRT
<213> ORGANISM: Artificial Sequence
<220> FEATURE:
<223> OTHER INFORMATION: Glycine Linker

<400> SEQUENCE: 80

Gly Gly Gly Gly Ser Gly Gly Gly Gly Ser Gly Gly Gly Gly Ser Gly
1               5                   10                  15

Gly Gly Gly Ser Gly Gly Gly Gly Ser
        20                  25

```
<210> SEQ ID NO 81
<211> LENGTH: 10
<212> TYPE: PRT
<213> ORGANISM: Artificial Sequence
<220> FEATURE:
<223> OTHER INFORMATION: Glycine Linker

<400> SEQUENCE: 81

Gly Gly Gly Gly Ser Gly Gly Gly Gly Ser
1               5                   10

<210> SEQ ID NO 82
<211> LENGTH: 5
<212> TYPE: PRT
<213> ORGANISM: Artificial Sequence
<220> FEATURE:
<223> OTHER INFORMATION: Glycine Linker

<400> SEQUENCE: 82

Gly Gly Gly Gly Ser
1               5

<210> SEQ ID NO 83
<211> LENGTH: 30
<212> TYPE: PRT
<213> ORGANISM: Artificial Sequence
<220> FEATURE:
<223> OTHER INFORMATION: Glycine Linker

<400> SEQUENCE: 83

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 84
<211> LENGTH: 25
<212> TYPE: PRT
<213> ORGANISM: Artificial Sequence
<220> FEATURE:
<223> OTHER INFORMATION: Glycine Linker

<400> SEQUENCE: 84

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 85
<211> LENGTH: 20
<212> TYPE: PRT
<213> ORGANISM: Artificial Sequence
<220> FEATURE:
<223> OTHER INFORMATION: polyadenylation signal sequence

<400> SEQUENCE: 85

Ala Ser Pro Ala Ala Pro Ala Pro Ala Ser Pro Ala Ala Pro Ala Pro
1               5                   10                  15

Ser Ala Pro Ala
            20

<210> SEQ ID NO 86
<211> LENGTH: 20
<212> TYPE: PRT
```

```
<213> ORGANISM: Artificial Sequence
<220> FEATURE:
<223> OTHER INFORMATION: polyadenylation signal sequence

<400> SEQUENCE: 86

Ala Ala Pro Ala Ser Pro Ala Pro Ala Ala Pro Ser Ala Pro Ala Pro
1               5                   10                  15

Ala Ala Pro Ser
            20

<210> SEQ ID NO 87
<211> LENGTH: 20
<212> TYPE: PRT
<213> ORGANISM: Artificial Sequence
<220> FEATURE:
<223> OTHER INFORMATION: polyadenylation signal sequence

<400> SEQUENCE: 87

Ala Pro Ser Ser Pro Ser Pro Ser Ala Pro Ser Ser Pro Ser Pro Ala
1               5                   10                  15

Ser Pro Ser Ser
            20

<210> SEQ ID NO 88
<211> LENGTH: 19
<212> TYPE: PRT
<213> ORGANISM: Artificial Sequence
<220> FEATURE:
<223> OTHER INFORMATION: polyadenylation signal sequence

<400> SEQUENCE: 88

Ala Pro Ser Ser Pro Ser Pro Ser Ala Pro Ser Ser Pro Ser Pro Ala
1               5                   10                  15

Ser Pro Ser

<210> SEQ ID NO 89
<211> LENGTH: 20
<212> TYPE: PRT
<213> ORGANISM: Artificial Sequence
<220> FEATURE:
<223> OTHER INFORMATION: polyadenylation signal sequence

<400> SEQUENCE: 89

Ser Ser Pro Ser Ala Pro Ser Pro Ser Ser Pro Ala Ser Pro Ser Pro
1               5                   10                  15

Ser Ser Pro Ala
            20

<210> SEQ ID NO 90
<211> LENGTH: 24
<212> TYPE: PRT
<213> ORGANISM: Artificial Sequence
<220> FEATURE:
<223> OTHER INFORMATION: polyadenylation signal sequence

<400> SEQUENCE: 90

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 91
<211> LENGTH: 20
<212> TYPE: PRT
```

```
<213> ORGANISM: Artificial Sequence
<220> FEATURE:
<223> OTHER INFORMATION: polyadenylation signal sequence

<400> SEQUENCE: 91

Ala Ser Ala Ala Ala Pro Ala Ala Ala Ser Ala Ala Ala Ser Ala Pro
1               5                   10                  15

Ser Ala Ala Ala
            20

<210> SEQ ID NO 92
<211> LENGTH: 66
<212> TYPE: DNA
<213> ORGANISM: Artificial Sequence
<220> FEATURE:
<223> OTHER INFORMATION: IL2 leader optimized Kozak sequenc

<400> SEQUENCE: 92
gccaccatgg acaggatgca actcctgtct tgcattgcac taagtcttgc acttgtcaca      60
aacagt                                                                66

<210> SEQ ID NO 93
<211> LENGTH: 7
<212> TYPE: PRT
<213> ORGANISM: Artificial Sequence
<220> FEATURE:
<223> OTHER INFORMATION: FC region

<400> SEQUENCE: 93

His Gln Ser Leu Gly Thr Gln
1               5

<210> SEQ ID NO 94
<211> LENGTH: 8
<212> TYPE: PRT
<213> ORGANISM: Artificial Sequence
<220> FEATURE:
<223> OTHER INFORMATION: FC region

<400> SEQUENCE: 94

His Gln Asn Leu Ser Asp Gly Lys
1               5

<210> SEQ ID NO 95
<211> LENGTH: 8
<212> TYPE: PRT
<213> ORGANISM: Artificial Sequence
<220> FEATURE:
<223> OTHER INFORMATION: FC region

<400> SEQUENCE: 95

His Gln Asn Ile Ser Asp Gly Lys
1               5

<210> SEQ ID NO 96
<211> LENGTH: 8
<212> TYPE: PRT
<213> ORGANISM: Artificial Sequence
<220> FEATURE:
<223> OTHER INFORMATION: FC region

<400> SEQUENCE: 96

Val Ile Ser Ser His Leu Gly Gln
1               5
```

<210> SEQ ID NO 97
<211> LENGTH: 35
<212> TYPE: PRT
<213> ORGANISM: Artificial Sequence
<220> FEATURE:
<223> OTHER INFORMATION: glycine linker

<400> SEQUENCE: 97

Gly Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Ser
        35

<210> SEQ ID NO 98
<211> LENGTH: 11
<212> TYPE: PRT
<213> ORGANISM: Artificial Sequence
<220> FEATURE:
<223> OTHER INFORMATION: FC region

<400> SEQUENCE: 98

Pro Lys Asn Ser Ser Met Ile Ser Asn Thr Pro
1               5                   10

<210> SEQ ID NO 99
<211> LENGTH: 10
<212> TYPE: DNA
<213> ORGANISM: Artificial Sequence
<220> FEATURE:
<223> OTHER INFORMATION: kozak sequence

<400> SEQUENCE: 99
gccaccatgg                                                          10

<210> SEQ ID NO 100
<211> LENGTH: 8
<212> TYPE: PRT
<213> ORGANISM: Artificial Sequence
<220> FEATURE:
<223> OTHER INFORMATION: His tag

<400> SEQUENCE: 100

Gly Gly His His His His His His
1               5

<210> SEQ ID NO 101
<211> LENGTH: 133
<212> TYPE: PRT
<213> ORGANISM: Artificial Sequence
<220> FEATURE:
<223> OTHER INFORMATION: IL2(21-153)

<400> SEQUENCE: 101

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu

```
                65                  70                  75                  80
Arg Pro Arg Asp Leu Ile Ser Asn Ile Asn Val Ile Val Leu Glu Leu
                    85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
            115                 120                 125
Ile Ser Thr Leu Thr
            130

<210> SEQ ID NO 102
<211> LENGTH: 133
<212> TYPE: PRT
<213> ORGANISM: Artificial Sequence
<220> FEATURE:
<223> OTHER INFORMATION: IL2(21-153)(C145S)

<400> SEQUENCE: 102

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
            35                  40                  45
Lys Ala Thr Glu Leu Lys His Leu Gln Cys Leu Glu Glu Leu Lys
        50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                    85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Ser Gln Ser Ile
            115                 120                 125
Ile Ser Thr Leu Thr
            130

<210> SEQ ID NO 103
<211> LENGTH: 133
<212> TYPE: PRT
<213> ORGANISM: Artificial Sequence
<220> FEATURE:
<223> OTHER INFORMATION: IL2(21-153)(C145A)

<400> SEQUENCE: 103

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
            35                  40                  45
Lys Ala Thr Glu Leu Lys His Leu Gln Cys Leu Glu Glu Leu Lys
        50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                    85                  90                  95
```

```
Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 104
<211> LENGTH: 133
<212> TYPE: PRT
<213> ORGANISM: Artificial Sequence
<220> FEATURE:
<223> OTHER INFORMATION: IL2(21-153)(C145V)

<400> SEQUENCE: 104

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Val Gln Ser Ile
            115                 120                 125

Ile Ser Thr Leu Thr
        130

<210> SEQ ID NO 105
<211> LENGTH: 133
<212> TYPE: PRT
<213> ORGANISM: Artificial Sequence
<220> FEATURE:
<223> OTHER INFORMATION: IL2(21-153)(T23A)

<400> SEQUENCE: 105

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125
```

Ile Ser Thr Leu Thr
    130

<210> SEQ ID NO 106
<211> LENGTH: 133
<212> TYPE: PRT
<213> ORGANISM: Artificial Sequence
<220> FEATURE:
<223> OTHER INFORMATION: IL2(21-153)(T23A+C145S)

<400> SEQUENCE: 106

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 107
<211> LENGTH: 133
<212> TYPE: PRT
<213> ORGANISM: Artificial Sequence
<220> FEATURE:
<223> OTHER INFORMATION: IL2(21-153)(T23A+C145A)

<400> SEQUENCE: 107

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

```
<210> SEQ ID NO 108
<211> LENGTH: 153
<212> TYPE: PRT
<213> ORGANISM: Artificial Sequence
<220> FEATURE:
<223> OTHER INFORMATION: NativeSigPep-IL2(1-153)

<400> SEQUENCE: 108

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 109
<211> LENGTH: 134
<212> TYPE: PRT
<213> ORGANISM: Artificial Sequence
<220> FEATURE:
<223> OTHER INFORMATION: M-IL2(C145S)

<400> SEQUENCE: 109

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ser Gln Ser
        115                 120                 125

Ile Ile Ser Thr Leu Thr
    130

<210> SEQ ID NO 110
<211> LENGTH: 134
```

```
<212> TYPE: PRT
<213> ORGANISM: Artificial Sequence
<220> FEATURE:
<223> OTHER INFORMATION: M-IL2(C145A)

<400> SEQUENCE: 110
```

Met Ala Pro Thr Ser Ser Ser Thr Lys Lys Thr Gln Leu Gln Leu Glu
1               5                   10                  15

His Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
            35                  40                  45

Lys Lys Ala Thr Glu Leu Lys His Leu Gln Cys Leu Glu Glu Glu Leu
50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
            115                 120                 125

Ile Ile Ser Thr Leu Thr
    130

```
<210> SEQ ID NO 111
<211> LENGTH: 132
<212> TYPE: PRT
<213> ORGANISM: Artificial Sequence
<220> FEATURE:
<223> OTHER INFORMATION: Del-A21-IL2

<400> SEQUENCE: 111
```

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
            115                 120                 125

Ser Thr Leu Thr
    130

```
<210> SEQ ID NO 112
<211> LENGTH: 132
<212> TYPE: PRT
<213> ORGANISM: Artificial Sequence
<220> FEATURE:
<223> OTHER INFORMATION: Del-A21-IL2(C145S)
```

<400> SEQUENCE: 112

```
Pro Thr Ser Ser Ser Thr Lys Lys Thr Gln Leu Gln Leu Glu His Leu
1               5                   10                  15
Leu Leu Asp Leu Gln Met Ile Leu Asn Gly Ile Asn Asn Tyr Lys Asn
            20                  25                  30
Pro Lys Leu Thr Arg Met Leu Thr Phe Lys Phe Tyr Met Pro Lys Lys
        35                  40                  45
Ala Thr Glu Leu Lys His Leu Gln Cys Leu Glu Glu Glu Leu Lys Pro
    50                  55                  60
Leu Glu Glu Val Leu Asn Leu Ala Gln Ser Lys Asn Phe His Leu Arg
65                  70                  75                  80
Pro Arg Asp Leu Ile Ser Asn Ile Asn Val Ile Val Leu Glu Leu Lys
                85                  90                  95
Gly Ser Glu Thr Thr Phe Met Cys Glu Tyr Ala Asp Glu Thr Ala Thr
            100                 105                 110
Ile Val Glu Phe Leu Asn Arg Trp Ile Thr Phe Ser Gln Ser Ile Ile
        115                 120                 125
Ser Thr Leu Thr
    130
```

<210> SEQ ID NO 113
<211> LENGTH: 132
<212> TYPE: PRT
<213> ORGANISM: Artificial Sequence
<220> FEATURE:
<223> OTHER INFORMATION: Del-A21-IL2(C145A)

<400> SEQUENCE: 113

```
Pro Thr Ser Ser Ser Thr Lys Lys Thr Gln Leu Gln Leu Glu His Leu
1               5                   10                  15
Leu Leu Asp Leu Gln Met Ile Leu Asn Gly Ile Asn Asn Tyr Lys Asn
            20                  25                  30
Pro Lys Leu Thr Arg Met Leu Thr Phe Lys Phe Tyr Met Pro Lys Lys
        35                  40                  45
Ala Thr Glu Leu Lys His Leu Gln Cys Leu Glu Glu Glu Leu Lys Pro
    50                  55                  60
Leu Glu Glu Val Leu Asn Leu Ala Gln Ser Lys Asn Phe His Leu Arg
65                  70                  75                  80
Pro Arg Asp Leu Ile Ser Asn Ile Asn Val Ile Val Leu Glu Leu Lys
                85                  90                  95
Gly Ser Glu Thr Thr Phe Met Cys Glu Tyr Ala Asp Glu Thr Ala Thr
            100                 105                 110
Ile Val Glu Phe Leu Asn Arg Trp Ile Thr Phe Ala Gln Ser Ile Ile
        115                 120                 125
Ser Thr Leu Thr
    130
```

<210> SEQ ID NO 114
<211> LENGTH: 133
<212> TYPE: PRT
<213> ORGANISM: Artificial Sequence
<220> FEATURE:
<223> OTHER INFORMATION: IL2(V111K)

<400> SEQUENCE: 114

```
Ala Pro Thr Ser Ser Ser Thr Lys Lys Thr Gln Leu Gln Leu Glu His
1               5                   10                  15
```

```
Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Lys Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130
```

<210> SEQ ID NO 115
<211> LENGTH: 133
<212> TYPE: PRT
<213> ORGANISM: Artificial Sequence
<220> FEATURE:
<223> OTHER INFORMATION: IL2(D40T)

<400> SEQUENCE: 115

```
Ala Pro Thr Ser Ser Ser Thr Lys Lys Thr Gln Leu Gln Leu Glu His
1               5                   10                  15

Leu Leu Leu Thr Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130
```

<210> SEQ ID NO 116
<211> LENGTH: 12
<212> TYPE: PRT
<213> ORGANISM: Artificial Sequence
<220> FEATURE:
<223> OTHER INFORMATION: L1-(G3S)3

<400> SEQUENCE: 116

```
Gly Gly Gly Ser Gly Gly Gly Ser Gly Gly Gly Ser
1               5                   10
```

<210> SEQ ID NO 117
<211> LENGTH: 12
<212> TYPE: PRT
<213> ORGANISM: Artificial Sequence

```
<220> FEATURE:
<223> OTHER INFORMATION: L2-G2S2

<400> SEQUENCE: 117

Gly Gly Ser Ser Gly Gly Ala Gly Gly Gly Ser
1               5                   10

<210> SEQ ID NO 118
<211> LENGTH: 20
<212> TYPE: PRT
<213> ORGANISM: Artificial Sequence
<220> FEATURE:
<223> OTHER INFORMATION: L3-(G3S)5

<400> SEQUENCE: 118

Gly Gly Gly Ser Gly Gly Gly Ser Gly Gly Gly Ser Gly Gly Gly Ser
1               5                   10                  15

Gly Gly Gly Ser
            20

<210> SEQ ID NO 119
<211> LENGTH: 9
<212> TYPE: PRT
<213> ORGANISM: Artificial Sequence
<220> FEATURE:
<223> OTHER INFORMATION: L4-(G2S)3

<400> SEQUENCE: 119

Gly Gly Ser Gly Gly Ser Gly Gly Ser
1               5

<210> SEQ ID NO 120
<211> LENGTH: 15
<212> TYPE: PRT
<213> ORGANISM: Artificial Sequence
<220> FEATURE:
<223> OTHER INFORMATION: L5-(G2S)5

<400> SEQUENCE: 120

Gly Gly Ser Gly Gly Ser Gly Gly Ser Gly Gly Ser Gly Gly Ser
1               5                   10                  15

<210> SEQ ID NO 121
<211> LENGTH: 12
<212> TYPE: PRT
<213> ORGANISM: Artificial Sequence
<220> FEATURE:
<223> OTHER INFORMATION: L6-GGEEE

<400> SEQUENCE: 121

Gly Gly Glu Glu Glu Gly Gly Glu Glu Glu Gly Ser
1               5                   10

<210> SEQ ID NO 122
<211> LENGTH: 12
<212> TYPE: PRT
<213> ORGANISM: Artificial Sequence
<220> FEATURE:
<223> OTHER INFORMATION: L7-12mer_Stiff

<400> SEQUENCE: 122

Glu Ser Pro Glu Pro Glu Thr Pro Glu Asp Glu Ser
1               5                   10

<210> SEQ ID NO 123
<211> LENGTH: 22
```

```
<212> TYPE: PRT
<213> ORGANISM: Artificial Sequence
<220> FEATURE:
<223> OTHER INFORMATION: L8-22mer_Helix

<400> SEQUENCE: 123

Gly Arg Gly Gly Glu Glu Lys Lys Lys Glu Lys Glu Lys Glu Glu Gln
1               5                   10                  15

Glu Glu Arg Glu Thr Lys
            20

<210> SEQ ID NO 124
<211> LENGTH: 1
<212> TYPE: PRT
<213> ORGANISM: Artificial Sequence
<220> FEATURE:
<223> OTHER INFORMATION: L9-G

<400> SEQUENCE: 124

Gly
1

<210> SEQ ID NO 125
<211> LENGTH: 2
<212> TYPE: PRT
<213> ORGANISM: Artificial Sequence
<220> FEATURE:
<223> OTHER INFORMATION: L10-GG

<400> SEQUENCE: 125

Gly Gly
1

<210> SEQ ID NO 126
<211> LENGTH: 1
<212> TYPE: PRT
<213> ORGANISM: Artificial Sequence
<220> FEATURE:
<223> OTHER INFORMATION: L11-S

<400> SEQUENCE: 126

Ser
1

<210> SEQ ID NO 127
<211> LENGTH: 2
<212> TYPE: PRT
<213> ORGANISM: Artificial Sequence
<220> FEATURE:
<223> OTHER INFORMATION: L12-GS

<400> SEQUENCE: 127

Gly Ser
1

<210> SEQ ID NO 128
<211> LENGTH: 219
<212> TYPE: PRT
<213> ORGANISM: Artificial Sequence
<220> FEATURE:
<223> OTHER INFORMATION: CD25(22-240)

<400> SEQUENCE: 128

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
```

```
            20                  25                  30
Gly Phe Arg Arg Ile Lys Ser Gly Ser Leu Tyr Met Leu Cys Thr Gly
         35                  40                  45

Asn Ser Ser His Ser Ser Trp Asp Asn Gln Cys Gln Cys Thr Ser Ser
 50                  55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                 85                  90                  95

Gln Ala Ser Leu Pro Gly His Cys Arg Glu Pro Pro Trp Glu Asn
             100                 105                 110

Glu Ala Thr Glu Arg Ile Tyr His Phe Val Val Gly Gln Met Val Tyr
             115                 120                 125

Tyr Gln Cys Val Gln Gly Tyr Arg Ala Leu His Arg Gly Pro Ala Glu
         130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln
    210                 215

<210> SEQ ID NO 129
<211> LENGTH: 191
<212> TYPE: PRT
<213> ORGANISM: Artificial Sequence
<220> FEATURE:
<223> OTHER INFORMATION: CD25(22-212)

<400> SEQUENCE: 129

Glu Leu Cys Asp Asp Pro Pro Glu Ile Pro His Ala Thr Phe Lys
 1               5                  10                  15

Ala Met Ala Tyr Lys Glu Gly Thr Met Leu Asn Cys Glu Cys Lys Arg
             20                  25                  30

Gly Phe Arg Arg Ile Lys Ser Gly Ser Leu Tyr Met Leu Cys Thr Gly
         35                  40                  45

Asn Ser Ser His Ser Ser Trp Asp Asn Gln Cys Gln Cys Thr Ser Ser
 50                  55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                 85                  90                  95

Gln Ala Ser Leu Pro Gly His Cys Arg Glu Pro Pro Trp Glu Asn
             100                 105                 110

Glu Ala Thr Glu Arg Ile Tyr His Phe Val Val Gly Gln Met Val Tyr
             115                 120                 125

Tyr Gln Cys Val Gln Gly Tyr Arg Ala Leu His Arg Gly Pro Ala Glu
         130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
```

```
                   165                 170                 175

Lys Pro Gln Ala Ser Pro Glu Gly Arg Pro Glu Ser Glu Thr Ser
            180                 185                 190

<210> SEQ ID NO 130
<211> LENGTH: 166
<212> TYPE: PRT
<213> ORGANISM: Artificial Sequence
<220> FEATURE:
<223> OTHER INFORMATION: CD25(22-187)

<400> SEQUENCE: 130

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu
                165

<210> SEQ ID NO 131
<211> LENGTH: 219
<212> TYPE: PRT
<213> ORGANISM: Artificial Sequence
<220> FEATURE:
<223> OTHER INFORMATION: CD25(22-240)(C213S)

<400> SEQUENCE: 131

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110
```

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Ser
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln
    210                 215

<210> SEQ ID NO 132
<211> LENGTH: 174
<212> TYPE: PRT
<213> ORGANISM: Artificial Sequence
<220> FEATURE:
<223> OTHER INFORMATION: CD25(22-192)-GGC

<400> SEQUENCE: 132

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
            85                  90                  95

Gln Ala Ser Leu Pro Gly His Cys Arg Glu Pro Pro Pro Trp Glu Asn
        100                 105                 110

Glu Ala Thr Glu Arg Ile Tyr His Phe Val Val Gly Gln Met Val Tyr
    115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Gly Gly Cys
                165                 170

<210> SEQ ID NO 133
<211> LENGTH: 192
<212> TYPE: PRT
<213> ORGANISM: Artificial Sequence
<220> FEATURE:
<223> OTHER INFORMATION: CD25(22-213)

<400> SEQUENCE: 133

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

```
Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
 50                      55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                 85                  90                  95

Gln Ala Ser Leu Pro Gly His Cys Arg Glu Pro Pro Trp Glu Asn
                100                 105                 110

Glu Ala Thr Glu Arg Ile Tyr His Phe Val Val Gly Gln Met Val Tyr
                115                 120                 125

Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                    165                 170                 175

Lys Pro Gln Ala Ser Pro Glu Gly Arg Pro Glu Ser Gly Thr Ser Cys
                180                 185                 190

<210> SEQ ID NO 134
<211> LENGTH: 166
<212> TYPE: PRT
<213> ORGANISM: Artificial Sequence
<220> FEATURE:
<223> OTHER INFORMATION: CD25(22-187)(N70C)

<400> SEQUENCE: 134

Glu Leu Cys Asp Asp Asp Pro Pro Glu Ile Pro His Ala Thr Phe Lys
 1               5                  10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Cys Ser Ser His Ser Ser Trp Asp Asn Gln Cys Gln Cys Thr Ser Ser
 50                      55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                 85                  90                  95

Gln Ala Ser Leu Pro Gly His Cys Arg Glu Pro Pro Trp Glu Asn
                100                 105                 110

Glu Ala Thr Glu Arg Ile Tyr His Phe Val Val Gly Gln Met Val Tyr
                115                 120                 125

Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu
                    165

<210> SEQ ID NO 135
<211> LENGTH: 166
<212> TYPE: PRT
<213> ORGANISM: Artificial Sequence
```

```
<220> FEATURE:
<223> OTHER INFORMATION: CD25(22-187)(N89C)

<400> SEQUENCE: 135

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Cys Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu
                165

<210> SEQ ID NO 136
<211> LENGTH: 167
<212> TYPE: PRT
<213> ORGANISM: Artificial Sequence
<220> FEATURE:
<223> OTHER INFORMATION: CD25(22-187)-C

<400> SEQUENCE: 136

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Cys
```

165

<210> SEQ ID NO 137
<211> LENGTH: 167
<212> TYPE: PRT
<213> ORGANISM: Artificial Sequence
<220> FEATURE:
<223> OTHER INFORMATION: CD25(22-187)-G

<400> SEQUENCE: 137

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Gly
                165

<210> SEQ ID NO 138
<211> LENGTH: 193
<212> TYPE: PRT
<213> ORGANISM: Artificial Sequence
<220> FEATURE:
<223> OTHER INFORMATION: CD25(22-212)-PP

<400> SEQUENCE: 138

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

```
Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Pro
            180                 185                 190

Pro

<210> SEQ ID NO 139
<211> LENGTH: 191
<212> TYPE: PRT
<213> ORGANISM: Artificial Sequence
<220> FEATURE:
<223> OTHER INFORMATION: CD25(22-212)(T106A)

<400> SEQUENCE: 139

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Ala Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
                115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser
            180                 185                 190

<210> SEQ ID NO 140
<211> LENGTH: 191
<212> TYPE: PRT
<213> ORGANISM: Artificial Sequence
<220> FEATURE:
<223> OTHER INFORMATION: CD25(22-212)(T95A)

<400> SEQUENCE: 140

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45
```

Asn Ser Ser His Ser Ser Trp Asp Asn Gln Cys Gln Cys Thr Ser Ser
            50                  55                  60

Ala Thr Arg Asn Thr Thr Lys Gln Val Ala Pro Gln Pro Glu Glu Gln
 65                  70                  75                  80

Lys Glu Arg Lys Thr Thr Glu Met Gln Ser Pro Met Gln Pro Val Asp
                 85                  90                  95

Gln Ala Ser Leu Pro Gly His Cys Arg Glu Pro Pro Trp Glu Asn
                100                 105                 110

Glu Ala Thr Glu Arg Ile Tyr His Phe Val Val Gly Gln Met Val Tyr
                115                 120                 125

Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser
                180                 185                 190

<210> SEQ ID NO 141
<211> LENGTH: 191
<212> TYPE: PRT
<213> ORGANISM: Artificial Sequence
<220> FEATURE:
<223> OTHER INFORMATION: CD25(22-212)(T95A+T106A)

<400> SEQUENCE: 141

Glu Leu Cys Asp Asp Asp Pro Pro Glu Ile Pro His Ala Thr Phe Lys
 1               5                  10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
 50                  55                  60

Ala Thr Arg Asn Thr Thr Lys Gln Val Ala Pro Gln Pro Glu Glu Gln
 65                  70                  75                  80

Lys Glu Arg Lys Ala Thr Glu Met Gln Ser Pro Met Gln Pro Val Asp
                 85                  90                  95

Gln Ala Ser Leu Pro Gly His Cys Arg Glu Pro Pro Trp Glu Asn
                100                 105                 110

Glu Ala Thr Glu Arg Ile Tyr His Phe Val Val Gly Gln Met Val Tyr
                115                 120                 125

Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser
                180                 185                 190

<210> SEQ ID NO 142
<211> LENGTH: 193
<212> TYPE: PRT
<213> ORGANISM: Artificial Sequence
<220> FEATURE:

<223> OTHER INFORMATION: CD25(22-212)-PG

<400> SEQUENCE: 142

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Pro
            180                 185                 190

Gly

<210> SEQ ID NO 143
<211> LENGTH: 166
<212> TYPE: PRT
<213> ORGANISM: Artificial Sequence
<220> FEATURE:
<223> OTHER INFORMATION: CD25(22-187)(N70Q+N89Q)

<400> SEQUENCE: 143

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Gln Ser Ser His Ser Ser Trp Asp Asn Gln Cys Gln Cys Thr Ser Ser
    50                  55                  60

Ala Thr Arg Gln Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

```
Ser Val Cys Lys Met Thr His Gly Lys Thr Arg Trp Thr Gln Pro Gln
145                 150                 155                 160

Leu Ile Cys Thr Gly Glu
                165
```

<210> SEQ ID NO 144
<211> LENGTH: 166
<212> TYPE: PRT
<213> ORGANISM: Artificial Sequence
<220> FEATURE:
<223> OTHER INFORMATION: CD25(22-187)(N89Q)

<400> SEQUENCE: 144

```
Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
                35                  40                  45

Asn Ser Ser His Ser Ser Trp Asp Asn Gln Cys Gln Cys Thr Ser Ser
    50                  55                  60

Ala Thr Arg Gln Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
                100                 105                 110

Glu Ala Thr Glu Arg Ile Tyr His Phe Val Val Gly Gln Met Val Tyr
                115                 120                 125

Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu
                165
```

<210> SEQ ID NO 145
<211> LENGTH: 166
<212> TYPE: PRT
<213> ORGANISM: Artificial Sequence
<220> FEATURE:
<223> OTHER INFORMATION: CD25(22-187)(N70Q)

<400> SEQUENCE: 145

```
Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
                35                  40                  45

Gln Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
                100                 105                 110
```

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu
                165

<210> SEQ ID NO 146
<211> LENGTH: 190
<212> TYPE: PRT
<213> ORGANISM: Artificial Sequence
<220> FEATURE:
<223> OTHER INFORMATION: CD25(22-211)

<400> SEQUENCE: 146

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr
            180                 185                 190

<210> SEQ ID NO 147
<211> LENGTH: 189
<212> TYPE: PRT
<213> ORGANISM: Artificial Sequence
<220> FEATURE:
<223> OTHER INFORMATION: CD25(22-210)

<400> SEQUENCE: 147

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser

```
                            50                  55                  60
Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                 85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu
            180                 185

<210> SEQ ID NO 148
<211> LENGTH: 188
<212> TYPE: PRT
<213> ORGANISM: Artificial Sequence
<220> FEATURE:
<223> OTHER INFORMATION: CD25(22-209)

<400> SEQUENCE: 148

Glu Leu Cys Asp Asp Pro Pro Glu Ile Pro His Ala Thr Phe Lys
 1               5                   10                  15

Ala Met Ala Tyr Lys Glu Gly Thr Met Leu Asn Cys Glu Cys Lys Arg
                 20                  25                  30

Gly Phe Arg Arg Ile Lys Ser Gly Ser Leu Tyr Met Leu Cys Thr Gly
             35                  40                  45

Asn Ser Ser His Ser Ser Trp Asp Asn Gln Cys Gln Cys Thr Ser Ser
 50                  55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                 85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser
            180                 185

<210> SEQ ID NO 149
<211> LENGTH: 187
<212> TYPE: PRT
<213> ORGANISM: Artificial Sequence
<220> FEATURE:
<223> OTHER INFORMATION: CD25(22-208)
```

<400> SEQUENCE: 149

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu
            180                 185

<210> SEQ ID NO 150
<211> LENGTH: 186
<212> TYPE: PRT
<213> ORGANISM: Artificial Sequence
<220> FEATURE:
<223> OTHER INFORMATION: CD25(22-207)

<400> SEQUENCE: 150

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro
            180                 185

<210> SEQ ID NO 151
<211> LENGTH: 185
<212> TYPE: PRT
<213> ORGANISM: Artificial Sequence
<220> FEATURE:
<223> OTHER INFORMATION: CD25(22-206)

<400> SEQUENCE: 151

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
        50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg
            180                 185

<210> SEQ ID NO 152
<211> LENGTH: 184
<212> TYPE: PRT
<213> ORGANISM: Artificial Sequence
<220> FEATURE:
<223> OTHER INFORMATION: CD25(22-205)

<400> SEQUENCE: 152

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
        50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

```
Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
            130                 135             140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly
            180
```

<210> SEQ ID NO 153
<211> LENGTH: 183
<212> TYPE: PRT
<213> ORGANISM: Artificial Sequence
<220> FEATURE:
<223> OTHER INFORMATION: CD25(22-204)

<400> SEQUENCE: 153

```
Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
            130                 135             140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu
            180
```

<210> SEQ ID NO 154
<211> LENGTH: 182
<212> TYPE: PRT
<213> ORGANISM: Artificial Sequence
<220> FEATURE:
<223> OTHER INFORMATION: CD25(22-203)

<400> SEQUENCE: 154

```
Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
```

```
                20              25              30
Gly Phe Arg Arg Ile Lys Ser Gly Ser Leu Tyr Met Leu Cys Thr Gly
            35              40              45

Asn Ser Ser His Ser Ser Trp Asp Asn Gln Cys Gln Cys Thr Ser Ser
 50              55              60

Ala Thr Arg Asn Thr Thr Lys Gln Val Thr Pro Gln Pro Glu Glu Gln
 65              70              75              80

Lys Glu Arg Lys Thr Thr Glu Met Gln Ser Pro Met Gln Pro Val Asp
            85              90              95

Gln Ala Ser Leu Pro Gly His Cys Arg Glu Pro Pro Pro Trp Glu Asn
            100             105             110

Glu Ala Thr Glu Arg Ile Tyr His Phe Val Val Gly Gln Met Val Tyr
            115             120             125

Tyr Gln Cys Val Gln Gly Tyr Arg Ala Leu His Arg Gly Pro Ala Glu
            130             135             140

Ser Val Cys Lys Met Thr His Gly Lys Thr Arg Trp Thr Gln Pro Gln
145             150             155             160

Leu Ile Cys Thr Gly Glu Met Glu Thr Ser Gln Phe Pro Gly Glu Glu
                165             170             175

Lys Pro Gln Ala Ser Pro
            180
```

<210> SEQ ID NO 155
<211> LENGTH: 181
<212> TYPE: PRT
<213> ORGANISM: Artificial Sequence
<220> FEATURE:
<223> OTHER INFORMATION: CD25(22-202)

<400> SEQUENCE: 155

```
Glu Leu Cys Asp Asp Asp Pro Pro Glu Ile Pro His Ala Thr Phe Lys
 1               5              10              15

Ala Met Ala Tyr Lys Glu Gly Thr Met Leu Asn Cys Glu Cys Lys Arg
            20              25              30

Gly Phe Arg Arg Ile Lys Ser Gly Ser Leu Tyr Met Leu Cys Thr Gly
            35              40              45

Asn Ser Ser His Ser Ser Trp Asp Asn Gln Cys Gln Cys Thr Ser Ser
 50              55              60

Ala Thr Arg Asn Thr Thr Lys Gln Val Thr Pro Gln Pro Glu Glu Gln
 65              70              75              80

Lys Glu Arg Lys Thr Thr Glu Met Gln Ser Pro Met Gln Pro Val Asp
            85              90              95

Gln Ala Ser Leu Pro Gly His Cys Arg Glu Pro Pro Pro Trp Glu Asn
            100             105             110

Glu Ala Thr Glu Arg Ile Tyr His Phe Val Val Gly Gln Met Val Tyr
            115             120             125

Tyr Gln Cys Val Gln Gly Tyr Arg Ala Leu His Arg Gly Pro Ala Glu
            130             135             140

Ser Val Cys Lys Met Thr His Gly Lys Thr Arg Trp Thr Gln Pro Gln
145             150             155             160

Leu Ile Cys Thr Gly Glu Met Glu Thr Ser Gln Phe Pro Gly Glu Glu
                165             170             175

Lys Pro Gln Ala Ser
            180
```

```
<210> SEQ ID NO 156
<211> LENGTH: 180
<212> TYPE: PRT
<213> ORGANISM: Artificial Sequence
<220> FEATURE:
<223> OTHER INFORMATION: CD25(22-201)

<400> SEQUENCE: 156

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala
            180

<210> SEQ ID NO 157
<211> LENGTH: 179
<212> TYPE: PRT
<213> ORGANISM: Artificial Sequence
<220> FEATURE:
<223> OTHER INFORMATION: CD25(22-200)

<400> SEQUENCE: 157

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
        115                 120                 125
```

```
Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln

<210> SEQ ID NO 158
<211> LENGTH: 178
<212> TYPE: PRT
<213> ORGANISM: Artificial Sequence
<220> FEATURE:
<223> OTHER INFORMATION: CD25(22-199)

<400> SEQUENCE: 158

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro

<210> SEQ ID NO 159
<211> LENGTH: 177
<212> TYPE: PRT
<213> ORGANISM: Artificial Sequence
<220> FEATURE:
<223> OTHER INFORMATION: CD25(22-198)

<400> SEQUENCE: 159

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
50                  55                  60

Ala Thr Arg Asn Thr Thr Lys Gln Val Thr Pro Gln Pro Glu Glu Gln
```

```
                65                  70                  75                  80
Lys Glu Arg Lys Thr Thr Glu Met Gln Ser Pro Met Gln Pro Val Asp
                    85                  90                  95

Gln Ala Ser Leu Pro Gly His Cys Arg Glu Pro Pro Trp Glu Asn
                100                 105                 110

Glu Ala Thr Glu Arg Ile Tyr His Phe Val Val Gly Gln Met Val Tyr
                115                 120                 125

Tyr Gln Cys Val Gln Gly Tyr Arg Ala Leu His Arg Gly Pro Ala Glu
                130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys

<210> SEQ ID NO 160
<211> LENGTH: 176
<212> TYPE: PRT
<213> ORGANISM: Artificial Sequence
<220> FEATURE:
<223> OTHER INFORMATION: CD25(22-197)

<400> SEQUENCE: 160

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
                35                  40                  45

Asn Ser Ser His Ser Ser Trp Asp Asn Gln Cys Gln Cys Thr Ser Ser
                50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                    85                  90                  95

Gln Ala Ser Leu Pro Gly His Cys Arg Glu Pro Pro Trp Glu Asn
                100                 105                 110

Glu Ala Thr Glu Arg Ile Tyr His Phe Val Val Gly Gln Met Val Tyr
                115                 120                 125

Tyr Gln Cys Val Gln Gly Tyr Arg Ala Leu His Arg Gly Pro Ala Glu
                130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

<210> SEQ ID NO 161
<211> LENGTH: 175
<212> TYPE: PRT
<213> ORGANISM: Artificial Sequence
<220> FEATURE:
<223> OTHER INFORMATION: CD25(22-196)

<400> SEQUENCE: 161

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
```

```
            20                  25                  30
Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
 50                      55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                     85                  90                  95

Gln Ala Ser Leu Pro Gly His Cys Arg Glu Pro Pro Pro Trp Glu Asn
                100                 105                 110

Glu Ala Thr Glu Arg Ile Tyr His Phe Val Val Gly Gln Met Val Tyr
                115                 120                 125

Tyr Gln Cys Val Gln Gly Tyr Arg Ala Leu His Arg Gly Pro Ala Glu
                130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu
                165                 170                 175
```

<210> SEQ ID NO 162
<211> LENGTH: 174
<212> TYPE: PRT
<213> ORGANISM: Artificial Sequence
<220> FEATURE:
<223> OTHER INFORMATION: CD25(22-195)

<400> SEQUENCE: 162

```
Glu Leu Cys Asp Asp Asp Pro Pro Glu Ile Pro His Ala Thr Phe Lys
 1               5                  10                  15

Ala Met Ala Tyr Lys Glu Gly Thr Met Leu Asn Cys Glu Cys Lys Arg
                 20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
 50                      55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                     85                  90                  95

Gln Ala Ser Leu Pro Gly His Cys Arg Glu Pro Pro Pro Trp Glu Asn
                100                 105                 110

Glu Ala Thr Glu Arg Ile Tyr His Phe Val Val Gly Gln Met Val Tyr
                115                 120                 125

Tyr Gln Cys Val Gln Gly Tyr Arg Ala Leu His Arg Gly Pro Ala Glu
                130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly
                165                 170
```

<210> SEQ ID NO 163
<211> LENGTH: 173
<212> TYPE: PRT
<213> ORGANISM: Artificial Sequence
<220> FEATURE:
<223> OTHER INFORMATION: CD25(22-194)

<400> SEQUENCE: 163

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro
                165                 170

<210> SEQ ID NO 164
<211> LENGTH: 172
<212> TYPE: PRT
<213> ORGANISM: Artificial Sequence
<220> FEATURE:
<223> OTHER INFORMATION: CD25(22-193)

<400> SEQUENCE: 164

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe
                165                 170

<210> SEQ ID NO 165
<211> LENGTH: 171
<212> TYPE: PRT
<213> ORGANISM: Artificial Sequence
<220> FEATURE:
<223> OTHER INFORMATION: CD25(22-192)

<400> SEQUENCE: 165

```
Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln
                165                 170
```

<210> SEQ ID NO 166
<211> LENGTH: 170
<212> TYPE: PRT
<213> ORGANISM: Artificial Sequence
<220> FEATURE:
<223> OTHER INFORMATION: CD25(22-191)

<400> SEQUENCE: 166

```
Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140
```

```
Ser Val Cys Lys Met Thr His Gly Lys Thr Arg Trp Thr Gln Pro Gln
145                 150                 155                 160

Leu Ile Cys Thr Gly Glu Met Glu Thr Ser
                165                 170

<210> SEQ ID NO 167
<211> LENGTH: 169
<212> TYPE: PRT
<213> ORGANISM: Artificial Sequence
<220> FEATURE:
<223> OTHER INFORMATION: CD25(22-190)

<400> SEQUENCE: 167

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
        50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
                100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr
                165

<210> SEQ ID NO 168
<211> LENGTH: 168
<212> TYPE: PRT
<213> ORGANISM: Artificial Sequence
<220> FEATURE:
<223> OTHER INFORMATION: CD25(22-189)

<400> SEQUENCE: 168

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
        50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
```

```
              100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu
            165
```

<210> SEQ ID NO 169
<211> LENGTH: 167
<212> TYPE: PRT
<213> ORGANISM: Artificial Sequence
<220> FEATURE:
<223> OTHER INFORMATION: CD25(22-188)

<400> SEQUENCE: 169

```
Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met
            165
```

<210> SEQ ID NO 170
<211> LENGTH: 1
<212> TYPE: PRT
<213> ORGANISM: Artificial Sequence
<220> FEATURE:
<223> OTHER INFORMATION: Linker sequence

<400> SEQUENCE: 170

Gly
1

<210> SEQ ID NO 171
<211> LENGTH: 2
<212> TYPE: PRT
<213> ORGANISM: Artificial Sequence
<220> FEATURE:
<223> OTHER INFORMATION: Linker sequence

<400> SEQUENCE: 171

```
Gly Gly
1

<210> SEQ ID NO 172
<211> LENGTH: 2
<212> TYPE: PRT
<213> ORGANISM: Artificial Sequence
<220> FEATURE:
<223> OTHER INFORMATION: Linker sequence

<400> SEQUENCE: 172

Gly Ser
1

<210> SEQ ID NO 173
<211> LENGTH: 3
<212> TYPE: PRT
<213> ORGANISM: Artificial Sequence
<220> FEATURE:
<223> OTHER INFORMATION: Linker sequence

<400> SEQUENCE: 173

Gly Gly Ser
1

<210> SEQ ID NO 174
<211> LENGTH: 4
<212> TYPE: PRT
<213> ORGANISM: Artificial Sequence
<220> FEATURE:
<223> OTHER INFORMATION: Linker sequence

<400> SEQUENCE: 174

Gly Gly Gly Ser
1

<210> SEQ ID NO 175
<211> LENGTH: 5
<212> TYPE: PRT
<213> ORGANISM: Artificial Sequence
<220> FEATURE:
<223> OTHER INFORMATION: Linker sequence

<400> SEQUENCE: 175

Gly Gly Ser Gly Gly
1               5

<210> SEQ ID NO 176
<211> LENGTH: 6
<212> TYPE: PRT
<213> ORGANISM: Artificial Sequence
<220> FEATURE:
<223> OTHER INFORMATION: Linker sequence

<400> SEQUENCE: 176

Gly Gly Gly Ser Gly Gly
1               5

<210> SEQ ID NO 177
<211> LENGTH: 7
<212> TYPE: PRT
<213> ORGANISM: Artificial Sequence
<220> FEATURE:
<223> OTHER INFORMATION: Linker sequence

<400> SEQUENCE: 177
```

Gly Gly Ser Gly Gly Ser Gly
1               5

<210> SEQ ID NO 178
<211> LENGTH: 8
<212> TYPE: PRT
<213> ORGANISM: Artificial Sequence
<220> FEATURE:
<223> OTHER INFORMATION: Linker sequence

<400> SEQUENCE: 178

Gly Gly Ser Gly Gly Gly Ser Gly
1               5

<210> SEQ ID NO 179
<211> LENGTH: 9
<212> TYPE: PRT
<213> ORGANISM: Artificial Sequence
<220> FEATURE:
<223> OTHER INFORMATION: Linker sequence

<400> SEQUENCE: 179

Gly Gly Gly Ser Gly Gly Gly Ser Gly
1               5

<210> SEQ ID NO 180
<211> LENGTH: 10
<212> TYPE: PRT
<213> ORGANISM: Artificial Sequence
<220> FEATURE:
<223> OTHER INFORMATION: Linker sequence

<400> SEQUENCE: 180

Gly Gly Gly Gly Ser Gly Gly Gly Gly Ser
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Linker sequence

<400> SEQUENCE: 181

Gly Gly Gly Gly Ser Gly Gly Gly Gly Ser Gly
1               5                   10

<210> SEQ ID NO 182
<211> LENGTH: 5
<212> TYPE: PRT
<213> ORGANISM: Artificial Sequence
<220> FEATURE:
<223> OTHER INFORMATION: Linker sequence

<400> SEQUENCE: 182

Glu Pro Lys Ser Ser
1               5

<210> SEQ ID NO 183
<211> LENGTH: 4
<212> TYPE: PRT
<213> ORGANISM: Artificial Sequence
<220> FEATURE:
<223> OTHER INFORMATION: Linker sequence

<400> SEQUENCE: 183

Pro Lys Ser Ser

```
<210> SEQ ID NO 184
<211> LENGTH: 3
<212> TYPE: PRT
<213> ORGANISM: Artificial Sequence
<220> FEATURE:
<223> OTHER INFORMATION: Linker sequence

<400> SEQUENCE: 184

Lys Ser Ser
1

<210> SEQ ID NO 185
<211> LENGTH: 2
<212> TYPE: PRT
<213> ORGANISM: Artificial Sequence
<220> FEATURE:
<223> OTHER INFORMATION: Linker sequence

<400> SEQUENCE: 185

Ser Ser
1

<210> SEQ ID NO 186
<211> LENGTH: 1
<212> TYPE: PRT
<213> ORGANISM: Artificial Sequence
<220> FEATURE:
<223> OTHER INFORMATION: Linker sequence

<400> SEQUENCE: 186

Ser
1

<210> SEQ ID NO 187
<211> LENGTH: 226
<212> TYPE: PRT
<213> ORGANISM: Artificial Sequence
<220> FEATURE:
<223> OTHER INFORMATION: IgG1-Fc

<400> SEQUENCE: 187

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
```

```
                145                 150                 155                 160
Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
            210                 215                 220

Pro Gly
225

<210> SEQ ID NO 188
<211> LENGTH: 226
<212> TYPE: PRT
<213> ORGANISM: Artificial Sequence
<220> FEATURE:
<223> OTHER INFORMATION: IgG1.1-Fc

<400> SEQUENCE: 188

Asp Lys Thr His Thr Cys Pro Pro Cys Pro Ala Pro Glu Ala Glu Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ser Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
            210                 215                 220

Pro Gly
225

<210> SEQ ID NO 189
<211> LENGTH: 226
<212> TYPE: PRT
<213> ORGANISM: Artificial Sequence
<220> FEATURE:
<223> OTHER INFORMATION: IgG1.3-Fc
```

<400> SEQUENCE: 189

```
Asp Lys Thr His Thr Cys Pro Pro Cys Pro Ala Pro Glu Ala Glu Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 190
<211> LENGTH: 226
<212> TYPE: PRT
<213> ORGANISM: Artificial Sequence
<220> FEATURE:
<223> OTHER INFORMATION: IgG1-Fc(P238K)

<400> SEQUENCE: 190

```
Asp Lys Thr His Thr Cys Pro Pro Cys Pro Ala Pro Glu Leu Leu Gly
1               5                   10                  15

Gly Lys Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly
225

<210> SEQ ID NO 191
<211> LENGTH: 229
<212> TYPE: PRT
<213> ORGANISM: Artificial Sequence
<220> FEATURE:
<223> OTHER INFORMATION: IgG4-Fc

<400> SEQUENCE: 191

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

```
<210> SEQ ID NO 192
<211> LENGTH: 229
<212> TYPE: PRT
<213> ORGANISM: Artificial Sequence
<220> FEATURE:
<223> OTHER INFORMATION: IgG4.1-F c

<400> SEQUENCE: 192

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 193
<211> LENGTH: 226
<212> TYPE: PRT
<213> ORGANISM: Artificial Sequence
<220> FEATURE:
<223> OTHER INFORMATION: IgG1.3-Fc-knob

<400> SEQUENCE: 193

Asp Lys Thr His Thr Cys Pro Pro Cys Pro Ala Pro Glu Ala Glu Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 194
<211> LENGTH: 226
<212> TYPE: PRT
<213> ORGANISM: Artificial Sequence
<220> FEATURE:
<223> OTHER INFORMATION: IgG1.3-Fc-hole

<400> SEQUENCE: 194

Asp Lys Thr His Thr Cys Pro Pro Cys Pro Ala Pro Glu Ala Glu Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Leu Ser
        210                 215                 220

Pro Gly
225

<210> SEQ ID NO 195
<211> LENGTH: 226
<212> TYPE: PRT
<213> ORGANISM: Artificial Sequence
<220> FEATURE:
<223> OTHER INFORMATION: IgG1-Fc(P238K)-knob

<400> SEQUENCE: 195

Asp Lys Thr His Thr Cys Pro Pro Cys Pro Ala Pro Glu Leu Leu Gly
1               5                   10                  15

Gly Lys Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 196
<211> LENGTH: 226
<212> TYPE: PRT
<213> ORGANISM: Artificial Sequence
<220> FEATURE:
<223> OTHER INFORMATION: IgG1-Fc(P238K)-hole

<400> SEQUENCE: 196

Asp Lys Thr His Thr Cys Pro Pro Cys Pro Ala Pro Glu Leu Leu Gly
1               5                   10                  15

Gly Lys Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His

```
            35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Glu Glu Met Thr Lys Asn Gln Val Ser
130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
210                 215                 220
Pro Gly
225

<210> SEQ ID NO 197
<211> LENGTH: 226
<212> TYPE: PRT
<213> ORGANISM: Artificial Sequence
<220> FEATURE:
<223> OTHER INFORMATION: IgG1.1-Fc(AZ1)

<400> SEQUENCE: 197

Asp Lys Thr His Thr Cys Pro Pro Cys Pro Ala Pro Glu Ala Glu Gly
 1               5                  10                  15
Ala Pro Ser Val Phe Leu Phe Pro Pro Lys Pro Lys Asp Thr Leu Met
             20                  25                  30
Ile Ser Arg Thr Pro Glu Val Thr Cys Val Val Val Asp Val Ser His
             35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ser Ser Ile
            100                 105                 110
Glu Lys Thr Ile Ser Lys Ala Lys Gly Gln Pro Arg Glu Pro Gln Val
            115                 120                 125
Tyr Val Tyr Pro Pro Ser Arg Glu Glu Met Thr Lys Asn Gln Val Ser
130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
```

```
                       165                 170                 175
Val Leu Asp Ser Asp Gly Ser Phe Ala Leu Val Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly
225

<210> SEQ ID NO 198
<211> LENGTH: 226
<212> TYPE: PRT
<213> ORGANISM: Artificial Sequence
<220> FEATURE:
<223> OTHER INFORMATION: IgG1.1-Fc(AZ2)

<400> SEQUENCE: 198

Asp Lys Thr His Thr Cys Pro Pro Cys Pro Ala Pro Glu Ala Glu Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ser Ser Ile
                100                 105                 110

Glu Lys Thr Ile Ser Lys Ala Lys Gly Gln Pro Arg Glu Pro Gln Val
            115                 120                 125

Tyr Val Leu Pro Pro Ser Arg Glu Glu Met Thr Lys Asn Gln Val Ser
        130                 135                 140

Leu Leu Cys Leu Val Lys Gly Phe Tyr Pro Ser Asp Ile Ala Val Glu
145                 150                 155                 160

Trp Glu Ser Asn Gly Gln Pro Glu Asn Asn Tyr Leu Thr Trp Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly
225

<210> SEQ ID NO 199
<211> LENGTH: 585
<212> TYPE: PRT
<213> ORGANISM: Artificial Sequence
<220> FEATURE:
<223> OTHER INFORMATION: Human Serum Albumin

<400> SEQUENCE: 199
```

-continued

```
Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
            20                  25                  30
Gln Cys Pro Phe Glu Asp His Val Lys Leu Val Asn Glu Val Thr Glu
        35                  40                  45
Phe Ala Lys Thr Cys Val Ala Asp Glu Ser Ala Glu Asn Cys Asp Lys
50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
```

```
            420                 425                 430
Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 200
<211> LENGTH: 585
<212> TYPE: PRT
<213> ORGANISM: Artificial Sequence
<220> FEATURE:
<223> OTHER INFORMATION: HSA(C34S)

<400> SEQUENCE: 200

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
```

```
            195                 200                 205
Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 201
<211> LENGTH: 585
<212> TYPE: PRT
<213> ORGANISM: Artificial Sequence
```

<220> FEATURE:
<223> OTHER INFORMATION: HSA(C35A)

<400> SEQUENCE: 201

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 202
<211> LENGTH: 311
<212> TYPE: PRT
<213> ORGANISM: Artificial Sequence
<220> FEATURE:
<223> OTHER INFORMATION: IL2-T3A-CD25(22-187)-N89Q-T95A-T106A

<400> SEQUENCE: 202

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Ser Gly Gly Gly Gly
    130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175
```

```
Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
            195                 200                 205

Ser Ala Thr Arg Gln Thr Thr Lys Gln Val Ala Pro Gln Pro Glu Glu
210                 215                 220

Gln Lys Glu Arg Lys Ala Thr Glu Met Gln Ser Pro Met Gln Pro Val
225                 230                 235                 240

Asp Gln Ala Ser Leu Pro Gly His Cys Arg Glu Pro Pro Pro Trp Glu
            245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
            275                 280                 285

Glu Ser Val Cys Lys Met Thr His Gly Lys Thr Arg Trp Thr Gln Pro
            290                 295                 300

Gln Leu Ile Cys Thr Gly Glu
305                 310

<210> SEQ ID NO 203
<211> LENGTH: 569
<212> TYPE: PRT
<213> ORGANISM: Artificial Sequence
<220> FEATURE:
<223> OTHER INFORMATION: Fc-(IL2(V91K)CD25)2 bivalent

<400> SEQUENCE: 203

Asp Lys Thr His Thr Cys Pro Pro Cys Pro Ala Pro Glu Leu Leu Gly
1               5                   10                  15

Gly Lys Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220
```

Pro Gly Gly Ser Gly Gly Ser Gly Gly Ala Pro Thr Ser Ser Ser Thr
225                 230                 235                 240

Lys Lys Thr Gln Leu Gln Leu Glu His Leu Leu Asp Leu Gln Met
            245                 250                 255

Ile Leu Asn Gly Ile Asn Asn Tyr Lys Asn Pro Lys Leu Thr Arg Met
                260                 265                 270

Leu Thr Phe Lys Phe Tyr Met Pro Lys Ala Thr Glu Leu Lys His
            275                 280                 285

Leu Gln Cys Leu Glu Glu Glu Leu Lys Pro Leu Glu Glu Val Leu Asn
            290                 295                 300

Leu Ala Gln Ser Lys Asn Phe His Leu Arg Pro Arg Asp Leu Ile Ser
305                 310                 315                 320

Asn Ile Asn Lys Ile Val Leu Glu Leu Lys Gly Ser Glu Thr Thr Phe
                325                 330                 335

Met Cys Glu Tyr Ala Asp Glu Thr Ala Thr Ile Val Glu Phe Leu Asn
                340                 345                 350

Arg Trp Ile Thr Phe Cys Gln Ser Ile Ile Ser Thr Leu Thr Gly Gly
                355                 360                 365

Gly Ser Gly Gly Ser Gly Gly Ser Glu Leu Cys Asp Asp
370                 375                 380

Pro Pro Glu Ile Pro His Ala Thr Phe Lys Ala Met Ala Tyr Lys Glu
385                 390                 395                 400

Gly Thr Met Leu Asn Cys Glu Cys Lys Arg Gly Phe Arg Arg Ile Lys
                405                 410                 415

Ser Gly Ser Leu Tyr Met Leu Cys Thr Gly Asn Ser Ser His Ser Ser
                420                 425                 430

Trp Asp Asn Gln Cys Gln Cys Thr Ser Ser Ala Thr Arg Asn Thr Thr
                435                 440                 445

Lys Gln Val Thr Pro Gln Pro Glu Glu Gln Lys Glu Arg Lys Thr Thr
                450                 455                 460

Glu Met Gln Ser Pro Met Gln Pro Val Asp Gln Ala Ser Leu Pro Gly
465                 470                 475                 480

His Cys Arg Glu Pro Pro Pro Trp Glu Asn Glu Ala Thr Glu Arg Ile
                485                 490                 495

Tyr His Phe Val Val Gly Gln Met Val Tyr Tyr Gln Cys Val Gln Gly
                500                 505                 510

Tyr Arg Ala Leu His Arg Gly Pro Ala Glu Ser Val Cys Lys Met Thr
                515                 520                 525

His Gly Lys Thr Arg Trp Thr Gln Pro Gln Leu Ile Cys Thr Gly Glu
                530                 535                 540

Met Glu Thr Ser Gln Phe Pro Gly Glu Glu Lys Pro Gln Ala Ser Pro
545                 550                 555                 560

Glu Gly Arg Pro Glu Ser Glu Thr Ser
                565

<210> SEQ ID NO 204
<211> LENGTH: 364
<212> TYPE: PRT
<213> ORGANISM: Artificial Sequence
<220> FEATURE:
<223> OTHER INFORMATION: IL2(21-153)-(G3S)3-CD25(22-240)

<400> SEQUENCE: 204

Ala Pro Thr Ser Ser Ser Thr Lys Lys Thr Gln Leu Gln Leu Glu His
1               5                   10                  15

```
Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Ser Gly Gly Gly Ser Gly Gly Gly
        130                 135                 140

Ser Glu Leu Cys Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
                180                 185                 190

Gly Asn Ser Ser His Ser Ser Trp Asp Asn Gln Cys Gln Cys Thr Ser
                195                 200                 205

Ser Ala Thr Arg Asn Thr Thr Lys Gln Val Thr Pro Gln Pro Glu Glu
                210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Trp Glu
                245                 250                 255

Asn Glu Ala Thr Glu Arg Ile Tyr His Phe Val Val Gly Gln Met Val
                260                 265                 270

Tyr Tyr Gln Cys Val Gln Gly Tyr Arg Ala Leu His Arg Gly Pro Ala
                275                 280                 285

Glu Ser Val Cys Lys Met Thr His Gly Lys Thr Arg Trp Thr Gln Pro
                290                 295                 300

Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

Cys Leu Val Thr Thr Thr Asp Phe Gln Ile Gln Thr Glu Met Ala Ala
                340                 345                 350

Thr Met Glu Thr Ser Ile Phe Thr Thr Glu Tyr Gln
                355                 360
```